(12) United States Patent
Cheng et al.

(10) Patent No.: US 12,414,990 B2
(45) Date of Patent: Sep. 16, 2025

(54) **USE OF HLA-A*11:01-RESTRICTED HEPATITIS B VIRUS (HBV) PEPTIDES FOR IDENTIFYING HBV-SPECIFIC CD8+ T CELLS**

(71) Applicant: AGENCY FOR SCIENCE, TECHNOLOGY AND RESEARCH, Singapore (SG)

(72) Inventors: Yang Cheng, Singapore (SG); Evan Newell, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 827 days.

(21) Appl. No.: 17/421,816

(22) PCT Filed: Jan. 13, 2020

(86) PCT No.: PCT/SG2020/050017
§ 371 (c)(1),
(2) Date: Jul. 9, 2021

(87) PCT Pub. No.: WO2020/145901
PCT Pub. Date: Jul. 16, 2020

(65) Prior Publication Data
US 2023/0087348 A1 Mar. 23, 2023

(30) Foreign Application Priority Data
Jan. 11, 2019 (SG) .............................. 10201900299V

(51) Int. Cl.
| A61K 39/29 | (2006.01) |
| A61K 35/17 | (2025.01) |
| A61K 40/11 | (2025.01) |
| A61K 40/32 | (2025.01) |
| A61K 40/46 | (2025.01) |
| C12N 15/86 | (2006.01) |

(52) U.S. Cl.
CPC ............ *A61K 39/292* (2013.01); *A61K 35/17* (2013.01); *A61K 40/11* (2025.01); *A61K 40/32* (2025.01); *A61K 40/46* (2025.01); *C12N 15/86* (2013.01)

(58) Field of Classification Search
CPC ...... A61K 39/292; A61K 40/46; A61K 40/32; A61K 40/11; A61K 35/17; A61K 2039/5158; C12N 15/86
See application file for complete search history.

(56) References Cited

U.S. PATENT DOCUMENTS

| 5,840,303 | A  | * | 11/1998 | Chisari .................. C07K 14/005 424/152.1 |
| 6,977,074 | B2 | * | 12/2005 | Kundig .................... A61P 31/12 536/23.5 |
| 9,896,483 | B2 | * | 2/2018  | Lu ........................... C07K 14/005 |
| 10,912,827 | B2 | * | 2/2021  | Protzer .................... C12N 15/86 |
| 11,918,645 | B2 | * | 3/2024  | Georges ................... A61K 39/12 |
| 2003/0152580 | A1 | * | 8/2003  | Sette ......................... C07K 7/06 424/193.1 |
| 2024/0066117 | A1 | * | 2/2024  | Balsitis .................. C12N 9/1252 |

FOREIGN PATENT DOCUMENTS

| CN | 102286075 A | 12/2011 | |
| WO | 93/03753 A1 | 3/1993 | |
| WO | WO-9945954 A1 * | 9/1999 | ............. C07K 14/36 |
| WO | 2009/136874 A1 | 11/2009 | |
| WO | WO-2017171631 A1 * | 10/2017 | ............. A61K 35/17 |
| WO | 1999/45954 A1 | 9/2019 | |
| WO | WO-2023146978 A2 * | 8/2023 | ............. G16B 15/30 |

OTHER PUBLICATIONS

GenBank Accession No. CDW17271.1. Rajput et al. Direct Submission. Jun. 11, 2014. (Year: 2014).*
GenBank Accession No. AHF95990.1. Saha et al. Direct Submission. Oct. 17, 2013. (Saha 1) (Year: 2013).*
GenBank Accession No. AHF95990.1. Saha et al. Direct Submission. Oct. 17, 2013. (Saha 2) (Year: 2013).*
GenBank Accession No. ACJ66105.1. Pourkarim et al. Direct Submission. Jun. 30, 2008. (Year: 2008).*
GenBank Accession No. AIW67756.1. Loureiro et al. Direct Submission. Sep. 22, 2014 (Year: 2014).*
GenBank Accession No. ATV92450.1. Li et al. Direct Submission. Mar. 31, 2017. (Year: 2017).*

(Continued)

*Primary Examiner* — Janet L Andres
*Assistant Examiner* — Carey Alexander Stuart
(74) *Attorney, Agent, or Firm* — Troutman Pepper Locke LLP

(57) ABSTRACT

The present invention relates to peptides and their ability to identify and bind to T cells specific for HBV-infected hepatocytes. In a first aspect of the invention, there is provided a peptide comprising an amino acid sequence selected from the group consisting of STLPETAVVRR (SEQ ID NO: 21), STLPETAVVR (SEQ ID NO: 22), STLPETTVVRR (SEQ ID NO: 23), STLPETTVTRR (SEQ ID NO: 24), STPPETTVVRR (SEQ ID NO: 25), STLPETTVVGR (SEQ ID NO: 26) and STIPETTVVRR (SEQ ID NO: 27), wherein the peptide is derived from Hepatitis B virus core169 and is capable of binding HLA-A*1101 and when bound to HLA-A*1101 is capable of identifying T cells specific for Hepatitis B virus. In a second aspect of the invention, there is provided a T cell expressing a T cell receptor (TCR) molecule, wherein the TCR molecule comprises an amino acid sequence selected from the group consisting of CASGDSNSPLHF (SEQ ID NO: 17), CASSGGQIVYEQYF (SEQ ID NO: 18), CSARGGRGGDYTF (SEQ ID NO: 19) and CASSQDWTEAFF (SEQ ID NO: 20), and wherein the TCR molecule is able to bind to a peptide according to the first aspect of the invention.

Figures 1A, 1B:
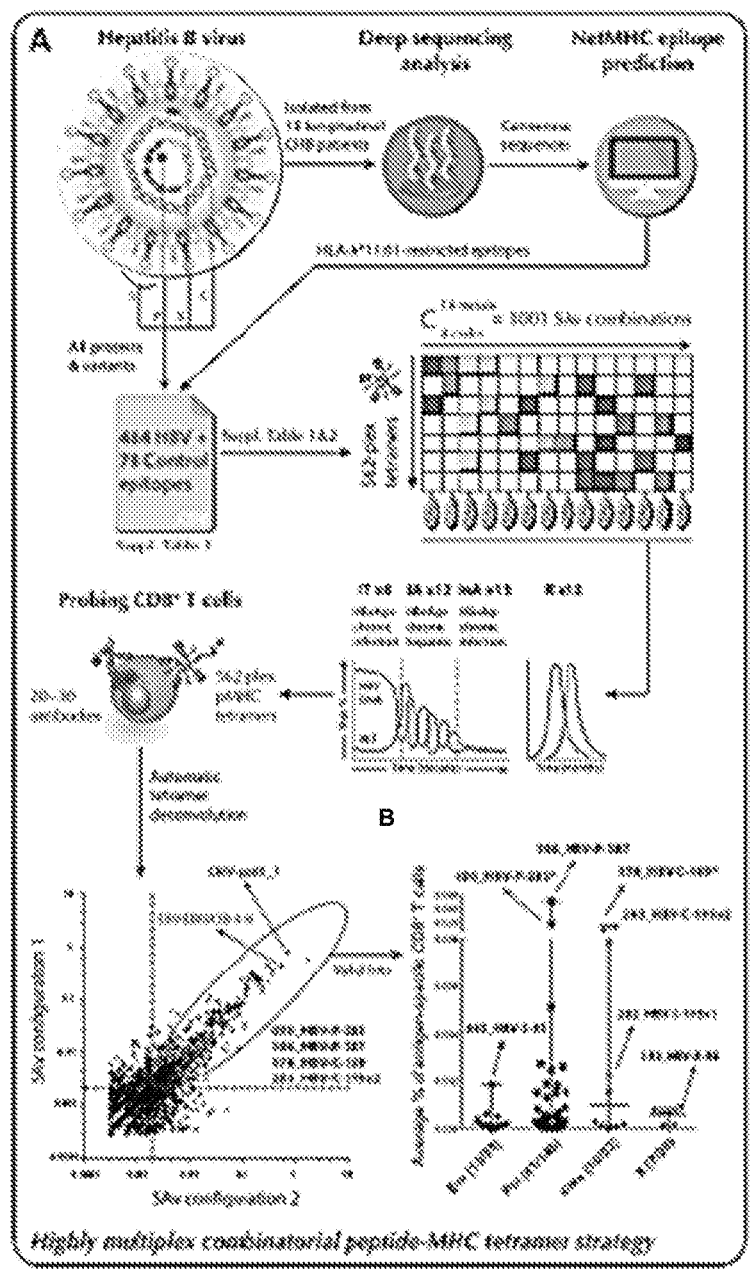

16 Claims, 23 Drawing Sheets
Specification includes a Sequence Listing.

(56) References Cited

OTHER PUBLICATIONS

GenBank Accession No. BAD91277.1. Shibayama et al. Direct Submission. Sep. 29, 2004. (Year: 2004).*
Kefalakes H. et al., "Adaptation of the hepatitis B virus core protein to CD8 T-cell selection pressure." Hepatology, Feb. 26, 2015, vol. 62, No. 1 pp. 47-56.
Huang M. et al., "Improved Transgenic Mouse Model for Studying HLA Class I Antigen Presentation." Sci Rep, Sep. 16, 2016, vol. 6, pp. e33612: 1-12.
Cheng Y. et al., "Multifactorial heterogeneity of virus-specific T cells and associate with the progression of human chronic hepatitis B infection." Sci Immunol, Feb. 8, 2019, vol. 4, No. 32, pp. eaau6905: 1-16.
International Search Report/Written Opinion dated Mar. 3, 2020 from corresponding application No. PCT/SG/2020/050017.
Extended European Search Report mailed Jan. 4, 2023 for EP Patent Application No. 20738835.6, Applicant: Agency for Science, Technology and Research; (10 pages).
Singapore Written Opinion mailed Jul. 6, 2022 for SG11202107510S filed Jan. 13, 2020, Examiner's Reference No. IPOS/SYY; (6 pages).
Chen Xiaoling et al: "An immmunodominant HLA-A*1101-restricted CD8+ T-cell response targeting hepatitis B surface antigen in chronic hepatitis B patients", Journal of General Virology, vol. 94, No. 12, Dec. 1, 2013; pp. 2717-2723, XP093009553, ISSN: 0022-1317, DOI: 10.1099/vir.0.052167-0.
Tickotsky Nili et al: "McPAS-TCR: a manually curated catalogue of pathology-associated T cell receptor sequences", Bioinformatics, vol. 33, No. 18, May 8, 2017, pp. 2924-2929, XP093009557, GB ISSN: 1367-4803, DOI: 10.1093/bioinformatics/btx286.
Qasim Waseem et al: "Immunotherapy of HCC 8-12 metastases with autologous T cell receptor redirected T cells, targeting HBsAg in a liver transplant patient", Journal of Hepatology, vol. 62, No. 2, Feb. 1, 2015, pp. 486-491, XP093009801, Amsterdam, NL ISSN: 0168-8278, DOI: 10.1016/j.jhep.2014.10.001.
Linda Wooldridge et al: "Tricks with tetramers: how to get the most from multimeric peptide-MHC", Cancer Research, Wiley-Blackwell Publishing Ltd, GB, vol. 126, No. 2, Jan. 5, 2009, pp. 147-164, XP071275787, ISSN: 0019-2805, DOI: 10.1111/J.1365-2567.2008.02848.X.
Gabriele Missale, et al., HLA-A31- and HLA-Aw68-restricted Cytotoxic T Cell Responses to a Single Hepatitis B Virus Nucleocapsid Epitope during Acute Viral Hepatitis, J. Exp. Med., vol. 177 ,Mar. 1993, 751-762, © The Rockefeller University Press • 0022-1007/93/03/0751/12.

* cited by examiner

USE OF HLA-A*11:01-RESTRICTED HEPATITIS B VIRUS (HBV) PEPTIDES FOR IDENTIFYING HBV-SPECIFIC CD8+ T CELLS

CROSS-REFERENCE TO RELATED APPLICATIONS

This application is a U.S. National Phase of International Patent Application No. PCT/SG2020/050017, filed on Jan. 13, 2020, which claims priority to Singapore Application No. 10201900299V, filed Jan. 11, 2019. The entire contents of these applications are incorporated herein by reference in their entirety.

SEQUENCE LISTING

The instant application contains a Sequence Listing which has been submitted electronically in ASCII format and is hereby incorporated by reference in its entirety. Said ASCII copy, created on Mar. 11, 2022, is named 245866.000006_ST25.txt and is 103,083 bytes in size.

The present invention relates to peptides and their ability to identify and bind to T cells specific for HBV-infected hepatocytes.

The listing or discussion of an apparently prior-published document in this specification should not necessarily be taken as an acknowledgement that the document is part of the state of the art or is common general knowledge.

Any document referred to herein is hereby incorporated by reference in its entirety.

Chronic HBV infection (CHB) remains a major health issue and is the leading causative agent of hepatocellular carcinoma (HCC) worldwide. Despite an effective vaccine, CHB has no cure and many patients are only diagnosed during the later stages of the disease where treatment efficacy is limited. The estimated mortality due to viral hepatitis has escalated by more than 50% in last decade. CHB develops into a series of stages that are defined by a few clinical parameters with limited associated immunological evidence. How adaptive immunity changes as young patients progress from the Immune Tolerant stage (IT, or HBeAg+ chronic infection, high viremia but limited liver inflammation), to progressive Immune Active stage (IA, or HBeAg+ chronic hepatitis, high viremia and high liver inflammation), and for some, spontaneously become HBeAg– Inactive Carriers (InA, or HBeAg– chronic infection, low-to-undetectable viral load and limited liver inflammation), is not thoroughly understood. Some argue that these definitions could affect early treatment opportunity and should be revisited.

Despite their low frequency in most CHB patients, the virus-specific T cell response has been of much interest for HBV immunologists. Seminal experiments on CHB patients and animal models such as HBV challenged chimpanzee has shown the indispensable function of virus-specific CD8+ T cells in viral control. Historically, mapping for potential virus-specific CD8+ T cells against HBV has mainly focused on HLA-A*02:01-restricted epitopes. For instance, numerous studies on a single epitope targeted by A*02:01-restricted HBVcore18-27-specific CD8+ T cells has provided many implications for immunotherapy. However, in Asia, which has high prevalence of HBV infection, the predominant allele in common East-Asian ethnicities is A*11:01, whose immunogenicity against chronic HBV is poorly defined. Hence, there is an unmet need to investigate A*11:01-restricted HBV-specific CD8+ T cells in CHB. Furthermore, regardless of MHC-restriction, due to the very low frequencies of HBV-specific T cells, information about their un-manipulated phenotypes are lacking.

In murine chronic lymphocytic choriomeningitis virus (LCMV) infection, prolonged and elevated viral antigenic exposure coincides with the upregulation of multiple inhibitory receptors on virus-specific T cells has led to the definition of the state of T cell exhaustion. The resemblance of exhausted T cells (TEX) observed in human chronicviral infection provides an explanation for the functional failure of immune response, but also pinpoints a valuable target to boost host immunity. Evidences suggest that such TEX cells arise from an altered path of memory T cell development. Besides several well-described defects, a hallmark of T cell exhaustion is a progressive loss of functional capacity, which correlates with the cumulative expression of inhibitory receptors over the course of persistent antigen stimulation. This functionally impaired T cell subset has been described in HIV and HCV infection, however, results from other studies do not necessary fit this model. Therefore, by simultaneously measuring a wide range of inhibitory receptors and memory-associated markers, we aimed to evaluate the extent to which the profiles of HBV-specific T cells fit with such model of "Hierarchical T cell exhaustion" in human CHB.

Here, to overcome challenges associated with identifying and deep-profiling un-manipulated HBV-specific T cells, mass cytometry together with a highly multiplexed combinatorial peptide-MHC (pMHC) tetramer strategy was used to simultaneously screen-for and interrogate 562 A*11:01-restricted Tcell candidate epitopes. Using a self-validated automatic tetramer deconvolution and unsupervised high-dimensional analyses, it is found that virus-specific CD8+ T cells targeting HBVpol387 and HBVcore169 displayed complex phenotypic profiles and T cell receptor sequence usages that co-varied with the HBV infection status.

Based on a high-dimensional trajectory analysis, it was also found that the profiles of HBV-specific T cells from blood are indicative of the degree of viral control in patients from two separately analyzed cohorts.

The present inventors have now identified amino acid sequences and compositions of peptides and its variants derived from HBVcore169 (also known as HBVcore141) that are restricted by HLA-A1101. Such epitopes can be used to induce cellular response and elicit multifunctional anti-viral T cell activity against HBV. In particular, the present invention discloses isolated peptides comprising seven oligopeptides, including STLPETAVVRR (SEQ ID No. 21), STLPETAVVR (SEQ ID No. 22), STLPETTVVRR (SEQ ID No. 23), STLPETTVIRR (SEQ ID No. 24), STPPETTVVRR (SEQ ID No. 25), STLPETTVVGR (SEQ ID No. 26), STIPETTVVRR (SEQ ID No. 27) that can be used as antigens in epitope-based therapeutics/vaccines or immunotherapy to prevent and/or treat a Hepatitis B virus (HBV) infection in a patient.

In addition, the present inventors have also identified the amino acid and nucleotide sequences comprising four HLA-A*11:01-restricted epitope-reactive T cell receptors (TCRs) that are specific for HBVcore169-CASGDSNSPLHF (SEQ ID No. 17), CASSGGQIVYEQYF (SEQ ID No. 18), CSARGGRGGDYTF (SEQ ID No. 19) and CASSQDWTEAFF (SEQ ID No. 20). Such TCR sequences can be constructed and encoded onto T cells to target HBV-infected hepatocytes using adoptive transfer immunotherapy for HLA-A11-1 positive patients.

The general structure of T cell receptors (TCRs), their domain structure and the organisation of genes that encode them is well known, for example see Chapter 11 in Immunology, second edition (1994), by Janis Kuby, W H Freeman & Co, New York, USA, and Garcia et al (1999) Ann. Rev. Immunol. 17, 369-397. One common class of natural TCRs is the αβ class in which the TCRs are made up of a separate alpha chain and a separate beta chain which form a heterodimer which is T cell membrane associated. Each alpha and beta chain is made up of regions which, in order from the N terminus to the C terminus are a leader sequence, a variable region, a constant region, a connecting sequence, a transmembrane region and a cytoplasmic tail region. The variable region of the alpha chain is called the Vα region and the variable region of the beta chain is called the Vβ region. Similarly, the constant region of the alpha chain is called the CI region and the constant region of the beta chain is called the Cβ region. The job of the αβ TCR is to recognise and bind to a peptide presented in a HLA molecule of a cell in the body. Generally speaking, the TCR cannot recognise and bind the peptide unless it is presented by a particular HLA molecule, and the TCR cannot recognise a HLA molecule unless it is presenting the specific peptide. T cells harboring a specific TCR will target cells which are presenting a specific peptide in a particular HLA molecule on a cell (ie a peptide-HLA complex), and this is the main principle of T cell-based immunity.

The peptide-HLA complex is recognised by the combined V regions of the alpha and beta chains of the TCR. In particular, it is the complementarity determining regions (CDRs) of the V regions which mediate recognition of the peptide-HLA complex. The V region of the alpha and beta chains of the natural TCR are made up of, in order in an N-terminal to C-terminal direction, FR1, CDR1, FR2, CDR2, FR3 and CDR3, where FR stands for "framework region" and CDR stands for "complementarity determining region". The FRs and CDRs of the alpha and beta chains are different. Of note, the CDR3 of beta chain was encoded by V(D)J segment, giving it the higher sequence diversity than alpha chain. It is also well-known that the CDR3 of beta chain is the key determinant for TCR to recognize peptide-MHC complex.

In a first aspect of the invention, there is provided a peptide comprising an amino sequence selected from the group consisting of STLPETAVVRR (SEQ ID No. 21), STLPETAVVR (SEQ ID No. 22), STLPETTVVRR (SEQ ID No. 23), STLPETTVIRR (SEQ ID No. 24), STPPETTVVRR (SEQ ID No. 25), STLPETTVVGR (SEQ ID No. 26) and STIPETTVVRR (SEQ ID No. 27), wherein the peptide is derived from Hepatitis B virus core169 and is capable of binding HLA-A*1101 and when bound to HLA-A*1101 is capable of identifying T cells specific for Hepatitis B virus.

Whether or not a peptide binds to HLA-DRB1*04 may be determined using any method known in the art.

The recognition of harmful pathogens or disease causing mutations within self tissue occurs through two mechanisms within the human immune system. Antibody molecules expressed by B cells bind with biological molecules, typically expressed on the surface of invading microorganisms or deviant self cells, in highly specific manner and will label these molecules in a manner which will trigger an appropriate immune response. In addition to the antibody response, pathogens and disease causing mutations can be detected due to unique proteins expressed by the pathogens or mutations. These proteins are broken down into small peptide fragments by natural and continuous protein degradation systems in the human cell. The peptide fragments will bind with special molecules, referred to as MHC Class I and MHC Class II molecules, expressed on the surface of all cells. In the human, these molecules are referred to as HLA molecules and are numbered according to the large number of alleles which exist across the human population.

In humans, the peptide fragments derived from pathogens bind with specific HLA molecules and are transported to the surface of the cell. The peptides are captured in a particular configuration which allows the peptides to be detected by T cell receptors ("TCRs") expressed on the surface of T cells. Through natural selection and development processes which are linked to the immune system's ability to detect danger signals in connection with the presence of a foreign organism, the human body produces T cells with TCRs which can recognize and distinguish between peptide fragments derived from a harmful pathogen and peptides which are derived from harmless microorganisms or healthy self tissue.

MHC Class I molecules present peptides derived mainly from proteins found within the cell to CD8+ T cells, also referred to as cytotoxic T cells or CTL. The peptides which bind with MHC Class I molecules are usually 8-10 amino acids in length. MHC Class 11 molecules present peptides derived from proteins or organisms which have been endocytosed from the extracellular milieu. MHC Class II molecules present peptides to CD4+ T cells, also referred to as T helper cells although CD4+ T cells may also have direct cytotoxic functions. The peptides which bind to MHC Class 11 molecules are relatively unconstrained in terms of length, although Class II peptides generally fall within a range of 13-17 amino acids, for example 14 or 15 or 16 amino acids.

A particular advantage of a peptide of the invention, is that it binds to the HLA-A*1101 molecule which is presented on a HLA allele that appears to be prevalent across the Asian patient population, a demographic that is not researched enough.

By "peptide" we include not only molecules in which amino acid residues are joined by peptide (—CO—NH—) linkages but also molecules in which the peptide bond is reversed. Such retro-inverso peptidomimetics may be made using methods known in the art, for example such as those described in Meziere et al (1997) J. Immunol. 159, 3230-3237. This approach involves making pseudopeptides containing changes involving the backbone, and not the orientation of side chains. Meziere et al (1997) show that, at least for MHC class II and T helper cell responses, these pseudopeptides are useful. Retro-inverse peptides, which contain NH—CO bonds instead of CO—NH peptide bonds, are much more resistant to proteolysis. We also include any protein or polypeptide that by virtue of its origin or source of derivation is not associated with naturally-associated components that accompany it in its native state; is substantially free of other proteins from the same source. A protein may be rendered substantially free of naturally associated components or substantially purified by isolation, using protein purification techniques known in the art. The peptides/proteins obtained in the invention may be "substantially purified" which is meant the protein is substantially free of contaminating agents, e.g., at least about 70% or 75% or 80% or 85% or 90% or 95% or 96% or 97% or 98% or 99% free of contaminating agents.

Similarly, the peptide bond may be dispensed with altogether provided that an appropriate linker moiety which retains the spacing between the Ca atoms of the amino acid residues is used; it is particularly preferred if the linker moiety has substantially the same charge distribution and substantially the same planarity of a peptide bond.

It will be appreciated that the peptide may conveniently be blocked at its N- or C-terminus so as to help reduce susceptibility to exoproteolytic digestion. Similarly, it will be appreciated that the peptide of the invention may be in salt form or may contain additional esters of —OH or —COOH groups or amides of —NH$_2$ groups. The peptides of the invention are defined in the claims, which would include any variants.

By a "variant" of the given amino acid sequence we mean that the side chains of one or two or three of the amino acid residues are altered (for example by replacing them with the side chain of another naturally occurring amino acid residue or some other side chain) such that the peptide is still able to bind to the HLA molecule in substantially the same way as a peptide consisting of the given amino acid sequence. For example, a peptide may be modified so that it at least maintains, if not improves, the ability to interact with and bind HLA-A*1101 and so that it at least maintains, if not improves, the ability to generate activated CD8* T cells which can recognise Hepatitis V virus. Typically, the amino acid alternatives are conservative in nature, such as from within the groups Gly, Ala; Ile, Leu, Val; Ser, Thr; Tyr, Phe, Trp; Glu, Asp; Gln, Asn, His, Met, Cys, Ser.

Peptides of at least 15 amino acids are preferred. Thus, the invention also includes peptides of 16 or 17 or 18 or 19 or 20 or 21 or 22 or 23 or 24 or 25 amino acids that contain an amino acid sequence selected from the group comprising: STLPETAVVRR (SEQ ID No. 21), STLPETAVVR (SEQ ID No. 22), STLPETTVVRR (SEQ ID No. 23), STLPETT-VIRR (SEQ ID No. 24), STPPETTVVRR (SEQ ID No. 25), STLPETTVVGR (SEQ ID No. 26) and STIPETTVVRR (SEQ ID No. 27). As noted above, the peptides of the invention are capable of binding HLA-A*1101.

Those amino acid residues that are not essential to interact with the T cell receptor can be modified by replacement with another amino acid whose incorporation does not substantially affect T cell reactivity and does not eliminate binding to the relevant HLA allele.

The peptides of the invention (and for use in the invention) are less than 5 000 and typically about 4 000 or 3 000 or 2 000. In terms of the number of amino acid residues, the peptides of the invention may have fewer than 30 or 20 or 19 or 18 or 17 or 16 or 15 or 14 or 13 or 12.

It will be appreciated from the following that in some applications the peptides of the invention may be used directly (i.e. they are not produced by expression of a polynucleotide in a patient's cell or in a cell given to a patient); in such applications it is preferred that the peptide has fewer than 30 or 25 or 24 or 23 or 22 or 21 or 20 or 19 or 18 or 17 or 16 or 15 or 14 or 13 or 12 residues.

The peptides of the invention are able to bind to HLA-A*1101. It is particularly preferred if the peptides bind selectively to HLA-A*1101.

It is further preferred that the peptides of the invention are ones which can be used to generate peptide-specific CD8+ T cells which mediate specific killing of Hepatitis B virus. The peptides of the invention (HBVcore169) are particularly useful in immunotherapeutic methods to combat a Hepatitis B virus. In particular, the peptide in combination with the specific HLA molecule can be used to select and define appropriate T cells, and trace them once they are put into the patient. It is particularly preferred that in all the immunotherapeutic methods of the invention that the patient to be treated is one who carries Class I HLA-A*1101 (ie has a Class I HLA-A*1101-positive genotype), and has antigen presenting cells which express HLA-A*1101.

The peptides of (and for use in) the invention are ones which bind HLA-A*1101 and when so bound the HLA-A*1101-peptide complex, when present on the surface of a suitable antigen-presenting cell, is capable of eliciting a T cell mediated immune response which mediates or helps to mediate the immune systems attack on Hepatitis B virus. In particular, the production of cytokines by a CD8+ T cell may mediate the attack on Hepatitis B virus.

Peptides (at least those containing peptide linkages between amino acid residues) may be synthesised using any method well known in the art, for example by the Fmoc-polyamide mode of solid-phase peptide synthesis as disclosed by Lu et al (1981) J. Org. Chem. 46, 3433 and references therein. Reagents for peptide synthesis are generally available from commercial providers of chemical and biological reagents. Purification may be effected by any one, or a combination of, techniques such as size exclusion chromatography, ion-exchange chromatography and (principally) reverse-phase high performance liquid chromatography. Analysis of peptides may be carried out using thin layer chromatography, reverse-phase high performance liquid chromatography, amino acid analysis after acid hydrolysis and by fast atom bombardment (FAB) mass spectrometric analysis.

In another aspect of the invention, there is provided a method for selecting Hepatitis B virus antigen specific T cells, the method comprising contacting a population of T cells with peptides according to the first aspect of the invention. Preferably, the method comprising contacting a population of T cells with a peptide or polypeptide of the invention presented in a HLA-A*1101 molecule to which said peptide binds.

In an embodiment, the population of T cells are from an individual who has been exposed to a Hepatitis B virus.

It is appreciated that the peptides of the invention may be used to generate an expansion of T cells specific for Hepatitis B virus for patients who are HLA-A*1101 positive and there are several ways in which the invention may be used.

The knowledge that the peptides of the invention bind the HLA-A*1101 molecule and is only recognised by T cells in this context means that the creation of peptide-MHC multimers that will directly bind the T cells can occur. This reagent can be used to directly select the Hepatitis B virus specific cells from the bulk culture in order to infuse cells with a high purity into a patient.

The invention also includes use of the MHC multimer in conjunction with additional multimers of other specificities (to be defined) to fully characterise the product prior to infusion to ensure purity and safety of the product. Following infusion of Hepatitis B virus T cells to the patient the reconstitution of Hepatitis B virus specific immunity could be monitored in the patient using the peptide/HLA-A*1101 multimer directly ex vivo.

An additional application of this technology would be that instead of relying on the innate antigen presentation ability of the patient's own cells to present the peptide of the invention in order to expand antigen presenting cells, an artificial antigen presenting cell could be used which consists of either cell lines deficient in all MHC but HLA-A*1101 pulsed with the peptide or artificial antigen presenting cells which can are engineered to supply the co-stimulation required for T cell expansion along with the HLA-A*1101 peptide combination in order to stimulate and expand the Hepatitis B virus specific T cells.

Suitable methods for selecting Hepatitis B virus-specific T cells include the use of ELISPOT analysis to confirm the responding T cells. Blood is obtained from HLA-A*1101- typed donors or patients. Peripheral blood mononuclear cells (PBMC) are isolated via centrifugation in Biocoll Separating Solution (Biochrom, Berlin, Germany) and either used directly after preparation or cryopreserved for later use. Cells are cultured in RPMI 1640 with L-Glutamine (Invitrogen, Karlsruhe, Germany), supplemented with 10% heat-inactivated, pooled human serum and 100 U/ml Penicillin-Streptomycin (invitrogen, Karlsruhe, Germany). Hepatitis B virus-specific T cell lines are generated by incubation of 1×107 whole PBMC per well in 6-well culture plates with the FHT peptide antigen for 7 days. Lymphocyte cultures are supplemented with 5 U/ml IL-2 (Proleukin, Chiron, Ratingen, Germany) every other day and culture medium replenished as needed. The T cell clones are generated by stimulating PBMCs repeatedly with 1 ua/ml FHT peptide once weekly for 4 weeks. Subsequently T cell clones are generated by limiting dilution in 96-well plates and expanded using the rapid expansion protocol as described by Beck et al. This small scale culture system may be scaled up and adapted to a "closed system" whereby clinical grade T cells suitable for infusion back into patients can be generated.

Suitable methods for selecting Hepatitis B virus-specific T cells include the use of a fluorescence-activated cell sorter (FACS). Following exposure of the donor or patient PBMCs to the peptides of the invention, the responding T cells are labeled based on activation markers or by behavioural characteristics. The labeling is achieved using an antibody specific for the activation marker or the secreted cytokine and such antibody is conjugated to a fluorochrome. The cells can then be separated and selected through a flow cytometer equipped for FACS analysis.

Alternatively, labeling of the responding T cells is based on the binding of an MHC multimer (HLA-A*1101), which is conjugated to a fluorescent marker, to the specific TCR on the surface of the Hepatitis B virus-specific T cell.

Suitable methods for selecting T cells include the Cytokine Secretion Assay System which is manufactured by Miltenyi Biotec.

Methods for making and using peptide-loaded MHC multimers are described, for example, in Altman et al (1996) Science 274, 94-96; Kuabel et al (2002) Nature Medicine 8, 631-637; and Neudorfer et al (2007) J. Immunol. Methods 320, 119-131.

The purity of a T cell population may be assessed using the fluorescently labelled MHC multimer/peptide complex.

Suitable methods for selecting T cells also include the MHC Multimer System, available through Proimmune and Stage Pharmaceutical, which works by creating an artificial construction of HLA molecules which bind, in the present case, the peptides of the invention. These soluble, standalone HLA molecules may be constructed in a multimeric configuration so that a single multimer has 4-5 HLA molecules each loaded with a peptide of the invention. These multimers may also be attached to a magnetic bead as above. The multimers are released into a blood sample, and the HLA: peptide construct will bind with T cell receptors that recognise the peptide and hence will label the T cells which will recognise and mount an immune response against Hepatitis B virus. The cell sample is passed through a magnetic column, and the labelled cells are retained and then released.

It will be appreciated from the above that the invention may include a complex comprising a HLA-A*1101 molecule bound to a peptide according to the first aspect of the invention. Conveniently, the complex is a soluble complex and is not cell-bound.

Preferably, the peptide in the complex is any one of the peptides of the invention, but may be any other peptide of the invention that will form a complex, and be useful in eliciting an anti-Hepatitis B virus T cell response. As is plain, the complex may be used for isolating Hepatitis B virus-specific T cells. The complex may also be used to identify an Hepatitis B virus-specific T cell in a sample.

Typically, the peptide is presented on a dendritic cell or monocyte which present the antigen to T cells. The T cells then secrete cytokines which in turn activate monocytes and neutrophils for enhanced killing of Hepatitis B virus.

In an aspect of the invention, there is provided A T cell expressing a T cell receptor (TCR) molecule, wherein the TCR molecule comprises an amino acid sequence selected from the group comprising: CASGDSNSPLHF (SEQ ID No. 17), CASSGGQIVYEQYF (SEQ ID No. 18), CSARG-GRGGDYTF (SEQ ID No. 19) and CASSQDWTEAFF (SEQ ID No. 20).

The invention also includes T cells, preferably CD8+ T cells, which have been transfected with a polynucleotide or expression vector which expressed the above mentioned TCR or functionally equivalent molecule. The T cells may be obtained from the patient or, in the case of an allogeneic HSCT patient, from a closely matched donor with respect to HLA type.

More particularly, the T cell of the invention is for use in inducing antiviral T cell activity against a Hepatitis B virus core169 epitope, wherein a polynucleotide or an expression vector of the invention has been introduced into the T cell, preferably patient-derived T cell, so that the T cell expresses the encoded TCR molecule.

As well as the TCR molecule, functionally equivalent molecules to the TCR are included in the invention. These include any molecule which is functionally equivalent to a TCR which can perform the same function as a TCR. In particular, such molecules include genetically engineered three-domain single-chain TCRs as made by the method described by Chung et al (1994) Proc. Natl. Acad. Sci. USA 91, 12654-12658, and referred to above.

Typically, the TCR or a functionally equivalent molecule to the TCR, recognises a human Class I HLA molecule expressed on the surface of an antigen-presenting cell and loaded with a peptide according to the first aspect of the invention.

In various embodiments of the invention, the Hepatitis B virus-specific T cell may be isolated for further use. With some techniques it is possible to isolate a sufficient number of specific T cells for therapeutic use directly, but it may be necessary to expand or clone the T cells to produce a sufficient number. For adoptive immunotherapy it is generally preferred to use a technique which allows for the isolation of sufficient numbers of cells directly since this can be achieved within a day (whereas cell expansion may take several weeks).

A suitable procedure for identifying pathogen-specific donor clones is described in Perruccio et al (2005) Blood 106, 4397-4406.

The Hepatitis B virus-specific T cells which are directed against the peptides of the invention are useful in therapy.

It will be appreciated that the skilled person can readily design and synthesise TCRs according to the invention using either or any nomenclature systems provided that the framework region (ie region not replaced by the CDRs) is compatible with the CDRs as is well known in the art.

By "TCR molecule" we include any molecule which contains the given CDRs and also contains FRs suitably situated within the molecule so that the TCR forms a recognition site (binding site) which is able to bind to HLA-A*11:01 presenting any one of the following peptides:

STLPETAVVRR (SEQ ID No. 21), STLPETAVVR (SEQ ID No. 22), STLPETTVVRR (SEQ ID No. 23), STLPETTVIRR (SEQ ID No. 24), STPPETTVVRR (SEQ ID No. 25), STLPETTVVGR (SEQ ID No. 26) and STIPETTVVRR (SEQ ID No. 27).

It is particularly preferred if the TCR molecules contain the precise amino acid sequences CASGDSNSPLHF (SEQ ID No. 17), CASSGGQIVYEQYF (SEQ ID No. 18), CSARGGRGGDYTF (SEQ ID No. 19) and CASSQDWTEAFF (SEQ ID No. 20). Where a variant to this precise sequence is present, it preferably varies by one or two or three (preferably one or two) amino acids. Typically, in these variants, the amino acids which are replaced are replaced with conservative amino acids. By conservative amino acids we include the groupings: G, A; S, A, T; F, Y, W; D, E; N, Q; and I, L, V.

In various embodiments, the amino acid encodes for a TCR beta chain portion, particularly CDR1, CDR1 and CD3 of the beta chain portion.

In another aspect of the invention, there is provided at least one polynucleotide encoding the TCR molecule as defined above. In an embodiment, the polynucleotide comprises sequences SEQ ID NOS 1 to 16 set out in the table below.

| SEQ ID NO. | TCR molecule amino acid sequence | Polynucleotide sequence |
| --- | --- | --- |
| 1 | CASGDSNSPLHF (SEQ ID No. 17) | CTAAACCTGAGCTCTCTGGAGCTGGGGGACTCAGCTTTGTAT TTCTGTGCCAGCGGGGATTCCAATTCACCCCTCCACTTTGGGA AC (SEQ ID No. 1) |
| 2 | CASGDSNSPLHF (SEQ ID No. 17) | ACTAAACTGAGCTCTCTGGAGCTGGGGGACTCAGCTTTGTAT TTCTGTGCCAGCGGGGATTCCAATTCACCCCTCCACTTTGGGA AC (SEQ ID No. 2) |
| 3 | CASGDSNSPLHF (SEQ ID No. 17) | ACTAAACCTGAGCTCTCTGGAGCTGGGGACTCAGCTTTGTAT TTCTGTGCCAGCGGGGATTCCAATTCACCCCTCCACTTTGGGA AC (SEQ ID No. 3) |
| 4 | CASGDSNSPLHF (SEQ ID No. 17) | ACTAACCTGAGCTCTCTGGAGCTGGGGGACTCAGCTTTGTAT TTCTGTGCCAGCGGGGATTCCAATTCACCCCTCCACTTTGGGA AC (SEQ ID No. 4) |
| 5 | CASGDSNSPLHF (SEQ ID No. 17) | TAAACCCTGAGCTCTCTGGAGCTGGGGGACTCAGCTTTGTAT TTCTGTGCCAGCGGGGATTCCAATTCACCCCTCCACTTTGGGA AC (SEQ ID No. 5) |
| 6 | CASGDSNSPLHF (SEQ ID No. 17) | CTAAACCTGAGCTCTCTGGAGCTGGGGGACTCAGCTTTGTAT TTCTGTGCCAGCGGGGATTCCAATTCACCCCTCCACTTTGGGA AC (SEQ ID No. 6) |
| 7 | CASGDSNSPLHF (SEQ ID No. 17) | CTAAACCTGAGCTCTCTGGAGCTGGGGGACTCAGCTTTGTAT TTCTGTGCCAGCGGGGATTCCAATTCACCCCTCCACTTTGGGA AC (SEQ ID No. 7) |
| 8 | CASSGGQIVYEQYF (SEQ ID No. 18) | GTGAACGCCTTGTTGCTGGGGGACTCGGCCCTGTATCTCTGT GCCAGCAGCGGGGGACAGATTGTATACGAGCAGTACTTCGG GCCG (SEQ ID No. 8) |
| 9 | CASSGGQIVYEQYF (SEQ ID No. 18) | TGTGAACGCCTTGTTGCTGGGGACTCGGCCCTGTATCTCTGT GCCAGCAGCGGGGGACAGATTGTATACGAGCAGTACTTCGG GCCG (SEQ ID No. 9) |
| 10 | CASSGGQIVYEQYF (SEQ ID No. 18) | GTGAACGCCTTGGAGCTGGACGACTCGGCCCTGTATCTCTGT GCCAGCAGCGGGGGACAGATTGTATACGAGCAGTACTTCGG GCCG (SEQ ID No. 10) |
| 11 | CASSGGQIVYEQYF (SEQ ID No. 18) | GTGAACGCCTTGTTGCTGGGGGACTCGGCCCTGTATCTCTGT GCCAGCAGCGGGGGACAGATTGTATACGAGCAGTACTTCGG GCCG (SEQ ID No. 11) |
| 12 | CSARGGRGGDYTF (SEQ ID No. 19) | ACAGTGACCAGTGCCCATCCTGAAGACAGCAGCTTCTACATC TGCAGTGCAAGGGGAGGAAGGGGCGGAGACTACACCTTCG GTTCG (SEQ ID No. 12) |
| 13 | CSARGGRGGDYTF (SEQ ID No. 19) | ACAGTGACCAGTGCCCATCCTGAAGACAGCAGCTTCTACATC TGCAGTGCAAGGGGAGGAAGGGGCGGAGACTACACCTTCG GTTCG (SEQ ID No. 13) |
| 14 | CSARGGRGGDYTF (SEQ ID No. 19) | ACAGTGACCAGTGCCCATCCTGAAGACAGCAGCTTCTACATC TGCAGTGCGAGGGGAGGAAGGGGCGGAGACTACACCTTCG GTTCG (SEQ ID No. 14) |
| 15 | CASSQDWTEAFF (SEQ ID No. 20) | CTGAAGGTGCAGCCTGCAGAACTGGAGGATTCTGGAGTTTA TTTCTGTGCCAGCAGCCAAGACTGGACTGAAGCTTTCTTTGG ACAA (SEQ ID No. 15) |

-continued

| SEQ ID NO. | TCR molecule amino acid sequence | Polynucleotide sequence |
|---|---|---|
| 16 | CASSQDWTEAFF (SEQ ID No. 20) | CTGAAGGTGCAGCCTGCAGAACTGGAGGATTCTGGAGTTTA TTTCTGTGCCAGCAGCCAAGATTGGACTGAAGCCTTCTTTGG ACAA (SEQ ID No. 16) |

The polynucleotide may be DNA or RNA, and it may or may not contain introns. Typically, the polynucleotide does not contain introns within the region that codes for the polypeptide of interest. It will be appreciated that different polynucleotides may encode the same polypeptide because of the degeneracy of the genetic code.

It will be appreciated that the polynucleotide is typically used in an HLA-A*1101-specific context.

The invention also provides an expression vector that contains the polynucleotide encoding the peptides and TCR molecule of the invention. Such expression vectors, when present in a suitable host cell, allow for the expression of the polypeptide(s) of interest. Preferably, the expression vector is an expression vector capable of expressing a polypeptide in a mammalian cell. More preferably, the expression vector is one which is able to express a polypeptide in a T cell, such as a human CTL. Typically, the expression vectors contain a promoter which is active in particular cell types, and which may be controllable (eg inducible).

It will be appreciated that the expression vector is typically used in an HLA-A*1101-specific context. The vector is suitably a retroviral vector which is capable of transfection into a mammalian host cell such as a human T cell. Typically, the vector is a lentiviral vector.

Other suitable expression vectors include viral based vectors such as retroviral or adenoviral or vaccinia virus vectors or lentiviral vectors or replication deficient MV vectors. Suitable general cloning vectors include plasmids, bacteriophages (including A and filamentous bacteriophage), phagemids and cosmids.

Methods for manipulating, changing and cloning nucleic acid molecules are well known in the art, for example Sambrook J and Russell, DW, Molecular Cloning, A Laboratory Manual, 3rd Edition, 2001, Cold Spring Harbor Laboratory Press describes such techniques including PCR methods.

A further aspect of the invention provides a host cell comprising a polynucleotide encoding the peptides and TCR molecules of the invention or a vector of the invention. The host cell may contain a polynucleotide or vector which encodes only the alpha chain portion or only the beta chain portion. However, if the host cell is to produce a TCR molecule of the invention, it contains one or more polynucleotides or vectors which encode both the alpha chain portion and the beta chain portion.

In various embodiments, the host cell is a T cell derived from an individual.

The host cell may be any cell such as a bacterial cell (e.g. *Escherichia coli, Bacillus subtilis* and *Salmonella typhimurium*), yeast cell (e.g. *Saccharomyces cerevisiae* and *Schizosaccharomyces pombe*), insect cell, plant cell or mammalian cell (e.g. CHO cells, COS cells and other mammalian cells such as antigen presenting cells), and methods of introducing polynucleotides into such cells are well known in the art. Typically, bacterial cells, such as *Escherichia coli* cells are used for general propagation and manipulation of the polynucleotides and vectors of the invention. Other host cells may be used to express the TCR molecules of the invention and, in particular, the cell may be a mammalian cell such as a human cell. As described below in relation to the therapeutic methods using the TCR molecules of the invention, it is particularly desirable if the host cell is a T cell such as (and preferably) a T cell derived from a patient to be treated, typically a patient with a WT1-expressing malignancy.

Typically, a retroviral vector (or, as the case may be vectors) encoding the TCR molecule of the invention is used based on its ability to infect mature human CD4+ or CD8+ T lymphocytes and to mediate gene expression: the retroviral vector system Kat is one preferred possibility (see Finer et al (1994) Blood 83, 43). High titre amphotrophic retrovirus are used to infect purified CD8+ T lymphocytes isolated from the peripheral blood of tumour patients following a protocol published by Roberts et al (1994) Blood 84, 2878-2889, incorporated herein by reference. Anti-CD3 antibodies are used to trigger proliferation T cells, which facilitates retroviral integration and stable expression of single chain TCRs. A combination of anti-CD3 and anti-CD8 antibodies may be more effective than anti-CD3 antibodies alone. Other suitable systems for introducing genes into CTL are described in Moritz et al (1994) Proc.Natl. Acad. Sci. USA 91, 4318-4322, incorporated herein by reference. Eshhar et al (1993) Proc.Natl. Acad. Sci. USA 90, 720-724 and Hwu et al (1993) J. Exp. Med. 178, 361-366 also describe the transfection of CTL. The commercially available Nuclofactor system, provided by AMAXA, Germany may be used to transfect T cells. Retroviral transduction of human CD8+ T cells is described in Stanislawski (2001) Nat. Immunol. 2, 962. Methods of cloning and genetic manipulation are well known in the art and are described in detail in standard manuals such as Sambrook & Russell (2001) Molecular Cloning, a laboratory manual, Cold Spring Harbor Press, Cold Spring Harbor, NY, USA.

In another aspect of the invention, there is provided a T cell according to an earlier aspect of the invention for use in inducing antiviral T cell activity against a Hepatitis B virus, and use of said T cell in the preparation of a medicament for inducing antiviral T cell activity against a Hepatitis B virus.

In an embodiment, the Hepatitis B virus expresses an epitope comprising an amino acid sequence selected from the group comprising: STLPETAVVRR (SEQ ID No. 21), STLPETAVVR (SEQ ID No. 22), STLPETTVVRR (SEQ ID No. 23), STLPETTVIRR (SEQ ID No. 24), STPPETTVVRR (SEQ ID No. 25), STLPETTVVGR (SEQ ID No. 26) and STIPETTVVRR (SEQ ID No. 27).

The phrase "inducing antiviral T cell activity against a Hepatitis B virus" is understood to mean that the antigen binding site of the present invention induces or enhances any one or more activities of the T cell, including but not limited to stimulating proliferation, cytotoxicity or maturation of NK cells, stimulating proliferation or differentiation of B cells and T cells; stimulating antibody production and affinity maturation in B cells; stimulating cytotoxicity of CD8+ T cells; stimulating interferon gamma production in T-cells and NK-cells; inhibiting dendridic cell (DC) activation and maturation; inhibiting release of inflammatory mediators from mast cells, enhancing phagocytosis of macrophages, inhibiting generation or survival of tReg cells, and stimulating the proliferation of bone marrow progenitor cells.

The peptides, TCR molecules, polypeptides, polynucleotides, expression vectors and T cells of the invention may be packaged and presented for use as a medicament. In particular, they are of use in treating or combating a Hepatitis B virus infection. By "Hepatitis B virus infection" we include treating patients who have Hepatitis B virus infection. We also include administering the peptides, TCR molecules, polypeptides, polynucleotides, expression vectors and T cells of the invention (either alone or in combination with, or present in or on, a suitable HLA matched antigen presenting cell such as a dendritic cell or B cell or monocytes or a synthetic APC) to not only patients who have a Hepatitis B virus infection, but also to those at risk of Hepatitis B virus infection.

Patients at risk of Hepatitis B virus infection include those who are immunocompromised or immunodepleted such as those undergoing allogeneic HSCT, organ transplant patients, autoimmune patients receiving immunosuppressive drugs, patients with genetic immune disorders, AIDS patients, or patients undergoing chemotherapy for cancer or leukaemia patients. Thus, it will be appreciated that "combating" includes preventing (or helping to prevent) Hepatitis B virus infection and treating a patient prophylactically.

In another aspect of the invention, there is provided a method of treating a Hepatitis B virus infection in an individual, the method comprising administering to the individual an effective amount of a peptide according to the first aspect of the invention or a polynucleotide according to various aspects of the invention described above or a T cell according to an aspect of the invention described above.

The term "effective amount" or "therapeutically effective amount" means a dosage sufficient to treat, inhibit, or alleviate one or more symptoms of a disease state being treated or to otherwise provide a desired pharmacologic and/or physiologic effect, especially enhancing T cell response to a selected antigen. The precise dosage will vary according to a variety of factors such as subject-dependent variables (e.g., age, immune system health, etc.), the disease, and the treatment being administered.

In another aspect of the invention, there is provided a pharmaceutical composition comprising a peptide according to the first aspect of the invention or a polynucleotide according an aspect of the invention or a T cell according an aspect of the invention and a pharmaceutically acceptable carrier.

A pharmaceutically acceptable carrier refers, generally, to materials that are suitable for administration to a subject wherein the carrier is not biologically harmful, or otherwise, causes undesirable effects. Such carriers are typically inert ingredients of a medicament. Typically a carrier is administered to a subject along with an active ingredient without causing any undesirable biological effects or interacting in a deleterious manner with any of the other components of a pharmaceutical composition in which it is contained. Suitable pharmaceutical carriers are described in Martin, Remington's Pharmaceutical Sciences, 18th Ed., Mack Publishing Co., Easton, Pa., (1990), incorporated by reference herein in its entirety.

In a more specific form of the disclosure there are provided pharmaceutical compositions comprising therapeutically effective amounts of the peptide, polynucleotide and T cell together with pharmaceutically acceptable diluents, preservatives, solubilizers, emulsifiers, adjuvants and/or carriers. Such compositions include diluents of various buffer content (e.g., phosphate, Tris-HCl, acetate), pH and ionic strength and additives such as detergents and solubilizing agents (e.g., Tween 80, Polysorbate 80), antioxidants (e.g., ascorbic acid, sodium metabisulfite), preservatives (e.g., Thimersol, benzyl alcohol) and bulking substances (e.g., lactose, mannitol). The material may be incorporated into particulate preparations of polymeric compounds such as, for example and without limitation, polylactic acid or polyglycolic acid, or into liposomes. Hylauronic acid may also be used. Such compositions may influence the physical state, stability, rate of in vivo release, and rate of in vivo clearance of the disclosed compositions. The compositions may be prepared in liquid form, or may be in dried powder, such as lyophilized form.

It will be appreciated that pharmaceutical compositions provided according to the disclosure may be administered by any means known in the art. Preferably, the pharmaceutical compositions for administration are administered by injection, orally, or by the pulmonary, or nasal route. The antisense polynucleotides are, in various embodiments, delivered by intravenous, intra-arterial, intraperitoneal, intramuscular, or subcutaneous routes of administration. In various embodiments, the composition is suitable for parenteral administration either naked or complexed with a delivery agent to a patient. The carrier may be selected from the group comprising of a nanoparticle, such as a polymeric nanoparticle; a liposome, such as pH-sensitive liposome, an antibody conjugated liposome; a viral vector, a cationic lipid, a polymer, a UsnRNA, such as U7 snRNA and a cell penetrating peptide.

The compositions or molecules of the invention may be administered orally, or rectal, or transmucosal, or intestinal, or intramuscular, or subcutaneous, or intramedullary, or intrathecal, or direct intraventricular, or intravenous, or intravitreal, or intraperitoneal, or intranasal, or intraocular.

The compositions or molecules of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such pro-drugs, and other bioequivalents.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

For polynucleotides, preferred examples of pharmaceutically acceptable salts include, but are not limited to, (a) salts formed with cations such as sodium, potassium, ammonium, magnesium, calcium, polyamines such as spermine and spermidine; (b) acid addition salts formed with inorganic acids, for example hydrochloric acid, hydrobromic acid, sulfuric acid, phosphoric acid, nitric acid; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid; and (d) salts formed from elemental anions such as chlorine, bromine, and iodine. The pharmaceutical compositions of the disclosure may be administered in a number of ways depending upon whether local or systemic treatment is desired and upon the area to be treated. Administration may be topical (including ophthalmic and to mucous membranes including rectal delivery), pulmonary, e.g., by inhalation of powders or aerosols, (including by nebulizer, intratracheal, intranasal, epidermal and transdermal), oral or parenteral. Parenteral administration includes intravenous, intra-arterial, subcutaneous, intraperitoneal or intramuscular injection or infusion; or intracranial, e.g., intrathecal or intraventricular, administration. Polynucleotides with at least one 2'-O-methoxyethyl modification are believed to be particularly useful for oral administration.

The pharmaceutical formulations of the disclosure, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly bringing into association the active ingredients with liquid carriers or finely divided solid carriers or both, and then, if necessary, shaping the product.

Combination therapy with an additional therapeutic agent is also contemplated by the disclosure. Examples of therapeutic agents that may be delivered concomitantly with a composition of the disclosure include, without limitation, a glucocorticoid steroid (for example and without limitation, prednisone and deflazacort), an angiotensin converting enzyme inhibitor, a beta adrenergic receptor blocker, an anti-fibrotic agent and a combination thereof.

In some embodiments, the present invention may be used in gene therapy such, e.g. using a vector (e.g., an expression vector) comprising a polynucleotide of the invention to direct expression of the polynucleotide in a suitable host cell. Such vectors are useful, e.g., for amplifying the polynucleotides in host cells to create useful quantities thereof, and for expressing proteins using recombinant techniques. In some embodiments, the vector is an expression vector wherein a polynucleotide of the invention is operatively linked to a polynucleotide comprising an expression control sequence.

The peptides of the invention, alone or in combination with antigens from other pathogen, may be used to activate immune cells within a blood or tissue sample or a cellular derivative thereof obtained from the patient or a donor without significant further selection or purification of cell types (an "Unselected Cell Formulation") with a view to infusing the Unselected Cell Formulation in a patient in order to treat or prevent infection by Hepatitis B virus whether on a targeted basis or as one of several pathogens which may cause infection in a patient.

The methods of combating or treating Hepatitis B virus infection, and the pharmaceutical compositions and medicaments, of the invention may be combined with other anti-Hepatitis B virus treatments.

In another aspect of the invention, there is provided vaccine against Hepatitis B virus infection comprising a peptide according to the first aspect of the invention or a polynucleotide or a T cell according to various aspects of the invention described above, and may be packaged and presented for use as a medicament.

In another aspect of the invention, there is provided a method of combating a Hepatitis B virus infection in a patient which carries HLA A*1101, the method comprising:

(a) obtaining T cells from the patient; (b) introducing into the T cells a polynucleotide encoding a TCR molecule according to an aspect of the invention; (c) introducing the T cells produced in step (b) into the patient.

The transfected T cells are able to help fight off the Hepatitis B virus. Preferably, the patients to be treated carry Class I HLA A*1101.

In various embodiments, the polynucleotide(s) is/are transfected or introduced to the T cells by electroporation. Other suitable systems for introducing genes into T cells are described in Moritz et al (1994) Proc. Natl. Acad. Sci. USA 91, 4318-4322. Eshhar et al (1993) Proc. Natl. Acad. Sci. USA 90, 720-724 and Hwu et al (1993) J. Exp. Med. 178, 361-366 also describe the transfection of T cells.

Methods for introducing a nucleic acid into the T cell, which are well known and routinely practiced in the art, include transformation, transfection, electroporation, nuclear injection, or fusion with carriers such as liposomes, micelles, ghost cells, and protoplasts. The host T-cell may be isolated and/or purified. The T-cell also may be a cell transformed in vivo to cause transient or permanent expression of the polypeptide in vivo. The T-cell may also be an isolated cell transformed ex vivo and introduced post-transformation, e.g., to produce the polypeptide in vivo for therapeutic purposes.

The polynucleotides of the present invention (particular SEQ ID Nos. 1 to 16) may be introduced into a T cell by methods of transfection well known in the art. These methods include sonophoresis, electric pulsing, electroporation, osmotic shock, calcium phosphate precipitation, and DEAE dextran transfection, lipid mediated delivery, passive delivery etc.

The language "transfecting T cells" is intended to include any means by which a nucleic acid molecule can be introduced into a T cell. The term "transfection" encompasses a variety of techniques useful for introduction of nucleic acids into mammalian cells including electroporation, calcium-phosphate precipitation, DEAE-dextran treatment, lipofection, microinjection, and viral infection. Suitable methods for transfecting mammalian cells can be found in Sambrook et al. (Molecular Cloning: A Laboratory Manual, 2nd Edition, Cold Spring Harbor Laboratory press (1989)) and other laboratory textbooks.

The polynucleotides may also be introduced into a T cell using a viral vector. Such viral vectors include, for example, recombinant retroviruses, adenovirus, adeno-associated virus, and herpes simplex virus-1. Retrovirus vectors and adeno-associated virus vectors are generally understood to be the recombinant gene delivery system of choice for the transfer of exogenous genes in vivo, particularly into humans. Alternatively they can be used for introducing exogenous genes ex vivo into T cells. These vectors provide efficient delivery of genes into T cells, and the transferred nucleic acids are stably integrated into the chromosomal DNA of the host cell.

Another viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. Yet another viral vector system useful for delivery of a nucleic acid molecule comprising a gene of interest is the adeno-associated virus.

The polynucleotides may be carried by and delivered into a T cell by a cell-delivery vehicle. Such vehicles include, for example, cationic liposomes (Lipofectin™) or derivatized (e.g. antibody conjugated) polylysine conjugates, gramicidin S, artificial viral envelopes. These vehicles can deliver a nucleic acid that is incorporated into a plasmid, vector, or viral DNA. In a specific embodiment, efficient introduction of the nucleic acid molecule in primary T lymphocytes is obtained by transfecting the primary T lymphocytes with adeno-associated virus plasmid DNA complexed to cationic liposomes, as described in Philip, R. et al. (1994) Mol. Cell. Biol. 14, 2411.

In another embodiment of the invention, the polynucleotides may be delivered in the form of a soluble molecular complex. The complex contains the nucleic acid releasably bound to a carrier comprised of a nucleic acid binding agent and a cell-specific binding agent which binds to a surface molecule of the specific T cell and is of a size that can be subsequently internalized by the cell.

In another embodiment of the invention the polynucleotides is introduced into T cells by particle bombardment.

In various embodiments, the polynucleotides may be passively delivered (i.e., deliver without additional transfection reagents) to the T cells, particularly during T cell expansion. Expansion as used herein includes the production of progeny cells by a transfected neural stem cell in containers and under conditions well known in the art. Expansion may occur in the presence of suitable media and cellular growth factors. The polynucleotides may be passively delivered to the T cells in culture (e.g., in culture plates, culture dishes, multiwell plates etc without limitation) under reduced serum conditions, including under 0% serum conditions. Such conditions include cells cultured in standard, art-tested reduced-serum media that are commercially available from numerous companies including Invitrogen, and HyClone. In one example, cells are first plated in serum medium, then the serum medium is replaced with reduced serum medium comprising a tripartite oligonucleotide complex of the disclosure for 24 hours, then the reduced serum medium is replaced with serum medium.

In various embodiments, the transfection reagent may be selected from the group consisting of polymers, lipids, lipid-polymers and/or their combinations and/or their derivatives containing a cell-targeting or an intracellular targeting moiety and/or a membrane-destabilizing component and one or more delivery enhancers.

In another aspect of the invention, the peptides according to the first aspect of the invention may be used to create a monoclonal or polyclonal antibody either on a patient-specific basis or batch manufacturing basis wherein the antibody is used to prevent or treat infection by Hepatitis B virus or to induce a primary or secondary humoral or cellular immune response to Hepatitis B virus in a patient. The antibody will include idiomatic derivations of antibodies specific for the peptides described above. Preferably, the antibody recognises the peptides of the invention when presented by a Class I HLA-A*1101 molecule.

In order that the present invention may be fully understood and readily put into practical effect, there shall now be described by way of non-limitative examples only preferred embodiments of the present invention, the description being with reference to the accompanying illustrative figures.

FIG. 1. Comprehensive epitope mapping against HBV using highly multiplexed combinatorial pMHC tetramer strategy. (A) The experimental workflows. The 562-plex pMHC tetramer library was generated from the deep sequencing of virus and epitope prediction. The library included 484 putative A*11:01-restricted HBV peptides and 78 known control peptides derived from other common virus or self-antigens. 1001 unique combinations of quadruple sAv-metal codings were used to code the entire library. A self-validated tetramer deconvolution algorithm automatically identified the signals on patient's T cells with statistical measurements. Validated antigen-specific CD8+ T cells targeting four viral epitopes were shown. (B) Mean frequency of HBV-specific CD8+ T cells from all patients tested across four different viral proteins. Plot only shows the detectable epitopes. Numbers at the bottom indicate the numbers of epitopes detected/screened for each viral protein. (C) Epitopes nomenclature and annotation used in this report are shown. * indicates a peptide cluster that contained more than one peptide (table S1). Peptide sequences in bold faces are previous unpublished sequences based on Immune Epitope Database (IEDB). (D) The frequencies of four antigen-specific CD8+ T cells across various patient groups as sorted. (E) The expression of cellular markers on four HBV-specific CD8+ T cells are shown in heatmaps. Boxes highlight the discriminative markers for each patient group.

Figure 2:
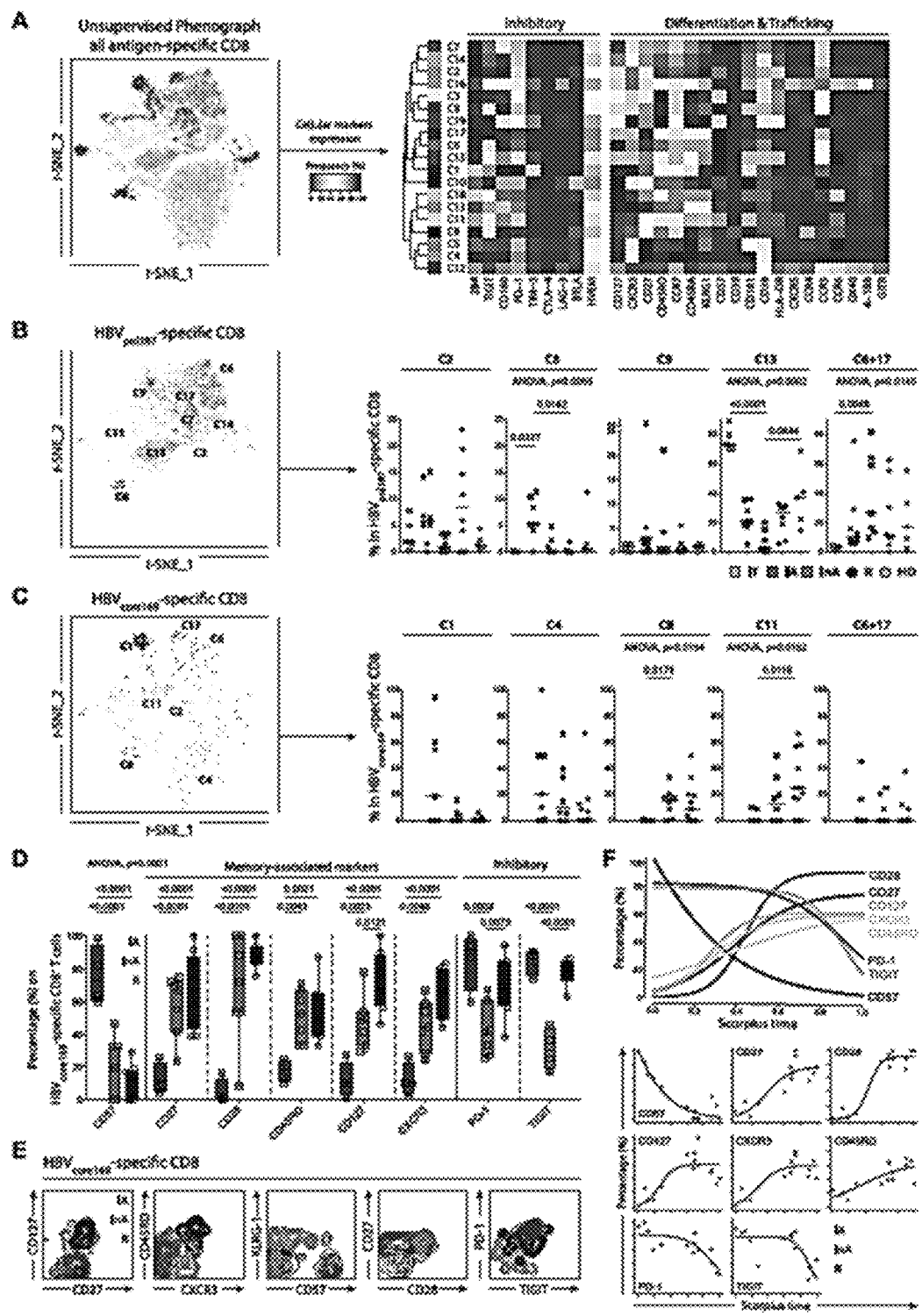

FIG. 2. Multifactorial memory atlas of HBVpol387 and HBVcore169-specific CD8+ T cells linked to HBV clinical stages. (A) Unsupervised Phenograph clustering of cellular subsets on all detected antigen-specific CD8+ T cells across patient groups. n=20, 4 patients per group. Nineteen cellular clusters objectively identified by Phenograph were sorted as indicated, and the expression levels of probed cellular proteins are shown. (B) Visualization of the Phenograph clustering of nine major cellular clusters of HBVpol387-specific CD8+ T cells is shown. The proportion of cellular clusters within HBVpol387-specific CD8+ T cells in individuals across various patient groups are shown. (C) The same analytical strategy for HBVcore169-specific CD8+ T cells is shown. (D) Bar graph indicates the discrepancy of T cell memory-associated markers (CD27, CD28, CD45RO, CD127 and CXCR3), inhibitory receptors (PD-1 and TIGIT) and CD57 expressed on HBVcore169-specific CD8+ T cells. Error bars are median and range, and values from individuals were imposed. (E) Representative contour plots show the expression level of markers on HBVcore169-specific CD8+ T cells between patient groups. Patients were sorted as indicated. (F) Logistic regression (Upper panel) of 8 phenotypic markers that showed significant difference between patient groups were stacked against pseudotime imputed using Scorpius. Logistic regression (black solid line, lower panel) was used to visualize the trend of these 8 cellular markers. Dots are individuals sorted by clinical stages, and showed the expression levels of these markers on HBVcore169-specific CD8+ T cells.

Figure 3:
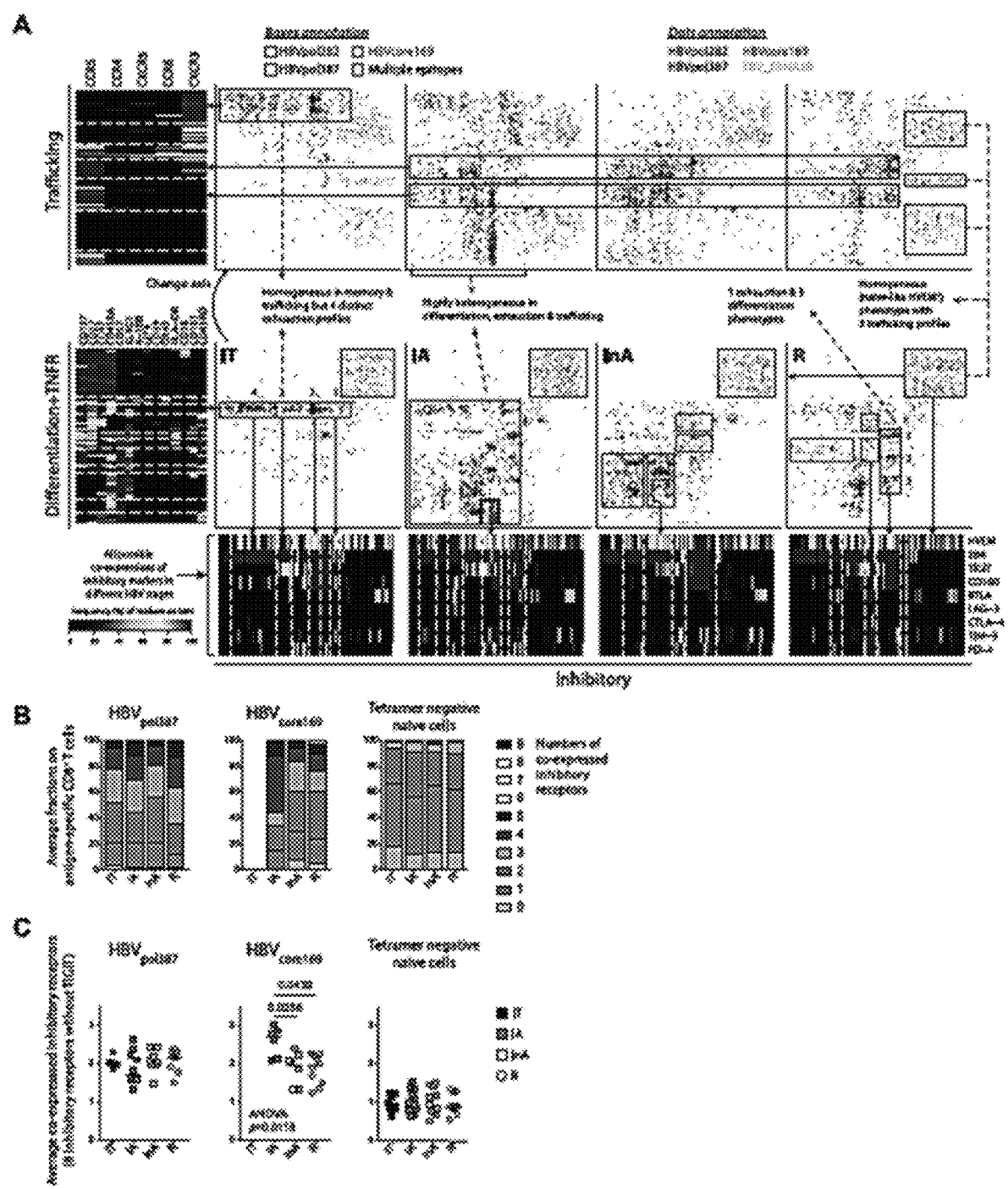

FIG. 3. Unsupervised analyses uncovered the complex model of inhibitory receptors (exhaustion markers) in CHB. (A) One-SENSE objectively related three different T cell categories (Differentiation+TNFR, Inhibitory and Trafficking) in 2D plots with visualization of the expression levels of cellular proteins. Dots are selected virus-specific CD8+ T cells as sorted. Boxes annotated the epitopes who were enriched in the given regions. (B) The average fractions of the numbers of co-expressed inhibitory receptors on four HBV-specific CD8+ T cells across patient groups. Plots were from a representative experiment with all nine inhibitory receptors. (C) The average co-expressed inhibitory receptors on four on four HBV-specific CD8+ T cells across patient groups. Plots were comprised of three experiments with simultaneously measurements of eight inhibitory receptors (without TIGIT). Each dot is an individual.

Figure 4:
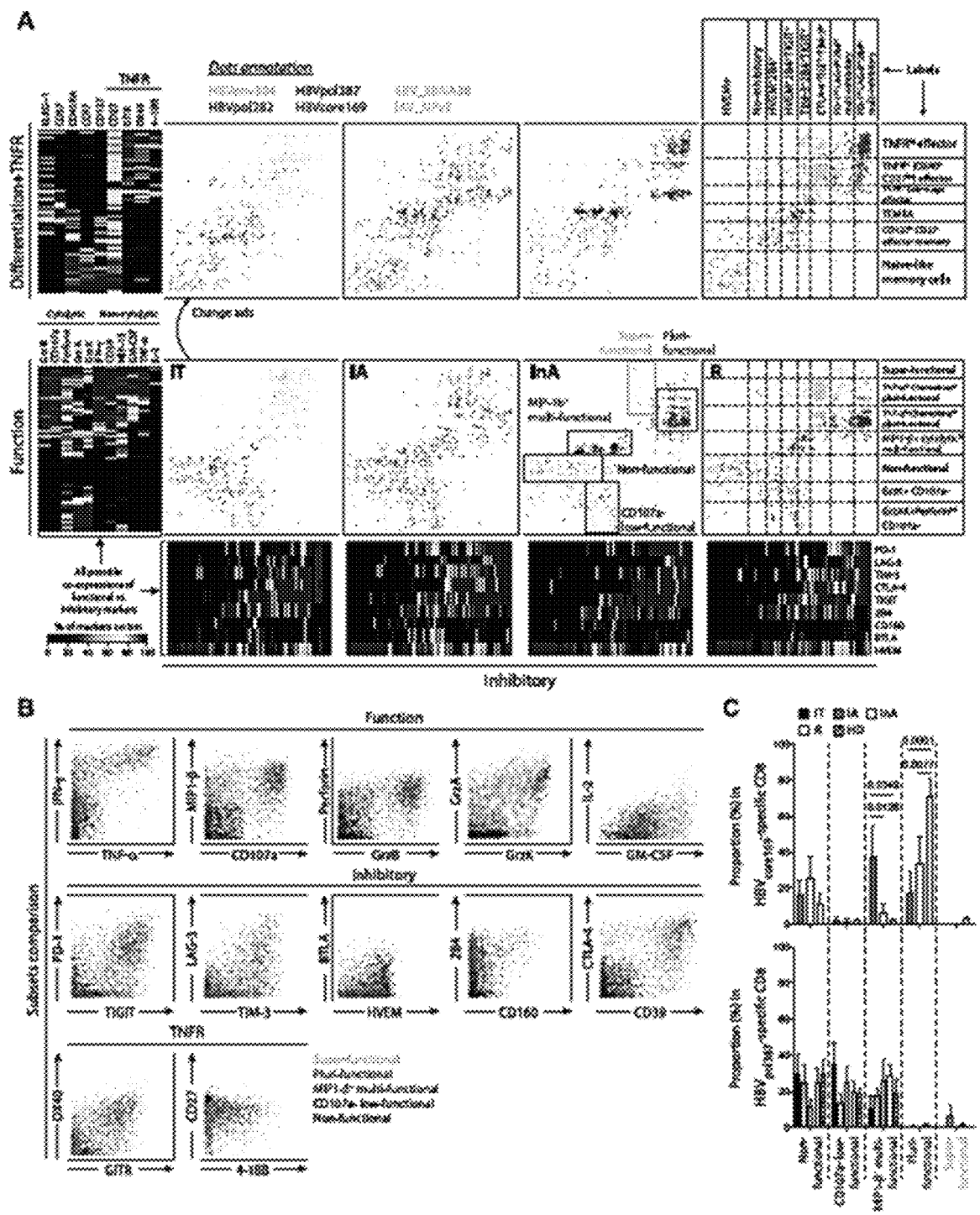

FIG. 4. Nonlinear correlations of multi-functionalities and inhibitory receptors by One-SENSE (A) Patient's PBMCs were stimulated with correspondent viral peptides for 10 days in vitro culture to measure the functional capacity. Categorical (Function, Inhibitory and Differentiation+

TNFR) analysis of One-SENSE revealed the diverse multifunctional virus-specific CD8+ T cells subsets and their corresponded co-expressions of inhibitory receptors. Dots are different virus-specific CD8+ T cells as annotated. Five different major functional subsets were labeled based on the aligned heatplots and sorted as indicated. (B) The expression levels of T cells functions, inhibitory receptors and TNFR costimulatory receptors were compared between these five functional subsets. (C) Bar graphs showed the proportion of each functional subset in HBVpol387 and HBVcore169-specific CD8+ T cells across patient groups. n=5 per group except for IT=4.

Figure 5:
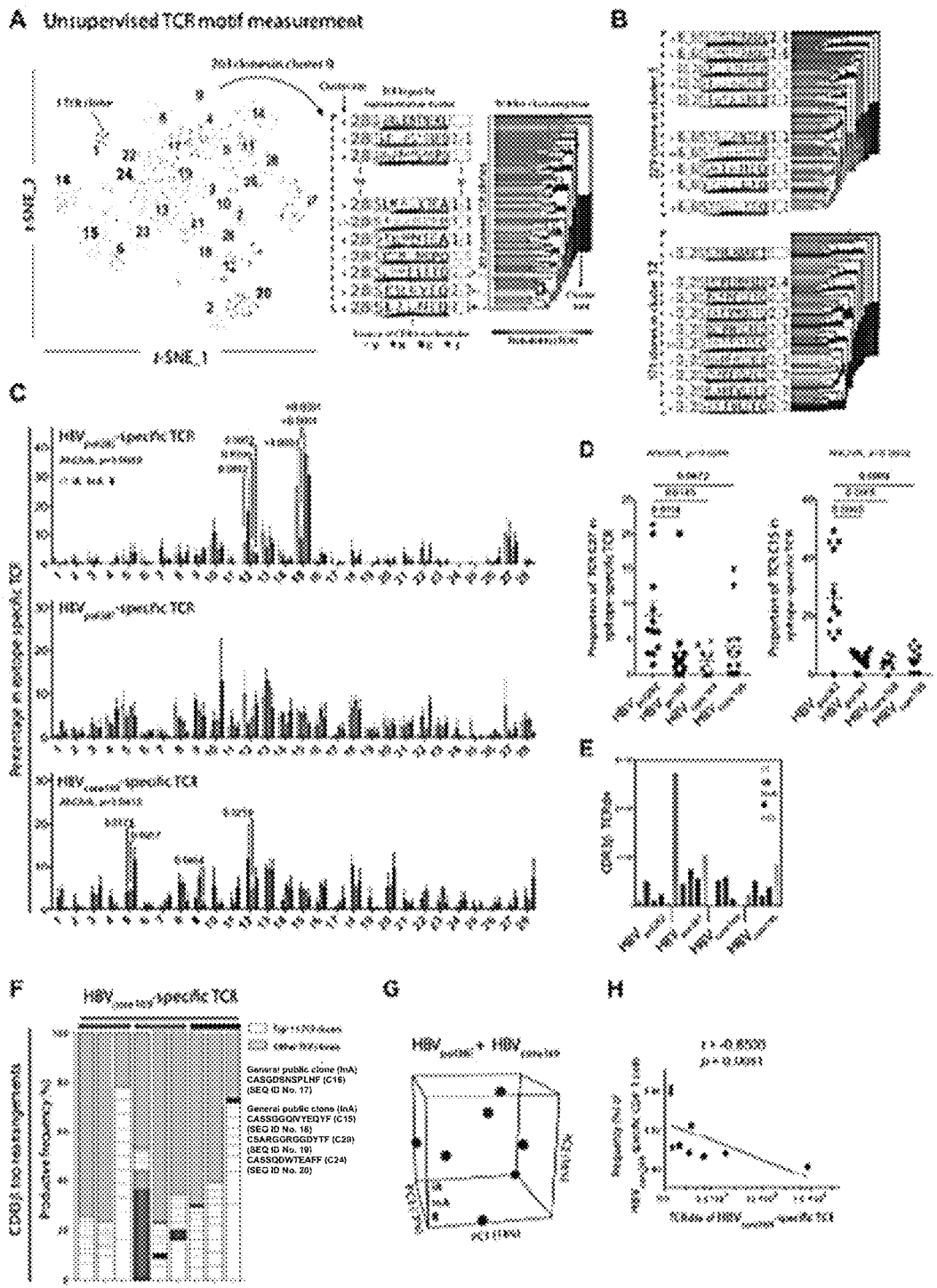

FIG. 5. Unsupervised quantifications of HBV-specific TCR were associated with disease stages in an epitope-dependent manner. (A) TCRdist measurements of epitope-specific TCRs were clustered by unsupervised Phenograph analysis and then projected by t-SNE. Each dot is one TCR clone. Twenty-eight TCR-sequence clusters on t-SNE map were labeled. (B) The sequence motifs (dashed boxes labeled with size) of representative TCR-sequence clusters were shown. Average-linkage dendrogram for each TCR in the given cluster was presented and sorted by generation probability. TCR logos display the frequency of V and J segments with CDR33 sequence in the middle. Bottom bars are source region as indicated (a total of four source regions). Light grey is V-region. Black is D for diversity. Dark grey is J-region. The remaining source region is N-region. (C) The percentages of the receptor in total epitope-specific TCRs for twenty-eight TCR-sequence clusters were shown. (D) The proportion of TCR cluster 27 (C27) and 15 (C15) in four different epitope-specific TCRs. (E) TCRdiv diversity measures for each epitope-specific TCR across patient groups. (F) Stacked bar charts show the Top eleven TCR clones in individual patient. The frequencies and sequences of public TCR clones were presented. (G) 3D PCA projection delineated patient's clinical stage using the epitope-specific TCR repertoires, tetramer response and cellular profiles from the same individuals. (H) Correlation between the frequency and TCRdiv diversity measures of HBVcore169-specific CD8+ T cells.

Figure 6:
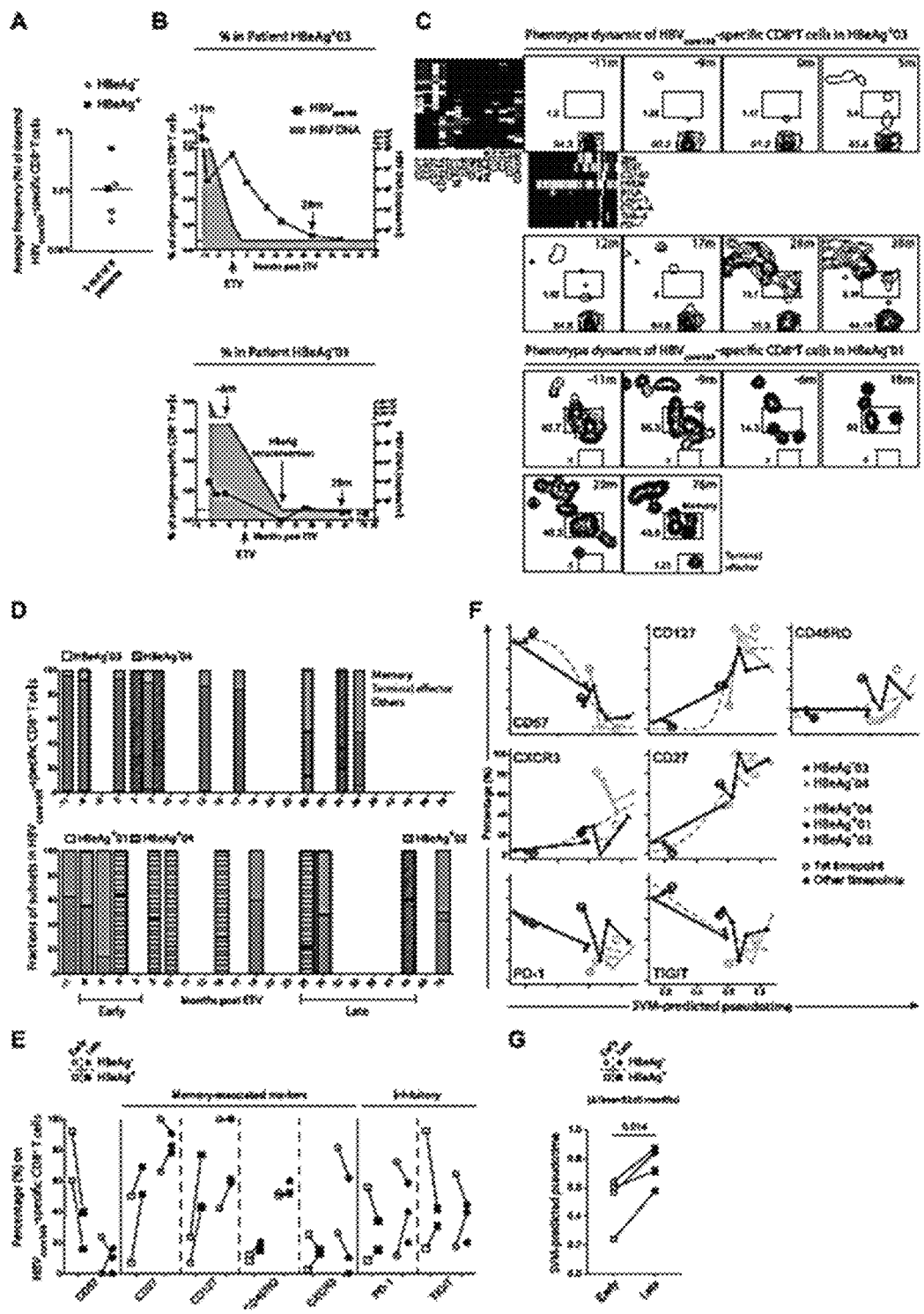

FIG. 6 The phenotypic dynamic and the machine learning-aided modeling of HBVcore169-specific CD8+ T cells. (A) A total of 14 patients (n=8 for HBeAg−, and n=6 for HBeAg+) were included in the longitudinal cohort. The average frequency of all detectable HBVcore169-specific CD8+ T cells across different time points was shown. Each dot is one patient who had detectable HBVcore169-specific CD8+ T cells. (B) Dynamics of HBVcore169-specific CD8+ T cells in two representative patients. (C) The phenotypic dynamic of HBVcore169-specific CD8+ T cells was shown using One-SENSE. Numbers are frequencies and boxes are annotated as indicated. (D) The fractions of memory and terminal effector cells were sorted in individual patients across longitudinal time points. (E) Plot showed the changes of selective cellular markers expression on HBVcore169-specific CD8+ T cells across patient's longitudinal time points (early and late, thick stacked bars in D). Two time points (early and late) were picked to roughly match the time points between patients based on the drug intervention. "Early" are pre-treatment time points besides one patient (HBeAg+04, whose earliest time point was 3 months post-treatment), and "Late" are roughly 30 months post-treatment. Plots showed the patients who had detectable HBVcore169-specific CD8+ T cells in both early and late time points. Statistical analysis was used to compare the cellular marker expressions between two time points (early and late, solid line), or patient groups (HBeAg+ and HBeAg−, dash line). (F) Logistic model (dashed grey line) of cellular markers expression (dependent variable) against SVM-predicted pseudotime (independent variable). Dots represent the expression levels of cellular markers on HBVcore169-specific CD8+ T cells across different patient's longitudinal time points. (G) Statistical analysis of SVM-predicted pseudotime during the progression of patient's longitudinal time points. A non-parametric paired t-test was used.

Figure 7:
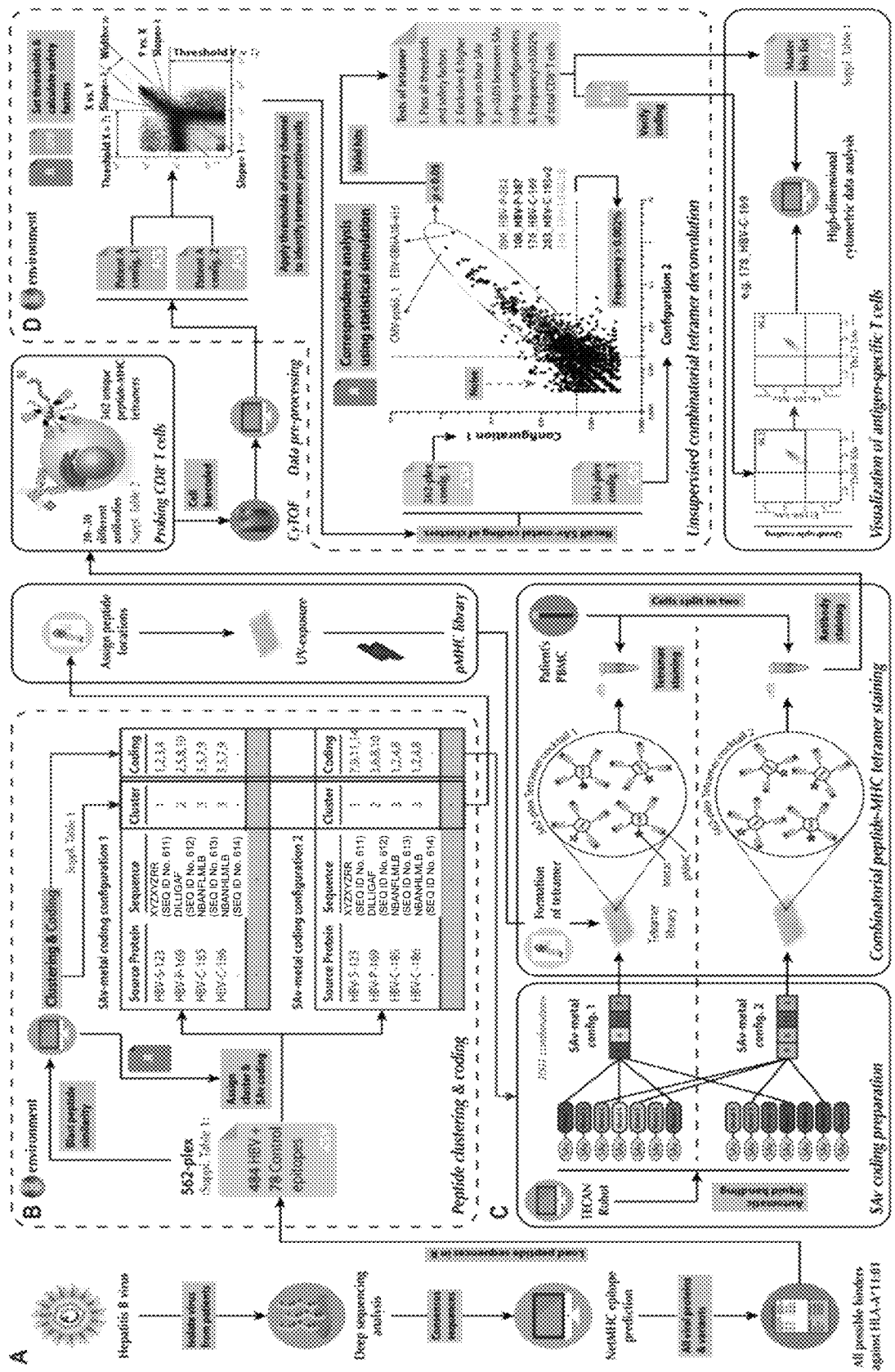

FIG. 7 Comprehensive epitope mapping strategy and experimental workflow.
(A) HBV was deep-sequenced using next-generation sequencing (NGS). NetMHC (v3.4) was used to predict HLA-A*11:01-restricted epitopes based on the consensus sequences. (B) 562 peptides were clustered based on the sequence homology and were further given unique combinations of four SAv-metal codes. (C) These unique combinations of four SAv-metal mixtures for two different coding configurations were prepared by automatic liquid handling robot. The quadruple SAv-metal coded pMHC tetramer library (for two coding configurations) was used to stain on patient's PBMC. (D) Tetramer positive cells were determined by an automatic tetramer deconvolution algorithm and the tetramer signals between the two coding configurations were calculated for their correspondence.

Figure 8:
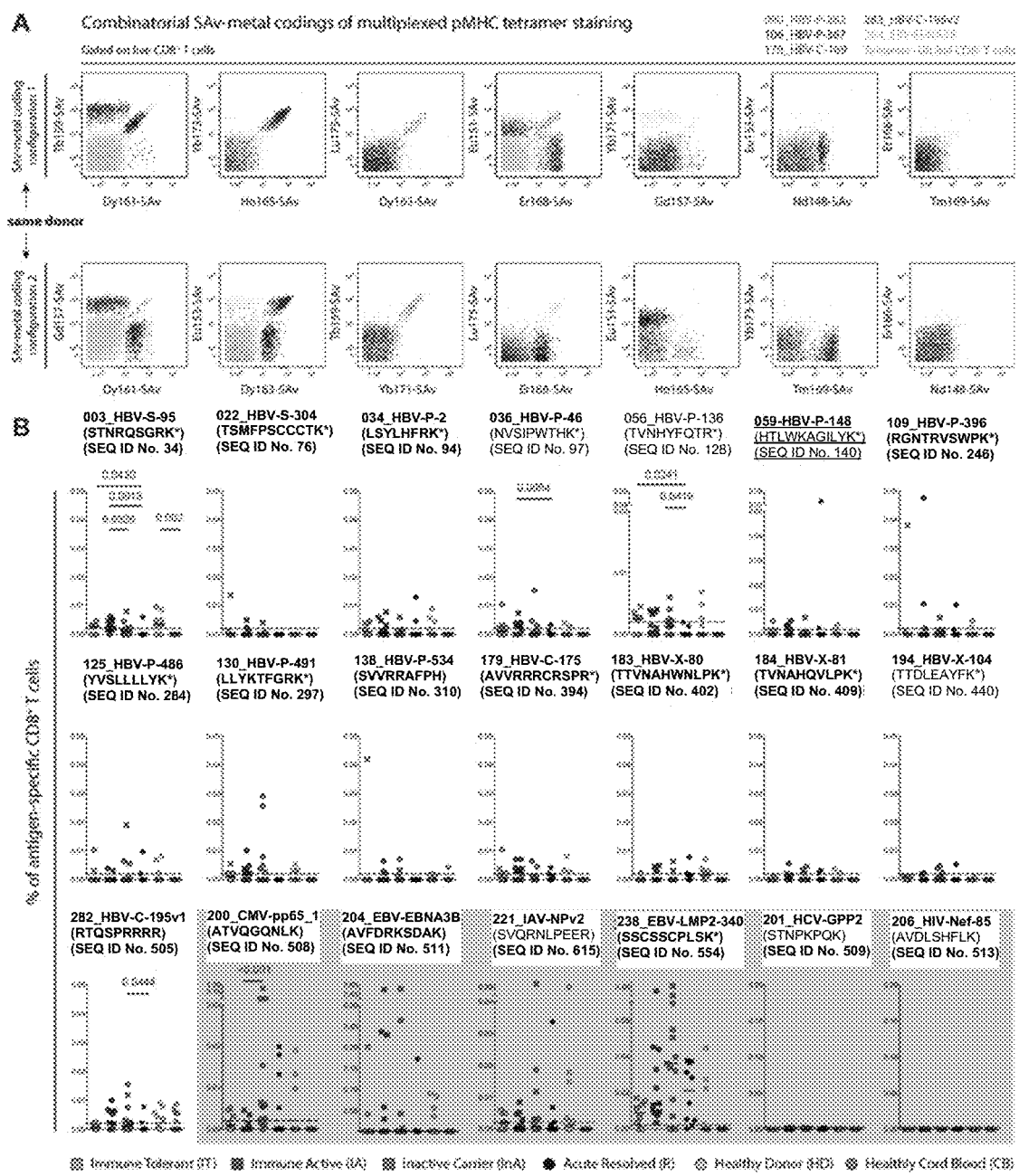

FIG. 8 The quality and detection of antigen-specific CD8+ T cells using highly multiplexed combinatorial pMHC tetramer staining and mass cytometry.
(A) The staining quality of quadruple SAv-metal coded pMHC tetramers using fourteen different SAv-metal channels from one representative CHB donor. The same vial of PBMC from each donor was stained in parallel with the same 562-plex pMHC tetramers but two different SAv-metal coding configurations as shown. (B) Magnitude of selected HBV-specific CD8+ T cells detected by highly multiplexed combinatorial pMHC tetramer strategy across various clinical stages of HBV infection. Plots show the frequency of antigen-specific CD8+ T cells for fifteen predictive HBV epitope clusters and six representative known control viral epitopes (shaded box). Epitope sequences in bold face indicate previously unpublished sequences. * means this epitope cluster contains more than one peptide (related to Supplementary Table 1). Dash lines on the y-axis are 0.002.

Figure 9:
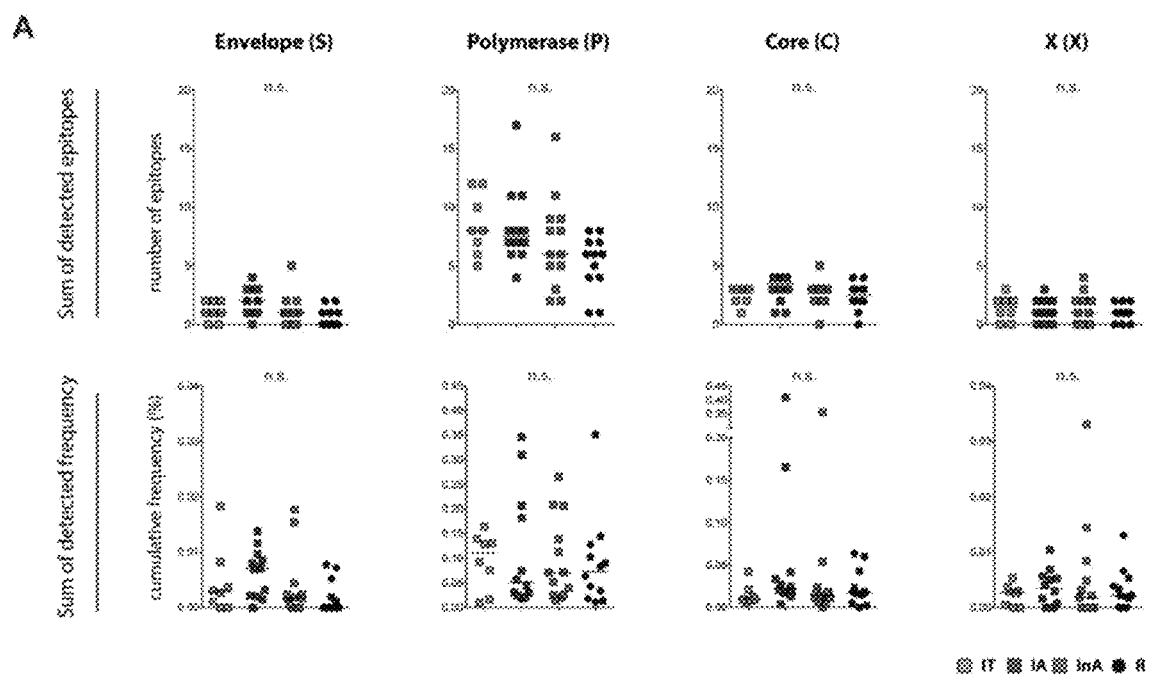

FIG. 9 The overall magnitudes of antigen-specific CD8+ T cells response in various clinical stages during HBV infection.
(A) Upper panel, the total number of different epitopes derived from four hepatitis B viral proteins (envelope, polymerase, core and x) detected in each individual patient across various clinical stages. Lower panel, the sum of frequency (%) of every detected antigen-specific CD8+ T cells for four different hepatitis B viral proteins in each individual patient across various clinical stages. n.s.=no significance.

Figure 10:
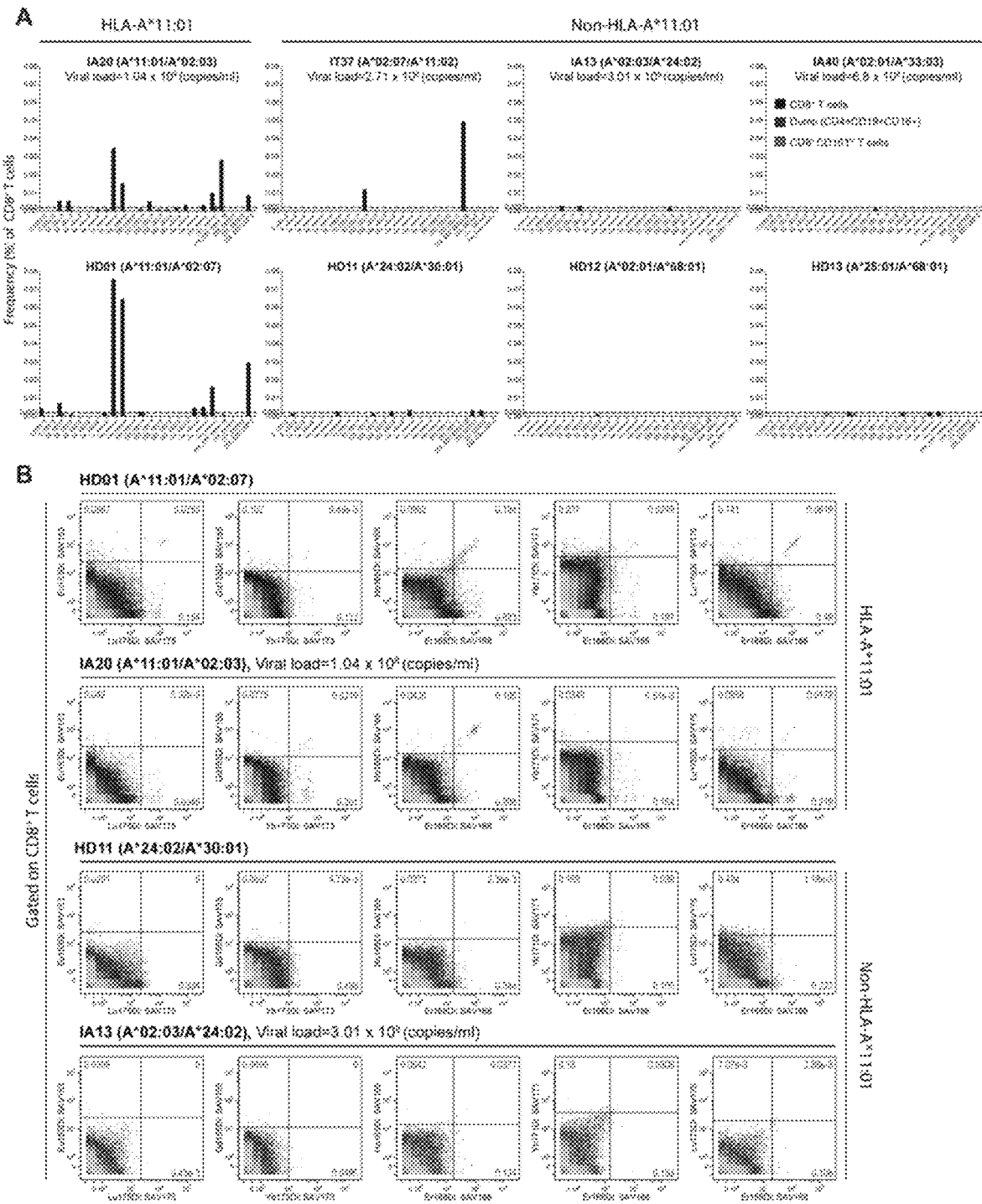

FIG. 10 The validation of highly multiplexed combinatorial pMHC tetramer strategy in HLA-A*11:01 and non-HLA-A*11:01 donors.
(A) Cells from each donorwere stained with selected 120-plex (Supplementary Table 1) pMHC tetramers coded with three different SAv-metal using two different sets of coding configurations. Experiments were performed independently and cells were stained and gated on live CD3+, Dump-(CD4+CD19+CD16+) and CD8+. Bar graphs indicate the frequencies for each epitope. (B) Representative dot plots show the pMHC tetramer positive cells and their signals of coded SAv-metals by different combinations of nine metal-tag SAv.

Figure 11:
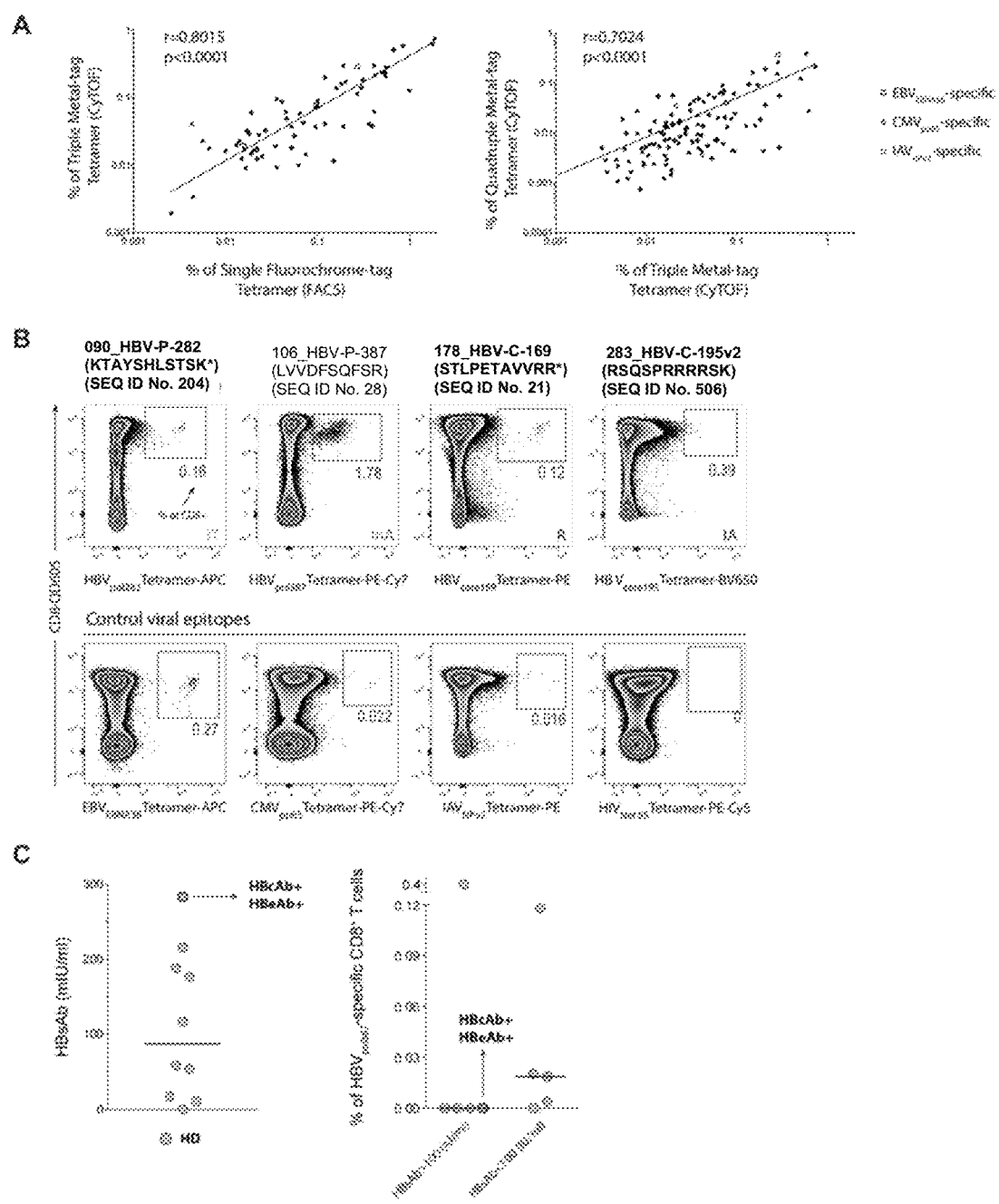

FIG. 11 The validation and reproducibility of antigen-specific CD8+ T cells using flow cytometry and the serological measurement of healthy donors.
(A) Correlations of the detected frequencies between FACS versus CyTOF based experiments. Each dot is one individual patient. (B) Representative FACS dotplots of selected HBV epitopes. The numbers are the frequencies of total CD8+ T cells. (C) Left, the hBsAb (anti-HBsAg antibody) titers in healthy donors (HD). Right, the frequency of HBVpol387-specific CD8+ T cells in HD in different HBV serological (HBsAb, HBcAb and HBeAb) status. The levels of serum antibodies against different HBV viral antigens were measured by ELISA. Circles denoted as HBcAb+ HBeAb indicate the only individual who was tested positive for HBcAb and HBeAb.

Figure 12:
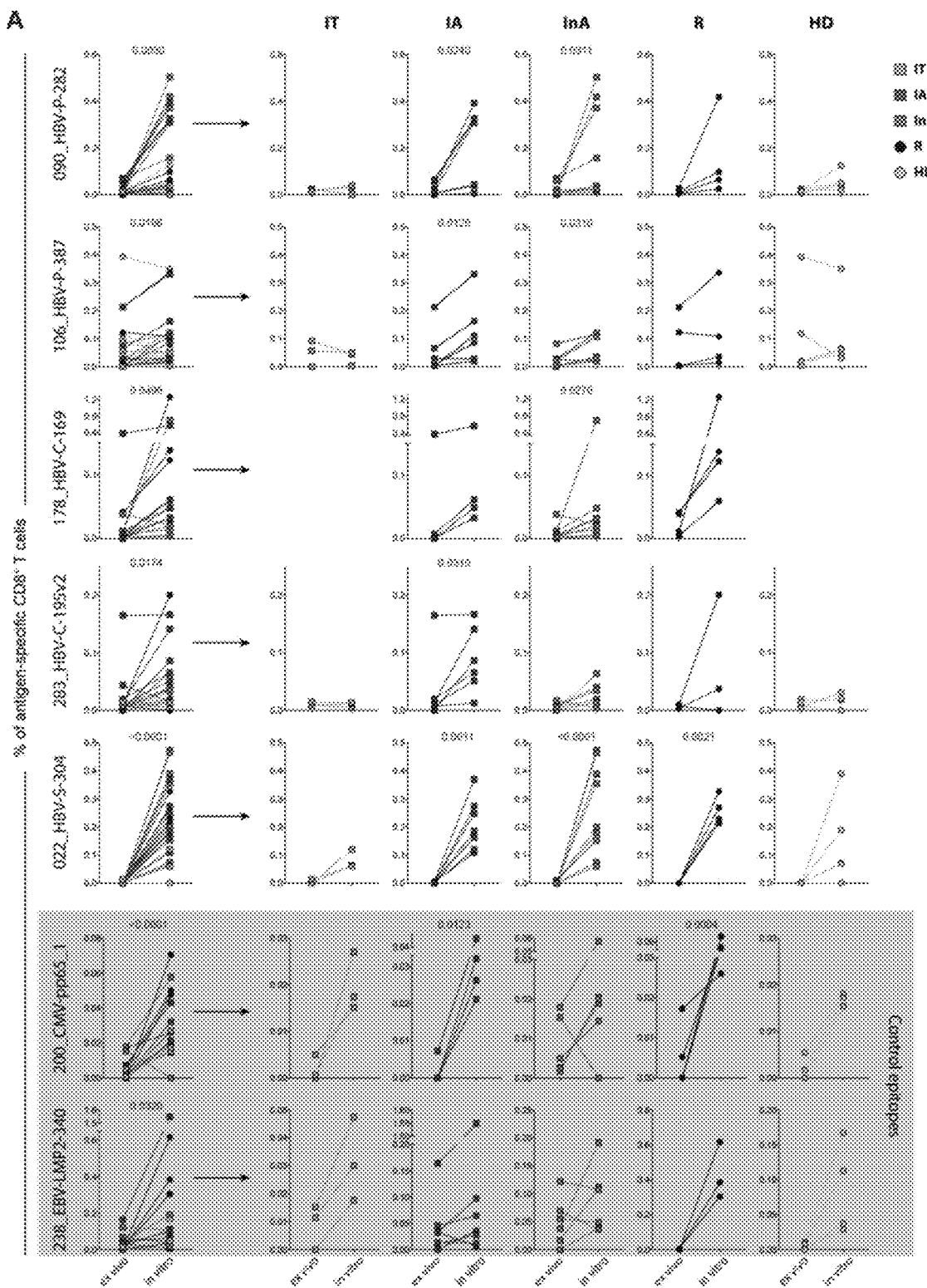

FIG. 12 In vitro expansion of antigen-specific CD8+ T cells upon peptide stimulation.
(A) PBMC from different patient groups were expanded by corresponded viral peptides for 10 days. The frequency of antigen-specific CD8+ T cells were determined as the same as ex vivo pMHC tetramer staining experiment. The number above each graph indicates the significant p value.

Figure 13:
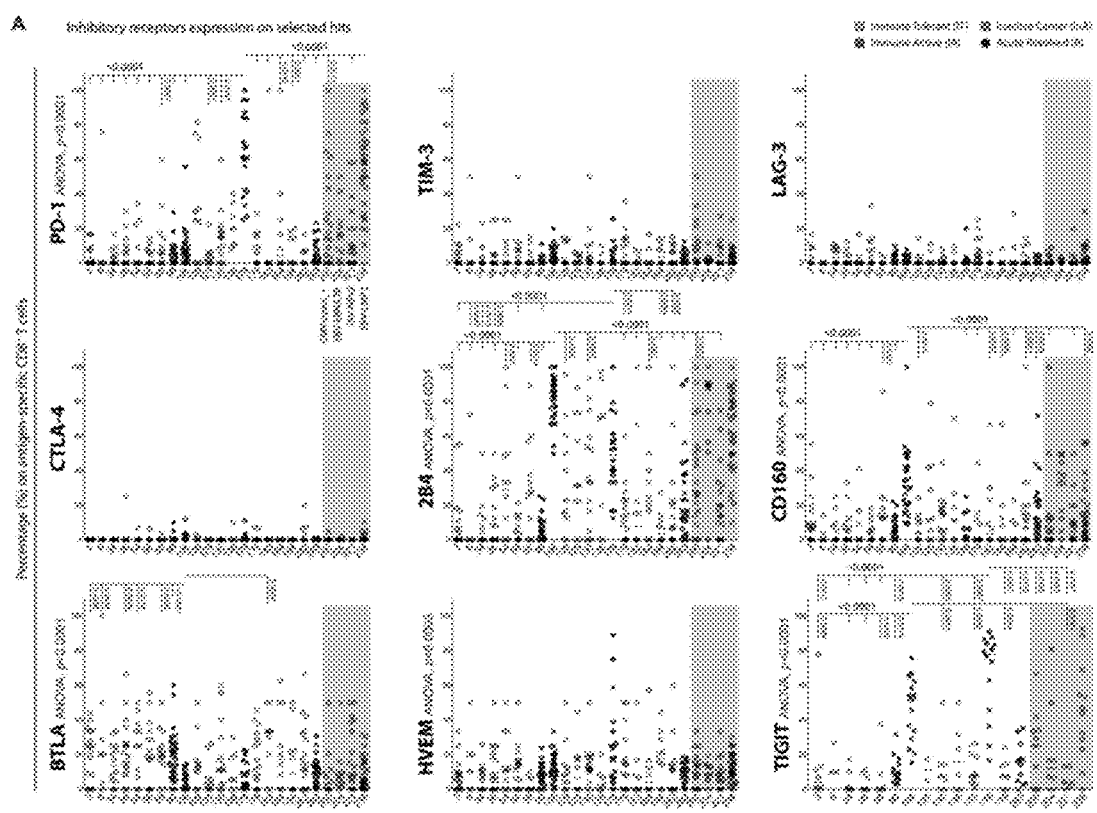

FIG. 13 The expression levels of nine different inhibitory receptors on antigen-specific CD8+ T cells.
(A) The expression level of inhibitory receptors on selected antigen-specific CD8+ T cells. The numbers on x-axis indicate the peptide cluster number for each specificity (epitopes) (see table_S1). Grey dots are the four selective HBV epitopes (090_HBV-P-282, 106_HBV-P-387, 178_HBV-C-169 and 283_HBV-C-195v2). Grey legends indicate the different HBV clinical stages. Grey highlighted areas are control viral epitopes. Statistical significances were only shown for selected epitopes. p value less than 0.0001 (short ticks) or other values (long ticks) are indicated.

Figure 14:
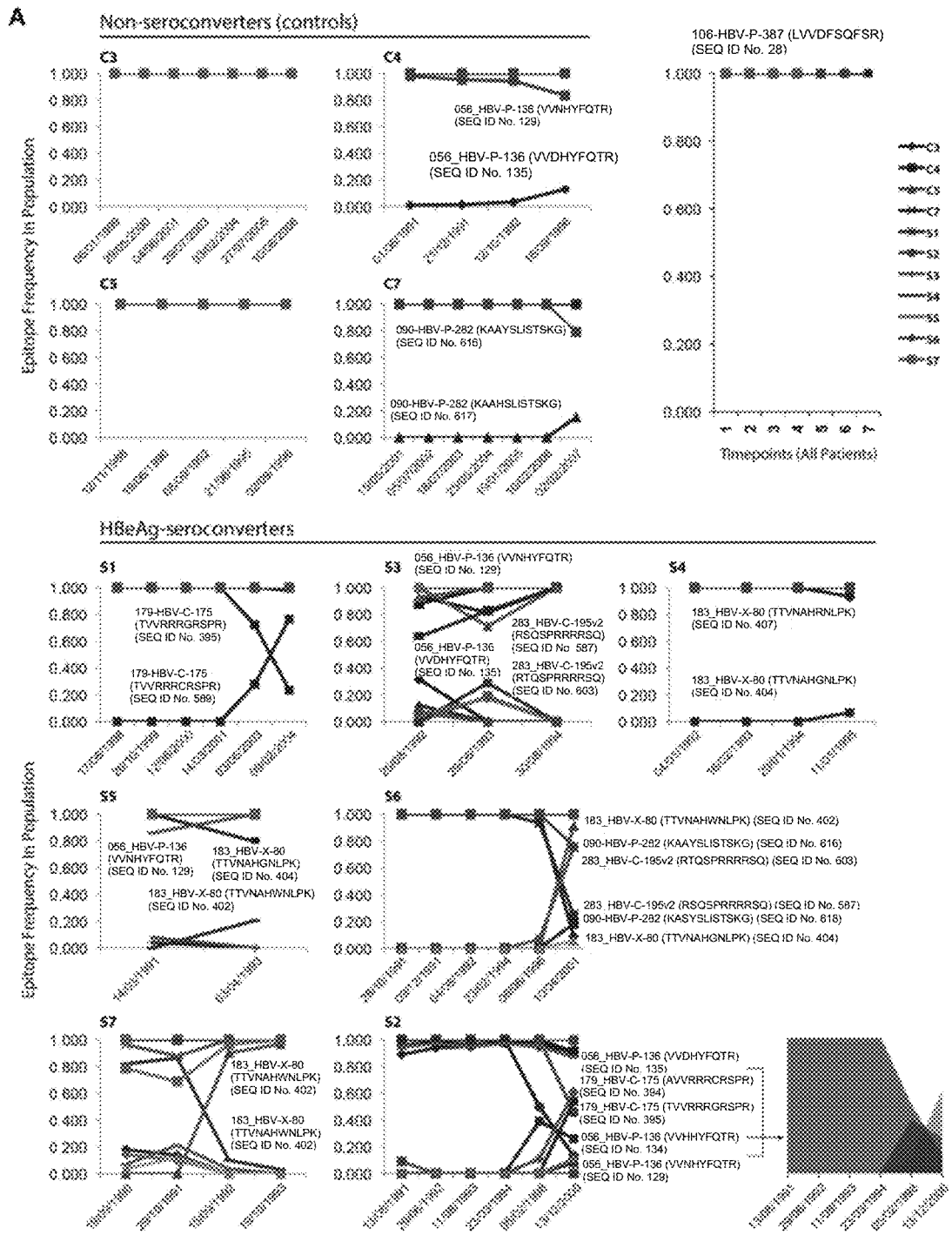

FIG. 14 The epitope frequencies in a longitudinal patient cohort of HBeAg-seroconverters.
(A) Deep sequencing analysis of HBV viral DNA showed the different dynamic of viral mutations on selective epitopes identified by highly multiplexed combinatorial pMHC tetramer strategy. A longitudinal patient cohort included treatment naive CHB patients who spontaneously underwent HBeAg-seroconversion (S, bottom) or Non-seroconversion (C, upper) across the similar time frame in chronological order. HBVpol387 (LVVDFSQFSR (SEQ ID No. 28)) proportion (upper right) in the viral population sequenced at each time point, out of a maximum of 1. This epitope remained fixed in all patients and no change was observed. Epitope ID and sequence was as listed in table S1. Detailed epitope mutation data can be found in table S4.

Figure 15:
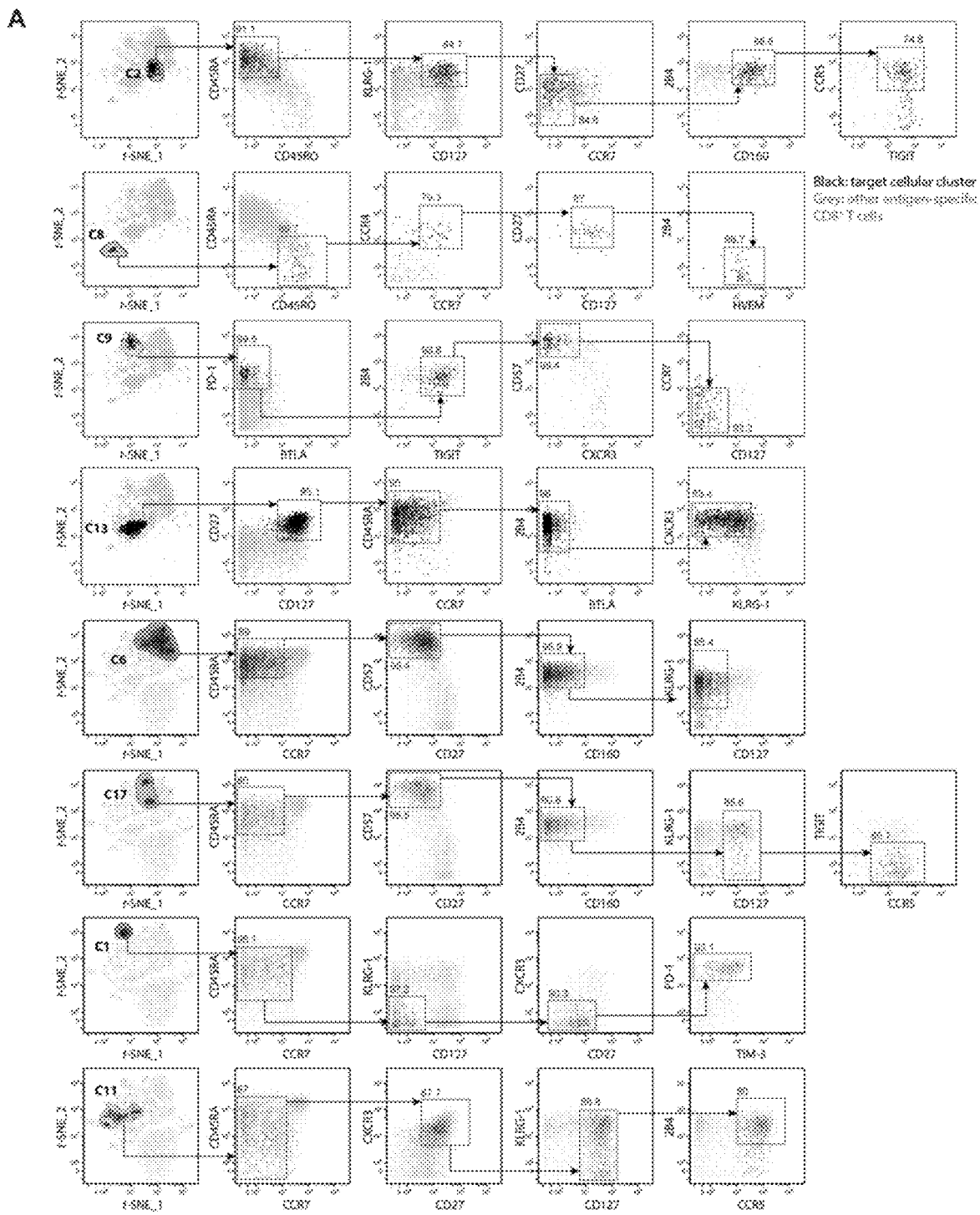

FIG. 15 Cellular profiles of subset clusters of HBV-specific CD8+ T cells identified by Phenograph and the enrichment strategy.
(A) Subset enrichment strategy for eight major Phenograph subset clusters of HBV-specific CD8+ T cells. Gating strategy was defined in a representative experiment and defining markers for each subset clusters were then applied onto three different batches of experiments to identify the proportion of each subset cluster within HBVpol387 and HBVcore169-specific CD8+ T cells. Shaded areas are the target clusters sorted as in FIG. 2A. Black dots are cells in the target cluster. Grey dots are other antigen-specific CD8+ T cells. The numbers indicate the frequencies.

Figure 16:
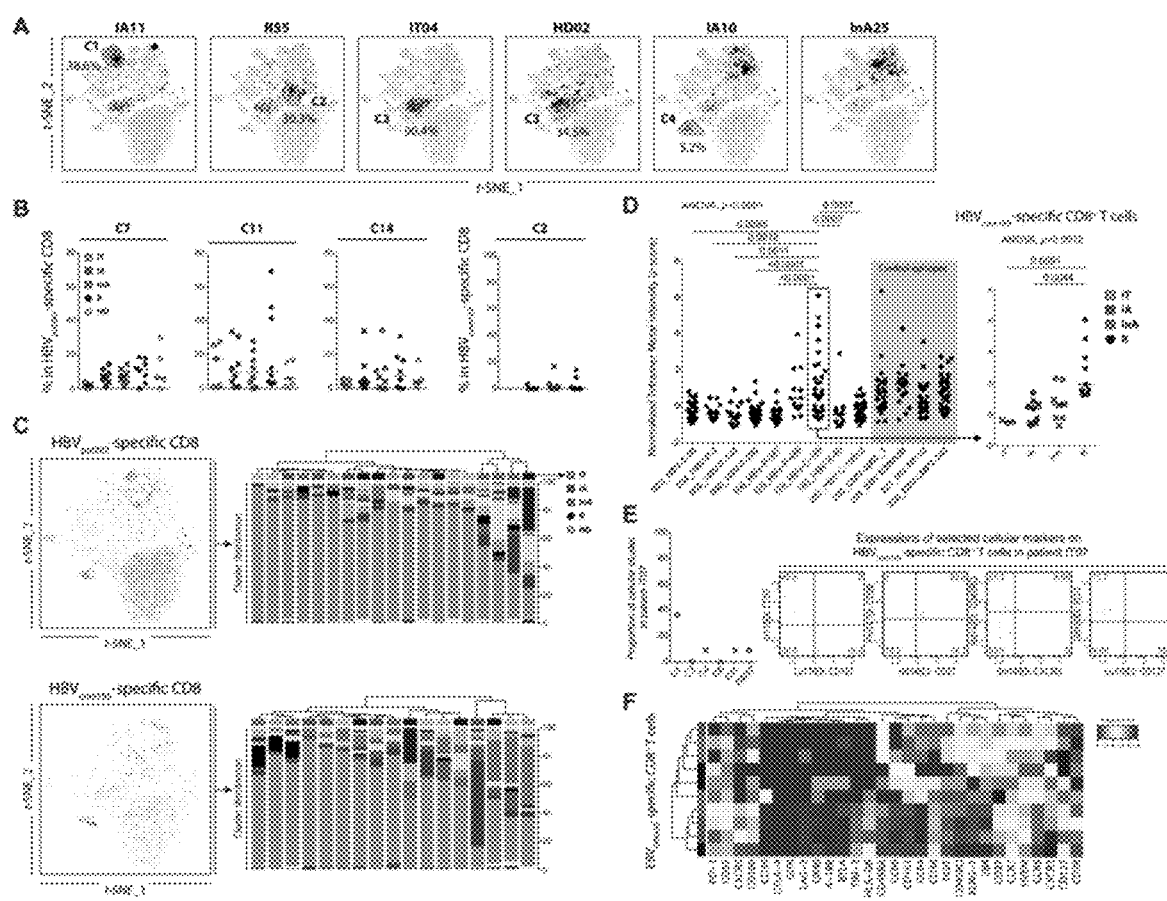

FIG. 16 Unsupervised Phenograph clustering analysis identified multifactorial T cell heterogeneity of HBV-specific CD8+ T cells.
(A) Representative plots of cellular cluster showed HBVpol387(LVVDFSQFSR (SEQ ID No. 28))-specific CD8+ T cells were enriched in distinct regions across patient groups. Related to FIG. 2A-B. Black dots are HBVpol387-specific CD8+ T cells from indicated donor. Grey dots are the combined of all antigen-specific CD8+ T cells of twenty individuals including all patient groups. The numbers indicate the proportion of highlighted clusters within HBVpol387-specific CD8+ T cells. (B) The proportion of three cellular clusters (C7, C11 and C14) in HBVpol387-specific CD8+ T cells. The proportion of cellular cluster C2 in HBVcore169-specific CD8+ T cells. (C) Unsupervised Phenograph clustering showed the phenotypic difference of HBVpol282 and HBVcore195. Stacked bar charts showed the distribution of nineteen cellular clusters (FIG. 2A) in individual across patient groups. (D) pMHC tetramer intensity was quantified by averaging the median numbers of metals of four different SAv-metals coded on tetramer positive cells. Plots show the normalized value (z-score) of tetramer intensity on different selected virus-specific CD8+ T cells (left), and HBVcore169-specific CD8+ T cells (right) across various patient groups. (E) The proportion of cellular cluster and the expressions of cellular markers of HBVcore169-specific CD8+ T cells derived from one IT patient (IT07), whose frequency (0.00193%) was just below the imposed cut-off. (F) Hierarchical clustering of cellular markers expression of EBVEBNA3B-specific CD8+ T cells from the same individuals as FIG. 1D across patient groups.

Figure 17:
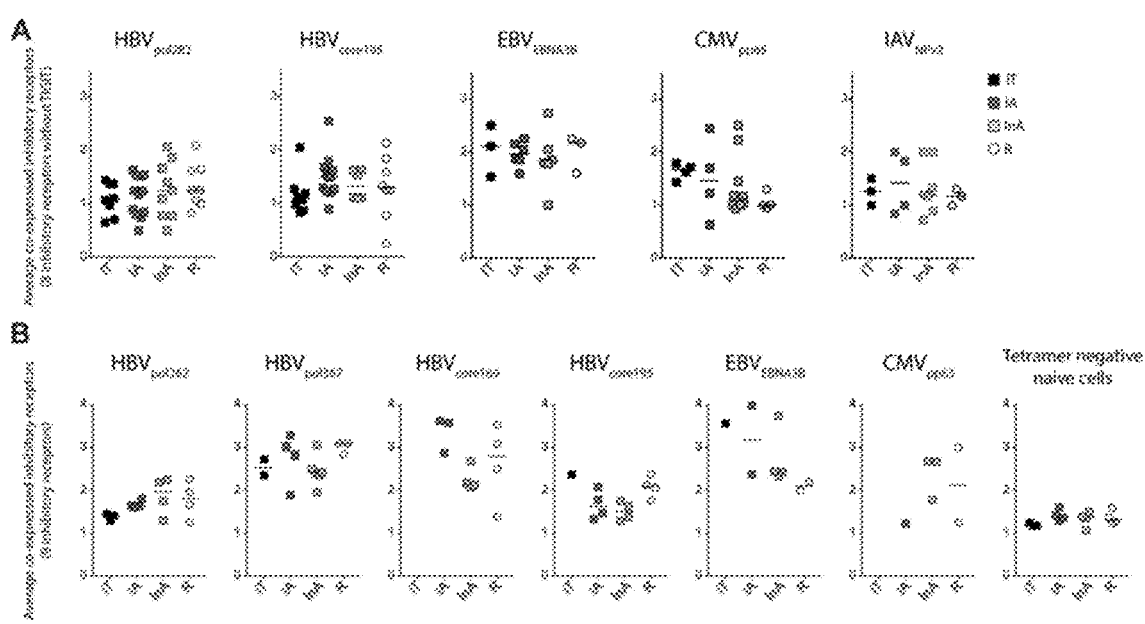

FIG. 17 The co-expressions of inhibitory receptors on virus-specific CD8+ T cells.
(A) The average numbers of co-expressed inhibitory receptors on different antigen-specific CD8+ T cells in individuals. Plots were combined of four independent experiments without the measurement of cellular marker TIGIT. Each dot is one individual. (B) The average numbers of co-expressed inhibitory receptors on different antigen-specific CD8+ T cells in individuals. Plots were from an experiment with the measurement of all nine inhibitory receptors.

Figure 18:
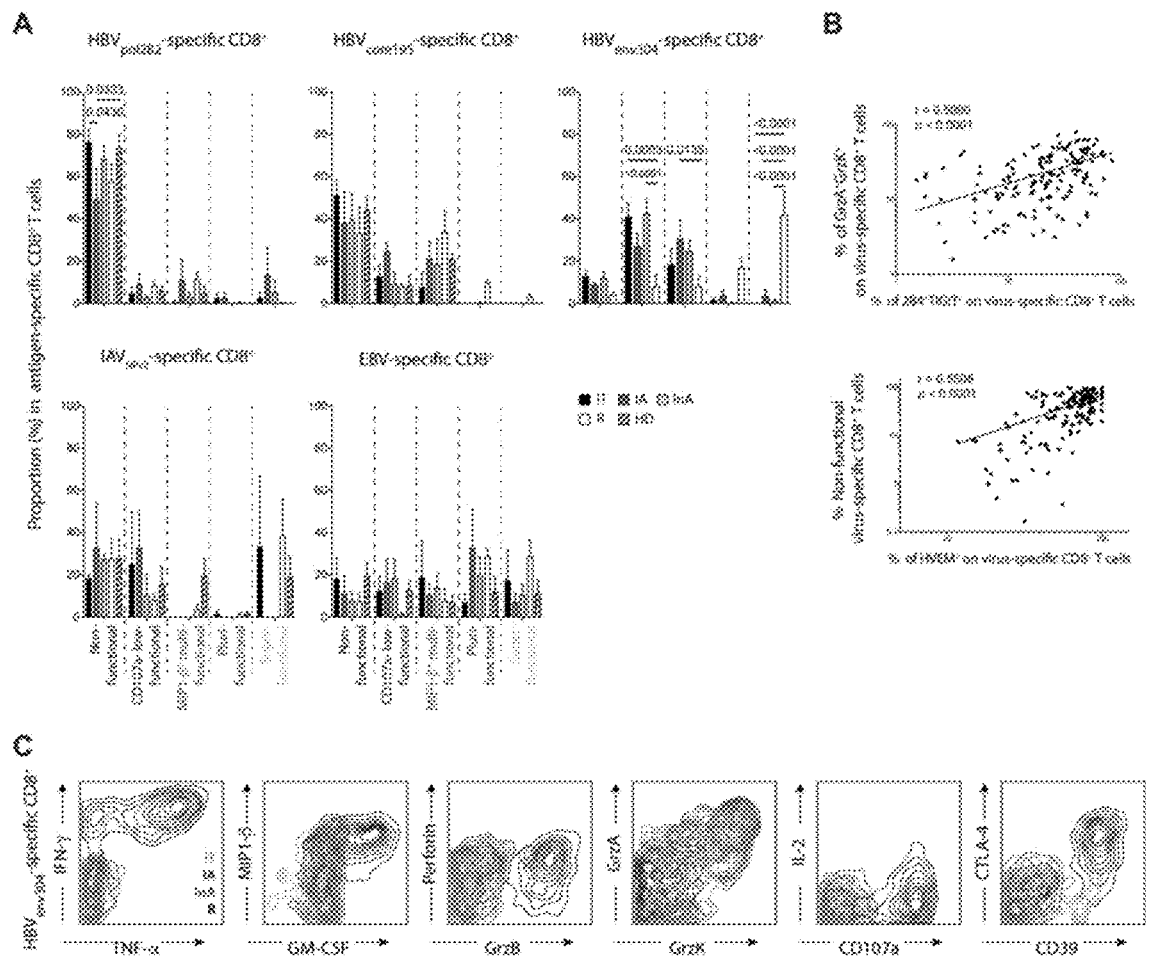

FIG. 18 The heterogeneous multi-functional subsets of virus-specific CD8+ T cells.
(A) The detailed One-SENSE functional clusters of different antigen-specific CD8+ T cells across patient groups. n=4~5 per patient group. Functional subsets were labelled as in FIG. 4A. (B) The correlation of co-producing Granzyme A and K with the co-expression of 2B4 and TIGIT on virus-specific CD8+ T cells. The proportion of Non-functional subset (black) was correlated to the sustained expression of HVEM on virus-specific CD8+ T cells. Dots were the different virus-specific CD8+ T cells from individual patients. (C) The representative contour plots of HBVenv304-specific CD8+ T cells showed the heterogeneous multi-functionality between patients.

Figure 19:
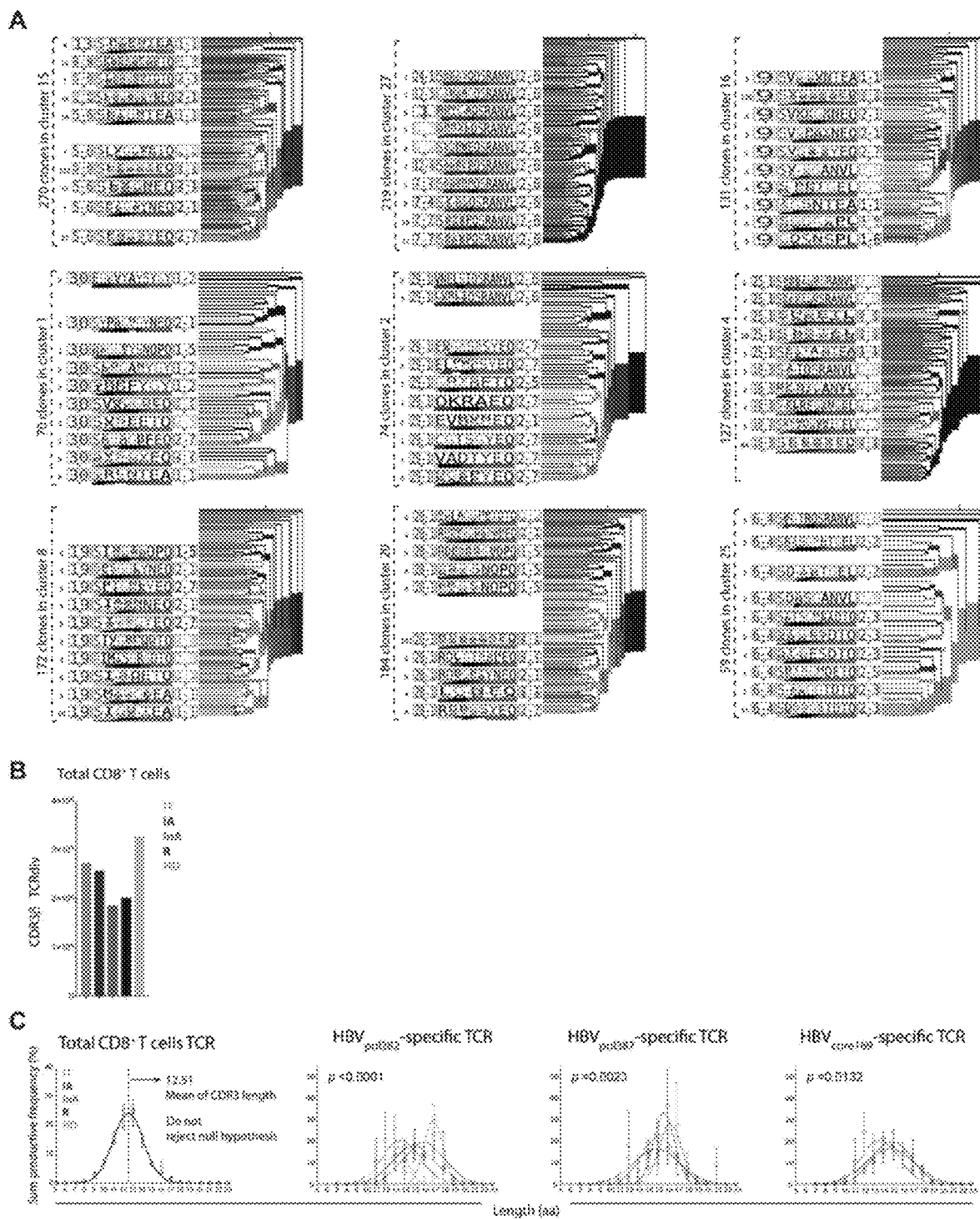

FIG. 19 Diverse characteristics of epitope-specific TCRβ repertoire using TCRdist.
(A) Nine TCR motif clusters identified by Phenograph were presented, and the representative TCR motifs were shown using average-linkage dendrogram using TCRdist algorithm. Related to FIG. 5. (B) TCRdiv diversity measures of total CD8+ T cells TCRβ repertoire between patient groups are shown. (C) The length (aa, amino acid) of CDR3β of total and epitope-specific CD8+ T cells across patient groups. Error bars are mean and SEM. Statistical analysis was calculated using Gaussian fit with the null hypothesis "one curve fits all groups".

Figure 20:
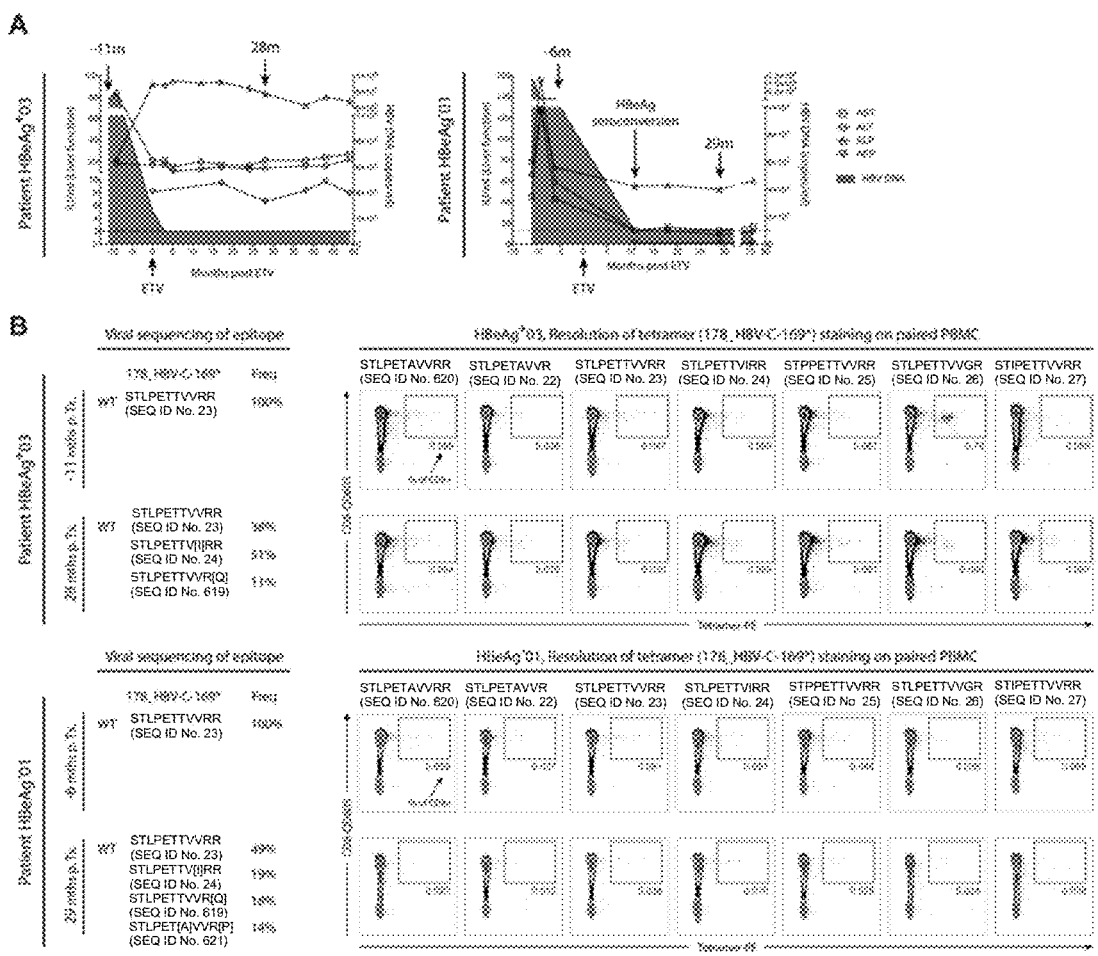

FIG. 20 The dynamic of cellular response and viral mutation of HBVcore169-specific CD8+ T cells in a longitudinal patient cohort.
(A) The liver inflammation scores of two patients (HBeAg+ 03 and HBeAg−01) from a longitudinal patient cohort were shown. ALT, alanine aminotransferase. AST, aspartate aminotransferase. AFP, alpha-fetoprotein. ALP, alkaline phosphatase. Related to FIG. 6A. (B) PBMCs from pre- and post-treatment of HBeAg+03 and HBeAg–01 were used to resolve the specific tetramer response for 7 different peptides in cluster 178 (see table S1). Cells were evenly split and stained with the corresponded (as indicated above) pMHC tetramer independently using flow cytometry. The numbers indicate the frequency of CD8+ T cells. Virus from paired serum samples were sequenced to determine the variants (in frequency) of the epitope (left). WT, wild type. The same sequences were sorted as indicated.

Figure 21:
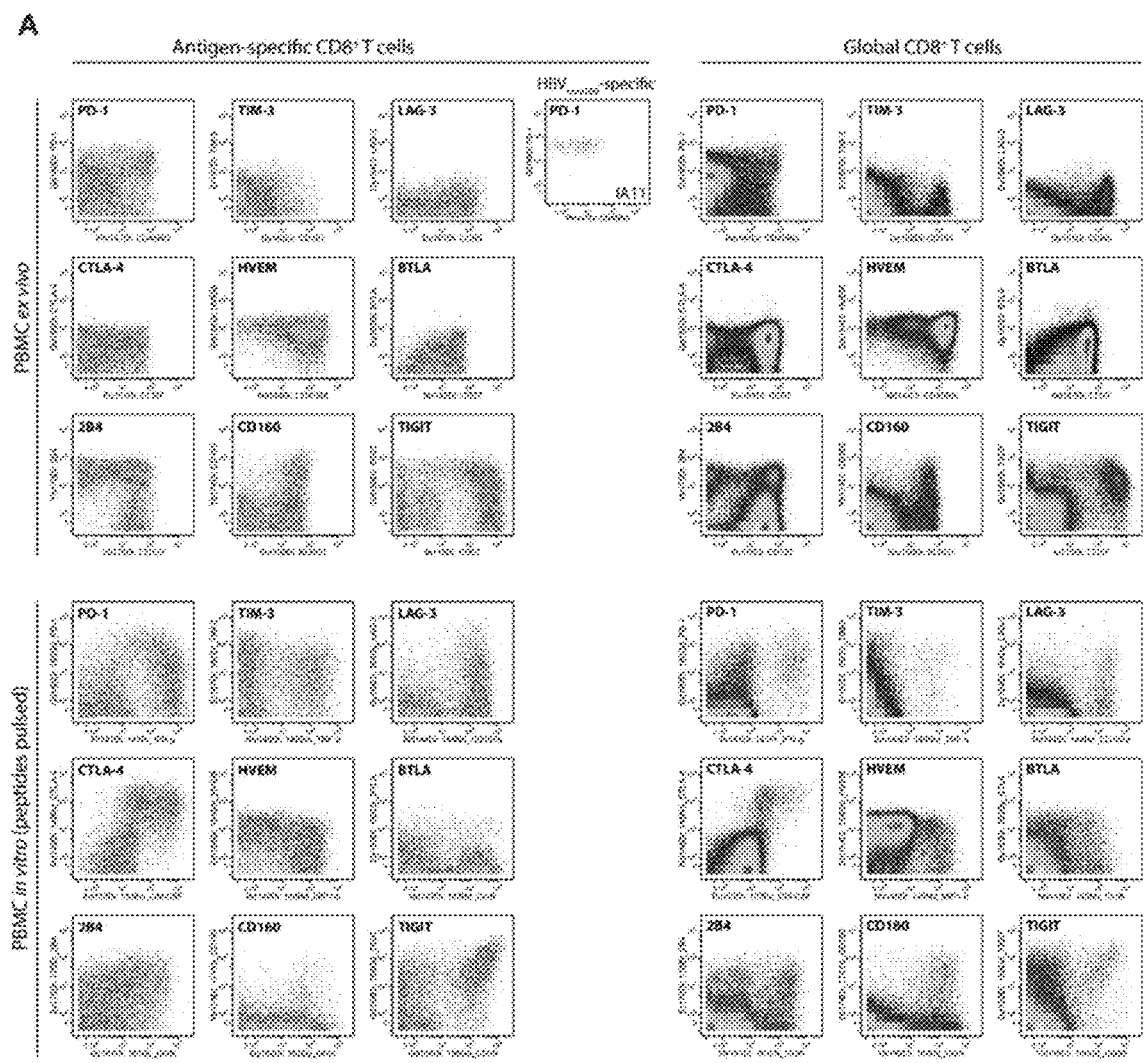

FIG. 21 The staining quality of cellular markers including nine inhibitory receptors using mass cytometry. (A) Dotplots show the expression levels of markers probed on antigen-specific (left) versus global (right) CD8+ T cells in patient's PBMC. Upper panels are ex vivo staining. Lower panels are cells from in vitro peptide stimulation. For the better visualization of dotplots, all detected antigen-specific CD8+ T cells were pooled from 18 patients (left panel, n=4~5 per patient group, including IT, IA, InA and R). PD-1-expressing HBVcore169-specific CD8+ T cells from a CHB patient is also showed. Plots were from two independent experiments (ex vivo and in vitro).

The present invention will be described with respect to particular embodiments and with reference to certain drawings, but the invention is not limited thereto but only by the claims.

Any reference signs in the claims shall not be construed as limiting the scope. The drawings described are only schematic and are non-limiting. In the drawings, the size of some of the elements may be exaggerated and not drawn on scale for illustrative purposes.

As used herein, except where the context requires otherwise, the term "comprise" and variations of the term, such as "comprising", "comprises" and "comprised", are not intended to exclude further additives, components, integers or steps. As used herein, except where the context requires otherwise, "comprise" and "include", or variations of the term such as "including" can be used interchangeably.

Where an indefinite or definite article is used when referring to a singular noun e.g. "a" or "an", "the", this includes a plural of that noun unless something else is specifically stated. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The following terms or definitions are provided solely to aid in the understanding of the invention. Unless specifically defined herein, all terms used herein have the same meaning as they would to one skilled in the art of the present invention. Practitioners are particularly directed to Sambrook et al., Molecular Cloning: A Laboratory Manual, 2nd ed., Cold Spring Harbor Press, Plainsview, New York (1989); and Ausubel et al., Current Protocols in Molecular Biology (Supplement 47), John Wiley & Sons, New York (1999), for definitions and terms of the art.

The definitions provided herein should not be construed to have a scope less than understood by a person of ordinary skill in the art.

EXAMPLE

Materials and Methods

1. Patient Samples and PBMC Isolation

Patients (table S3) with HBV infection were recruited with fully informed written consent from Division of Gastroenterology and Hepatology at National University Health System, Singapore. The respective local ethical institutional review boards approved the study, and the recruitment and sampling of suitable patients was completed at hospital. Up to 60 ml of blood was taken, peripheral blood mononucleated cells (PBMC) were further isolated by using Ficoll-separation (Ficoll-Paque PLUS, GE Healthcare). All patients had clinical, serological and virological evidences of chronic hepatitis B infection with detection of HBsAg and HBV DNA, and no positive result for the presence of HIV-1 and -2, and HCV. Three CHB patient groups, Immune Tolerant (IT, HBV DNA>2000 Iu/ml, ALT<40 IU/ml, HBeAg+), Immune Active (IA, HBV DNA>2000 Iu/ml, ALT>40 IU/ml, HBeAg+), Inactive Carrier (InA, HBV DNA<200 IU/ml or undetectable, ALT<40 IU/ml, HBeAg–) and one group of acute resolved patients (R, undetectable HBV DNA, HBsAg- and anti-HBc antibody+) were enrolled in this study. Each CHB patient had at least three adjacent time points indicating consistent virological and serological evidences for the referring clinical stages. All patients were treatment free from any antiviral drug or clinical intervention at the time of blood draw. Patients received Entecavir (ETV) were followed up longitudinally and enrolled. Serological and virological scores (serum HBV DNA, HBeAg and HBsAg) and liver function test were determined by clinical laboratory at hospital or ELISA. Blood from anonymous healthy donors were recruited underSingapore immunology Network (SIgN) institutional review board. Healthy cord blood samples were purchased from Singapore Cord Blood Bank under the institutional review board, without detection of HIV-1 and -2, HTLV-i and II, HCV, CMV, HBsAg and anti-HBc antibody. HLA-A*11:01 was confirmed by typing service from BGI Genomics.

TABLE S3

Supplementary Table 3: List of the patient samples and the clinical and serological informations.

| Tissue types | Patient group | n | Tx | Age | HBV DNA (IU/ml) | ALT (IU/ml) | AST (IU/ml) | HBsAg (ng/ml) | HBeAg (ng/ml) | HBsAb mIU/ml) | HBeAb (ng/ml) |
|---|---|---|---|---|---|---|---|---|---|---|---|
| PBMC | Immune Tolerant (IT) | 11 | N | 32.5 (30~54) | $4.5 \times 10^7$ ($2.0 \times 10^4$~ $9.2 \times 10^8$) | 30 (23~40) | 25.5 (2~46) | $5.1 \times 10^4$ ($5.3 \times 10^3$~ $9.7 \times 10^4$) | $2.4 \times 10^3$ ($9.3 \times 10^1$~ $4.0 \times 10^3$) | Not detected | 4.1 (0~12.0) |
| | Immune Active (IA) | 20 | N | 33.3 (20~60) | | | | | | Not detected | 4.5 (0~20.8) |
| | Inactive Carrier (InA) | 16 | N | 33.3 (31~72) | | | | | | 0 (0-59.9) | 140.3 (18.5~ 368.6) |

TABLE S3-continued

Supplementary Table 3: List of the patient samples and the clinical and serological informations.

|   |   |   |   |   |   |   |   |   |   |   |   |
|---|---|---|---|---|---|---|---|---|---|---|---|
|   | Acute Resolved (R)* | 13 | N | N/A | Not detected | N/A | N/A | Negative | Negative | >1000 | positive |
|   | Healthy Donor (HD) | 13 | N | 34 (29~45) | N/A | N/A | N/A | N/A | N/A | N/A | N/A |
|   | Healthy Cord Blood (CB) | 10 | N | N/A | N/A | N/A | N/A | N/A | N/A | N/A | N/A |

|   | Longitudinal patient group | n | Tx | # of timepoints | HBV DNA (IU/ml) | ALT (IU/ml) | AST (IU/ml) | HBsAg (ng/ml) | HBeAg (ng/ml) | HBsAb mIU/ml) | HBeAb (ng/ml) |
|---|---|---|---|---|---|---|---|---|---|---|---|
| PBMC | HBeAg– | 8 | ETV | 5~7 | 0 (0~1.8 × $10^8$) | 33.5 (9~210) | 28.5 (13~128) | Positive | Negative** | N/A | Positive** |
|   | HBeAg+ | 6 | ETV | 4~8 | 0 (0~1.4 × $10^7$) | 18.5 (11~42) | 24 (15~84) | Positive | Positive | N/A | Negative |

|   | Longitudinal patient group |   |   | # of timepoints | HBV DNA (log10, copies/ml) | ALT (IU/ml) |   |   |   |   |   |
|---|---|---|---|---|---|---|---|---|---|---|---|
| Serum | HBeAg-sero-converter (S) | 8 | N | 4~8 | 8 (4.40~9.67) | 33 (7~121) |   |   |   |   |   |
|   | Non-sero-converter (C) | 7 | N | 5~7 | 9 (6.00~10.29) | 48 (19~87) |   |   |   |   |   |

2. 562-Plex Combinatorial (Quadruple/Triple SAv-Metal Coded) pMHC Tetramers

Fourteen different SAv-metals were made by labelling streptavidin with fourteen different metal isotopes. Similar to previous work reported in E. W. Newell et al., Combinatorial tetramer staining and mass cytometry analysis facilitate T-cell epitope mapping and characterization, each SAv-metal was diluted into 20 μg/ml in EDTA-free W-buffer on the same day of tetramerization of pMHC. Two different configurations of quadruple SAv-metal coding for 562-plex pMHC tetramers were generated using a R-based script for a 14-choose-4 scheme (for 1001 combinations). The script was then loaded onto TECAN Freedom EVO200 automatic liquid distribution robot to prepare the designed combinations of quadruple SAv-metal mixtures (each mixture contains 4 different SAv-metals) in 2 ml 96-well deep well plates. To form pMHC tetramers, each peptide-loaded HLA-A*1101 monomer (562 different pMHC monomers) was randomly assigned for four different SAv-metals. To reach a 1:4 ratio of streptavidin to pMHC, quadruple SAv-metal mixtures were added to the corresponded pMHC monomer in a stepwise manner of four additions, each has 10 min incubation at room temperature. 10 μM D-biotin was added into the reaction at the end for another 10 min at room temperature to saturate unbound streptavidins. The 562-plex pMHC tetramers were combined and concentrated down to 5 μg/ml per pMHC tetramer in 10% FBS CyFACS buffer using Amicon 50 kDa cut-off concentrator (Millipore). The total amount of protein in each concentrator was limited to 300 ag. To reach the desired concentration and volume, multiple spins were performed at 700 xg for 5 min. The 562-plex tetramers were then filtered by 0.1 m filter tube (Millipore) at 2000 xg for 25 min. The cocktail of tetramers was kept on ice, and then spin at 14,000 xg for 1 min in a 1.5 ml Eppendorf tube to remove the remaining aggregates prior the staining.

The combinatorial streptavidin codings were re-scrambled for every independent 562-plex combinatorial pMHC tetramer staining experiment.

For selected experiments, a 9-choose-3 (84 combinations) or 8-choose-3 (56 combinations) scheme were used to cover 120-plex (40 peptide clusters) or 50-plex (17 peptide clusters) combinatorial triple coded pMHC tetramers staining preferentially selected (table S1) for more phenotypic analysis, or in vitro peptide stimulation (table S2).

TABLE S1

Supplementary Table 1.
List of detected HLA-A*1101-restricted epitopes and the frequency across various patient groups

| Cluster | Source Protein & Position | 1st Peptide Sequence | Peptides in Cluster | | | | Hits (Freq > 0.002%) | | | | Average of hits (%) | | | |
|---|---|---|---|---|---|---|---|---|---|---|---|---|---|---|
| | | | | | | | IT | IA | InA | R | IT | IA | InA | R |

Antigen Source-Hepatitis B virus

| 1 | HBV-S-27 | HQLDPAFK (SEQ ID No. 32) | | | | | | | | | | | | |
| 2 | HBV-S-94 | ASTNRQSGRK (SEQ ID No. 33) | | | | | | | | | | | | |
| 3 | HBV-S-95* | STNRQSGRK* (SEQ ID No. 34) | STNRQSGRK (SEQ ID No. 34) | STNRQSGR (SEQ ID No. 35) | | | 5/8 | 7/12 | 4/13 | 1/12 | 0.003228 | 0.004132 | 0.005883 | |
| 4 | HBV-S-124* | STFHQALLDPR* (SEQ ID No. 36) | STFHQALLDPR (SEQ ID No. 36) | TTFHQALLDPR (SEQ ID No. 37) | TTFHQTLQDPR (SEQ ID No. 38) | | | 1/12 | | | | 0.008353 | | |
| 5 | HBV-S-129* | TLQDPRVRALY* (SEQ ID No. 39) | TLQDPRVRALY (SEQ ID No. 39) | ALLDPRVRGLY (SEQ ID No. 40) | | | | | | | | | | |
| 6 | HBV-S-156* | TVSAISSILSK* (SEQ ID No. 41) | TVSAISSILSK (SEQ ID No. 41) | TVSTISSILSK (SEQ ID No. 42) | TASPISSIFSK (SEQ ID No. 43) | TASPISSIFSR (SEQ ID No. 44) | 1/8 | 2/12 | | 1/12 | 0.00508 | 0.002307 | | 0.005196 |
| 7 | HBV-S-157* | VSAISSILSK* (SEQ ID No. 45) | VSAISSILSK (SEQ ID No. 45) | ASPISSIFSK (SEQ ID No. 46) | VSTISSILSK (SEQ ID No. 47) | ASPISSIFSR (SEQ ID No. 48) | | 1/12 | | | | 0.005228 | | |
| 8 | HBV-S-158* | STISSILSK* (SEQ ID No. 49) | STISSILSK (SEQ ID No. 49) | SAISSILSK (SEQ ID No. 50) | SPISSIFSK (SEQ ID No. 51) | SPISSIFSR (SEQ ID No. 52) | | 1/12 | 1/13 | | | 0.003020 | 0.015373 | |
| 9 | HBV-S-159* | TISSILSK* (SEQ ID No. 53) | TISSILSK (SEQ ID No. 53) | AISSILSK (SEQ ID No. 54) | PISSIFSK (SEQ ID No. 55) | | | | | | | | | |
| 10 | HBV-S-187* | VLQAGFFLLTK (SEQ ID No. 56) | VLQAGFFLLTK (SEQ ID No. 56) | VLQAGFFSLTK (SEQ ID No. 57) | VLQAGFFLLTR (SEQ ID No. 58) | | | | | | | | | |

TABLE S1-continued

Supplementary Table 1.
List of detected HLA-A*1101-restricted epitopes and the frequency across various patient groups

| # | ID | Peptide | | | | | | | | |
|---|---|---|---|---|---|---|---|---|---|---|
| 11 | HBV-S-188* | LQAGFFLLTK* (SEQ ID No. 59) | LQAGFFLLTK (SEQ ID No. 60) | LQAGFFSLTK (SEQ ID No. 61) | LQAGFFLLTR | 1/12 | | | | 0.002898 |
| 12 | HBV-S-189* | QAGFFLLTK* (SEQ ID No. 62) | QAGFFLLTK (SEQ ID No. 63) | QAGFFSLTK | | | | | | |
| 13 | HBV-S-190* | AGFFLLTK* (SEQ ID No. 64) | AGFFLLTK (SEQ ID No. 65) | AGFFSLTK | | 1/13 | | | | 0.002499 |
| 14 | HBV-S-210 | TSLNFLGGAPK (SEQ ID No. 66) | | | | | | | | |
| 15 | HBV-S-211 | SLNFLGGAPK (SEQ ID No. 67) | | | | | | | | |
| 16 | HBV-S-236 | TSCPPICPGYR (SEQ ID No. 68) | | | | | | | | |
| 17 | HBV-S-264 | LIFLLVLLDY (SEQ ID No. 69) | | | | | | | | |
| 18 | HBV-S-285* | GTSTTSTGPCK (SEQ ID No. 70) | GSSTTSTGPCK (SEQ ID No. 71) | | | | | | | |
| 19 | HBV-S-286* | SSTTSTGPCK* (SEQ ID No. 72) | TSTTSTGPCK (SEQ ID No. 73) | | | | | | | |
| 20 | HBV-S-287 | STTSTGPCK (SEQ ID No. 74) | | | | | | | | |
| 21 | HBV-S-288 | TTSTGPCK (SEQ ID No. 75) | | | | 1/12 | 1/12 | | 0.02665 | 0.006913 |
| 22 | HBV-S-304 | TSMFPSCCCTK (SEQ ID No. 76) | | | | 1/8 | 2/12 | 1/13 | 0.013587 | 0.003647 0.004037 |

TABLE S1-continued

Supplementary Table 1.
List of detected HLA-A*1101-restricted epitopes and the frequency across various patient groups

| | | | | | | | | | | | |
|---|---|---|---|---|---|---|---|---|---|---|---|
| 23 | HBV-S-305* | SMFPSCCCTK (SEQ ID No. 77) | SMFPSCCCTK (SEQ ID No. 77) | SMYPSCCCTK (SEQ ID No. 78) | | | | | | | |
| 24 | HBV-S-323 | IPIPSSWAFAK (SEQ ID No. 79) | | | | | | | | | |
| 25 | HBV-S-324 | PIPSSWAFAK (SEQ ID No. 80) | | | | | | | | | |
| 26 | HBV-S-325 | IPSSWAFAK (SEQ ID No. 81) | | | | | | | | | |
| 27 | HBV-S-326 | PSSWAFAK (SEQ ID No. 82) | | | | | | | | | |
| 28 | HBV-S-327 | SSWAFAKY (SEQ ID No. 83) | | | | | | | | | |
| 29 | HBV-S-366* | SVIWMMWY* (SEQ ID No. 84) | SVIWMMWY (SEQ ID No. 84) | SVIWMMWF (SEQ ID No. 85) | SVIWMMWY (SEQ ID No. 86) | | | | | | |
| 30 | HBV-S-369* | WMMWFWG PSLY* (SEQ ID No. 87) | WMMWFWG PSLY (SEQ ID No. 87) | WMMWYWG PSLY (SEQ ID No. 88) | | | | | | | |
| 31 | HBV-S-370 | MMWFWGPS LY (SEQ ID No. 89) | | | | | | | | | |
| 32 | HBV-P-0* | MPLSYLHFRK* (SEQ ID No. 90) | MPLSYLHFRK (SEQ ID No. 90) | MPLSYQHFRK (SEQ ID No. 91) | | | | | | | |
| 33 | HBV-P-1* | PLSYLHFRK* (SEQ ID No. 92) | PLSYLHFRK (SEQ ID No. 92) | PLSYQHFRK (SEQ ID No. 93) | | | | | | | |
| 34 | HBV-P-2* | LSYLHFRK* (SEQ ID No. 94) | LSYLHFRK (SEQ ID No. 94) | LSYQHFRK (SEQ ID No. 95) | | 3/8 | 4/12 | 1/13 | 2/12 | 0.004069 | 0.005406 0.005959 | 0.008759 |

TABLE S1-continued

Supplementary Table 1.
List of detected HLA-A*1101-restricted epitopes and the frequency across various patient groups

| | | | | | | | | | | | |
|---|---|---|---|---|---|---|---|---|---|---|---|
| 35 | HBV-P-44 | NLNVSIPWTHK (SEQ ID No. 96) | 4/8 | 8/12 | 3/13 | 1/12 | 0.004481 | 0.003864 | 0.007687 | 0.003309 |
| 36 | HBV-P-46 | NVSIPWTHK (SEQ ID No. 97) | | | | | | | | |
| 37 | HBV-P-47 | VSIPWTHK (SEQ ID No. 98) | | | | | | | | |
| 38 | HBV-P-54 | KVGNFTGLY (SEQ ID No. 99) | | | | | | | | |
| 39 | HBV-P-62 | YSSTVPCFNPK (SEQ ID No. 100) | | | | | | | | |
| 40 | HBV-P-63 | SSTVPCFNPK (SEQ ID No. 101) | | | | | | | | |
| 41 | HBV-P-64 | STVPCFNPK (SEQ ID No. 102) | | | | 1/12 | | | | 0.002033 |
| 42 | HBV-P-65 | TVPCFNPK (SEQ ID No. 103) | | | 1/13 | | | | 0.013511 | |
| 43 | HBV-P-74 | QTPSFPHIHLK (SEQ ID No. 104) | | | | | | | | |
| 44 | HBV-P-75 | TPSFPHIHLK (SEQ ID No. 105) | | | | | | | | |
| 45 | HBV-P-76 | PSFPHIHLK (SEQ ID No. 106) | 1/8 | | | 1/12 | 0.009268851 | | | 0.002264 |
| 46 | HBV-P-77 | SFPHIHLK (SEQ ID No. 107) | | | | | | | | |

TABLE S1-continued

Supplementary Table 1.
List of detected HLA-A*1101-restricted epitopes and the frequency across various patient groups

| # | ID | Epitopes (SEQ ID No.) | Frequency | Values |
|---|---|---|---|---|
| 47 | HBV-P-94 | YVGPLTVNEK (SEQ ID No. 108) | | 0.003304 |
| 48 | HBV-P-98* | LTINENRRLK (SEQ ID No. 109); LTVNETRRLK (SEQ ID No. 110); LTVNENRRLK (SEQ ID No. 111); LTVNEKRRLK (SEQ ID No. 112) | 1/12 | |
| 49 | HBV-P-99* | TVNETRRLK (SEQ ID No. 113); TVNENRRLK (SEQ ID No. 114); TVNEKRRLK (SEQ ID No. 115); TINENRRLK (SEQ ID No. 116) | 1/8  2/12  2/13 | 0.003505  0.004665  0.007724 |
| 50 | HBV-P-107 | KLIMPARFY (SEQ ID No. 117) | | |
| 51 | HBV-P-108 | LVMPARFY (SEQ ID No. 118) | | |
| 52 | HBV-P-113* | RFYPNLTK (SEQ ID No. 119); RFYPNVTK (SEQ ID No. 120) | | |
| 53 | HBV-P-117 | NVTKYLPLDK (SEQ ID No. 121) | | |
| 54 | HBV-P-118* | VTKYLPLDK (SEQ ID No. 122); LTKYLPLDK (SEQ ID No. 123) | 1/8  3/13  2/12 | 0.004096  0.019158  0.003800 |
| 55 | HBV-P-135* | HTVNHYFK (SEQ ID No. 124); HTVNHYFQTR (SEQ ID No. 125); HVVDHYFQTR (SEQ ID No. 126); HVVNHYFQTR (SEQ ID No. 127) | | |
| 56 | HBV-P-136* | TVNHYFQTR (SEQ ID No. 128); VVNHYFQTR (SEQ ID No. 129); TVNHYFKTR (SEQ ID No. 130); IVNHYFQTR (SEQ ID No. 131); TVNHYFQTRHY (SEQ ID No. 132); TVNHYFTRH (SEQ ID No. 133); VVHHYFQTR (SEQ ID No. 134); VVDHYFQTR (SEQ ID No. 135); VVNHYFQTRHY (SEQ ID No. 136) | 5/8  4/12  5/13 | 0.003132  0.003651  0.003352 |
| 57 | HBV-P-142* | KTRHYLHTLW (SEQ ID No. 137); QTRHYLHTLW (SEQ ID No. 138) | | |
| 58 | HBV-P-144 | RHYLHTLWK (SEQ ID No. 139) | | |

TABLE S1-continued

Supplementary Table 1.
List of detected HLA-A*1101-restricted epitopes and the frequency across various patient groups

| # | ID | Epitope 1 | Epitope 2 | Epitope 3 | Epitope 4 | Freq 1 | Freq 2 | Freq 3 | Freq 4 | Val 1 | Val 2 | Val 3 | Val 4 |
|---|---|---|---|---|---|---|---|---|---|---|---|---|---|
| 59 | HBV-P-148* | HTLWKAGILYK* (SEQ ID No. 140) | HTLWEAGILYK (SEQ ID No. 141) | HTLMKAGILYK (SEQ ID No. 142) | HTLWEAGILY (SEQ ID No. 143) | 1/8 | 4/12 | 1/13 | 2/12 | 0.005276 | 0.003741 | 0.006728 | 0.037610 |
| 60 | HBV-P-149* | TLWEAGILYK* (SEQ ID No. 144) | TLWKAGILYK (SEQ ID No. 145) | | | | | | | | | | |
| 61 | HBV-P-161 | STRSASFY (SEQ ID No. 146) | | | | | | | | | | | |
| 62 | HBV-P-163* | RSASFYGSPY* (SEQ ID No. 147) | RSASFCGSPY (SEQ ID No. 148) | | | | | | | | | | |
| 63 | HBV-P-164* | SASFYGSPY* (SEQ ID No. 149) | SASFCGSPY (SEQ ID No. 150) | | | | | | | | | | |
| 64 | HBV-P-165* | ASFYGSPY* (SEQ ID No. 151) | ASFCGSPY (SEQ ID No. 152) | | | | | | | | | | |
| 65 | HBV-P-182 | RLVFQTSK (SEQ ID No. 153) | | | | | | | | | | | |
| 66 | HBV-P-183* | LVFQTSER* (SEQ ID No. 154) | LVFQTSER (SEQ ID No. 155) | LVFQTSTR (SEQ ID No. 156) | | | | 1/13 | 1/12 | | | 0.003668 | 0.002847 |
| 67 | HBV-P-186* | QTSERHGDK* (SEQ ID No. 157) | QTSERHGDK (SEQ ID No. 158) | | | | | 1/13 | 1/12 | | | 0.015373 | 0.002615 |
| 68 | HBV-P-187* | TSERHGDK* (SEQ ID No. 159) | TSKRHGDK (SEQ ID No. 160) | | | | | | | | | | |
| 69 | HBV-P-197 | CSQSSGIILSR (SEQ ID No. 161) | | | | | | | | | | | |
| 70 | HBV-P-198 | SQSSGIILSR (SEQ ID No. 162) | | | | | | | | | | | |

TABLE S1-continued

Supplementary Table 1.
List of detected HLA-A*1101-restricted epitopes and the frequency across various patient groups

| | | | | | | | |
|---|---|---|---|---|---|---|---|
| 71 | HBV-P-199 | QSSGILSR (SEQ ID No. 163) | | | 1/12 | | 0.003660 |
| 72 | HBV-P-202 | GILPRSSVGPR (SEQ ID No. 164) | | 1/12 | 3/13 | | 0.002828 0.072039 |
| 73 | HBV-P-208 | SVGSCIQSQLR* (SEQ ID No. 165) SVGSCIQSQLR (SEQ ID No. 166) SVGPRIQSQLR (SEQ ID No. 167) SVGPCIQSQLR (SEQ ID No. 167) | | | | | |
| 74 | HBV-P-210* | GSCIQSQLRK* (SEQ ID No. 168) GSCIQSQLRK (SEQ ID No. 169) | 1/8 | | | 0.002406 | |
| 75 | HBV-P-211 | SCIQSQLRK (SEQ ID No. 170) | | | | | |
| 76 | HBV-P-212* | RIQSQLRK* (SEQ ID No. 171) RIQSQLRK (SEQ ID No. 172) GIQSQLRK (SEQ ID No. 173) CIQSQLRK | | | | | |
| 77 | HBV-P-214 | RSQFKQSR (SEQ ID No. 174) | | | | | |
| 78 | HBV-P-215 | SQLRKSRLGPK (SEQ ID No. 175) | | | | | |
| 79 | HBV-P-227 | QQGSMASGK (SEQ ID No. 176) | | | 1/13 | | 0.004808 |
| 80 | HBV-P-229* | RSMASGKPGR* (SEQ ID No. 177) RSMASGKPG (SEQ ID No. 178) RGSMASGKPG GSMARGKSG (SEQ ID No. 179) | | | | | |
| 81 | HBV-P-241 | SIRARVHPTSR (SEQ ID No. 180) | | | | | |
| 82 | HBV-P-245* | RVHSSPWR* (SEQ ID No. 181) RVHSSPWR (SEQ ID No. 182) RVHPTSRR | | | | | |

TABLE S1-continued

Supplementary Table 1.
List of detected HLA-A*1101-restricted epitopes and the frequency across various patient groups

| # | Name | Epitopes (SEQ ID NOs) | Frequencies |
|---|---|---|---|
| 83 | HBV-P-267* | SASSASSCLY* (SEQ ID No. 183), SASSASSCLY (SEQ ID No. 183), STSSASYCLH (SEQ ID No. 184) | |
| 84 | HBV-P-268 | ASSASSCLY (SEQ ID No. 185) | |
| 85 | HBV-P-269 | SSASSCLY (SEQ ID No. 186) | |
| 86 | HBV-P-271* | ASYCLHQSAVR* (SEQ ID No. 187), ASYCLHQSAV (SEQ ID No. 187), SSSCLHQPAV (SEQ ID No. 188), SSSCLYQSAV (SEQ ID No. 189), ASSCLHQSAVR (SEQ ID No. 190), ASSCLYQSAVR (SEQ ID No. 191) | |
| 87 | HBV-P-272* | SSCLHQPAVRK* (SEQ ID No. 192), SSCLHQPAVRK (SEQ ID No. 192), SSCLHQSAVR (SEQ ID No. 192), SSCLYQSAVR (SEQ ID No. 193), KSSCLHQSAVR (SEQ ID No. 194), SSCLYQSAVR (SEQ ID No. 195), SSCLHQPAVR (SEQ ID No. 196), SYCLHQSAVR (SEQ ID No. 197) | 1/12; 0.009064 |
| 88 | HBV-P-274* | CLYQSAVRK* (SEQ ID No. 199), CLYQSAVRK (SEQ ID No. 199), CLYQSAVRKK (SEQ ID No. 200), CLHQPAVRKN (SEQ ID No. 201), CLHQSAVRK (SEQ ID No. 202) | |
| 89 | HBV-P-276 | YQSAVRKK (SEQ ID No. 203) | |
| 90 | HBV-P-282* | KTAYSHLSTSK* (SEQ ID No. 204), KTAYSHLSTSK (SEQ ID No. 204), KTAYSLISTSK (SEQ ID No. 205), KAAYSLISTSK (SEQ ID No. 206), KAAYSLNSTSK (SEQ ID No. 207) | 8/8; 12/12; 11/13; 7/12; 0.025309; 0.021343; 0.020005; 0.014202 |
| 91 | HBV-P-283* | KAYSHLSSSK* (SEQ ID No. 208), KAYSHLSSSK (SEQ ID No. 208), TAYSHLSTSK (SEQ ID No. 209), TAYLISTSK (SEQ ID No. 210), AAYSLISTSK (SEQ ID No. 211), AAYSLNSTSK (SEQ ID No. 212), TAYSHLSTSK (SEQ ID No. 208), TAYSLISTSKR (SEQ ID No. 213), TAYSLISTSKR (SEQ ID No. 213), KAYSHLSSSKR (SEQ ID No. 215) | |
| 92 | HBV-P-284* | AYSHLSSSK* (SEQ ID No. 216), AYSHLSSSK (SEQ ID No. 216), AYSHLSTSK (SEQ ID No. 217), AYSLISTSK (SEQ ID No. 218), AYSLNSTSK (SEQ ID No. 219) | |
| 93 | HBV-P-285* | YSLNSTSK* (SEQ ID No. 220), YSLNSTSK (SEQ ID No. 220), YSLISTSK (SEQ ID No. 221), YSHLSSSK (SEQ ID No. 222), YSHLSTSK (SEQ ID No. 223) | |

TABLE S1-continued

Supplementary Table 1.
List of detected HLA-A*1101-restricted epitopes and the frequency across various patient groups

| | ID | Sequence | | | | | | Freq | Freq |
|---|---|---|---|---|---|---|---|---|---|
| 94 | HBV-P-286 | SLISTSKR (SEQ ID No. 224) | | | | | | | |
| 95 | HBV-P-289* | STSKGHSSSR* (SEQ ID No. 225) | STSKGHSSSR (SEQ ID No. 226) | | | | | | |
| 96 | HBV-P-290 | TSKGHSSSR (SEQ ID No. 227) | | | | | | | |
| 97 | HBV-P-295 | SSSRHAVELR (SEQ ID No. 228) | | | | | | | |
| 98 | HBV-P-304 | RQFPPNTSR (SEQ ID No. 229) | | | | | | | |
| 99 | HBV-P-309 | SSARSQSER (SEQ ID No. 230) | | | | | 1/13 | 0.002307 | |
| 100 | HBV-P-318* | SVLSCWWLQFR* (SEQ ID No. 231) | SVLSCWWLQ (SEQ ID No. 232) | SVLSCWWLQFR (SEQ ID No. 232) | PVLSCWWLQFR (SEQ ID No. 233) | | | | |
| 101 | HBV-P-319* | VLSCWWLQFR* (SEQ ID No. 234) | VLSCWWLQFR (SEQ ID No. 234) | ILSCWWLQPR (SEQ ID No. 235) | | | | | |
| 102 | HBV-P-320* | LSCWWLQPR* (SEQ ID No. 236) | LSCWWLQPR (SEQ ID No. 236) | PSCWWLQPR (SEQ ID No. 237) | | | | | |
| 103 | HBV-P-324 | WLQPRNSK (SEQ ID No. 238) | | | | | | | |
| 104 | HBV-P-367* | RVTGGVFLVDK* (SEQ ID No. 239) | RVTGGVFLVDK (SEQ ID No. 239) | RITGGVPLVDK (SEQ ID No. 240) | | | 1/12 | | 0.002254 |
| 105 | HBV-P-368* | VTGGVFLVDK* (SEQ ID No. 241) | VTGGVFLVDK (SEQ ID No. 241) | ITGGVPLVDK (SEQ ID No. 242) | | | 1/12 | | 0.002254 |

TABLE S1-continued

Supplementary Table 1.
List of detected HLA-A*1101-restricted epitopes and the frequency across various patient groups

| # | Name | Sequences | | | | | | | | | |
|---|------|-----------|---|---|---|---|---|---|---|---|---|
| 106 | HBV-P-387 | LVVDFSQFSR (SEQ ID No. 28) | | | | | 5/8 | 9/12 | 9/13 | 9/12 | 0.06119 8525 | 0.086237 | 0.055185 | 0.066603 |
| 107 | HBV-P-388 | VVDFSQFSR (SEQ ID No. 243) | | | | | | | | | | |
| 108 | HBV-P-392* | SQFSRGSTR* (SEQ ID No. 244) | SQFSRGSTR (SEQ ID No. 244) | SQFSRGNTR (SEQ ID No. 245) | | | | | | | | |
| 109 | HBV-P-396* | RGNTRVSWPK* (SEQ ID No. 246) | RGNTRVSWPK (SEQ ID No. 246) | RGSTHVSWPK (SEQ ID No. 247) | RGSTRVSWPK (SEQ ID No. 248) | | 1/8 | 2/12 | 1/13 | 1/12 | 0.03816 5858 | 0.029153 | 0.005767 | 0.010167 |
| 110 | HBV-P-397* | GSTHVSWPK* (SEQ ID No. 249) | GSTHVSWPK (SEQ ID No. 249) | GSTRVSWPK (SEQ ID No. 250) | GSTQVSWPK (SEQ ID No. 251) | | 1/8 | 1/12 | | | 0.00763 3172 | 0.002506 | | |
| 111 | HBV-P-398* | STQVSWPK* (SEQ ID No. 252) | STQVSWPK (SEQ ID No. 252) | STHVSWPK (SEQ ID No. 253) | STRVSWPK (SEQ ID No. 253) | NTRVSWPK (SEQ ID No. 254) | 2/8 | 1/12 | | | 0.004475 | 0.004529 | | |
| 112 | HBV-P-431 | AAFYHLPLH (SEQ ID No. 256) | | | | | | | | | | |
| 113 | HBV-P-447* | LVGSSGLPR* (SEQ ID No. 257) | LVGSSGLPR (SEQ ID No. 257) | LVGSSGLSR (SEQ ID No. 258) | | | | | | | | |
| 114 | HBV-P-449* | GSSGLSRYVAR* (SEQ ID No. 259) | GSSGLSRYVAR (SEQ ID No. 259) | GSSGLPRYVAR (SEQ ID No. 260) | | | | | | | | |
| 115 | HBV-P-450* | SSGLSRYVAR* (SEQ ID No. 261) | SSGLSRYVAR (SEQ ID No. 261) | SSGLPRYVAR (SEQ ID No. 262) | | | | | | | | |
| 116 | HBV-P-456* | YVARLSSTSR* (SEQ ID No. 263) | YVARLSSTSR (SEQ ID No. 263) | YVARLSSNSR (SEQ ID No. 264) | | | | | | | | |
| 117 | HBV-P-461 | SSTSRNINY (SEQ ID No. 265) | | | | | | | | | | |

TABLE S1-continued

Supplementary Table 1.
List of detected HLA-A*1101-restricted epitopes and the frequency across various patient groups

| # | ID | Epitopes | | | | | | | |
|---|---|---|---|---|---|---|---|---|---|
| 118 | HBV-P-462* | STSRIINNQHR* (SEQ ID No. 266) | STSRIINNQHR (SEQ ID No. 266) | STSRNINY (SEQ ID No. 267) | STSRIINDQHR (SEQ ID No. 268) | | | | |
| 119 | HBV-P-465 | RIINNQHR (SEQ ID No. 269) | | | | | 1/12 | | |
| 120 | HBV-P-473* | TMQNLHSSCS (SEQ ID No. 270) | TMQDLHNSCS (SEQ ID No. 271) | TMQNLHNSCS (SEQ ID No. 272) | TMQNLHDSCSR (SEQ ID No. 273) | TMQNLHDSCSR (SEQ ID No. 274) | 1/12 | | 0.008372 |
| | | AMQDLHDSC (SEQ ID No. 275) | | | | | | | |
| 121 | HBV-P-474 | MQNLHSSCSR (SEQ ID No. 276) | | | | | | | |
| 122 | HBV-P-479 | SSCSRNLY (SEQ ID No. 277) | | | | | | | |
| 123 | HBV-P-484* | NLYVSLMLLYK* (SEQ ID No. 278) | NLYVSLMLLYK (SEQ ID No. 278) | NLYVSLLLLYK (SEQ ID No. 279) | NLYVSLMLLY (SEQ ID No. 280) | NLYVSLLLLY (SEQ ID No. 281) | | | 0.012989 |
| 124 | HBV-P-485* | LYVSLMLLYK (SEQ ID No. 282) | LYVSLMLLYK (SEQ ID No. 282) | LYVSLLLLYK (SEQ ID No. 283) | | | | | |
| 125 | HBV-P-486* | YVSLLLLYK* (SEQ ID No. 284) | YVSLMLLYK (SEQ ID No. 285) | YVSLMLLYK (SEQ ID No. 285) | YVSLMLLY (SEQ ID No. 286) | VVSLLLLY (SEQ ID No. 287) | 2/8 2/12 3/13 1/12 0.006757 | | 0.003553 0.010339 0.009762 |
| 126 | HBV-P-487* | VSLMLLYK* (SEQ ID No. 288) | VSLMLLYK (SEQ ID No. 288) | VSLLLLYK (SEQ ID No. 289) | | | | 1/12 | 0.002615 |
| 127 | HBV-P-488* | SLMLLYKTYGR* (SEQ ID No. 290) | SLMLLYKTYGR (SEQ ID No. 290) | SLLLLYKTFGR (SEQ ID No. 291) | | | | | |
| 128 | HBV-P-489* | LMLLYKTYGRK* (SEQ ID No. 292) | LMLLYKTYGRK (SEQ ID No. 292) | LLLLYKTFGRK (SEQ ID No. 293) | | | | | |
| 129 | HBV-P-490* | MLLYKTYGRK* (SEQ ID No. 294) | MLLYKTYGRK (SEQ ID No. 294) | LLLYKTFGRK (SEQ ID No. 295) | MLLYKTFGR | | | 1/13 | 0.002855 |

TABLE S1-continued

Supplementary Table 1.
List of detected HLA-A*1101-restricted epitopes and the frequency across various patient groups

| # | ID | Sequence | Epitope | Epitope | Epitope | Freq1 | Freq2 | Freq3 | Freq4 | Val1 | Val2 | Val3 | Val4 |
|---|---|---|---|---|---|---|---|---|---|---|---|---|---|
| 130 | HBV-P-491* | LLYKTFGRK* (SEQ ID No. 297) | LLYKTFGRK (SEQ ID No. 298) | LLYKTFGRK (SEQ ID No. 299) | | 4/8 | 5/12 | 5/13 | 1/12 | 0.003012655 | 0.004777 | 0.009704 | 0.025620 |
| 131 | HBV-P-494* | KTYGRKLHLY* (SEQ ID No. 300) | KTFGRKLHLY (SEQ ID No. 301) | | | 1/8 | | | | 0.002007 | | | |
| 132 | HBV-P-503 | YSHPIILGFRK (SEQ ID No. 302) | | | | | | | | | | | |
| 133 | HBV-P-506 | PIILGFRK (SEQ ID No. 303) | | | | | | | | | | | |
| 134 | HBV-P-528 | FTSAICSVVRR (SEQ ID No. 304) | | | | | | | | | | | |
| 135 | HBV-P-529* | TSAICSVVRR* (SEQ ID No. 305) | TSAICSVVR (SEQ ID No. 306) | | | | | | | | | | |
| 136 | HBV-P-590* | SAICSVVRR* (SEQ ID No. 307) | SAICSVVR (SEQ ID No. 308) | | | | | | | | | | |
| 137 | HBV-P-531 | AICSVVRR (SEQ ID No. 309) | | | | | | | | | | | |
| 138 | HBV-P-534 | SVVRRAFPH (SEQ ID No. 310) | | | | 1/8 | 3/12 | 2/13 | | 0.041982 | 0.003832 | 0.005224 | |
| 139 | HBV-P-538 | RAFPHCLAFSY (SEQ ID No. 311) | | | | | | | | | | | |
| 140 | HBV-P-547 | SYMDDVVLGAK (SEQ ID No. 312) | | | | | | | | | | | |
| 141 | HBV-P-548 | YMDDVVLGAK (SEQ ID No. 313) | | | | | | | | | | | |

TABLE S1-continued

Supplementary Table 1.
List of detected HLA-A*1101-restricted epitopes and the frequency across various patient groups

| | | | | | | | |
|---|---|---|---|---|---|---|---|
| 142 | HBV-P-558* | SVQHLESLY* (SEQ ID No. 313) | SVQHLESLY (SEQ ID No. 314) | SVQHLESVY (SEQ ID No. 315) | | 3/12 1/13 | 0. 0. 004279 002691 |
| 143 | HBV-P-564 | SVYAAVTNFLL (SEQ ID No. 316) | | | | | |
| 144 | HBV-P-574* | LSLGIHLNPNK* (SEQ ID No. 317) | LSLGIHLNPNK (SEQ ID No. 317) | LSLGIHLNPHK (SEQ ID No. 318) | | | |
| 145 | HBV-P-575* | SLGIHLNPNK* (SEQ ID No. 319) | SLGIHLNPNK (SEQ ID No. 319) | SLGIHLNPHK (SEQ ID No. 320) | | | |
| 146 | HBV-P-577* | GIHLNPNK* (SEQ ID No. 321) | GIHLNPNK (SEQ ID No. 321) | GIHLNPHK (SEQ ID No. 322) | GIHLNPHKTK (SEQ ID No. 323) | GIHLNPNKTK (SEQ ID No. 324) | |
| 147 | HBV-P-590 | YSLNFMGY (SEQ ID No. 325) | | | | | |
| 148 | HBV-P-603* | GTLPQEHIVLK* (SEQ ID No. 326) | GTLPQEHIVLK (SEQ ID No. 326) | GTLPQEHIVQK (SEQ ID No. 327) | | 1/12 | 0. 004185 |
| 149 | HBV-P-604* | TLPQEHIVLK* (SEQ ID No. 328) | TLPQEHIVLK (SEQ ID No. 328) | TLPQEHIVQK (SEQ ID No. 329) | | | |
| 150 | HBV-P-609 | HIVQKIKMCFK (SEQ ID No. 330) | | | | | |
| 151 | HBV-P-610* | IVQKIKMCFRK* (SEQ ID No. 331) | IVQKIKMCFRK (SEQ ID No. 331) | IVQKIKMCFK (SEQ ID No. 332) | IVQKIKLCFRK (SEQ ID No. 333) | IVQKIKMCRKK (SEQ ID No. 334) | IVLKLKQCFRK (SEQ ID No. 335) 1/8 1/12 2/12 0.00227 0. 8415 009584 |
| | | IVQKIKQCFRK (SEQ ID No. 336) | IVQKIKMCFR (SEQ ID No. 337) | IVQKIKLCFR (SEQ ID No. 338) | IVLKLKQCFR (SEQ ID No. 339) | IVQKIKQCFR (SEQ ID No. 340) | |
| 152 | HBV-P-611* | VQKIKMCFK* (SEQ ID No. 341) | VQKIKMCFK (SEQ ID No. 341) | VQKIKMCFRK (SEQ ID No. 342) | VQKIKLCRFK (SEQ ID No. 343) | VQKIKMCFKK (SEQ ID No. 344) | VLKLKQCFRK (SEQ ID No. 345) 0. 004296 |
| | | VQKIKQCFRK (SEQ ID No. 346) | | | | | |

TABLE S1-continued

Supplementary Table 1.
List of detected HLA-A*1101-restricted epitopes and the frequency across various patient groups

| | | | | | | | | | | | | |
|---|---|---|---|---|---|---|---|---|---|---|---|---|
| 153 | HBV-P-613* | KIKMCFRK* (SEQ ID No. 347) | KIKMCFRK (SEQ ID No. 348) | KIKMCFKK (SEQ ID No. 349) | KIKLCFRK (SEQ ID No. 349) | KIKQCFRK (SEQ ID No. 350) | KLKQCFRK (SEQ ID No. 351) | | 2/8 | | 1/12 | 0.005047506 | 0.005196 |
| 154 | HBV-P-615* | KMCFRKLPVNR* (SEQ ID No. 352) | KMCFRKLPVNR (SEQ ID No. 352) | KQCFRKLPINR (SEQ ID No. 353) | KMCFKKLPVNR (SEQ ID No. 354) | KQCFRKLPVNR (SEQ ID No. 355) | KLCFRKLPVNR (SEQ ID No. 356) | | | | | | |
| 155 | HBV-P-622 | PVNRPIDWK (SEQ ID No. 357) | | | | | | 1/8 | 3/12 | | | | 0.000000 |
| 156 | HBV-P-655* | PLYACIQAK* (SEQ ID No. 358) | PLYACIQAK (SEQ ID No. 358) | PLYACIQTK (SEQ ID No. 359) | | | | | | | | 0.005276 | |
| 157 | HBV-P-663* | KQAFTFSPTYK* (SEQ ID No. 360) | KQAFTFSPTYK (SEQ ID No. 360) | KQAFTFSPTY (SEQ ID No. 361) | | | | | | | | | |
| 158 | HBV-P-664* | QAFTFSPTYK* (SEQ ID No. 362) | QAFTFSPTYK (SEQ ID No. 362) | QAFTFSPTY (SEQ ID No. 363) | | | | | 2/12 | 2/13 | | 0.010664 | 0.005043 | 0.002264 |
| 159 | HBV-P-665 | AFTFSPTYK (SEQ ID No. 364) | | | | | | | | | | | |
| 160 | HBV-P-666 | FTFSPTYK (SEQ ID No. 365) | | | | | | | | | | | |
| 161 | HBV-P-668* | FSPTYKAFLSK* (SEQ ID No. 366) | FSPTYKAFLSK (SEQ ID No. 366) | FSPTYKAFLCK (SEQ ID No. 367) | | | | | | | | | |
| 162 | HBV-P-669* | SPTYKAFLCK* (SEQ ID No. 368) | SPTYKAFLCK (SEQ ID No. 368) | SPTYKAFLSK (SEQ ID No. 369) | | | | | | | | | |
| 163 | HBV-P-670* | PTYKAFLSK* (SEQ ID No. 370) | PTYKAFLSK (SEQ ID No. 370) | PTYKAFLCK (SEQ ID No. 371) | | | | 1/8 | 2/12 | 2/13 | 1/12 | 0.007914106 | 0.003032 | 0.003198 | 0.002264 |
| 164 | HBV-P-671* | TYKAFLSK* (SEQ ID No. 372) | TYKAFLSK (SEQ ID No. 372) | TYKAFLCK (SEQ ID No. 373) | | | | | | | | | |

TABLE S1-continued

Supplementary Table 1.
List of detected HLA-A*1101-restricted epitopes and the frequency across various patient groups

| | | | | | | |
|---|---|---|---|---|---|---|
| 165 | HBV-P-678* | KQYLHLYPVAR* (SEQ ID No. 374) | KQYLHLYPVAR (SEQ ID No. 374) | KQYLNLYPVA (SEQ ID No. 375) | | |
| 166 | HBV-P-731 | AACFARSR (SEQ ID No. 376) | | | | |
| 167 | HBV-P-745* | GTDNSVVLSRK* (SEQ ID No. 377) | GTDNSVVLSRK (SEQ ID No. 377) | GTDNSVVLSR (SEQ ID No. 378) | | |
| 168 | HBV-P-748 | NSVVLSRK (SEQ ID No. 379) | | | | |
| 169 | HBV-P-765 | CAANWILR (SEQ ID No. 380) | | | | |
| 170 | HBV-P-781 | SALNPADDPSR (SEQ ID No. 381) | | | | |
| 171 | HBV-P-795* | GLYRPLLR* (SEQ ID No. 382) | GLYRPLLR (SEQ ID No. 382) | GLYRPLLRLLY (SEQ ID No. 383) | GLYRPLLRLIVY (SEQ ID No. 384) | |
| 172 | HBV-P-803 | LVYRPTTGR (SEQ ID No. 385) | | | 1/12 1/13 | 0. 0. 002566 002594 |
| 173 | HBV-P-808 | TTGRTSLY (SEQ ID No. 386) | | | | |
| 174 | HBV-P-820* | SVPSHLPVR* (SEQ ID No. 387) | SVPSHLPVR (SEQ ID No. 387) | SVPFHLPDR (SEQ ID No. 388) | SVPSHLPDR (SEQ ID No. 389) | SVPSHPPDR (SEQ ID No. 390) |
| 175 | HBV-P-831 | FASPLHVAWK (SEQ ID No. 391) | | | | |
| 176 | HBV-P-832 | ASPLHVAWK (SEQ ID No. 392) | | | | |

TABLE S1-continued

Supplementary Table 1.
List of detected HLA-A*1101-restricted epitopes and the frequency across various patient groups

| # | Name | Epitopes (SEQ ID NOs) | Frequencies / Values |
|---|------|-----------------------|----------------------|
| 177 | HBV-P-833 | SPLHVAWK (SEQ ID No. 393) | |
| 178 | HBV-C-169* | STLPETAVVRR (SEQ ID No. 21), STLPETAVVRR (SEQ ID No. 22), STLPETAVVR (SEQ ID No. 23), STLPETTVVRR (SEQ ID No. 24), STLPETTVVRR (SEQ ID No. 25), STLPETTVVGR (SEQ ID No. 21), STIPETTVVRR (SEQ ID No. 21) | 4/12 7/13 9/12   0.098664 0.010236 0.026518 |
| 179 | HBV-C-175* | AVVRRRCRSPR (SEQ ID No. 394), TVVRRRGRSP (SEQ ID No. 395), TVVRRRGRSPR (SEQ ID No. 396), TVIRRRGRSPR (SEQ ID No. 396), TVVGRRGRSPR (SEQ ID No. 397) | 3/8 6/12 2/13 1/12 0.00546 0555   0.004748 0.005453 0.004136 |
| 180 | HBV-X-3 | RVCCQLDPAR (SEQ ID No. 398) | |
| 181 | HBV-X-63* | SSAGPCALR (SEQ ID No. 399), SSTGPCALR (SEQ ID No. 400) | 2/13   0.015895 |
| 182 | HBV-X-64 | STGPCALR (SEQ ID No. 401) | |
| 183 | HBV-X-80* | TTVNAHWNL (SEQ ID No. 402), TTVNALGNLP (SEQ ID No. 403), TTVNAHGNLP (SEQ ID No. 404), TTVNAPGNLPK (SEQ ID No. 405), TTVNAHQVLPK (SEQ ID No. 406), TTVNAHRNLP (SEQ ID No. 407), TTVNARQVLP (SEQ ID No. 408) | 1/8 3/12 2/13 1/12 0.00231 5941   0.004083 0.004750 0.007793 |
| 184 | HBV-X-81* | TVNAHQVLPK (SEQ ID No. 409), TVNAHRNLPK (SEQ ID No. 410), TVNAHWNLPK (SEQ ID No. 411), TVNAHGNLPK (SEQ ID No. 412), TVNALGNLPK (SEQ ID No. 413), TVNAPGNLPK (SEQ ID No. 414), TVNARQVLPK (SEQ ID No. 415) | 1/12 3/13 2/12   0.005656 0.003399 0.002743 |
| 185 | HBV-X-82 | VNAHWNLPK (SEQ ID No. 416) | |
| 186 | HBV-X-83* | NAHWNLPK (SEQ ID No. 417), NALGNLPK (SEQ ID No. 418), NAHQVLPK (SEQ ID No. 419), NAHGNLPK (SEQ ID No. 420), NAHRNLPK (SEQ ID No. 421) | |

TABLE S1-continued

Supplementary Table 1.
List of detected HLA-A*1101-restricted epitopes and the frequency across various patient groups

| | | | | | | | |
|---|---|---|---|---|---|---|---|
| 187 | HBV-X-84 | ALGNLPKVLHK (SEQ ID No. 422) | | | | | |
| 188 | HBV-X-85* | RQVLPKVLHK (SEQ ID No. 423) | RQVLPKVLHK (SEQ ID No. 423) | HQVLPKVLHK (SEQ ID No. 424) | | | |
| 189 | HBV-X-86* | QVLPKVLHK* (SEQ ID No. 425) | QVLPKVLHK (SEQ ID No. 425) | QVLPKVLHKR (SEQ ID No. 426) | | 1/12 | 0.002715 |
| 190 | HBV-X-87 | VLPKVLHK (SEQ ID No. 427) | | | | | |
| 191 | HBV-X-100* | SVMSMTDLEAY* (SEQ ID No. 428) | SVMSMTDLEAY (SEQ ID No. 428) | SVMSTTDLEAY (SEQ ID No. 429) | SAMSTTDLEAY (SEQ ID No. 430) | SAMSATDLEAY (SEQ ID No. 431) | |
| 192 | HBV-X-102* | MSMTDLEAYFK* (SEQ ID No. 432) | MSMTDLEAYFK (SEQ ID No. 432) | MSATDLEAYFK (SEQ ID No. 433) | MSTTDLEAYFAK (SEQ ID No. 434) | MSMTDLEAY (SEQ ID No. 435) | 1/12 | 0.003997 |
| 193 | HBV-X-103* | STTDLEAYFK* (SEQ ID No. 436) | STTDLEAYFK (SEQ ID No. 436) | SMTDLEAYFK (SEQ ID No. 437) | SATDLEAYFK (SEQ ID No. 438) | STTDLEAY (SEQ ID No. 439) | | |
| 194 | HBV-X-104* | TTDLEAYFK* (SEQ ID No. 440) | TTDLEAYFK (SEQ ID No. 440) | MTDLEAYFK (SEQ ID No. 441) | ATDLEAYFK (SEQ ID No. 442) | | 1/12 3/13 1/12 | 0.002297 0.003752 0.005196 |
| 195 | HBV-X-108 | EAYFKDCVFK (SEQ ID No. 441) | | | | | |
| 196 | HBV-X-109 | AYFKDCVFK (SEQ ID No. 444) | | | | | |
| 197 | HBV-X-127 | RLMIFVLGGCR (SEQ ID No. 445) | | | | | |
| 198 | HBV-X-129* | KVFVLGGCRHK* (SEQ ID No. 442) MIFVLGGCR (SEQ ID No. 451) | KVFVLGGCRHK (SEQ ID No. 442) | MIFVLGGCRHK (SEQ ID No. 442) | KIIVLGGCRHK (SEQ ID No. 442) | KVFVLGGGR (SEQ ID No. 442) | KIIVLGGCR (SEQ ID No. 442) | 1/8 1/12 2/12 0.005276 | 0.007552 0.004401 |

TABLE S1-continued

Supplementary Table 1.
List of detected HLA-A*1101-restricted epitopes and the frequency across various patient groups

| # | Name | Sequences | | | | Freq | Value |
|---|---|---|---|---|---|---|---|
| 199 | HBV-X-131 | YVLGGCRHK (SEQ ID No. 452) | | | | | |
| 202 | HBV-C-88* | YVNVNMGLK (SEQ ID No. 453) | YVNVNMGLK (SEQ ID No. 453) | YVNTNMGLK (SEQ ID No. 454) | YVNVNMGPK (SEQ ID No. 455) | YVNVNTGLK (SEQ ID No. 456) | YVNVNMGK (SEQ ID No. 457) | 1/12 | 0.003396 |
| | | YANVNMGIK (SEQ ID No. 458) | YVNVNMRLK (SEQ ID No. 459) | YVNVIMGLK (SEQ ID No. 460) | | | |
| 265 | HBV-C-11* | CSCPTVQASK* (SEQ ID No. 461) | CSCSTVQASK (SEQ ID No. 462) | CSCPTVQTSK (SEQ ID No. 463) | CTCPTVQASK (SEQ ID No. 464) | CSCPTVQVSK (SEQ ID No. 465) | 2/13 | 0.002576 |
| 266 | HBV-C-13 | CSTVQASK (SEQ ID No. 466) | | | | | |
| 267 | HBV-C-15 | TVQASKICLGR (SEQ ID No. 467) | | | | | |
| 268 | HBV-C-15v1 | TVQASKIY (SEQ ID No. 468) | | | | | |
| 269 | HBV-C-25 | RLWGMDIDPYK (SEQ ID No. 469) | | | | | |
| 270 | HBV-C-28* | GMDIDPYK* (SEQ ID No. 470) | GMDIDPYK (SEQ ID No. 470) | GMNIDPYK (SEQ ID No. 471) | GMDIDAYK (SEQ ID No. 472) | GMDIDTYK (SEQ ID No. 473) | 1/12 | 0.171478 |
| 271 | HBV-C-113 | VVSYVNVNMR (SEQ ID No. 474) | | | | | |
| 272 | HBV-C-114* | VSYVNVNMG (SEQ ID No. 475) | VSYVNVNMG (SEQ ID No. 475) | VSYVNVNMG (SEQ ID No. 476) | VSYVNVNTGL (SEQ ID No. 477) | VSYVNVNMGIK (SEQ ID No. 478) | VSYANVNMGIK (SEQ ID No. 479) | 1/12 | 0.002033 |
| | | VSYVNVNMR (SEQ ID No. 480) | VSYVNVIMGL (SEQ ID No. 481) | | | | |
| 273 | HBV-C-114v6 | VSYVNVNMR (SEQ ID No. 482) | | | | | |

TABLE S1-continued

Supplementary Table 1.
List of detected HLA-A*1101-restricted epitopes and the frequency across various patient groups

| | | | | | | | | | | | |
|---|---|---|---|---|---|---|---|---|---|---|---|
| 274 | HBV-C-115* | SYVNVNMGLK* (SEQ ID No. 483) | SYVNVNMGLK (SEQ ID No. 483) | SYVNVNMGPK (SEQ ID No. 484) | SYVNVNTGLK (SEQ ID No. 485) | GYVNVNMGLK (SEQ ID No. 486) | SYVNVNMRLK (SEQ ID No. 487) | | | | |
| | | | SYVNVIMGLK (SEQ ID No. 488) | | | | | | | | |
| 275 | HBV-C-126 | RQLLWFHISCR (SEQ ID No. 489) | | | | | | | | | |
| 276 | HBV-C-132 | HISCLTFGR (SEQ ID No. 490) | | | | | | | | | |
| 277 | HBV-C-136* | LTFGRETVLE* (SEQ ID No. 491) | LTFGRETVLEY (SEQ ID No. 492) | RTFGRETVLEY (SEQ ID No. 493) | LTFGRQTVLEY (SEQ ID No. 493) | | | 1/13 | 1/12 | | 0.003706 | 0.003309 |
| 278 | HBV-C-151* | GVWIRTPPAYR* (SEQ ID No. 494) | GVWIRTPPAYR (SEQ ID No. 494) | GVWIRTPPAFR (SEQ ID No. 495) | GVWIRTPTAY (SEQ ID No. 496) | GVWIRTPSAYR (SEQ ID No. 497) | GVWIRTPLAYR (SEQ ID No. 483) | 1/13 | | | 0.010397 | |
| | | GVWIRAPPAYR (SEQ ID No. 499) | | | | | | | | | |
| 279 | HBV-C-169v3* | STLPETTVVR* (SEQ ID No. 500) | STLPETTVIR (SEQ ID No. 501) | STIPETTVVR (SEQ ID No. 502) | | | | 1/13 | 1/12 | | 0.010508 | 0.004473 |
| 280 | HBV-C-175v3 | TVIRRRGR (SEQ ID No. 503) | | | | | | | | | |
| 281 | HBV-C-195 | RTQSPRRR (SEQ ID No. 504) | | | | | | | | | |
| 282 | HBV-C-195v1 | RTQSPRRRR (SEQ ID No. 505) | | | | | | 1/8 | 6/12 5/13 2/12 | 0.002316 | 0.006087 0.008052 | 0.005029 |
| 283 | HBV-C-195v2 | RSQSPRRRRSK (SEQ ID No. 506) | | | | | | 8/8 | 12/12 6/13 6/12 | 0.010887 | 0.026361 0.077769 | 0.007808 |
| 284 | HBV-C-196 | SQSPRRRRSK (SEQ ID No. 507) | | | | | | | | | |

TABLE S1-continued

Supplementary Table 1.
List of detected HLA-A*1101-restricted epitopes and the frequency across various patient groups control antigens

| # | Name | Sequence (SEQ ID No.) | | | | | | | | | |
|---|---|---|---|---|---|---|---|---|---|---|---|
| 200 | CMV-pp65_1 | ATVQGQNLK (SEQ ID No. 507) | | | 3/8 | 2/12 | 9/13 | 4/12 | 0.00422 0616 | 0.004034 | 0.145515 | 0.014064 |
| 201 | HCV-GPP-2 | STNPKPQK (SEQ ID No. 508) | | | | | | | | | | |
| 203 | Survivin-53 | DLAQCFCFK (SEQ ID No. 510) | | | | | | | | | | |
| 204 | EBV-EVNA3B | AVFDRKSDAK (SEQ ID No. 511) | | | 2/8 | 5/12 | 4/13 | 1/12 | 0.121349 | 0.211809 | 0.209514 | 0.172746 |
| 205 | EBV-EBNA3B-416 | IVTDFSVIK (SEQ ID No. 512) | | | | | 1/12 | | | | | 0.003396 |
| 206 | HIV-Nef-85 | AVDLSHFLK (SEQ ID No. 513) | | | | | | | | | | |
| 207 | HPV33-E6-86 | NTLEQTVKK (SEQ ID No. 514) | | | | | | | | | | |
| 208 | DENV1-1-PP* | GTSGSPIVNR* (SEQ ID No. 515) GTSGSPIVNR (SEQ ID No. 515) | GTSGSPIIDK (SEQ ID No. 516) GTSGSPIINR (SEQ ID No. 520) | GTSGSPIVDR (SEQ ID No. 517) GTSGSPIIDK (SEQ ID No. 521) | GTSGSPIVDK (SEQ ID No. 518) | GTSGSPIADK (SEQ ID No. 519) | 5/8 | 4/12 | 4/13 | 4/12 | 0.013932 | 0.066662 | 0.016159 | 0.046505 |
| 209 | CMV-pp65_2 | SVLGPISGHVLK (SEQ ID No. 522) | | | | | 2/13 | | | | | 0.005887 |
| 210 | CMV-2 | TVRAFSRAYHHRINR (SEQ ID No. 523) | | | | | 1/12 | | | | | 0.004067 |
| 211 | MTB-EsxR | QIMYNYPAM (SEQ ID No. 524) | | | | | | | | | | |

TABLE S1-continued

Supplementary Table 1.
List of detected HLA-A*1101-restricted epitopes and the frequency across various patient groups

| | | | | | | | |
|---|---|---|---|---|---|---|---|
| 212 | MTB-EsxH | ANTMAMMAR (SEQ ID No. 525) | | | | | |
| 213 | TG-MS* | KSFKDILPK* (SEQ ID No. 526) | KSFKDILPK (SEQ ID No. 526) | RSFKDLLKK (SEQ ID No. 527) | | | |
| 214 | TG-DG_1 | AMLTAFFLR (SEQ ID No. 528) | | | | | |
| 215 | TG-SAG_1 | STFWPCLLR (SEQ ID No. 529) | | | | | |
| 216 | TG-SAG_2 | SSAYVPSVK (SEQ ID No. 530) | | | | | |
| 217 | TG-DG_2 | AVVSLLRLLK (SEQ ID No. 531) | | | | | |
| 218 | AV-MP1_1 | ASCMGLIYNR (SEQ ID No. 532) | 1/8 | | 1/13 | 1/12 | 0.00247 0337 | 0.003668 018185 |
| 219 | IAV-MP2 | RLFFKCIYRR (SEQ ID No. 533) | | | | | |
| 220 | IAV-NPv1 | SVQPTFSVQR (SEQ ID No. 534) | 2/8 | 3/12 | 4/13 | 1/12 | 0.01239 4747 | 0.005795 009134 016267 |
| 221 | IAV-NPv2 | SVQRNLPFER (SEQ ID No. 535) | 4/8 | 4/12 | 6/13 | 3/12 | 0.00453 5774 | 0.005311 044947 014219 |
| 222 | IAV-PA_1 | KFLPDLYDYK (SEQ ID No. 536) | | | 1/13 | | | |
| 223 | IAV-PCS_1 | KLVGINMSKK (SEQ ID No. 537) | | | | | | 0.003386 |

TABLE S1-continued

Supplementary Table 1.
List of detected HLA-A*1101-restricted epitopes and the frequency across various patient groups

| | Name | Epitope (SEQ ID NO.) | | | | | | | | |
|---|---|---|---|---|---|---|---|---|---|---|
| 224 | IAV-PCS_2 | GTFEFTSFFY (SEQ ID No. 538) | | | | | | | | |
| 225 | IAV-PB2_1 | SFSFGGFTFK (SEQ ID No. 539) | | 2/12 | 2/13 | 1/12 | | 0.003073 | 0.056170 | 0.008540 |
| 226 | IAV-PB2_2 | VLRGFLILGK (SEQ ID No. 540) | | | | | | | | |
| 227 | DENV2-5-PP | SQIGAGVYK (SEQ ID No. 541) | 1/8 | 3/12 | 2/13 | 1/12 | 0.002624733 | 0.003189 | 0.002960 | 0.002847 |
| 228 | DENV2-7-PP | KTFDSEYVK (SEQ ID No. 542) | | | 1/12 | | | | | 0.026576 |
| 229 | DENV2-8-PP | RIYSDPLALK (SEQ ID No. 543) | | | | | | | | |
| 230 | DENV2-9-PP | ATVLMGLGK (SEQ ID No. 544) | 1/8 | 1/12 | 1/13 | | 0.007914106 | 0.002360 | 0.002428 | |
| 231 | DENV2-10-PP* | STYGWNLVR* STYGWNLVR (SEQ ID No. 545) ATYGWNLVK (SEQ ID No. 546) STYGWNIVK (SEQ ID No. 547) | 5/8 | 7/12 | 4/13 | 3/12 | 0.002984029 | 0.004907 | 0.003946 | 0.006023 |
| 232 | DENV1-2-PP | TVMDIISRR (SEQ ID No. 548) | 2/8 | | | | 0.006980396 | | | |
| 233 | DENV2-11-PP | RTTWSIHAK (SEQ ID No. 549) | 2/8 | 5/12 | 3/13 | 3/12 | 0.00349347 | 0.003315 | 0.003655 | 0.003184 |
| 234 | DENV2-12-PP | RQMEGEGVFK (SEQ ID No. 550) | | | | | | | | |
| 235 | AV-MP2-70 | KSMREEYRK (SEQ ID No. 551) | | | | | | | | |

TABLE S1-continued

Supplementary Table 1.
List of detected HLA-A*1101-restricted epitopes and the frequency across various patient groups

| # | Name | Sequence | | | | | | | |
|---|---|---|---|---|---|---|---|---|---|
| 236 | IAV-MP1-178 | RMVLASTTAK (SEQ ID No. 552) | | 6/8 | 12/12 | 11/13 | 8/12 | 0.01116 2901 | 0.031328 061079 | 0.024404 |
| 237 | IAV-MP1-13 | SIIPSGPLK (SEQ ID No. 553) | | | | | | | | |
| 238 | EBV-LMP2-340* | SSCSSCPLSK* (SEQ ID No. 554) | SSCSSCPLSK (SEQ ID No. 555) | | | | | | | |
| 239 | DENV2-PP | AVQTKPCLFK (SEQ ID No. 556) | | | | | | | | |
| 240 | DENV3-PP | GAMLFLISGK (SEQ ID No. 557) | | | | | | | | |
| 241 | DENV4-PP | KSGAIKVLK (SEQ ID No. 558) | | | | 1/13 | | | 0.002257 | |
| 242 | DENV5-PP | KTFVDLMRR (SEQ ID No. 559) | | | 1/12 | | | | 0.003485 | |
| 243 | DENV6-PP | MANEMGFLEK (SEQ ID No. 560) | | | | | | | | |
| 244 | DENV7-PP* | MATYGWNLVK* (SEQ ID No. 561) | MSTYGWNLVK (SEQ ID No. 562) | | 1/12 | 1/13 | | | 0.002438 | 0.011825 |
| 245 | DENV9-PP | MSYTMCSGK (SEQ ID No. 563) | | | | | | | | |
| 246 | DENV10-PP | MVSRLLLNR (SEQ ID No. 564) | | | 1/12 | | | | 0.004186 | |
| 247 | DENV11-PP | RQLANAIFK (SEQ ID No. 565) | | | | | | | | |

TABLE S1-continued

Supplementary Table 1.
List of detected HLA-A*1101-restricted epitopes and the frequency across various patient groups

| # | Name | Sequence | | | Frequencies |
|---|---|---|---|---|---|
| 248 | DENV12-PP* | RVIDPRRCLK* (SEQ ID No. 566) | RVIDPRRCLK (SEQ ID No. 566) | RVIDPRRCMK (SEQ ID No. 567) | 1/8  0.002802527 |
| 249 | DENV15-PP | TSGSPIIDK (SEQ ID No. 568) | | | 1/8  0.00527609 |
| 250 | DENV16-PP | TTKRDLGMSK (SEQ ID No. 569) | | | 1/8  2/12  0.003551109  0.014267 |
| 251 | DENV17-PP | VTRGAVLMHK (SEQ ID No. 570) | | | |
| 252 | DENV18-PP | YVSAIAQTEK (SEQ ID No. 571) | | | |
| 253 | DENV19-PP | SPGTSGSPIIDKKGK (SEQ ID No. 572) | | | |
| 254 | EBV-BRLF1 | ATIGTAMYK (SEQ ID No. 573) | | | 1/8  3/12  3/13  2/13  0.004156485  0.018045  0.078450  0.011428 |
| 255 | CMV-pp65_3 | GPISGHVLK (SEQ ID No. 574) | | | |
| 256 | IAV-MP1_2 | AYQKRMGVQM (SEQ ID No. 575) | | | |
| 257 | IAV-PA_2 | LYASPQLEGF (SEQ ID No. 576) | | | |
| 258 | LMAV-GP | LVTFLLLCGR (SEQ ID No. 577) | | | |
| 258 | LCMV-GP_1 | LVSFLLLAGR (SEQ ID No. 578) | | | |

TABLE S1-continued

Supplementary Table 1.
List of detected HLA-A*1101-restricted epitopes and the frequency across various patient groups

| | | | | |
|---|---|---|---|---|
| 259 | LCMV-GP_2 | FTNDSIISH (SEQ ID No. 579) | | |
| 260 | LCMV-RING-Z | TTYLGPLSCK (SEQ ID No. 580) | | |
| 261 | Mus musculus-GP | AINSEMFLR (SEQ ID No. 581) | | |
| 262 | Mus musculus-Insulin-1 | LALEVARQKR (SEQ ID No. 582) | LALEVARQKR (SEQ ID No. 582) | TLALEVARQK (SEQ ID No. 583) |
| 263 | Mus musculus-Insulin-2 | TLALEVAQQK (SEQ ID No. 584) | | |
| 264 | MTB-Ag85B | AMGDAGGYK (SEQ ID No. 585) | 1/13 | 0.002307 |

TABLE S2

Supplementary Table 2: List of the antibody staining panels used for mass cytometry and high-dimensional cytometric data analysis

| Metal-Isotope | PBMC ex vivo panel 1, 14(SAv)-choose-4 | | | |
|---|---|---|---|---|
| | Antibody (or label) | Clone | Company | t-SNE |
| Y-89 | CD45 | HI30 | Fluidigm (DVS) | |
| Pd-102 | Cell barcode | | | |
| Rh-103 | DNA Intercalator | | Fluidigm (DVS) | |
| Pd-104 | Cell barcode | | | |
| Pd-105 | Cell barcode | | | |
| Pd-106 | Cell barcode | | | |
| Pd-108 | Cell barcode | | | |
| Pd-110 | Cell barcode | | | |
| Cd-112/114 | Qdt800-CD14 | TuK4 | Molecular Probes | |
| In-113 | Empty | | | |
| In-115 | CD57 (Differentiation) | HCD57 | Biolegend | ✓ |
| La-139 | Va7.2 (Differentiation) | 3C10 | Biolegend | ✓ |
| Ce-140 | CD3 | UCHT1 | BioXcell | |
| Pr-141 | HLA-DR (Differentiation) | L243 | Biolegend | ✓ |
| Nd-142 | CD45RO (Differentiation) | UCHL1 | Biolegend | ✓ |
| Nd-143 | CD38 (Differentiation) | HIT2 | Biolegend | ✓ |
| Nd-144 | CCR7 (Differentiation) | 150503 | R&D Systems | ✓ |
| Nd-145 | CD27 (Differentiation) | LG.7F9 | eBioscience | ✓ |
| Nd-146 | CD8b | SK1 | Biolegend | |
| Sm-147 | CD28 (Differentiation) | CD28.2 | Biolegend | ✓ |
| Nd-148 | SAv-Nd-148 | | in-house | |
| Sm-149 | CXCR3 (Differentiation) | 1C6 | BD Bioscience | ✓ |
| Nd-150 | KLRG-1 (Differentiation) | 13F12F2 | eBioscience | ✓ |
| Eu-151 | SAv-Eu-151 | | in-house | |
| Sm-152 | CXCR5 (Differentiation) | RF8B2 | BD Bioscience | ✓ |
| Eu-153 | SAv-Eu-153 | | in-house | |
| Sm-154 | HVEM (Exhaustion) | 94801 | R&D Systems | ✓ |
| Gd-155 | CTLA-4 (Exhaustion) | BNI3 | BD Bioscience | ✓ |
| Gd-156 | CD39 (Differentiation) | A1 | Biolegend | ✓ |
| Gd-157 | SAv-Gd-157 | | in-house | |
| Gd-158 | CD45RA (Differentiation) | HI100 | BD Bioscience | ✓ |
| Tb-159 | SAv-Tb-159 | | in-house | |
| Gd-160 | PD-1 (Exhaustion) | eBioJ105 | eBioscience | ✓ |
| Dy-161 | SAv-Dy-161 | | in-house | |
| Dy-162 | CD4 | SK3 | Biolegend | |
| Dy-162 | CD19 | HIB19 | Biolegend | |
| Dy-162 | CD56 | NCAM16.2 | BD Bioscience | |
| Dy-163 | SAv-Dy-163 | | in-house | |
| Dy-164 | LAG-3 (Exhaustion) | 874501 | R&D Systems | ✓ |
| Ho-165 | SAv-Ho-165 | | in-house | |
| Er-166 | SAv-Er-166 | | in-house | |
| Er-167 | TIM-3 (Exhaustion) | 344823 | R&D Systems | ✓ |
| Er-168 | SAv-Er-168 | | in-house | |
| Tm-169 | SAv-Tm-169 | | in-house | |
| Er-170 | 2B4 (Exhaustion) | C1.7 | Biolegend | ✓ |
| Yb-171 | SAv-Yb-171 | | in-house | |
| Yb-172 | BTLA (Exhaustion) | MIH26 | eBioscience | ✓ |
| Yb-173 | SAv-Yb-173 | | in-house | |
| Yb-174 | CD160 (Exhaustion) | 688327 | R&D Systems | ✓ |
| Lu-175 | SAv-Yb-175 | | in-house | |
| Yb-176 | CD127 (Differentiation) | A019D5 | Biolegend | ✓ |
| Ir-191/193 | CD161 (Differentiation) | HP-3G10 | Biolegend | ✓ |
| Pt-194 | | | | |
| Pt-195 | Live/Dead | | | |
| Pt-198 | | | | |
| Bi-209 | | | | |
| One-SENSE category | Differentiation Exhaustion Trafficking | | | |

| Metal-Isotope | PBMC ex vivo panel 2, , 9(SAv)-choose-3 | | | |
|---|---|---|---|---|
| | Antibody (or label) | Clone | Company | t-SNE |
| Y-89 | CD45 | HI30 | Fluidigm (DVS) | |
| Pd-102 | Cell barcode | | | |
| Rh-103 | Live/Dead | | | |
| Pd-104 | Cell barcode | | | |
| Pd-105 | Cell barcode | | | |
| Pd-106 | Cell barcode | | | |
| Pd-108 | Cell barcode | | | |

TABLE S2-continued

Supplementary Table 2: List of the antibody staining panels used for mass cytometry and high-dimensional cytometric data analysis

| Metal-Isotope | Antibody (or label) | Clone | Company | t-SNE |
|---|---|---|---|---|
| Pd-110 | Cell barcode | | | |
| Cd-112/114 | Qdt800-CD14 | TuK4 | Molecular Probes | |
| In-113 | Empty | | | |
| In-115 | CD57 (Differentiation + TNFR) | HCD57 | Biolegend | ✓ |
| La-139 | Va7.2 (Differentiation + TNFR) | 3C10 | Biolegend | ✓ |
| Ce-140 | CD3 | UCHT1 | BioXcell | |
| Pr-141 | HLA-DR (Differentiation + TNFR) | L243 | Biolegend | ✓ |
| Nd-142 | CD27 (Differentiation + TNFR) | LG.7F9 | eBioscience | ✓ |
| Nd-143 | CD38 (Differentiation + TNFR) | HIT2 | Biolegend | ✓ |
| Nd-144 | CCR4 (Trafficking) | 205410 | R&D Systems | ✓ |
| Nd-145 | CD45RA (Differentiation + TNFR) | HI100 | BD Bioscience | ✓ |
| Nd-146 | CCR6 (Trafficking) | G034E3 | Biolegend | ✓ |
| Sm-147 | CD45RO (Differentiation + TNFR) | UCHL1 | Biolegend | ✓ |
| Nd-148 | CTLA-4 (Exhaustion) | BNI3 | BD Bioscience | ✓ |
| Sm-149 | CXCR3 (Trafficking) | 1C6 | BD Bioscience | ✓ |
| Nd-150 | KLRG-1 (Differentiation + TNFR) | 13F12F2 | eBioscience | ✓ |
| Eu-151 | CCR7 (Differentiation + TNFR) | 150503 | R&D Systems | ✓ |
| Sm-152 | CXCR5 (Trafficking) | RF8B2 | BD Bioscience | ✓ |
| Eu-153 | SAv-Eu-153 | | in-house | |
| Sm-154 | HVEM (Exhaustion) | 94801 | R&D Systems | ✓ |
| Gd-155 | SAv-Gd-155 | | in-house | |
| Gd-156 | CD39 (Differentiation + TNFR) | A1 | Biolegend | ✓ |
| Gd-157 | 0X40 (Differentiation + TNFR) | 443318 | R&D Systems | ✓ |
| Gd-158 | TIGIT (Exhaustion) | MBSA43 | eBioscience | ✓ |
| Tb-159 | GITR (Differentiation + TNFR) | 110416 | R&D Systems | ✓ |
| Gd-160 | PD-1 (Exhaustion) | eBioJ105 | eBioscience | ✓ |
| Dy-161 | CCR5 (Trafficking) | HEK/1/85a | Abcam | ✓ |
| Dy-162 | CD161 (Differentiation + TNFR) | HP-3G10 | Biolegend | ✓ |
| Dy-162 | | | | |
| Dy-162 | | | | |
| Dy-163 | BTLA (Exhaustion) | MIH26 | Fluidigm (DVS) | ✓ ✓ |
| Dy-164 | LAG-3 (Exhaustion) | 874501 | R&D Systems | |
| Ho-165 | SAv-Ho-165 | | in-house | |
| Er-166 | SAv-Er-166 | | in-house | |
| Er-167 | TIM-3 (Exhaustion) | 874501 | R&D Systems | ✓ |
| Er-168 | SAv-Er-168 | | in-house | |
| Tm-169 | SAv-Tm-169 | | in-house | |
| Er-170 | 2B4 (Exhaustion) | C1.7 | Biolegend | ✓ |
| Yb-171 | SAv-Yb-171 | | in-house | |
| Yb-172 | 4-1BB (Differentiation + TNFR) | 4B4-1 | Biolegend | ✓ |
| Yb-173 | SAv-Yb-173 | | in-house | |
| Yb-174 | CD160 (Exhaustion) | 688327 | R&D Systems | ✓ |
| Lu-175 | SAv-Yb-175 | | in-house | |
| Yb-176 | CD127 (Differentiation + TNFR) | A019D5 | Biolegend | ✓ |
| Ir-191/193 | DNA Intercalator | | (DVS) | |
| Pt-194 | CD8b | SKI | Biolegend | |
| Pt-195 | Empty | | | |
| Pt-198 | CD4 | SK3 | Biolegend | |
| | CD19 | HIB19 | Biolegend | |
| Bi-209 | CD16 | 3G8 | Fluidigm (DVS) | |
| One-SENSE category | Differentiation + TNFR Exhaustion Trafficking | | | |

PBMC in vitro panel, 8(SAv)-choose-3

| Metal-Isotope | Antibody (or label) | Clone | Company | t-SNE |
|---|---|---|---|---|
| Y-89 | CD45 | HI30 | Fluidigm (DVS) | |
| Pd-102 | Cell barcode | | | |
| Rh-103 | Live/Dead | | | |
| Pd-104 | Cell barcode | | | |
| Pd-105 | Cell barcode | | | |
| Pd-106 | Cell barcode | | | |
| Pd-108 | Cell barcode | | | |
| Pd-110 | Cell barcode | | | |
| Cd-112/114 | Qdt800-CD14 | TuK4 | Molecular Probes | |
| | Qdt800-CD19 | HIB19 | Molecular Probes | |
| In-113 | Empty | | | |
| In-115 | CD57 (Differentiation + TNFR) | HCD57 | Biolegend | ✓ |
| La-139 | IL-15Ra (Differentiation + TNFR) | | R&D Systems | |
| Ce-140 | CD3 | UCHT1 | BioXcell | |
| Pr-141 | IFN-g (Function) | 4S.B3 | eBioscience | ✓ |

TABLE S2-continued

Supplementary Table 2: List of the antibody staining panels used for mass cytometry and high-dimensional cytometric data analysis

| | | | | |
|---|---|---|---|---|
| Nd-142 | CD27 (Differentiation + TNFR) | LG.7F9 | eBioscience | ✓ |
| Nd-143 | Granzyme B (Function) | CLB-GB11 | Abcam | ✓ |
| Nd-144 | CD107a (Function) | H4A3 | BD Bioscience | ✓ |
| Nd-145 | CD45RA (Differentiation + TNFR) | HI100 | BD Bioscience | ✓ |
| Nd-146 | MIP1-b (Function) | D21-1351 | BD Bioscience | ✓ |
| Sm-147 | IL-2 (Function) | MQ1-17H12 | eBioscience | ✓ |
| Nd-148 | CTLA-4 (Exhaustion) | BNI3 | BD Bioscience | ✓ |
| Sm-149 | TNF-a (Function) | Mab11 | eBioscience | ✓ |
| Nd-150 | KLRG-1 (Differentiation + TNFR) | 13F12F2 | eBioscience | ✓ |
| Eu-151 | CCR7 (Differentiation + TNFR) | 150503 | R&D Systems | ✓ |
| Sm-152 | Perforin (Function) | B-D48 | Abcam | ✓ |
| Eu-153 | GM-CSF (Function) | BVD2-21C11 | Biolegend | ✓ |
| Sm-154 | HVEM (Exhaustion) | 94801 | R&D Systems | ✓ |
| Gd-155 | SAv-Gd-155 | | in-house | |
| Gd-156 | CD39 (Differentiation + TNFR) | A1 | Biolegend | ✓ |
| Gd-157 | OX40 (Differentiation + TNFR) | 443318 | R&D Systems | ✓ |
| Gd-158 | TIGIT (Exhaustion) | MBSA43 | eBioscience | ✓ |
| Tb-159 | GITR (Differentiation + TNFR) | 110416 | R&D System | ✓ |
| Gd-160 | PD-1 (Exhaustion) | eBioJ105 | eBioscience | ✓ |
| Dy-161 | Granzyme K (Function) | GM6C3 | Biolegend | ✓ |
| Dy-162 | Granzyme A (Function) | CB9 | Biolegend | ✓ |
| Dy-162 | | | | |
| Dy-162 | | | | |
| Dy-163 | BTLA (Exhaustion) | MIH26 | Fluidigm (DVS) | ✓ |
| Dy-164 | LAG-3 (Exhaustion) | 874501 | R&D Systems | ✓ |
| Ho-165 | SAv-Ho-165 | | in-house | |
| Er-166 | SAv-Er-166 | | in-house | |
| Er-167 | TIM-3 (Exhaustion) | 874501 | R&D Systems | ✓ |
| Er-168 | SAv-Er-168 | | in-house | |
| Tm-169 | SAv-Tm-169 | | in-house | |
| Er-170 | 2B4 (Exhaustion) | C1.7 | Biolegend | ✓ |
| Yb-171 | SAv-Yb-171 | | in-house | |
| Yb-172 | 4-1BB (Differentiation + TNFR) | 4B4-1 | Biolegend | ✓ |
| Yb-173 | SAv-Yb-173 | | in-house | |
| Yb-174 | CD160 (Exhaustion) | 688327 | R&D Systems | ✓ |
| Lu-175 | SAv-Yb-175 | | in-house | |
| Yb-176 | CD127 (Differentiation + TNFR) | A019D5 | Biolegend | ✓ |
| Ir-191/193 | DNA Intercalator | | Fluidigm (DVS) | |
| Pt-194 | CD8b | SK1 | Biolegend | |
| Pt-195 | Empty | | | |
| Pt-198 | CD4 | SK3 | Biolegend | |
| Bi-209 | CD16 | 3G8 | Fluidigm (DVS) | |
| One-SENSE category | Differentiation + TNFR Exhaustion Function | | | |

3. Highly Multiplexed pMHC Tetramer, Antibody Staining and CD8 T Cell Enrichment Cryopreserved PBMC were thawed and washed with complete RPMI (10% FBS+1% penicillin/streptomycin/L-glutamine+1% 1M HEPES) (Gibco, Invitrogen), and rest for 3 hours at 37° C. After the recovery, cells were harvested and seeded on a non-treated 96-well plate, and about 10 million cells per patient were used and split evenly in two separated wells for two configurations of 562-plex combinatorial pMHC tetramer staining. 50 µM dasatinib was incubated with cells for 30 min at 37° C., 5% CO2, to prevent the downregulation of TCR (30). Cells were washed with CyFACS buffer (2 mM EDTA+0.05% sodium azide+4% FBS in PBS) and incubated with 200 mM cisplatin (Pt-195) for 5 min on ice, or rhodium (Rh-103) for 20 min at room temperature (table S2) for viability measurement. After wash once with CyFACS buffer, cells from the same donor in separated wells were stained with 50 µl of cocktail containing the same 562-plex pMHC tetramers but completely different SAv-metal coding configurations for 1 hour in room temperature in the presence of 1:100 Fc block (Biolegend). Cells were washed twice with CyFACS buffer after incubation, and resuspend in 50 µl of T cells or CD8 T cells enrichment kit (STEMCELL) antibody cocktail in 1:10 in CyFACS buffer for 30 min on ice. Cells were then washed, and stained with 50 l of primary antibody cocktail (table S2 and FIG. 21) for 30 min on ice. Excessive antibodies were removed by washing the cells twice with CyFACS buffer, and cells were resuspended with 4 µl of enrichment beads (STEMCELL)+46 µl of CyFACS buffer for 15 min on ice. After the staining, cells were washed with PBS and fixed with 200 µl of 2% PFA (paraformaldehyde, Electron Microscopy Sciences) overnight at 4° C. On the next day, PFA was removed and cells were incubated with permeabilization buffer (Biolegend) at room temperature for 10 min, and then resuspended with 50 µl of intracellular antibody cocktail for 30 min at room temperature. For subsequent dual mass-tag cellular barcoding, 2 mM bromo-acetamidobenzyl-EDTA (BABE; Dojindo) with 0.5 mM PbCl2 was dissolved in HEPES buffer, and each sample was given a unique combination of metal-barcode (BABE-Pd-102, BABE-Pd-104, BABE-Pd-106, BABE-Pd-108, BABE-Pd-110) on ice for 30 min. After 5 min incubation with CyFACS buffer on ice, cells were labeled by Iridium DNA interchelator (Ir-191/193, Fluidigm DVS) in 2% PFA at room temperature for 20 min. Cells were then washed with CyFACS buffer and CD8 T cells were negatively selected using EasySep™ Magnet (STEMCELL) according to manufacturer's instruction. Enriched cells were washed twice by MilliQ water and ready for mass cytometry acquisition.

4. Statistical Analysis

Non-parametric analysis of variance (ANOVA) was used for group comparison unless Indicated elsewhere. p<0.05 by non-parametric ANOVA allowed the subsequent multiple comparison test. P values were calculated using Prism software (GraphPad). All error bars are median and SEM.

5. Amplification of HBV Genome and Library Construction

Seven treatment-naïve HBeAg non-seroconverters and eight HBeAg seroconverters of patients chronically infected by HBV (including genotype B and C) were recruited in National University Health System, Singapore. Multiple longitudinal serum samples (5 to 15 time points per patient) from each patient were taken across the event of HBeAg seroconversion. Deep sequencing analysis was performed in all serums samples by sequencing the whole HBV viral genome. Similar to previously description, primers (5'-GCTCTTCT1T1TCACCTCTGCCTAATCA-3' (SEQ ID No. 29) and 5'-GCTCTTCAAAAAGTTG-CATGGTGCTGG-3' (SEQ ID No. 30)) were used to generate full-length amplicons of the HBV genome. Polymerase chain reaction (PCR) was performed using the PfuUltra™ II Fusion HS DNA Polymerase (Stratagene, La Jolla, California, USA) according to the manufacturer's instructions. The 3.1 kb fragment was extracted from 1% agarose gel prepared in 1×TBE buffer, using the QiAquick Gel Extraction Kit (Qiagen, Valencia, CA, USA) and the concentration of the extracted product was measured using the NanoDrop ND 1000 Spectrophotometer (Thermo Fisher Scientific, Waltham, MA, USA). Each sample was fragmented into 100-300 bp using the Covaris S2 (Covaris, Woburn, MA, USA). (Shearing conditions—Duty cycle: 20%; Intensity: 5; Cycles per burst: 200; Time: 110 seconds). After fragmentation, the samples were purified using the QiAquick PCR purification kit (Qiagen, Valencia, CA, USA). The DNA 1000 Chip was used with the 2100 bioanalyzer (Agilent Technologies, Santa Clara, CA, USA) to check the size and quality of the fragmented products. For library construction, the KAPA Library Preparation Kit (KAPA Biosystems) was used according to the manufacturer's instructions. The library construction includes end repair, A-tailing, ligation of adapters and a final PCR step that incorporates the indexes into the samples. Illumina TrueSeq adapters and indexes were used (Illumina, San Diego, CA, USA). PfuUltra™ II Fusion HS DNA Polymerase was used for this final PCR step according to the manufacturer's instructions. The samples were then cleaned up using the Agentcourt AMPure XP (Beckman Coulter) on a 1:1 ratio of beads to sample. To check on the size and concentration of the ligated products, the 2100 Bioanalyzerwith DNA 1000 Chipwas used. The quality and quantity of the products were determined by running a quantitative PCR. The reactions were prepared using the KAPA Library Quantification kit (KAPA Biosystems) and the run was done on the LightCycler 480 II real time thermal cycler (Roche Applied Science, Indianapolis, IN, USA) according to the manufacturer's instructions.

Samples were sequenced in the Genome Institute of Singapore on the Illumina HiSeq 2500 to obtain multiplexed 101 bp paired-end reads.

6. SNV Analysis on Viral Epitope

We modified the reference genome P121214 such that ambiguous positions (e.g. R/W/Y) were replaced by one of the relevant bases (A/C/G/T) randomly. 101 bp paired-end reads were mapped to the modified reference genome with BWA-MEM version 0.7.10-r789 and Single-nucleotide variant (SNV) calling was carried out with LoFreq version 2.1.2. Coverage depth averaged around 104~105 for all samples. SNVs were filtered by frequency (>5%), SNV quality (>1000), and coverage depth (>100) to remove false positives. SNVs within PCR primer regions were also ignored due to high error rates. SNVs passing quality filters were then sorted and only non-synonymous mutations that changed >20% in frequency between the early and late time points were kept (custom per script). These SNVs were candidates for adaptive epitopes, and were matched to known epitope sequences for further tetramer experiments.

7. HBV Epitope Prediction and Peptide Synthesis

The consensus sequences of HBV from each patient were further determined and translated into amino acid sequence for each open reading frame (ORF). The predicted binders (peptides) restricted to HLA-A*1101 were then generated by NetMHC software (v3.4 server, cbs.dtu.dk/services/NetMHC/) based on the consensus sequences derived from HBV proteins (core, polymerase, x and envelope), including all possible binding variants for 8-, 9-, 10-, and 11-mer peptides that above the binding threshold (for score>0.4 predicting weak binding and score>0.6 predicting strong binding). The prediction scheme produced 484 unique HLA-A*1101-restricted HBV epitopes, together with 78 known HLA-A*1101-restricted epitopes derived from other pathogens or self-proteins, a total of 562 different pMHC tetramers (table S1) were therefore made from these peptides for subsequent highly multiplexed combinatorial pMHC tetramer mapping. Immune Epitope Database (IEDB) was used to report previously unidentified epitope sequences. All peptides were synthesized by Mimotopes (Australia) with purity>85%.

8. Peptides Sequence Similarity and Cluster Assignment

To avoid the incorrect interpretation from cross-reactive T cell epitopes in the 562-plex pMHC library that comprised of all viral proteins and variants, sequences of the library were pooled and loaded onto a Biostrings-based R-written environment. Similar to BLAST (Basic Local Alignment Search Tool), the biological sequence and matching algorithm performed pairwise alignment to calculate the peptide binding score based on their sequence similarity. Total of 284 peptide clusters were assigned, and the peptides in each cluster are listed (table S1). Peptides within the same cluster were then given the same quadruple SAv-metal coding for highly multiplexed combinatorial pMHC tetramer strategy.

9. Generation of HLA-A*11:01 Monomer and 562-Plex pMHC Library

The inclusion bodies of HLA-A*1101 were produced (76, 77), and refolded with a UV-cleavable peptide H-RVFA(J)SFIK-OH (SEQ ID No. 31), where J is ANP (3-Amino-3-(2-nitrophenyl) propionic acid) linker. The protein was purified and biotinylated, and stored in PBS+50% glycerol at −20° C. Peptide exchange was performed at 0.1 mg/ml of HLA-A*1101 monomer in 100 µl PBS with 25 µM of peptide of interest in a 96-well plate. The reaction was exposed to 365 nm UV irradiation for 5 min twice using UVP CL-1000 Ultraviolet Crosslinker, the plate was further sealed and stored at 4° C. overnight to complete the exchange.

10. Streptavidin (SAv) Production and Metal Labeling

Streptavidin with free cysteines residues separated by glycine linkers were used for recombinant expression. Briefly, purified streptavidin was made in-house and stored in 10 mM TCEP in 20 mM HEPES (pH 7.2) buffered saline as frozen aliquots at −80° C. After conjugation using DN3 polymer labeling kits and filtering using 0.1 μm filters (Amicon), the metal-tag streptavidin conjugates (SAv-metal) were transferred to a new 30 kD concentrator (Merck) to perform five washes with eDTA-free W-buffer. SAv-metal was adjusted to final concentration at 200 μg/ml prior the formation of tetrameric pMHC complex.

11. Antibody-Metal Conjugation

Purified antibodies without carrier proteins were purchased as listed (table S2). 50 or 100 ag of antibody was conjugated with metal-attached maleimide-coupled DN3 MAXPAR (Fluidigm DVS) chelating polymer according to manufacturer's instruction (Fluidigm DVS) as previously described. All metal isotopes were purchased from Fluidigm DVS or TRACE Sciences International Inc. as listed (table S2).

12. Mass Cytometry and Data Pre-Processing

All experiments were acquired by CyTOF2 (Fluidigm DVS) systems. Cells were wash by MilliQ water twice, filtered, and immediately acquired by mass cytometry with an acquisition rate of 300~350 cells/sec. 2% of Four EQ beads (Fluidigm DVS) were mixed with cell suspension. To normalize signal variations of CyTOF2, the output FCS files were normalized based on the added beads that has been previously described. Normalized FCS files were further loaded onto a Unix-based R-written script and all zero values were randomized into values between 0 to −1 using uniform distribution.

13. Self-Validated Automatic Deconvolution of Antigen-Specific T Cells

After data pre-processing, lived CD8+ T cells were gated using FlowJo v9.7.6 (Tree Star Inc.) and individual samples were de-barcoded based on the dual mass-tag cellular barcodes using Boolean gates. Two SAv-metal coding configurations from the same donor were barcoded and exported independently. For optimal automatic identification of tetramer positive cells, multiple safety parameters and thresholds were built and subjectively defined using an R-written script, respectively (FIG. 1 and FIG. 7). Briefly, thresholds for each SAv-metal channel were manually defined by gating a tetramer negative population for all fourteen SAv-metal channels. Based on thresholds (Threshold X=Tx and Threshold Y=Ty) of every SAv-metal channel, the safety factors then objectively identify the tetramer positive population using the pre-set geometric criteria (Y/X Slope=k, X/Y Slope=k, and Width=w) (FIG. 7). All antigen-specific CD8+ T cells identified by highly multiplexed combinatorial pMHC tetramer strategy in this report have to firstly pass both the thresholds and auto-gating stringency parameters. Secondly, the corresponded four SAv-metals coded on each pMHC tetramer must have exclusive and higher metal intensity than rest of the ten SAv-metal channels. The deconvolution algorithm excluded any tetramer positive cells that have less, or more than four SAv-metals coding. The tetramer positive cells identified in two different SAv-metal coding configurations of the same donor were further calculated for their signals correspondence by using statistical simulation (FIG. 7), with $p<0.05$ was considerate a confident detection. Finally, antigen-specific CD8+ T cells who passed all the above-mentioned tests with frequency>0.002 of total CD8+ T cells were selected for further high-dimensional data analysis.

14. High-Dimensional Cytometric Data Visualization

Validated antigen-specific CD8+ T cells were exported individually from each donor for dimensionality reduction analysis. Detailed methodology for t-SNE and One-SENSE can be found elsewhere. Briefly, t-SNE and One-SENSE were performed using custom R scripts based on "flowCore" and "Rtsne" packages downloaded from The Comprehensive R Archive Network (CRAN). All data were transformed using the "logicleTransform" function and w=0.25, t=16409, m=4.5, a=0 as input parameters to roughly match scaling historically used in FlowJo. Cellular markers analyzed by t-SNE and One-SENSE were indicated (table S2). For One-SENSE, cellular markers in each T cell category ("Differentiation+TNFR", "Exhaustion" and "Trafficking") were subjectively assigned for categorical analysis. Aligned heatplots represent the distribution of marker positive cells in percentage on each "bin" on the axis (category) constructed by cells residing in small ranges of values. Positive population of markers was manually defined and markers of the same category were combined for each dimension using 250 bins.

The 3D visualization of One-SENSE was built from numerous consecutive 3D images supported by "rgl" package based on the three dimensions of One-SENSE analysis. The continuous image sequences were subsequently combined by Sequimago (AppleScript) to generate 3D movies.

Logistic regression was performed using the drc R package (v 3.0.1) using a 3-parameters logistic model. Support vector machines was trained on the 7 parameters common across the two datasets usingthe e1071R package (v 1.6-8) using default parameters (epsilon-regression with radial kernel, gamma of ⅐ and epsilon of 0.1).

15. Flow Cytometry and Cell Sorting

Cells were prepared as the same fashion as mass cytometry experiments. After incubation with dasatinib, cells were washed with PBS and incubated with 50 μl of Live/Dead-Pacific Orange (Thermo Fisher) on ice for 20 min in dark. For single fluorochrome-tag pMHC tetramers, peptide-exchange and tetramer formation were done using the same method as metal-tag pMHC tetramers in dark. PE-SAv (ebioscience), PE-Cy7-SAv (ebioscience), PE-Cy5-SAv (eBioscience), BV650-SAv (BD) and APC-SAv (Biolegend) were diluted to 20 μg/ml in PBS and added into pMHC monomer loaded with different peptides in the same manner as mentioned above. Cells then washed, and stained by tetramer cocktail in the same condition as mass cytometry experiment in dark. After two washed with FACS buffer, cells were stained with primary antibodies, Pacific Blue-CD14 (Biolegend), Pacific Blue-CD16 (Biolegend), Pacific Blue-CD19 (Biolegend), Alexa Fluor 700-CD3 (Biolegend), FITC-CD4 (Biolegend) and QD605-CD8 (Thermo Fisher) in FACS buffer for 30 min on ice in dark. Cells were then washed twice, filtered, and analyzed by LSRFortessa (BD). Fluorochrome-tag tetramer positive cells were stained using the same method and live-sorted using Aria II 5 lasers system (BD).

16. TCR High-Throughput Sequencing and Spectratyping

Five populations, including four different tetramer-stained virus-specific CD8+ T cells plus the total CD8+ T cells from each donor were live-sorted, and genomic DNA were freshly extracted using Qiagen Blood & Tissue kit according to manufacturer's instruction. Cells from three donors per patient group, with five groups and 75 samples in total, were used for TCR sequencing. Briefly, TCRβ chains were amplified using a bias-controlled two-step multiplex PCR by ImmunoSEQ platform (Adaptive Biotechnologies). The first PCR amplified the CDR3 region of sorted T cells, followed by adding the adaptor sequences in second PCR, and subsequently sequenced by next-generation sequencing (NGS). Productive reads were generated from the reduction of amplification and sequencing bias. 1000, 5000, 1500, 2000 and 10000 cells were live sorted for HBVpol282-, HBVpol387-, HBVcore169-, HBVcore195-specific and total CD8+ T cells, respectively.

TCR sequences were then exported from ImmunoSEQ Analyzer and the genes were defined by IMGT/HighV-Quest nomenclature. CDR33 length analysis was calculated by Prism using Gaussian fit with the null hypothesis "one curve fits all". The null hypothesis was rejected with statistical significance.

17. TCRdist Measurements for Quantifying Epitope-Specific Repertoires

Quantifiable distances of epitope-specific TCR3 (TCRdist) were computed to be the similarity-weighted Hamming distances between the contacting regions of two TCR's CDR1, 2 and 3 as recently developed (53). TCRdist pipeline was downloaded (github.com/phbradley/tcr-dist) and installed in Python. TCR3 sequences were loaded and executed with additional command "—make_fake_alpha" and "—make_fake_quals". The unsupervised visualization of t-SNE maps were constructed based on the kernel PCA coordinates and the TCRdist distance matrix of TCR clones generated by TCRdist pipeline using a custom R-written script. The implementation for unsupervised clustering Phenograph algorithm, Rphenograph, was installed in R (github.com/JinmiaoChenLab/Rphenograph). A repertoire diversity metric (TCRdiv) that generalizes Simpson's diversity index was used to measure the diversity of epitope-specific TCRs by accounting both the similarity and identity of the sequences.

18. In Vitro Virus-Specific CD8+ T Cells Expansion

PBMC from patients were thawed and recovered, and then resuspend in AIM-V medium (with 2% human AB serum, 1% penicillin/streptomycin/L-glutamine, 1% 1M HEPES) (Gibco, Invitrogen) with 20 IU/ml of recombinant human IL-2 (R&D). Cells were pulsed with corresponded HBV or control peptides at 1 µM per 1 million cells in 200 µl medium in 96-well round-bottom tissue culture plate and cultured for 10 days at 37° C. Half of the medium was replaced as supplementary every three days without any peptide. On day 10, cells were restimulated with or without the corresponded peptides for 7 hours in the presence of Brefeldin A (eBioscience), monensin (eBioscience) and 0.5 µg/ml anti-CD107a at 37° C. After incubation, cells were collected and then stained with the 50-plex pMHC tetramers (table S1) and surface antibodies. Intracellular cytokine staining was performed on the second day as indicated in (table S2). All staining, cellular barcoding, and CD8 T cell enrichment were done in the same manner as ex vivo staining described above.

19. Enzyme-Linked Immunosorbent Assay (ELISA)

Paired serum samples from patients were serially diluted in PBS, and level of HbeAg, HBsAg, HBeAb, HBsAb and HBcAb were determined using quantitative sandwich ELISA kits (Abnova and MyBioSource) according to manufacturer's instruction.

Results

1. Comprehensive HBV Epitope Mapping

To generate a comprehensive HBV targeting pMHC library, viral DNA was isolated and deep sequenced from serum samples of 15 longitudinal CHB patients to determine viral consensus sequences and common variants (FIG. 1A and FIG. 7A, see Materials and Methods). The sequences were loaded onto the NetMHC platform to predict possible A*11:01-restricted binders. 484 unique putative HBV epitopes above the predictive "weak binding" threshold were combined with 78 known epitopes derived from other common antigens to arrive at a total of 562 peptides, listed in table S1. Sequence homology was analyzed to group relatively similar peptides into the same cluster by a pairwise matching algorithm (FIG. 7B and table S1). The resulting 284 peptide clusters were randomly assigned for unique combinations of quadruple streptavidin-metal (SAv-metal) coding (FIG. 1A and FIG. 7C). This approach avoided false interpretation of the combinatorial pMHC tetramer strategy (29) that would result from T cells expected to cross-react with multiple minor variants of the same peptide. The coded 562-plex pMHC tetramers library was pooled and simultaneously probed on each patient's peripheral lymphocytes (FIG. 7C) (30). To increase confidence of detection, patient's cells were evenly divided and independently interrogated by the same 562-plex pMHC tetramers library of two entirely different SAv-metal coding configurations (FIG. 7C-D and S2A). Together with >26 cellular markers (table S2), the signals of 562-plex pMHC tetramers were determined by mass cytometry. A self-validated automatic combinatorial tetramer deconvolution algorithm was used to identify tetramer positive events in an unbiased way (Materials and Methods, FIG. 7D). The correspondences between matching tetramers from two coding configurations were calculated using a bootstrapping statistical analysis (see Materials and Methods, FIG. 1A and FIG. 7D). Finally, the validated antigen-specific CD8$^+$ T cells for those passing all the deconvolution criteria between two configurations were enumerated, and such approach can be verified by the correlation of control epitopes (e.g. CMV and EBV) detected between the configurations (FIG. 7 and S2A). Using this objective strategy, we were able to detect many unidentified candidate epitopes and their variants in CHB patients, as well as the previous identified epitopes (table S1).

Figures 1C, 1D:
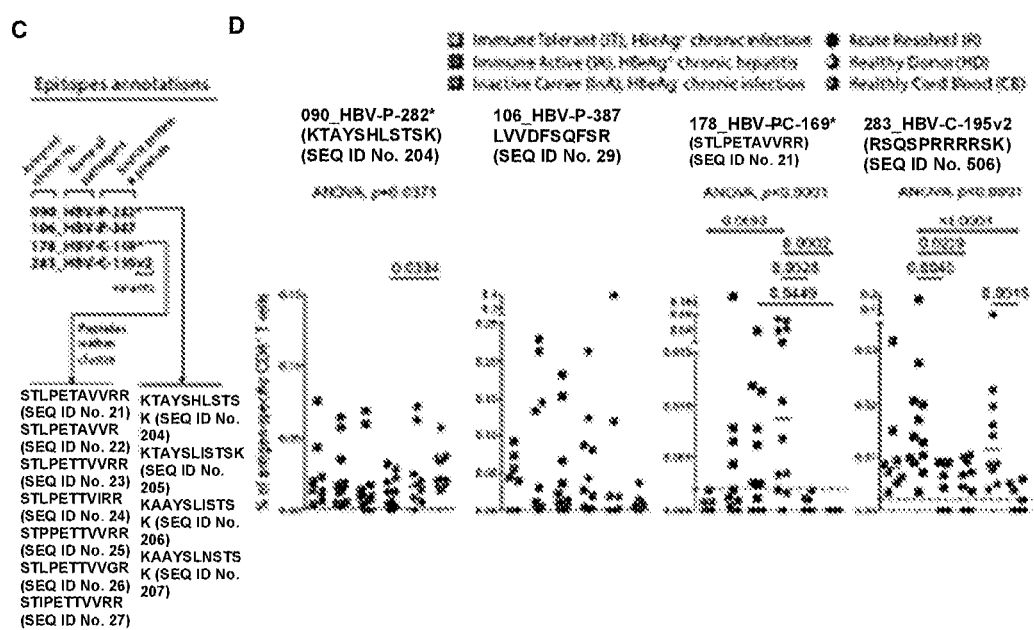

It was hypothesized that the antigen-specific T cell responses could vary across different clinical stages and reflect CHB disease progression. Therefore, this strategy to map potential T cell epitopes across three CHB patient groups (IT, IA and InA) and one group of acutely resolved patients (R) (table S3) was applied. There was no difference in the overall magnitudes of detected antigen-specificities between patient groups (FIG. 9). However, across all tested patients, T cells specific for more epitopes derived from polymerase (P) and core (C) compared to envelope (S) and x (X) proteins were detected, including four epitopes with the highest frequencies observed (FIG. 1B). These were HBV-P-282 (cluster 090, 4 peptide variants), HBV-P-387 (cluster 106, 1 unique peptide), HBV-C-169 (cluster 178, 7 peptide variants), and HBV-C-195v2 (cluster 283, 1 unique peptide) (FIG. 1B-C, FIG. 8 and table S1).

Figure 1E:
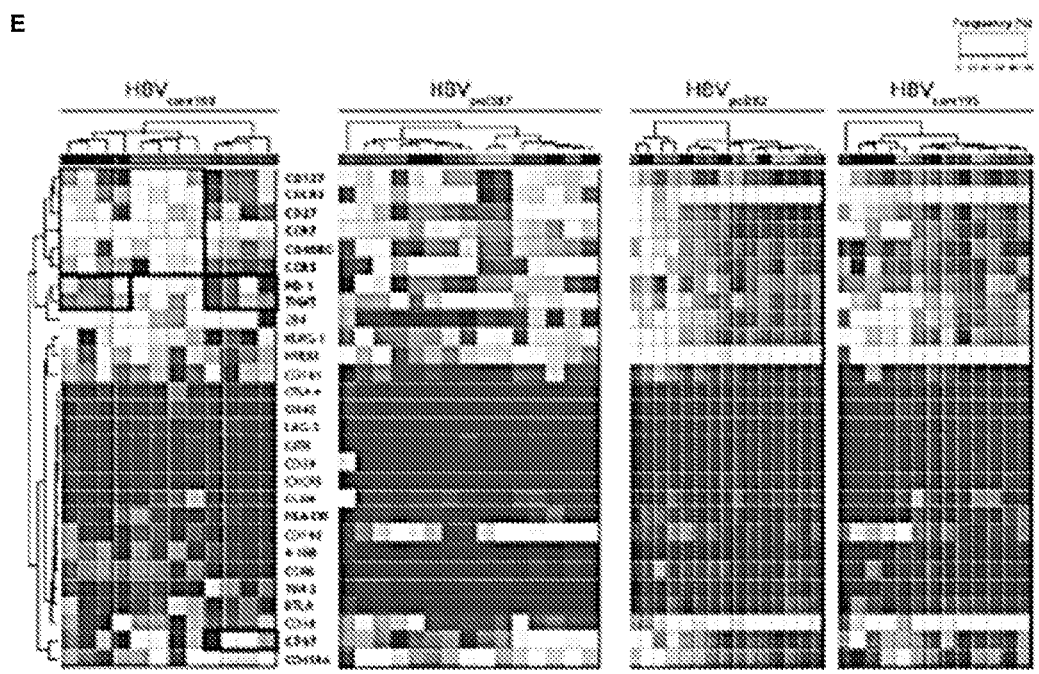

Several experiments were performed to validate and assess the HBV relevance of these four epitopes. For three out of four of these epitopes, antigen-specific T cells were detected in some healthy donor (HD) or cord blood (CB) samples (FIG. 1D), but not in HLA-mismatched patients (FIG. 10). The detection of these cells was further reproduced and confirmed by fluorescence flow cytometry pMHC tetramer staining, which showed consistent results (FIG. 11A-B). These T cells could also proliferate upon the stimulation by corresponding viral peptides (FIG. 12), except the seemingly unresponsiveness of cells from IT and HD. Although the results obtained were clear in confirming the specificity of T cells stained with HBV-P-282 and HBV-C-195v2 peptide-loaded pMHC tetramers, these cells displayed a mostly naïve-like phenotype (FIG. 1E). It is likely that T cells specific for these epitopes could be naïve T cells with relatively high precursor frequencies due to the non-random nature of TCR recombination, and were similar to HCV-specific CD8$^+$ naïve precursors that previously described.

A previously identified epitope, HBV-P-387 was observed with relatively high frequency in CHB and also in half of the HD tested, but to a lesser extent in CB samples. As described further in subsequent sections, the heterogeneous phenotypes of these cells were highly variable between patients (FIG. 1E), suggesting the relevant HBV-specific immune response. Given the high prevalence of HBV in Singapore, where the HD were collected, we postulate that such unexpected detection of HBV-specific T cells could be due to the high coverage of vaccination or subclinical infection without the development of anti-HBc antibody (HBcAb), as reported in HBV-exposed health workers (FIG. 1D and FIG. 11C). This remains to be determined. Lastly, among the validated epitopes, T cells specific for HBV-C-169 were only detected in HBV-infected individuals and elevated in patients with viral control (InA and R) (FIG. 1D) compared to patients with high viral load (IT), where these cells were undetectable. Such HBV-specific T cells displayed phenotypic profiles that differed according to the status of HBV-infection (FIG. 1E). These results prompted us to further evaluate the profiles of HBV$_{pol387}$ and HBV$_{core169}$-specific CD8$^+$ T cells.

2. High-Dimensional Phenotypic Profiling of HBV-Specific CD8$^+$ T Cells

Further analyses were directed at HBV$_{pol387}$ and HBV$_{core169}$-specific CD8$^+$ T cells because of their higher degrees of phenotypic heterogeneity observed across patients at various stages of CHB. Although both HBV-P-387 (LVVDFSQFSR (SEQ ID No. 28)) and one of the peptides within the HBV-C-169 (STLPETTVVRR (SEQ ID No. 23)) have been previously reported, the phenotypes of these reactive T cells have not been investigated. Unique to HBV$_{pol387}$ and HBV$_{core169}$-specific CD8$^+$ T cells is the higher expression of TIGIT compared to other HBV-specific CD8$^+$ T cells (FIG. 13), as well as elevated PD-1 expression on HBV$_{core169}$-specific CD8+ T cells (FIG. 13).

Unsupervised high-dimensional t-SNE visualization and Phenograph cellular clustering were applied to describe the phenotypes of virus-specific CD8$^+$ T cells across individuals from one large batch of samples run in parallel (FIG. 2). Based on the expression levels of markers indicative of T cell activation, differentiation, trafficking and inhibitory receptors typically associated with T cell exhaustion, 19 cellular clusters were objectively identified and annotated (FIG. 2A).

From this analysis, remarkable heterogeneity of HBV$_{pol387}$-specific CD8$^+$ T cells was observed. In many instances, several distinct populations specific for this one epitope could be seen even within individual patients. Despite such diverse phenotypes, this epitope sequence was highly conserved across all patients and time-points subjected to HBV viral sequencing over a decade (FIG. 14, table S4). Quantification of cellular clusters within each T cell antigen-specificity were performed across all batches of experiments using cluster-specific gating strategies (FIG. 15) to test for compositional differences associated with the status of HBV infection. Besides cluster 8 (C8), all of the cellular clusters occupied by HBV$_{pol387}$-specific CD8$^+$ T cells expressed 2B4 with heterogeneous phenotype indicative of different T cell memory status, whereas only cluster 9 (C9) showed elevated expression of PD-1 (FIG. 2). In terms of relationships with the status of infection, a significant enrichment of cells with C13-like phenotypes (~80%) in IT patients, expressing CXCR3$^+$CD27$^{hi}$CD127$^{hi}$ (FIG. 2A-B and FIG. 16A-C) was observed. Significant differences were also seen for C8 in IA patients, which was highlighted by the co-expression of CD45ROh$^{hi}$CCR4$^+$HVEM$^+$ with a T$_{CM}$ phenotype. The phenotypically similar region C6+C17 was preferentially occupied by InA, which were notably absent from IT patients (FIG. 2B and FIG. 16A-C). Such subset was similar to terminal effector memory RA (TEMRA) but expressed CD127$^{int}$, perhaps suggesting an ongoing T cell response specific for InA but not IT patients. Given that these cells were less expanded in IT patients (FIG. 12) and expressed several memory-associated markers, it suggests that they were experienced but not fully activated, and perhaps such inactivation was regulated by 2B4 in a PD-1-independent manner (FIG. 2A).

TABLE S4

Supplementary Table 4:
The frequency of viral mutation on selective epitopes in longitudinal patient cohort across HBeAg-seroconversion.

| Patient group | Patient ID | Epitope | Sequence | Time | | | | | | | | |
|---|---|---|---|---|---|---|---|---|---|---|---|---|
| | | | | 6-Jan-1999 | 29-May-2000 | 4-Jun-2001 | 29-Jul-2003 | 3-Feb-2004 | 27-Jul-2005 | 10-Aug-2006 | | |
| Non-seroconverters | C3 | 003_HBV-S-95* | STNRQSGRQ (SEQ ID No. 586) | 0.9623 | 0.9608 | 0.9601 | 0.9569 | 0.9623 | 0.9607 | 0.9611 | | |
| | | 056_HBV-P-136* | VVNHYFQTR (SEQ ID No. 129) | 0.9704 | 0.9692 | 0.9681 | 0.9666 | 0.9698 | 0.9689 | 0.9677 | | |
| | | 090_HBV-P-282* | KAAYSLISTSK (SEQ ID No. 206) | 0.9448 | 0.9436 | 0.9390 | 0.9396 | 0.9443 | 0.9426 | 0.9442 | | |
| | | 106_HBV-P-387 | LVVDFSQFSR (SEQ ID No. 28) | 0.9556 | 0.9558 | 0.9542 | 0.9509 | 0.9581 | 0.9558 | 0.9556 | | |
| | | 125_HBV-P-486* | Y[V]SLMLLYK (SEQ ID No. 285) | 0.9552 | 0.9541 | 0.9537 | 0.9514 | 0.9548 | 0.9521 | 0.9560 | | |
| | | 178_HBV-C-169* | STLPETTWRR (SEQ ID No. 23) | 0.9601 | 0.9631 | 0.9616 | 0.9592 | 0.9618 | 0.9598 | 0.9578 | | |
| | | 179_HBV-C-175* | TWRRGRSPR (SEQ ID No. 395) | 0.9570 | 0.9572 | 0.9578 | 0.9556 | 0.9584 | 0.9559 | 0.9563 | | |
| | | 183_HBV-X-80* | TTVNAH[G]NLPK (SEQ ID No. 404) | 0.9474 | 0.9462 | 0.9443 | 0.9411 | 0.9500 | 0.9480 | 0.9455 | | |
| | | 283_HBV-C-195v2 | RSQSPRRRRSQ (SEQ ID No. 587) | 0.9568 | 0.9555 | 0.9551 | 0.9517 | 0.9557 | 0.9542 | 0.9550 | | |
| | | | | 1-Jun-1991 | 21-Dec-1991 | 12-Oct-1992 | 16-Sep-1996 | | | | | |
| | C4 | 003_HBV-S-95* | STNRQSGRQ (SEQ ID No. 586) | 0.9851 | 0.9605 | 0.9841 | 0.9599 | | | | | |
| | | 056_HBV-P-136* | VVNHYFQTR (SEQ ID No. 129) | 0.9784 | 0.9519 | 0.9419 | 0.8340 | | | | | |
| | | | VV[D]HYFQTR (SEQ ID No. 135) | 0.0106 | 0.0158 | 0.0351 | 0.1301 | | | | | |
| | | 090_HBV-P-282* | KAAYSLISTSK (SEQ ID No. 206) | 0.9784 | 0.9415 | 0.9656 | 0.9380 | | | | | |
| | | 106_HBV-P-387 | LVVDFSQFSR (SEQ ID No. 28) | 0.9805 | 0.9573 | 0.9815 | 0.9518 | | | | | |
| | | 125_HBV-P-486* | Y[V]SLMLLYK (SEQ ID No. 285) | 0.9739 | 0.9460 | 0.9706 | 0.9451 | | | | | |
| | | 178_HBV-C-169* | STLPETTWRR (SEQ ID No. 23) | 0.9832 | 0.9622 | 0.9824 | 0.9571 | | | | | |
| | | 179_HBV-C-175* | TVVRRGRSPR (SEQ ID No. 395) | 0.9801 | 0.9601 | 0.9807 | 0.9540 | | | | | |
| | | 183_HBV-X-80* | TTVNAH[G]NLPK (SEQ ID No. 404) | 0.9751 | 0.9412 | 0.9716 | 0.9406 | | | | | |
| | | 283_HBV-C-195v2 | RSQSPRRRRSQ (SEQ ID No. 587) | 0.9768 | 0.9538 | 0.9749 | 0.9454 | | | | | |

TABLE S4-continued

Supplementary Table 4:
The frequency of viral mutation on selective epitopes in longitudinal patient cohort across HBeAg-seroconversion.

| | | 12-Nov-1988 | 19-Jun-1990 | 8-Sep-1992 | 21-Jun-1995 | 2-Sep-1996 |
|---|---|---|---|---|---|---|
| C5 | 003_HBV-S-95* STNRQSGRQ (SEQ ID No. 586) | 0.9639 | 0.9635 | 0.9655 | 0.9632 | 0.9801 |
| | 056_HBV-P-136* WNHYFQTR (SEQ ID No. 129) | 0.9614 | 0.9594 | 0.9636 | 0.9633 | 0.9808 |
| | 090_HBV-P-282* KAAYSLISTSK (SEQ ID No. 206) | 0.9480 | 0.9462 | 0.9494 | 0.9470 | 0.9715 |
| | 106_HBV-P-387 LVVDFSQFSR (SEQ ID No. 28) | 0.9617 | 0.9595 | 0.9625 | 0.9638 | 0.9810 |
| | 125_HBV-P-486* Y[V]SLMLLYK (SEQ ID No. 285) | 0.9577 | 0.9579 | 0.9614 | 0.9606 | 0.9819 |
| | 178_HBV-C-169* STLPETTVIRR (SEQ ID No. 24) | 0.9612 | 0.9615 | 0.9646 | 0.9663 | 0.9818 |
| | 179_HBV-C-175* TVIRRGRSPR (SEQ ID No. 396) | 0.9566 | 0.9597 | 0.9615 | 0.9607 | 0.9786 |
| | 183_HBV-X-80* TTVNAHRNLPK (SEQ ID No. 407) | 0.9481 | 0.9477 | 0.9546 | 0.9515 | 0.9735 |
| | 283_HBV-C-195v2 RSQSPRRRSQ (SEQ ID No. 587) | 0.9611 | 0.9593 | 0.9608 | 0.9616 | 0.9760 |

| | | 15-May-2001 | 5-Jul-2002 | 18-Jul-2003 | 25-May-2004 | 19-Jan-2005 | 10-Feb-2006 | 2-Feb-2007 |
|---|---|---|---|---|---|---|---|---|
| C7 | 003_HBV-S-95* STNRQSGRQ (SEQ ID No. 586) | 0.9629 | 0.9630 | 0.9594 | 0.9610 | 0.9643 | 0.9624 | 0.9623 |
| | 056_HBV-P-136* WNHYFQTR (SEQ ID No. 129) | 0.9593 | 0.9600 | 0.9592 | 0.9564 | 0.9595 | 0.9586 | 0.9587 |
| | 090_HBV-P-282* KAAYSLISTSK (SEQ ID No. 206) | 0.9454 | 0.9458 | 0.9412 | 0.9436 | 0.9471 | 0.9430 | 0.7917 |
| | KAA[H]SLISTSK (SEQ ID No. 588) | | | | | | | 0.1527 |
| | 106_HBV-P-387 LWDFSQFSR (SEQ ID No. 28) | 0.9556 | 0.9569 | 0.9530 | 0.9567 | 0.9587 | 0.9564 | 0.9566 |
| | 125_HBV-P-486* Y[V]SLMLLYK (SEQ ID No. 285) | 0.9494 | 0.9513 | 0.9473 | 0.9490 | 0.9517 | 0.9489 | 0.9484 |
| | 178_HBV-C-169* STLPETTVRR (SEQ ID No. 23) | 0.9595 | 0.9619 | 0.9597 | 0.9610 | 0.9611 | 0.9591 | 0.9595 |
| | 179_HBV-C-175* TVVRRRGRSPR (SEQ ID No. 395) | 0.9570 | 0.9579 | 0.9579 | 0.9578 | 0.9589 | 0.9566 | 0.9529 |
| | 183_HBV-X-80* TTVNAHRNLPK SEQ ID No. 407 | 0.9430 | 0.9449 | 0.9405 | 0.9398 | 0.9484 | 0.9436 | 0.9425 |
| | 283_HBV-C-195v2 RSQSPRRRSQ (SEQ ID No. 587) | 0.9544 | 0.9553 | 0.9570 | 0.9525 | 0.9552 | 0.9521 | 0.9493 |

Numbers indicate the frequenies of the given variants. Grey shaded sequences, are wild type sequences.

TABLE S4-continued

Supplementary Table 4:
The frequency of viral mutation on selective epitopes in longitudinal patient cohort across HBeAg-seroconversion.

| Patient group | Patient ID | Epitope | Sequence | Time | | | | | | | | | |
|---|---|---|---|---|---|---|---|---|---|---|---|---|---|
| | | | | 13-Aug-1991 | 17-Aug-1998 | 26-Oct-1999 | 12-Jun-2000 | 11-Aug-1993 | 23-Mar-1994 | 14-Mar-2001 | 3-Jun-2003 | 9-Feb-2004 | 24-Mar-2004 |
| HBeAg-seroconverters | S1 | 003_HBV-S-95* | STNRQSGRQ (SEQ ID No. 586) | 0.9624 | 0.9799 | 0.9815 | 0.9812 | 0.9659 | 0.9804 | 0.9852 | 0.9584 | 0.9770 | |
| | | 056_HBV-P-136* | WNHYFQTR (SEQ ID No. 129) | 0.9680 | 0.9854 | 0.9862 | 0.9853 | 0.9685 | 0.9811 | 0.9874 | 0.9626 | 0.9747 | |
| | | | W[D]HYFQTR (SEQ ID No. 135) | | | | | | | | | 0.0109 | |
| | | 090_HBV-P-282* | KAAYSLISTSK (SEQ ID No. 206) | | 0.9748 | 0.9725 | 0.9758 | | | 0.9709 | 0.9420 | 0.9697 | |
| | | 106_HBV-P-387 | LVVDFSQFSR (SEQ ID No. 28) | | 0.9822 | 0.9821 | 0.9816 | | | 0.9806 | 0.9526 | 0.9801 | |
| | | 125_HBV-P-486* | Y[V]SLMLLYK (SEQ ID No. 285) | | 0.9819 | 0.9810 | 0.9818 | | | 0.9547 | 0.9485 | 0.9784 | |
| | | 178_HBV-C-169* | STLPETTWRR (SEQ ID No. 23) | | 0.9825 | 0.9827 | 0.9835 | | | 0.9828 | 0.9590 | 0.9820 | |
| | | 179_HBV-C-175* | TWRRGRSPR (SEQ ID No. 395) | | 0.9793 | 0.9804 | 0.9790 | | | 0.9795 | 0.7738 | 0.2946 | |
| | | | TVVRRR[C]RSPR (SEQ ID No. 589) | | | 0.0628 | | | | | 0.1824 | 0.6858 | |
| | | 183_HBV-X-80* | TTVNAHRNLPK (SEQ ID No. 407) | | 0.9731 | 0.9126 | 0.9751 | | | 0.9484 | 0.9382 | 0.9749 | |
| | | | TTVNAH[G]NLPK (SEQ ID No. 404) | | | | | | | 0.0194 | | | |
| | | | TTVNA[L][G]NLPK (SEQ ID No. 403) | | | | | | | | | | |
| | | 283_HBV-C-195v2 | RSQSPRRRRSQ (SEQ ID No. 587) | | 0.9772 | 0.9786 | 0.9777 | | | 0.9828 | 0.9565 | 0.9779 | |
| | | | | 13-Aug-1991 | | 29-Jun-1992 | | | | | 5-Feb-1998 | 13-Dec-2000 | 24-Mar-2004 |
| | S2 | 003_HBV-S-95* | STNRQSGRQ | | | 0.9794 | | | | | 0.9658 | 0.9858 | 0.9858 |
| | | 056_HBV-P-136* | (SEQ ID No. 586) VVNHYFQTR (SEQ ID No. 129) | | | 0.9815 | | | | | 0.5004 | | 0.9811 |
| | | | VV[H]HYFQTR (SEQ ID No. 134) | | | | | | | | 0.3335 | 0.3654 | |
| | | | VV[D]HYFQTR (SEQ ID No. 135) | | | | | | | | 0.1079 | 0.5556 | |
| | | | VV[S]HYFQTR (SEQ ID No. 590) | | | | | | | | 0.0247 | | |
| | | | [I]VNHYFQTR (SEQ ID No. 131) | | | | | | | | | 0.0617 | |

TABLE S4-continued

Supplementary Table 4:
The frequency of viral mutation on selective epitopes in longitudinal patient cohort across HBeAg-seroconversion.

| | | | | | | | |
|---|---|---|---|---|---|---|---|
| 090_HBV-P-282* | KAAYSLISTSK (SEQ ID No. 206) | 0.9474 | 0.9713 | 0.9477 | 0.9727 | 0.9516 | 0.8700 | 0.8100 |
| | [E][T]AYS[H][L][T]TSK (SEQ ID No. 591) | | | | 0.1082 | | | |
| | [E]AAYS[F]ISTS[E] (SEQ ID No. 592) | | | | | 0.1900 | | |
| 106_HBV-P-387 | LVVDFSQFSR (SEQ ID No. 28) | 0.9613 | 0.9816 | 0.9625 | 0.9822 | 0.9784 | 0.9800 | 0.9999 |
| 125_HBV-P-486* | Y[V]SLMLLYK (SEQ ID No. 285) | 0.9573 | 0.9827 | 0.9619 | 0.9839 | 0.9801 | 0.8944 | 0.9700 |
| | Y[V]SL[L]LLYK (SEQ ID No. 284) | | | | | | 0.0900 | |
| 178_HBV-C-169* | STLPETTWRR (SEQ ID No. 23) | 0.9640 | 0.9822 | 0.9647 | 0.9821 | 0.9703 | 0.3558 | 0.7700 |
| | STLPETTVVR[C] (SEQ ID No. 593) | | | | | | 0.0879 | |
| | STLPETT[A]WRR (SEQ ID No. 21) | | | | | | 0.5395 | 0.1500 |
| | STLPETTV[I]RR (SEQ ID No. 24) | | | | | | | 0.0800 |
| 179_HBV-C-175* | TVVRRGRSPR (SEQ ID No. 395) | 0.9553 | 0.9704 | 0.8969 | 0.9068 | 0.5168 | 0.0873 | 0.7920 |
| | TVVRRR[C]RSPR (SEQ ID No. 589) | | | | 0.0654 | 0.0698 | 0.4472 | 0.2718 |
| | TWR[C]RGRS[T]R (SEQ ID No. 594) | | | | | | | 0.1021 |
| | [A]WRRR[C]RSPR (SEQ ID No. 394) | | | | | | 0.5225 | 0.2000 |
| | TV[I]RRRGR[T]PR (SEQ ID No. 595) | | | | | | | 0.0080 |
| 183_HBV-X-80* | TTVNAHRNLPK (SEQ ID No. 407) | 0.0547 | 0.0327 | 0.0249 | | 0.0198 | | |
| | TTVNAH[G]NLPK (SEQ ID No. 404) | 0.8972 | 0.9429 | 0.9310 | 0.9712 | 0.9456 | 0.9041 | 0.1600 |
| | TTVNA[R][Q][V]LPK (SEQ ID No. 408) | | | | | | 0.0764 | |
| 283_HBV-C-195v2 | RSQSPRRRRSQ (SEQ ID No. 587) | 0.9589 | 0.9790 | 0.9639 | 0.9788 | 0.9604 | 0.9809 | 0.9809 |

TABLE S4-continued

Supplementary Table 4:
The frequency of viral mutation on selective epitopes in longitudinal patient cohort across HBeAg-seroconversion.

| | | | 25-Aug-1992 | 29-Jun-1993 | 30-Aug-1994 |
|---|---|---|---|---|---|
| S3 | 003_HBV-S-95* | STNRQSGRQ (SEQ ID No. 586) | 0.9864 | 0.9428 | 0.9839 |
| | | S[N]NRQSGRQ (SEQ ID No. 596) | | 0.0231 | |
| | 056_HBV-P-136* | WNHYFQTR (SEQ ID No. 129) | 0.6202 | 0.8098 | 0.9752 |
| | | W[D]HYFQTR (SEQ ID No. 135) | 0.3160 | | |
| | | VV[H]HYFQTR (SEQ ID No. 134) | 0.0527 | 0.1735 | 0.0114 |
| | 090_HBV-P-282* | KAAYSLISTSK (SEQ ID No. 206) | 0.9040 | 0.9318 | 0.9785 |
| | | KAA[N]SLISTSK (SEQ ID No. 597) | 0.0744 | | |
| | | KAAYSLISTS[T] (SEQ ID No. 598) | 0.0102 | | |
| | | KAAYSL[N]STSK (SEQ ID No. 207) | 0.0147 | | |
| | | KAAYS[R]ISTSK (SEQ ID No. 599) | | | |
| | 106_HBV-P-387 | LVVDFSQFSR (SEQ ID No. 28) | 0.9833 | 0.9820 | 0.9800 |
| | 125_HBV-P-486* | Y[V]SLMLLYK (SEQ ID No. 285) | 0.8413 | 0.9841 | 0.9812 |
| | | Y[D]SL[I]LLYK (SEQ ID No. 600) | 0.1217 | | |
| | | Y[D]SLMLLYK (SEQ ID No. 601) | 0.0227 | | |
| | 178_HBV-C-169* | STLPETTWRR (SEQ ID No. 23) | 0.9837 | 0.9830 | 0.9794 |
| | 179_HBV-C-175* | TVVRRGRSPR (SEQ ID No. 395) | 0.9807 | 0.9806 | 0.9773 |
| | 183_HBV-X-80* | TTVNAH[G]NLPK (SEQ ID No. 404) | 0.9138 | 0.7518 | 0.9617 |
| | | TTVN[T]H[G]NLPK (SEQ ID No. 602) | 0.0664 | | |
| | | TTVNAH[W]NLPK (SEQ ID No. 402) | | 0.0242 | 0.0127 |
| | | TTVNA[P][G]NLPK (SEQ ID No. 405) | | 0.1872 | |

TABLE S4-continued

Supplementary Table 4:
The frequency of viral mutation on selective epitopes in longitudinal patient cohort across HBeAg-seroconversion.

|  |  |  |  |  |  |  |
|---|---|---|---|---|---|---|
|  | 283_HBV-C-195v2 | RSQSPRRRSQ (SEQ ID No. 587) |  | 0.9838 | 0.6616 | 0.9712 |
|  |  | R[T]QSPRRRSQ (SEQ ID No. 603) |  |  | 0.2879 | 0.0118 |
|  |  | RSQSPRRRS[K] (SEQ ID No. 506) |  |  | 0.0244 |  |

| | | | 4-Jan-1992 | 16-Feb-1993 | 20-Jan-1994 | 11-Jan-1995 |
|---|---|---|---|---|---|---|
| HBeAg-seroconverters | S4 | 003_HBV-S-95* STNRQSGRQ (SEQ ID No. 586) | 0.9635 | 0.9588 | 0.9654 | 0.9790 |
| | | 056_HBV-P-136* WNHYFQTR (SEQ ID No. 129) | 0.9632 | 0.9600 | 0.9645 | 0.9799 |
| | | 090_HBV-P-282* KAAYSLISTSK (SEQ ID No. 206) | 0.9413 | 0.9273 | 0.9454 | 0.9252 |
| | | KAAYS[R]ISTSK (SEQ ID No. 599) | | | | 0.0301 |
| | | 106_HBV-P-387 LVVDFSQFSR (SEQ ID No. 28) | 0.9578 | 0.9587 | 0.9555 | 0.9819 |
| | | 125_HBV-P-486* Y[V]SLMLLYK (SEQ ID No. 285) | 0.9539 | 0.9472 | 0.9530 | 0.9815 |
| | | 178_HBV-C-169* STLPETTWRR (SEQ ID No. 23) | 0.9614 | 0.9616 | 0.9596 | 0.9805 |
| | | 179_HBV-C-175* TWRRGRSPR (SEQ ID No. 395) | 0.9585 | 0.9569 | 0.9545 | 0.9763 |
| | | 183_HBV-X-80* TTVNAHRNLPK (SEQ ID No. 407) | 0.9395 | 0.9425 | 0.9397 | 0.8980 |
| | | TTVNAH[G]NLPK (SEQ ID No. 404) | | | | 0.0671 |
| | | 283_HBV-C-195v2 RSQSPRRRSQ (SEQ ID No. 587) | 0.9607 | 0.9588 | 0.9589 | 0.9794 |

| | | | 14-Mar-1991 | 3-Apr-1993 |
|---|---|---|---|---|
| | S5 | 003_HBV-S-95* STNRQSGRQ (SEQ ID No. 586) | 0.9813 | 0.9594 |
| | | 056_HBV-P-136* WNHYFQTR (SEQ ID No. 129) | 0.8592 | 0.9603 |
| | | W[D]HYFQTR (SEQ ID No. 135) | 0.0417 | |
| | | W[H]HYFQTR (SEQ ID No. 134) | 0.0783 | |
| | | 090_HBV-P-282* KAAYSLISTSK (SEQ ID No. 206) | 0.9749 | 0.9080 |
| | | KAAYSL[N]STSK (SEQ ID No. 207) | | 0.0367 |

TABLE S4-continued

Supplementary Table 4:
The frequency of viral mutation on selective epitopes in longitudinal patient cohort across HBeAg-seroconversion.

| | | 28-Oct-1991 | 9-Dec-1991 | 4-Aug-1992 | 23-Feb-1994 | 6-Jun-1996 | 10-Apr-2001 |
|---|---|---|---|---|---|---|---|
| | 106_HBV-P-387 LWDFSQFSR (SEQ ID No. 28) | 0.9823 | 0.9586 | | | | |
| | 125_HBV-P-486* Y[V]SLMLLYK (SEQ ID No. 285) | 0.9822 | 0.9560 | | | | |
| | 178_HBV-C-169* STLPETTVVRR (SEQ ID No. 23) | 0.9833 | 0.9611 | | | | |
| | 179_HBV-C-175* TVVRRRGRSPR (SEQ ID No. 395) | 0.9463 | 0.9413 | | | | |
| | TVVRRRGRS[T]R (SEQ ID No. 604) | 0.0316 | 0.0101 | | | | |
| | 183_HBV-X-80* TTVNAHRNLPK (SEQ ID No. 407) | 0.0289 | 0.0181 | | | | |
| | TTVNAH[G]NLPK (SEQ ID No. 404) | 0.9308 | 0.6834 | | | | |
| | TTVNAH[W]NLPK (SEQ ID No. 402) | | 0.2053 | | | | |
| | TTVNAH[E]NLPK (SEQ ID No. 605) | | 0.0360 | | | | |
| | 283_HBV-C-195v2 RSQSPRRRSQ (SEQ ID No. 587) | 0.9755 | 0.9578 | | | | |
| S6 | 003_HBV-S-95* STNRQSGRQ (SEQ ID No. 586) | 0.9678 | 0.9796 | 0.9793 | 0.9792 | 0.9799 | 0.9825 |
| | 056_HBV-P-136* WNHYFQTR (SEQ ID No. 129) | 0.9617 | 0.9836 | 0.9848 | 0.9871 | 0.9775 | 0.9770 |
| | WNHY[L]QTR (SEQ ID No. 606) | 0.0111 | | 0.0110 | | | |
| | 090_HBV-P-282* KAAYSLISTSK (SEQ ID No. 206) | 0.9547 | 0.9627 | 0.9565 | 0.9639 | 0.9594 | 0.7289 |
| | KA[S]YSLISTSK (SEQ ID No. 607) | 0.0117 | | | | | 0.1834 |
| | KAA[N]SLISTSK (SEQ ID No. 597) | | | | | | 0.0537 |
| | 106_HBV-P-387 LVVDFSQFSR (SEQ ID No. 28) | 0.9810 | 0.9826 | 0.9819 | 0.9819 | 0.9818 | 0.9794 |
| | 125_HBV-P-486* Y[V]SLMLLYK (SEQ ID No. 285) | 0.9848 | 0.9825 | 0.9838 | 0.9719 | 0.9811 | 0.9770 |
| | 178_HBV-C-169* STLPETTVVRR (SEQ ID No. 23) | 0.9830 | 0.9806 | 0.9832 | 0.9827 | 0.9812 | 0.9661 |
| | STLPETTV[I]RR (SEQ ID No. 24) | | | | | | 0.0170 |
| | 179_HBV-C-175* TVVRRRGRSPR (SEQ ID No. 395) | 0.9794 | 0.9784 | 0.9779 | 0.9807 | 0.9789 | 0.9627 |
| | TV[I]RRRGRSPR (SEQ ID No. 396) | | | | | | 0.0162 |

TABLE S4-continued

Supplementary Table 4:
The frequency of viral mutation on selective epitopes in longitudinal patient cohort across HBeAg-seroconversion.

| | | 19-Sep-1990 | 29-Oct-1991 | 15-Sep-1992 | 19-Oct-1993 |
|---|---|---|---|---|---|
| | 183_HBV-X-80* | TTVNAHRNLPK (SEQ ID No. 407) | | | 0.0158 |
| | | TTVNAH[G]NLPK (SEQ ID No. 404) | 0.9807 | 0.9753 | 0.9780 | 0.9594 0.9716 0.0872 |
| | | TTVNAH[W]NLPK (SEQ ID No. 402) | | | | 0.8652 |
| | 283_HBV-C-195v2 | RSQSPRRRRSQ (SEQ ID No. 587) | 0.9835 | 0.9783 | 0.9760 | 0.9816 0.9113 0.2492 |
| | | R[T]QSPRRRRSQ (SEQ ID No. 603) | | | | 0.0658 0.7290 |
| S7 | 003_HBV-S-95* | STNRQSGRQ (SEQ ID No. 586) | 0.9645 | 0.9831 | 0.9841 | 0.9822 |
| | 056_HBV-P-136* | WNHYFQTR (SEQ ID No. 129) | 0.7695 | 0.6757 | 0.9503 | 0.9840 |
| | | W[D]HYFQTR (SEQ ID No. 135) | 0.0699 | 0.2116 | 0.0345 | |
| | | VV[H]HYFQTR (SEQ ID No. 13r) | 0.1436 | 0.1007 | | |
| | 090_HBV-P-282* | KAAYSLISTSK (SEQ ID No. 206) | 0.9152 | 0.8284 | 0.9782 | 0.9792 |
| | | KAA[N]SLISTSK (SEQ ID No. 597) | 0.0365 | 0.1220 | | |
| | | KAAYS[I]ISTSK (SEQ ID No. 608) | | 0.0223 | | |
| | 106_HBV-P-387 | LVVDFSQFSR (SEQ ID No. 28) | 0.9817 | 0.9826 | 0.9819 | 0.9850 |
| | 125_HBV-P-486* | Y[V]SLMLLYK (SEQ ID No. 285) | 0.9791 | 0.9414 | 0.9605 | 0.9848 |
| | | Y[D]SLMLLYK (SEQ ID No. 609) | | 0.0441 | 0.0233 | |

TABLE S4-continued

Supplementary Table 4:
The frequency of viral mutation on selective epitopes in longitudinal patient cohort across HBeAg-seroconversion.

| | | | | |
|---|---|---|---|---|
| 178_HBV-C-169* | STLPETTWRR (SEQ ID No. 23) | 0.9798 | 0.9568 | 0.9832 | 0.9846 |
| | STLPE[I]TWRR (SEQ ID No. 610) | | 0.0270 | | |
| 179_HBV-C-175* | TWRRRGRSPR (SEQ ID No. 395) | 0.9277 | 0.9381 | 0.9786 | 0.9808 |
| | TVRRR[C]RSPR (SEQ ID No. 589) | 0.0468 | 0.0406 | | |
| 183_HBV-X-80* | TTVNAHRNLPK (SEQ ID No. 407) | | | 0.8787 | 0.9438 |
| | TTVNAH[G]NLPK (SEQ ID No. 404) | 0.7742 | 0.8143 | 0.0994 | 0.0308 |
| | TTVN[T]H[G]NLPK (SEQ ID No. 602) | 0.1802 | 0.1366 | | |
| | TTVNA[L][G]NLPK (SEQ ID No. 403) | | 0.0214 | | |
| 283_HBV-C-195v2 | RSQSPRRRRSQ (SEQ ID No. 587) | 0.9733 | 0.9409 | 0.9814 | 0.9799 |
| | RSQSPRRRRS[K] (SEQ ID No. 506) | | 0.0406 | | |

Comprised of seven peptide-sequence variants (FIG. 1C and table S1), $HBV_{core169}$-specific $CD8^+$ T cells had significantly greater frequencies (FIG. 1D) and pMHC tetramer staining intensity in patients with viral control (InA and R) (FIG. 16D). No T cells specific for this epitope were detected in IT patients or HD (FIG. 1D), except one IT patient had detectable cells (0.00193%) just below the imposed cut-off frequency (0.002%) (FIG. 16E). t-SNE and Phenograph analysis showed that C8 and C11 were significantly enriched in InA and R, whereas C1 and C4 tended to be more prevalent in IA and InA patients. This is in-line with hierarchical clustering (FIG. 1E) that segregated individuals into different clinical stages based on the phenotypes of $HBV_{core169}$-specific $CD8^+$ T cells (FIG. 1E), which was not observed for EBV-specific $CD8^+$ T cells analyzed in parallel (FIG. 16F). In contrast to the elevated expression of CD57, PD-1 and TIGIT seen for these cells in IA patients, $HBV_{core169}$-specific $CD8^+$ T cells from InA and R patients significantly expressed CD27, CD28, CD45RO, CD127 and CXCR3 (FIG. 2D-E), suggesting they were long-lived memory T cells that were associated with a high degree of viral control. However, it is interesting to note that these cells from R patients expressed relatively high levels of PD-1 and TIGIT despite their presumed clearance of virus. Albeit, these cells derived from R patients differed in the expression of other memory-associated markers and CD57 compared to IA patients. Importantly, the PD-1-expressing $HBV_{core169}$-specific $CD8^+$ T cells from R patients exhibited high level of IL-7R (CD127), indicating they were not $T_{EX}$, but likely to be long-lived memory cells. It is plausible that such PD-1 expression denoted a sign of activation, or adaptation rather than exhaustion, and was induced by strong TCR-viral antigen engagement (FIG. 16D). It is also possible that the R patients were not completely cleared of the virus, and these PD-1-expressing $HBV_{core169}$-specific $CD8^+$ T cells still actively inhibit the virus. In contrast, $HBV_{core169}$-specific $CD8^+$ T cells from InA patients displayed intermediate levels of CD127 and CXCR3, and similar levels of CD27, CD28 and CD45RO compared to R patients. These cells in InA also had diminished expression of PD-1 compared to other groups (FIG. 2D-E). This can be explained by the low-to-undetectable viral load during the stage of InA, leading to lesser TCR-viral antigen engagement compared to IA patients who had high viral load.

Lastly, Scorpius (R. Cannoodt et al., SCORPIUS improves trajectory inference and identifies novel modules in dendritic cell development. bioRxiv), a trajectory inference method, was applied to compute the trajectory of $HBV_{core169}$-specific $CD8^+$ T cells across three clinical stages using the patient-wise expression of eight phenotypic markers that showed statistical significances (FIG. 2F). Our analysis indicated that decreased expression of PD-1, TIGIT and CD57 together with the increased expression of CD27, CD28, CXCR3, CD45RO and CD127 were associated with the inferred status of infection. Furthermore, patients associated with viral control (InA and R) were nicely separated and toward the end of the trajectory, whereas IA patients were on the opposite side. Thus, it was demonstrated the highly heterogeneous HBV-specific $CD8^+$ T cells during the progression of CHB using several high-dimensional analytical approaches, and such multifactorial cellular responses targeting $HBV_{pol387}$ and $HBV_{core169}$ were able to delineate patients into their clinical stages.

3. Multifactorial Interrelations of Inhibitory Receptors on Virus-Specific T Cells Next, the relationships between various categories of cellular markers expressed by each of the antigen-specific T cells analyzed, with a special focus on nine different inhibitory receptors was evaluated. To directly assess these relationships, One-Dimensional *Soli*-Expression by Nonlinear Stochastic Embedding (One-SENSE) was employed. One-SENSE works by reducing dimensionality of each category of markers into a one-dimensional t-SNE map that can be plotted in conjunction with alternative categories of markers mapped into additional one-dimensional t-SNE maps. In this way, cells are separately arranged based on their categorical expression and then relationships between the categories can be intuitively visualized and described.

In this case, the categories assigned (table S2) were: "Differentiation+TNFR" (markers of differentiation and tumor necrosis factor receptor superfamily), "Inhibitory" (inhibitory receptors) and "Trafficking" (chemokine receptors). The three derived axes called out the cellular subsets objectively with all possible protein co-expressions (FIG. 3A). The profiles of T cells specific for four different epitopes, including $HBV_{pol282}$, $HBV_{pol387}$ and $HBV_{core169}$, and one that derived from EBV ($EBV_{EBNA3B}$) were plotted and compared. In general, of the observed combinations of inhibitory receptors expressed by the antigen-specific T cells across patients, one subset displayed $HVEM^{int}2B4^+TIGIT^+ CD160^+PD\text{-}1^{lo}$, and was mainly contributed by subpopulations of $HBV_{pol387}$ and $EBV_{EBNA3B}$-specific $CD8^+$ T cells. One-SENSE analysis also showed that 2B4 and $HVEM^{lo}$ were expressed by most of the antigen-specific T cells, but limited expressions of LAG-3, TIM-3 and CTLA-4 (FIG. 3A and FIG. 13). Additionally, it was found that the majority of $PD\text{-}1^+$ cells did not express 2B4 and TIGIT but not CD160.

By plotting the cells based on the patient groups, it was noted that the phenotypes of $HBV_{pol387}$ and $HBV_{core169}$-specific $CD8^+$ T cells (blue and red) were most heavily influenced by status of infection the distinguishing features of these highly diverse cells are labeled. This heterogeneity can be best presented by $HBV_{pol387}$ and $HBV_{core169}$-specific $CD8^+$ T cells. $HBV_{pol387}$ from IT had a relatively homogeneous phenotype of in terms of memory-associated and trafficking receptors, but varied in four distinct co-expressions of inhibitory receptors (FIG. 3A). In other clinical stages, greater diversity was observed for $HBV_{pol387}$-specific $CD8^+$ T cells in terms of memory versus effector-associated markers and these also had complex relationships with the patterns of inhibitory receptors co-expressed (FIG. 3A). Similar examination of $HBV_{core169}$-specific $CD8^+$ T cells was somewhat limited due to the low cell numbers but also showed a greater degree of heterogeneity than might be expected. Nonetheless, this representation was consistent with that described above (FIG. 2).

The numbers of co-expressed inhibitory receptors on these cells using a Boolean strategy (FIG. 3B-C) were further quantified. In line with One-SENSE analysis, no HBV-specific cellular subsets that accumulated all inhibitory receptors (FIG. 3A-C and FIG. 11) were detected. Although the different co-expressions of inhibitory receptors on $HBV_{pol387}$-specific $CD8^+$ T cells can be shown by One-SENSE, there were no differences in terms of the numbers accumulated on the cells across patient groups. Conversely, IA patients had significant higher numbers of inhibitory receptors on $HBV_{core169}$-specific $CD8^+$ T cells compared to patients with viral control (FIG. 3C). Together with the visualization of One-SENSE, our data suggested a highly heterogeneous antigen-specific phenotype rather than a simple accumulation of so-called "Exhaustion markers" during CHB, and the diverse co-expressions of inhibitory receptors had different relationships with cellular differentiation and trafficking profiles that may associate with disease stages.

5. Functional Capacity of HBV-Specific CD8$^+$ T Cells

To address the relationships of functional capacity and inhibitory receptors, patient's cells were pulsed and expanded using short-term in vitro peptide stimulation and then assessed their functional responses using intracellular cytokine staining (FIG. 12). One-SENSE analysis was used to delineate virus-specific CD8$^+$ T cells into five major heterogeneous functional subsets on the basis of the relationships between categories of "Functions", "Inhibitory" and "Differentiation+TNFR" (FIG. 4A and table S2). For each category (axes of One-SENSE plots), all possible cellular subsets were described by heatplots and descriptive labels. Biaxial plots of the most relevant markers for these five functionally distinct subsets were also represented (FIG. 4B), and the relative composition of these subsets was quantified (FIG. 4C). Overall, this analysis highlights nonlinear relationships between inhibitory receptors and functional capacity on virus-specific CD8$^+$ T cells upon antigen recall in CHB.

Regardless of patient groups, a multi-functional subset was present (FIG. 4A, green box) and mainly contributed by HBV$_{pol387}$ and HBV$_{env304}$-specific CD8$^+$ T cells expressing MIP-1β$^+$GrzA$^+$GrzK$^{lo}$ Perforin$^+$ but CD107a$^{lo}$ (FIG. 4A-B and FIG. 18A). Another population of these cells (blue box) with otherwise similar phenotypic profiles were distinctly less able to produce cytokines but were GrzA$^+$GrzK$^+$Perforin$^{Int}$ without the degranulation marker CD107a, suggesting an alternative form of dysfunctional T cells that was associated with the expression of 2B4 and TIGIT but not PD-1 (FIG. 4A-B and FIG. 18B). These cells were mostly composed of HBV$_{env304}$-specific CD8$^+$ T cells from CHB patients (FIG. 4A and FIG. 18A), which had expanded greatly in response to in vitro peptide stimulation (FIG. 12). Unlike the other inhibitory receptors, CD160 and HVEM were largely reduced on cells producing effector functions upon TCR stimulation. The sustained HVEM was mostly expressed by the non-functional (black box) subset of HBV$_{pol282}$-specific cells (FIG. 4A-B and FIG. 18A-B). Such naïve-like and unresponsive T cells present a different type of dysfunctional T cells, perhaps associated with their expression of BTLA and CD160 prior to antigen recall (FIG. 13). It was also found that a fraction of HBV$_{env304}$-specific CD8$^+$ T cells from R patients had similar functional profiles as EBV and IAV-specific CD8$^+$ T cells that were PD-1·LAG-3·TIM-3, expressing IFN-γ$^+$TNF-α$^{hi}$MIP-1β$^{hi}$GM-CSF$^{hi}$ (yellow box) (FIG. 4A and FIG. 18A and C). Moreover, HBV$_{core169}$-specific CD8$^+$ T cells were in the unique plurifunctional (red box) subset co-producing various non-cytolytic and cell recruiting factors (GrzA$^-$GrzK$^-$IFN-γ$^+$TNF-α$^{lo}$MIP-1β$^+$GM-CSF$^{int}$CD107a$^+$) despite reciprocally co-expressed five inhibitory receptors including PD-1 (FIG. 4A-B). Interestingly, this subset exhibited high levels of TNFR costimulatory receptors (OX40, GITR, 4-1BB and CD27), suggesting the greater activation and memory status. In this analysis, the major differences observed between patient groups were in the profiles of HBV$_{core169}$-specific CD8$^+$ T cells. Patients with better viral control (R>InA>IA) displayed significantly higher the frequencies of pluri-functional subset of HBV$_{core169}$-specific CD8$^+$ T cells. In contrast, the opposite trend was observed for the frequencies of HBV$_{core169}$-specific CD8$^+$ T cells within the MIP1-β$^+$ multi-functional subset (FIG. 4C).

Together with the abovementioned data, it was concluded that the immune responses of HBV$_{core169}$-specific CD8$^+$ T cells were linked to viral control. The analysis also displays complex orchestrations rather than a simple linear relationship between inhibitory receptors and functional capacity on virus-specific CD8$^+$ T cells during CHB.

6. Clinical Stage-Dependent Landscapes of Virus-Specific TCR

How T cell receptors are selected over the course of CHB is largely unknown. Hence, the pMHC tetramer-stained cells (FIG. 11B) were sorted and sequenced the β chain of epitope-specific TCRs (HBV$_{pol282}$, HBV$_{pol387}$, HBV$_{core169}$ and HBV$_{core195}$) across various clinical stages. To map the TCR landscapes of these epitopes, TCRdist was applied, an algorithm that generates a distance matrix to quantify and obtain the relative motif similarity of TCR based on their sequences of amino acid (P. Dash et al., Quantifiable predictive features define epitope-specific T cell receptor repertoires). TCRdist distance matrix was used to cluster similar TCRs using the unsupervised Phenograph clustering algorithm (J. H. Levine et al., Data-Driven Phenotypic Dissection of AML Reveals Progenitor-like Cells that Correlate with Prognosis) and then visualized by the t-SNE dimensionality reduction algorithm (FIG. 5A). Thereafter, the sequence motifs that formed the basis of each TCR-sequence cluster can be presented (FIG. 5B and FIG. 19A), and the composition of these clusters in terms of the antigen-specificity of each sequence derived from patients can be quantified (FIG. 5C). It was found that TCR cluster 15 and 27 were significantly increased in HBV$_{pol282}$-specific TCRs compared with other epitopes (FIG. 5C-D), suggesting that these motifs were important determinants for recognition of this HBV epitope, and may associate with naïve-like phenotypes. In addition, the relative usage of each of these TCR-sequence clusters differed significantly between patients grouped by status of HBV infection. Dominated by TRBV5-6, TCR cluster 15 could be observed in all patients except for IA patients, which were instead enriched for the TRBV3-2$^+$ TCR cluster 12. Interestingly, TCR cluster 27 was solely joined by TRBJ2-6 with highly conserved CDR3 (FIG. 19A). Clusters of TCR-sequence usages were more diverse for T cells specific for HBV$_{core169}$ and HBV$_{pol387}$. Nonetheless, HBV$_{core169}$-specific TCR sequences also differed between patient groups. The TRBV3-2$^+$ TCR cluster 12 (also enriched in HBV$_{pol282}$-specific TCRs) was similarly enriched in IA patients within HBV$_{core169}$-specific TCRs. In addition, HBV$_{core169}$-specific TCRs of R and InA had significant higher usages of TRBV6-6$^+$ cluster 5 and TRBV28$^+$ cluster 9, respectively (FIG. 5C).

Repertoire diversity and density for each TCR sequence from various cell populations using a TCR diversity metric (TCRdiv) was calculated (P. Dash et al., Quantifiable predictive features define epitope-specific T cell receptor repertoires). Various patterns of this measure were observed among the epitope and patient groups (FIG. 5E). Of note, the TCRdiv scores for HBV$_{pol387}$-specific TCRs have striking similar pattern with the proportion of cellular cluster 13 in HBV$_{pol387}$-specific CD8$^+$ T cells across patient groups (FIG. 2B), which may be attributed to their relative enrichment in IT and HD groups. Importantly, both epitope-specific and bulk TCRs from HD had overall greater diversity (FIG. 19B), which separated them from CHB patients at the molecular level. In contrast to the uniformity of total CD8$^+$ T cells (FIG. 19C), CDR3 lengths were skewed between epitopes and patient groups. Overall, these findings fit with the previously described phenotypic differences observed in different patient groups. Thus, our analysis indicated the biased TCR repertoire usages during CHB were epitope and clinical stage-dependent.

7. Shared HBV$_{core169}$-Specific TCR Clones in Patients with Viral Control

Focusing on the HBV$_{core169}$-specific response and inquiring a recently curated TCR database, several previously unidentified public HBV$_{core169}$-specific TCRβ clones that were shared between individuals in a clinical stage-dependent manner were discovered (FIG. 5F). In particular, a general public clone CASGDSNSPLHF (SEQ ID No. 17) was within the top three TCR clones in all three InA patients tested. Two other special public clones CASSGGQI-VYEQYF (SEQ ID No. 18) and CSARGGRGGDYTF (SEQ ID No. 19) were each identified in two InA patients.

An additional special public clone CASSQDWTEAFF (SEQ ID No. 20) was found at low frequencies in two acute resolved patients. That these public TCR clones were not shared across patient groups, further highlights differences in the qualities of T cell responses that occur in acute versus chronic viral infection. Failure to detect public clones in IA patients suggested that the presence of public TCRs were essential for HBV viral control. By using PCA to combine the characteristics of HBV$_{pol387}$ and HBV$_{core169}$-specific TCR repertoire and cellular response in the same donors, patient's clinical status can be delineated (FIG. 5G). Lastly, it was found that the observed frequency of HBV$_{core169}$-specific CD8$^+$ T cells inversely correlated with their TCR repertoire diversity (FIG. 5H), suggesting the selective expansion of T cell clonotypes after viral clearance.

8. Phenotypic Dynamic of HBV$_{core169}$-Specific CD8+ T Cells

To assess the characteristic changes of antigen-specific T cells over the course of infection, selected HBV epitopes in a (n=14, HLA-A*1101$^+$ patients) longitudinally studied patient cohort who received Entecavir (ETV) over the course of several years were examined. ETV is a nucleotide analogue that inhibits viral replication and leads to improved viral control in most patients. Although it does not inhibit HBeAg production by infected hepatocytes, it can also lead to HBeAg seroconversion and established anti-HBeAg antibody (HBeAb) in some patients, and this is a serological marker of further improved viral suppression. For 10 out of 14 patients who had detectable HBV$_{core169}$-specific CD8$^+$ T cells (FIG. 6A), we compared the profiles of these cells in patients that later lost HBeAg and produced HBeAb (HBeAg–, n=6) over the course of the study vs. those that did not (HBeAg$^+$, n=4). Consistent with a previous work, decreased frequencies of HBV$_{core169}$-specific CD8$^+$ T cells were observed in some patients (FIG. 6B and FIG. 20A). Further experiments were performed to dissect the longitudinal viral mutation and tetramer response on this given epitope (FIG. 20B), showing that these HBV-specific CD8$^+$ T cells can recognize different variants beyond the database consensus peptide sequence. Based on the analysis of these cells at multiple time-points, the detailed features could be tracked over time and major changes in the phenotypes of these cells were often observed (FIG. 6C). For instance, at early time points, HBV$_{core169}$-specific CD8$^+$ T cells from patient HBeAg$^+$03 (a patient that did not lost HBeAg during the study time-frame) displayed a terminally differentiated effector phenotype (CD57$^+$CD45RA$^+$CCR7$^-$). Whereas, at later time points, more than half of this phenotype was shift. In contrast, HBV$_{core169}$-specific CD8$^+$ T cells from a HBeAg$^-$ patient (HBeAg$^-$01, a patient that lost HBeAg and established HBeAb) displayed a memory T cell phenotype (CD27$^+$CD127$^+$CD45RO$^+$) at all time points tested that was maintained for more than 6 years post treatment. Similar trends were observed for the other patients studied and detectable HBV$_{core169}$-specific CD8$^+$ T cells were described quantitatively (FIG. 6D).

In addition to summarizing the composition of these cells in terms of their memory vs. effector phenotypes over time (FIG. 6D), the same markers found that vary the most across patients in our cross-sectional cohort (FIGS. 1E and 2D-E) were focussed on. In general, the fraction of memory cell subset in HBV$_{core169}$-specific CD8+ T cells were associated with lower HBeAg level over time (FIG. 6D). This was supported by the increased expression of T cell memory-associated markers (CD27, CD127, CD45RO and CXCR3) (FIG. 6E) and the decreased expression of CD57 on HBV$_{core169}$-specific CD8$^+$ T cells, in line with similar observation in InA and R patients from the cross-sectional cohort (FIGS. 1E and 2D). In patients who sustained high HBeAg level, HBV$_{core169}$-specific CD8+ T cells displayed significantly lower levels of CD57 and higher levels of CD27 and CD127 after the virus was suppressed, whereas the cells derived from HBeAg$^-$ patients already possessed such a cellular profile (CD57$^{lo}$CD27$^{hi}$CD127$^{hi}$CD45RO$^+$) before the treatment and this was maintained for several years. To further quantify these changes, trajectory analysis using Scorpius was applied to these samples. To examine the reproducibility of the trajectory detection in this longitudinal cohort as it compared with the cross-sectional cohort (FIG. 2F), support vector machines (SVM) were used to map data from the longitudinal samples onto the pseudotime metric developed using Scorpius from the cross-sectional cohort (FIG. 2F, see methods). In other words, using the data from the cross-sectional cohort as a training set, we computed the pseudotime across patient's time points in the testing set (longitudinal cohort, FIG. 6F). Of these seven cellular markers, the trajectories of HBV$_{core169}$-specific CD8$^+$ T cells between the two independent patient cohorts were consistent (even when Scorpius was run independently without the use of SVM). In addition to validating the trajectory model on this independent cohort, this allowed the hypothesis that the HBV-specific T cell phenotypic evolution would track with the extent of viral control to be tested. Indeed, the phenotypes of HBV$_{core169}$-specific CD8$^+$ T cells did show the expected progression along this pseudotime metric over the course of treatment for all patients (FIG. 6G). This implies that the virus-specific T cell response associated with viral control improved for each patient over the course of antiviral therapy, as would be expected. In addition, patients who lost HBeAg and established HBeAb had a more progressed (higher expression of T cell memory markers, lower PD-1 and TIGIT expression) phenotype at earlier time points than non-HBeAg seroconverting patients, suggesting that these patients had better virus-specific T cell response at the start of treatment. Thus, our data showed that HBV$_{core169}$-specific CD8$^+$ T cells expressing increased cellular markers associated with long-term T cell memory development but decreased CD57 and two inhibitory receptor PD-1 and TIGIT was linked to viral control, and such machine learning-aided model could have predictive value for prognosis in CHB.

DISCUSSION

By fully leveraging a highly multiplexed combinatorial pMHC tetramer staining strategy, mass cytometry and unsupervised high-dimensional analyses, we investigated 562 unique A*11:01-restricted candidate epitopes during the progression of HBV. Analysis of HBV-specific T cell responses is difficult due to the very low frequencies of these cells. In this regard, we show the importance of investigating both the specificity and phenotypic profiles of the antigen-specific T cells to verify their involvement in the HBV-specific immune response. Beyond this, our data highlights the heterogeneity of the virus-specific T cell response that was associated with disease stages and provides quantifiable analyses of HBV-specific TCRβ repertoires that corresponded to cellular phenotypes during chronic viral infection.

Host defense against HBV weighs on immune response driven largely by virus-specific T cells. The number of A*11:01-restricted epitopes detected by this comprehensive approach were relatively limited compared to the reported epitopes in the context of A*02:01. It is possible that some epitope-specific T cells were only detectable in the liver but not in the periphery. Future investigation on HBV-specific intrahepatic lymphocytes is needed. The presence and frequencies of well-described A*02:01-restricted $HBV_{core18-27}$-specific CD8$^+$ T cells have been shown to associate with viral control. Many therapeutics have been therefore developed based on this T cells, including the blockade of overexpressed PD-1 to reinstate T cell function, adoptive transfer of engineering virus-specific T cells, and TCR-like (TCR-L) antibody to deliver interferon-α (IFN-α) directly onto infected hepatocytes. Here, evidence was presented that showed that the specific responses and characteristics of A*11:01-restricted $HBV_{core169}$-specific CD8$^+$ T cells were linked to viral control, with public TCR clones used by these T cells. Comparative analysis showed that these cells had differing profiles across clinical stages. Furthermore, high-dimensional trajectory analysis allowed the use of the profiles of $HBV_{core169}$-specific CD8$^+$ T cells to assign each patient a value along an objective pseudotime metric. The underlying features of $HBV_{core169}$-specific T cells along this trajectory were consistent across two independent patient cohorts, both showing correlations with viral control. Based on this metric, it is also conceivable that these antiviral-treated patients and possessing T cells with the most-progressed features of viral control could be eligible for safe discontinuation of antiviral drug once they mounted $HBV_{core169}$-specific memory T cells response, in line with a recent report showing the predictive utility of HBV-specific T cells (63). This is important because even the most advanced serological measures are unable to accurately predict such outcomes. Collectively, our findings should impact HBV immunotherapy design, and could be useful to predict patient's clinical outcome based on the phenotypic response of $HBV_{core169}$-specific CD8$^+$ T cells. It is also anticipated that the utility of this approach could be extended of other epitopes associated with viral control derived from HBV core or other proteins that are restricted to other HLA alleles.

By comprehensively probing HBV epitopes on numerous HBV-infected patients, the inventors here failed to identify $T_{EX}$ expressing all inhibitory receptors or overt evidence for "Hierarchical T cell exhaustion". Instead, unsupervised visualization using One-SENSE showed complex non-linear relationships between the expression of inhibitory receptors. Moreover, the dysfunctionality of HBV-specific T cells did not correlate to the linear accumulation of inhibitory receptors, indicating these cells were not completely functional inert. One interpretation is that these HBV-specific T cells do not nicely fit the definition of $T_{EX}$ as reported in LCMV-specific T cells, but instead a different type of subset that were mostly absent, with the remaining dysfunctional T cells expressing various combinations of inhibitory receptors. Based on present data, it is proposed that these T cell profiles, at least in the peripheral blood, could fit better with the description of functional adaption in CHB. Nonetheless, it is noteworthy that our functional assessment was relied on in vitro peptide stimulation due to the rare detection of HBV-specific T cells, and this might limit its relevance to in vivo response. Unlike during chronic LCMV infection, where maintenance of the $T_{EX}$ phenotype requires persistent and high antigen level, $HBV_{core169}$-specific CD8$^+$ T cells expressing high level of CD27 and IL-7Rα (CD127) found in InA patients were not $T_{EX}$ and are likely to be maintained for decades with a limited amount of viral antigen present. HBV-specific T cells from these patients were PD-1$^{int}$TIG-IT$^{int}$ with elevated expression of memory-associated markers and functional capacities that seem to be associated with control of the virus. On the other hand, for IA patients who have high and fluctuating viremia, HBV-specific T cells were detected that better matched the expected features of $T_{EX}$. These included a strong co-expression of PD-1 and TIGIT and limited expression of memory-associated markers such as CD127. Additionally, the inventors also found substantial expression of CD57 on HBV-specific T cells from IA patients, a cellular marker that is indicative of more differentiated effector cells with low proliferative capacity, suggesting these cells were not long-lived memory cells. Overall, cellular profiles of HBV-specific T cells in IA stage are consistent with persistent high antigen-exposure. At later stages (InA) in patients with better viral control, HBV-specific T cells had a memory phenotype expressing lower CD57 but elevated CXCR3, CD45RO, CD27 and CD127. The lack of the detectable $HBV_{core169}$-specific CD8$^+$ T cells in IT patients who has high viremia suggests that they might be largely deleted, and the absence of such particular T cells could contribute to the minimum liver inflammation in this stage. Future studies involve larger volume of blood samples from IT patients or using more sensitive approaches may help to address this issue. Further investigation of the expression level of EOMES and T-bet, or the epigenetic modification that better defined the bona fide $T_{EX}$ is important to address this aspect in CHB. It is also important to note that this report is limited to the analysis of circulating HBV-specific CD8$^+$ T cells, further examination of the exhaustion profile in intrahepatic lymphocytes is needed to address this question.

Previous studies have suggested the link between the different inhibitory receptors and T cell differentiation, which is in relative disagreement with the present One-SENSE analysis objectively showing more complex relationships between the co-expressed inhibitory receptors and T cell differentiation on several virus-specific T cells across multiple clinical stages of HBV infection. This is because many studies in human chronic viral infection often examined less than four inhibitory receptors within T cell subsets that were simply defined by few differentiation-associated markers, or on limited numbers of virus-specific T cells from one type of patient. Secondly, traditional analysis using hierarchical gating on biaxial dot plots to assess the expression level of cellular protein can easily underestimate the phenotypic complexity.

Despite the TCR sequence diversity of T cells specific for the $HBV_{core169}$ epitope, several public clones at relatively high abundance were detected in multiple patients. In line with the CMV-specific TCR repertoire, it was noted that these previously unidentified public TCRs were different when derived from patients showing viral control (R and InA) vs. viremia (IA), suggesting the functional importance of these T cells. The public virus-specific TCR clones may be selected over the course of viral clearance (i.e. from IA into InA) and contraction of the effector response. As previously reported for CMV and EBV infection, virus-specific CD8+ T cells do not express IL-7Rα (CD127) until T cell memory had been established, and such selection is thought to be driven by high affinity TCR-viral epitope binding. This is consistent with the characteristics of $HBV_{core169}$-specific CD8+ T cells in InA and R patients who carried public TCRs and elevated expression of T cell memory-associated markers including CD127, indicating their long-lived and self-renewing ability to maintain memory T cells pool after the reduction of viral antigen. Analogously, intrahepatic and peripheral public TCR clones have been linked to viral clearance in HCV-infected chimpanzees.

Despite the challenges highlighted associated with detecting HBV-specific T cells due to their low prevalence, the present invention explores the previously unappreciated complexity of virus-specific T cells in lifelong human HBV viral infection. The cellular responses of $HBV_{core169}$-specific CD8+ T cells and TCR sequences used were associated with the status of HBV infection and could be used as an indicator of the relative extent of viral control. Thus, the results provided here could have important implications for the development of new biomarkers, treatment strategies and immunotherapy aiming at HBV cure.

Whilst there has been described in the foregoing description preferred embodiments of the present invention, it will be understood by those skilled in the technology concerned that many variations or modifications in details of design or construction may be made without departing from the present invention.

The invention claimed is:

1. A method for identifying Hepatitis B virus antigen-specific T cells, the method comprising contacting a population of T cells with a peptide comprising an amino acid sequence selected from the group consisting of STLPETAVVRR (SEQ ID NO: 21), STLPETAVVR (SEQ ID NO: 22), STLPETTVTRR (SEQ ID NO: 24), STPPETTVVRR (SEQ ID NO: 25), STLPETTVVGR (SEQ ID NO: 26) and STIPETTVVRR (SEQ ID NO: 27), wherein the peptide is less than 30 amino acids long and is capable of binding HLA-A* 1101 and when bound to HLA-A* 1101 is capable of identifying T cells specific for Hepatitis B virus.

2. A T cell receptor (TCR) molecule comprising a TCR beta chain complementarity determining region 3 (CDR3) comprising an amino acid sequence selected from the group consisting of: CASGDSNSPLHF (SEQ ID NO: 17), CASSGGQIVYEQYF (SEQ ID NO: 18), CSARGGRGGDYTF (SEQ ID NO: 19) and CASSQDWTEAFF (SEQ ID NO: 20), wherein the TCR molecule is able to bind to a peptide, wherein the peptide comprises an amino acid sequence selected from the group consisting of STLPETAVVRR (SEQ ID NO: 21), STLPETAVVR (SEQ ID NO: 22), STLPETTVIRR (SEQ ID NO: 24), STPPETTVVRR (SEQ ID NO: 25), STLPETTVVGR (SEQ ID NO: 26) and STIPETTVVRR (SEQ ID NO: 27).

3. A polynucleotide encoding the TCR molecule according to claim 2.

4. The polynucleotide according to claim 3, comprising a sequence selected from the group consisting of SEQ ID NOs: 1 to 16.

5. An expression vector comprising the polynucleotide according to claim 3.

6. An isolated host cell comprising the polynucleotide according to claim 3.

7. The isolated host cell according to claim 6, wherein the host cell is a T cell derived from a patient.

8. An isolated T cell modified to express the TCR molecule according to claim 2.

9. A pharmaceutical composition comprising a peptide and a pharmaceutically acceptable carrier, wherein the peptide comprises an amino acid sequence selected from the group consisting of STLPETAVVRR (SEQ ID NO: 21), STLPETAVVR (SEQ ID NO: 22), STLPETTVTRR (SEQ ID NO: 24), STPPETTVVRR (SEQ ID NO: 25), STLPETTVVGR (SEQ ID NO: 26) and STIPETTVVRR (SEQ ID NO: 27), wherein the peptide is less than 30 amino acids long and is capable of binding HLA-A*1101.

10. A method of treating a Hepatitis B virus infection in an individual, the method comprising administering to the individual an effective amount of a peptide, wherein the peptide comprises an amino acid sequence selected from the group consisting of STLPETAVVRR (SEQ ID NO: 21), STLPETAVVR (SEQ ID NO: 22), STLPETTVIRR (SEQ ID NO: 24), STPPETTVVRR (SEQ ID NO: 25), STLPETTVVGR (SEQ ID NO: 26) and STIPETTVVRR (SEQ ID NO: 27), wherein the peptide is less than 30 amino acids long and is capable of binding HLA-A*1101.

11. A method of combating a Hepatitis B virus infection in a patient which carries HLA-A*1101, the method comprising:
  (a) obtaining T cells from the patient;
  (b) introducing into the T cells a polynucleotide encoding the TCR molecule according to claim 2; and
  (c) introducing the T cells produced in step (b) into the patient.

12. The method according to claim 11, wherein the polynucleotide is transfected into or introduced to the T cells by electroporation.

13. An isolated host cell comprising the expression vector according to claim 5.

14. A pharmaceutical composition comprising the isolated host cell according to claim 7 and a pharmaceutically acceptable carrier.

15. A vaccine against Hepatitis B virus infection comprising the isolated T cell according to claim 8.

16. A method of treating a Hepatitis B virus infection in an individual, the method comprising administering to the individual an effective amount of the isolated T cell according to claim 8.

* * * * *

SEQUENCE LISTING

```
<160> NUMBER OF SEQ ID NOS: 621

<210> SEQ ID NO 1
<211> LENGTH: 87
<212> TYPE: DNA
<213> ORGANISM: Artificial Sequence
<220> FEATURE:
<223> OTHER INFORMATION: Synthetic polynucleotide

<400> SEQUENCE: 1
ctaaacctga gctctctgga gctgggggac tcagctttgt atttctgtgc cagcggggat       60
tccaattcac ccctccactt tgggaac                                           87

<210> SEQ ID NO 2
<211> LENGTH: 87
<212> TYPE: DNA
<213> ORGANISM: Artificial Sequence
<220> FEATURE:
<223> OTHER INFORMATION: Synthetic polynucleotide

<400> SEQUENCE: 2
actaaactga gctctctgga gctgggggac tcagctttgt atttctgtgc cagcggggat       60
tccaattcac ccctccactt tgggaac                                           87

<210> SEQ ID NO 3
<211> LENGTH: 87
<212> TYPE: DNA
<213> ORGANISM: Artificial Sequence
<220> FEATURE:
<223> OTHER INFORMATION: Synthetic polynucleotide

<400> SEQUENCE: 3
actaaacctg agctctctgg agctggggac tcagctttgt atttctgtgc cagcggggat       60
tccaattcac ccctccactt tgggaac                                           87

<210> SEQ ID NO 4
<211> LENGTH: 87
<212> TYPE: DNA
<213> ORGANISM: Artificial Sequence
<220> FEATURE:
<223> OTHER INFORMATION: Synthetic polynucleotide

<400> SEQUENCE: 4
actaacctga gctctctgga gctgggggac tcagctttgt atttctgtgc cagcggggat       60
tccaattcac ccctccactt tgggaac                                           87
```

```
<210> SEQ ID NO 5
<211> LENGTH: 87
<212> TYPE: DNA
<213> ORGANISM: Artificial Sequence
<220> FEATURE:
<223> OTHER INFORMATION: Synthetic polynucleotide

<400> SEQUENCE: 5
taaaccctga gctctctgga gctgggggac tcagctttgt atttctgtgc cagcggggat      60
tccaattcac ccctccactt tgggaac                                          87

<210> SEQ ID NO 6
<211> LENGTH: 87
<212> TYPE: DNA
<213> ORGANISM: Artificial Sequence
<220> FEATURE:
<223> OTHER INFORMATION: Synthetic polynucleotide

<400> SEQUENCE: 6
ctaaacctga gctctctgga gctgggggac tcagctttgt atttctgtgc cagcggggat      60
tccaattcac ccctccactt tgggaac                                          87

<210> SEQ ID NO 7
<211> LENGTH: 87
<212> TYPE: DNA
<213> ORGANISM: Artificial Sequence
<220> FEATURE:
<223> OTHER INFORMATION: Synthetic polynucleotide

<400> SEQUENCE: 7
ctaaacctga gctctctgga gctgggggac tcagctttgt atttctgtgc cagcggggat      60
tccaattcac ccctccactt tgggaac                                          87

<210> SEQ ID NO 8
<211> LENGTH: 87
<212> TYPE: DNA
<213> ORGANISM: Artificial Sequence
<220> FEATURE:
<223> OTHER INFORMATION: Synthetic polynucleotide

<400> SEQUENCE: 8
gtgaacgcct tgttgctggg ggactcggcc ctgtatctct gtgccagcag cgggggacag      60
attgtatacg agcagtactt cgggccg                                          87

<210> SEQ ID NO 9
<211> LENGTH: 87
<212> TYPE: DNA
<213> ORGANISM: Artificial Sequence
<220> FEATURE:
<223> OTHER INFORMATION: Synthetic polynucleotide

<400> SEQUENCE: 9
tgtgaacgcc ttgttgctgg ggactcggcc ctgtatctct gtgccagcag cgggggacag      60
attgtatacg agcagtactt cgggccg                                          87

<210> SEQ ID NO 10
<211> LENGTH: 87
<212> TYPE: DNA
<213> ORGANISM: Artificial Sequence
<220> FEATURE:
<223> OTHER INFORMATION: Synthetic polynucleotide

<400> SEQUENCE: 10
```

```
gtgaacgcct tggagctgga cgactcggcc ctgtatctct gtgccagcag cggggacag      60 attgtatacg agcagtactt cgggccg                                          87

<210> SEQ ID NO 11
<211> LENGTH: 87
<212> TYPE: DNA
<213> ORGANISM: Artificial Sequence
<220> FEATURE:
<223> OTHER INFORMATION: Synthetic polynucleotide

<400> SEQUENCE: 11
gtgaacgcct tgttgctggg ggactcggcc ctgtatctct gtgccagcag cggggacag      60 attgtatacg agcagtactt cgggccg                                          87

<210> SEQ ID NO 12
<211> LENGTH: 87
<212> TYPE: DNA
<213> ORGANISM: Artificial Sequence
<220> FEATURE:
<223> OTHER INFORMATION: Synthetic polynucleotide

<400> SEQUENCE: 12
acagtgacca gtgcccatcc tgaagacagc agcttctaca tctgcagtgc aaggggagga    60
aggggcggag actacacctt cggttcg                                          87

<210> SEQ ID NO 13
<211> LENGTH: 87
<212> TYPE: DNA
<213> ORGANISM: Artificial Sequence
<220> FEATURE:
<223> OTHER INFORMATION: Synthetic polynucleotide

<400> SEQUENCE: 13
acagtgacca gtgcccatcc tgaagacagc agcttctaca tctgcagtgc aaggggagga    60
aggggcggag actacacctt cggttcg                                          87

<210> SEQ ID NO 14
<211> LENGTH: 87
<212> TYPE: DNA
<213> ORGANISM: Artificial Sequence
<220> FEATURE:
<223> OTHER INFORMATION: Synthetic polynucleotide

<400> SEQUENCE: 14
acagtgacca gtgcccatcc tgaagacagc agcttctaca tctgcagtgc gaggggagga    60
aggggcggag actacacctt cggttcg                                          87

<210> SEQ ID NO 15
<211> LENGTH: 87
<212> TYPE: DNA
<213> ORGANISM: Artificial Sequence
<220> FEATURE:
<223> OTHER INFORMATION: Synthetic polynucleotide

<400> SEQUENCE: 15
ctgaaggtgc agcctgcaga actggaggat tctggagttt atttctgtgc cagcagccaa    60
gactggactg aagctttctt tggacaa                                          87

<210> SEQ ID NO 16
<211> LENGTH: 87
<212> TYPE: DNA
```

```
<213> ORGANISM: Artificial Sequence
<220> FEATURE:
<223> OTHER INFORMATION: Synthetic polynucleotide

<400> SEQUENCE: 16
ctgaaggtgc agcctgcaga actggaggat tctggagttt atttctgtgc cagcagccaa    60
gattggactg aagctttctt tggacaa                                        87

<210> SEQ ID NO 17
<211> LENGTH: 12
<212> TYPE: PRT
<213> ORGANISM: Artificial Sequence
<220> FEATURE:
<223> OTHER INFORMATION: Synthetic TCR molecule

<400> SEQUENCE: 17

Cys Ala Ser Gly Asp Ser Asn Ser Pro Leu His Phe
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Synthetic TCR molecule

<400> SEQUENCE: 18

Cys Ala Ser Ser Gly Gly Gln Ile Val Tyr Glu Gln Tyr Phe
1               5                   10

<210> SEQ ID NO 19
<211> LENGTH: 13
<212> TYPE: PRT
<213> ORGANISM: Artificial Sequence
<220> FEATURE:
<223> OTHER INFORMATION: Synthetic TCR molecule

<400> SEQUENCE: 19

Cys Ser Ala Arg Gly Gly Arg Gly Gly Asp Tyr Thr Phe
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Synthetic TCR molecule

<400> SEQUENCE: 20

Cys Ala Ser Ser Gln Asp Trp Thr Glu Ala Phe Phe
1               5                   10

<210> SEQ ID NO 21
<211> LENGTH: 11
<212> TYPE: PRT
<213> ORGANISM: Hepatitis B virus

<400> SEQUENCE: 21

Ser Thr Leu Pro Glu Thr Ala Val Val Arg Arg
1               5                   10

<210> SEQ ID NO 22
<211> LENGTH: 10
<212> TYPE: PRT
<213> ORGANISM: Hepatitis B virus
```

```
<400> SEQUENCE: 22

Ser Thr Leu Pro Glu Thr Ala Val Val Arg
1               5                   10

<210> SEQ ID NO 23
<211> LENGTH: 11
<212> TYPE: PRT
<213> ORGANISM: Hepatitis B virus

<400> SEQUENCE: 23

Ser Thr Leu Pro Glu Thr Thr Val Val Arg Arg
1               5                   10

<210> SEQ ID NO 24
<211> LENGTH: 11
<212> TYPE: PRT
<213> ORGANISM: Hepatitis B virus

<400> SEQUENCE: 24

Ser Thr Leu Pro Glu Thr Thr Val Ile Arg Arg
1               5                   10

<210> SEQ ID NO 25
<211> LENGTH: 11
<212> TYPE: PRT
<213> ORGANISM: Hepatitis B virus

<400> SEQUENCE: 25

Ser Thr Pro Pro Glu Thr Thr Val Val Arg Arg
1               5                   10

<210> SEQ ID NO 26
<211> LENGTH: 11
<212> TYPE: PRT
<213> ORGANISM: Hepatitis B virus

<400> SEQUENCE: 26

Ser Thr Leu Pro Glu Thr Thr Val Val Gly Arg
1               5                   10

<210> SEQ ID NO 27
<211> LENGTH: 11
<212> TYPE: PRT
<213> ORGANISM: Hepatitis B virus

<400> SEQUENCE: 27

Ser Thr Ile Pro Glu Thr Thr Val Val Arg Arg
1               5                   10

<210> SEQ ID NO 28
<211> LENGTH: 10
<212> TYPE: PRT
<213> ORGANISM: Hepatitis B virus

<400> SEQUENCE: 28

Leu Val Val Asp Phe Ser Gln Phe Ser Arg
1               5                   10

<210> SEQ ID NO 29
<211> LENGTH: 28
<212> TYPE: DNA
<213> ORGANISM: Artificial Sequence
<220> FEATURE:
<223> OTHER INFORMATION: Synthetic polynucleotide
```

```
<400> SEQUENCE: 29
gctcttcttt ttcacctctg cctaatca                                          28

<210> SEQ ID NO 30
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 30
gctcttcaaa aagttgcatg gtgctgg                                           27

<210> SEQ ID NO 31
<211> LENGTH: 9
<212> TYPE: PRT
<213> ORGANISM: Artificial Sequence
<220> FEATURE:
<223> OTHER INFORMATION: UV cleavable peptide
<220> FEATURE:
<221> NAME/KEY: MISC_FEATURE
<222> LOCATION: (5)..(5)
<223> OTHER INFORMATION: X is 3-Amino-3-(2-nitrophenyl) propionic acid

<400> SEQUENCE: 31

Arg Val Phe Ala Xaa Ser Phe Ile Lys
1               5

<210> SEQ ID NO 32
<211> LENGTH: 8
<212> TYPE: PRT
<213> ORGANISM: Hepatitis B virus

<400> SEQUENCE: 32

His Gln Leu Asp Pro Ala Phe Lys
1               5

<210> SEQ ID NO 33
<211> LENGTH: 10
<212> TYPE: PRT
<213> ORGANISM: Hepatitis B virus

<400> SEQUENCE: 33

Ala Ser Thr Asn Arg Gln Ser Gly Arg Lys
1               5                   10

<210> SEQ ID NO 34
<211> LENGTH: 9
<212> TYPE: PRT
<213> ORGANISM: Hepatitis B virus

<400> SEQUENCE: 34

Ser Thr Asn Arg Gln Ser Gly Arg Lys
1               5

<210> SEQ ID NO 35
<211> LENGTH: 8
<212> TYPE: PRT
<213> ORGANISM: Hepatitis B virus

<400> SEQUENCE: 35

Ser Thr Asn Arg Gln Ser Gly Arg
1               5

<210> SEQ ID NO 36
```

```
<211> LENGTH: 11
<212> TYPE: PRT
<213> ORGANISM: Hepatitis B virus

<400> SEQUENCE: 36

Ser Thr Phe His Gln Ala Leu Leu Asp Pro Arg
1               5                   10

<210> SEQ ID NO 37
<211> LENGTH: 11
<212> TYPE: PRT
<213> ORGANISM: Hepatitis B virus

<400> SEQUENCE: 37

Thr Thr Phe His Gln Ala Leu Leu Asp Pro Arg
1               5                   10

<210> SEQ ID NO 38
<211> LENGTH: 11
<212> TYPE: PRT
<213> ORGANISM: Hepatitis B virus

<400> SEQUENCE: 38

Thr Thr Phe His Gln Thr Leu Gln Asp Pro Arg
1               5                   10

<210> SEQ ID NO 39
<211> LENGTH: 11
<212> TYPE: PRT
<213> ORGANISM: Hepatitis B virus

<400> SEQUENCE: 39

Thr Leu Gln Asp Pro Arg Val Arg Ala Leu Tyr
1               5                   10

<210> SEQ ID NO 40
<211> LENGTH: 11
<212> TYPE: PRT
<213> ORGANISM: Hepatitis B virus

<400> SEQUENCE: 40

Ala Leu Leu Asp Pro Arg Val Arg Gly Leu Tyr
1               5                   10

<210> SEQ ID NO 41
<211> LENGTH: 11
<212> TYPE: PRT
<213> ORGANISM: Hepatitis B virus

<400> SEQUENCE: 41

Thr Val Ser Ala Ile Ser Ser Ile Leu Ser Lys
1               5                   10

<210> SEQ ID NO 42
<211> LENGTH: 11
<212> TYPE: PRT
<213> ORGANISM: Hepatitis B virus

<400> SEQUENCE: 42

Thr Val Ser Thr Ile Ser Ser Ile Leu Ser Lys
1               5                   10

<210> SEQ ID NO 43
<211> LENGTH: 11
<212> TYPE: PRT
```

<213> ORGANISM: Hepatitis B virus

<400> SEQUENCE: 43

Thr Ala Ser Pro Ile Ser Ser Ile Phe Ser Lys
1               5                   10

<210> SEQ ID NO 44
<211> LENGTH: 11
<212> TYPE: PRT
<213> ORGANISM: Hepatitis B virus

<400> SEQUENCE: 44

Thr Ala Ser Pro Ile Ser Ser Ile Phe Ser Arg
1 5 10

<210> SEQ ID NO 45
<211> LENGTH: 10
<212> TYPE: PRT
<213> ORGANISM: Hepatitis B virus

<400> SEQUENCE: 45

Val Ser Ala Ile Ser Ser Ile Leu Ser Lys
1 5 10

<210> SEQ ID NO 46
<211> LENGTH: 10
<212> TYPE: PRT
<213> ORGANISM: Hepatitis B virus

<400> SEQUENCE: 46

Ala Ser Pro Ile Ser Ser Ile Phe Ser Lys
1 5 10

<210> SEQ ID NO 47
<211> LENGTH: 10
<212> TYPE: PRT
<213> ORGANISM: Hepatitis B virus

<400> SEQUENCE: 47

Val Ser Thr Ile Ser Ser Ile Leu Ser Lys
1 5 10

<210> SEQ ID NO 48
<211> LENGTH: 10
<212> TYPE: PRT
<213> ORGANISM: Hepatitis B virus

<400> SEQUENCE: 48

Ala Ser Pro Ile Ser Ser Ile Phe Ser Arg
1 5 10

<210> SEQ ID NO 49
<211> LENGTH: 9
<212> TYPE: PRT
<213> ORGANISM: Hepatitis B virus

<400> SEQUENCE: 49

Ser Thr Ile Ser Ser Ile Leu Ser Lys
1 5

<210> SEQ ID NO 50
<211> LENGTH: 9
<212> TYPE: PRT
<213> ORGANISM: Hepatitis B virus

```
<400> SEQUENCE: 50

Ser Ala Ile Ser Ser Ile Leu Ser Lys
1               5

<210> SEQ ID NO 51
<211> LENGTH: 9
<212> TYPE: PRT
<213> ORGANISM: Hepatitis B virus

<400> SEQUENCE: 51

Ser Pro Ile Ser Ser Ile Phe Ser Lys
1               5

<210> SEQ ID NO 52
<211> LENGTH: 9
<212> TYPE: PRT
<213> ORGANISM: Hepatitis B virus

<400> SEQUENCE: 52

Ser Pro Ile Ser Ser Ile Phe Ser Arg
1               5

<210> SEQ ID NO 53
<211> LENGTH: 8
<212> TYPE: PRT
<213> ORGANISM: Hepatitis B virus

<400> SEQUENCE: 53

Thr Ile Ser Ser Ile Leu Ser Lys
1               5

<210> SEQ ID NO 54
<211> LENGTH: 8
<212> TYPE: PRT
<213> ORGANISM: Hepatitis B virus

<400> SEQUENCE: 54

Ala Ile Ser Ser Ile Leu Ser Lys
1               5

<210> SEQ ID NO 55
<211> LENGTH: 8
<212> TYPE: PRT
<213> ORGANISM: Hepatitis B virus

<400> SEQUENCE: 55

Pro Ile Ser Ser Ile Phe Ser Lys
1               5

<210> SEQ ID NO 56
<211> LENGTH: 11
<212> TYPE: PRT
<213> ORGANISM: Hepatitis B virus

<400> SEQUENCE: 56

Val Leu Gln Ala Gly Phe Phe Leu Leu Thr Lys
1               5                   10

<210> SEQ ID NO 57
<211> LENGTH: 11
<212> TYPE: PRT
<213> ORGANISM: Hepatitis B virus

<400> SEQUENCE: 57
```

Val Leu Gln Ala Gly Phe Phe Ser Leu Thr Lys
1               5                   10

<210> SEQ ID NO 58
<211> LENGTH: 11
<212> TYPE: PRT
<213> ORGANISM: Hepatitis B virus

<400> SEQUENCE: 58

Val Leu Gln Ala Gly Phe Phe Leu Leu Thr Arg
1               5                   10

<210> SEQ ID NO 59
<211> LENGTH: 10
<212> TYPE: PRT
<213> ORGANISM: Hepatitis B virus

<400> SEQUENCE: 59

Leu Gln Ala Gly Phe Phe Leu Leu Thr Lys
1               5                   10

<210> SEQ ID NO 60
<211> LENGTH: 10
<212> TYPE: PRT
<213> ORGANISM: Hepatitis B virus

<400> SEQUENCE: 60

Leu Gln Ala Gly Phe Phe Ser Leu Thr Lys
1               5                   10

<210> SEQ ID NO 61
<211> LENGTH: 10
<212> TYPE: PRT
<213> ORGANISM: Hepatitis B virus

<400> SEQUENCE: 61

Leu Gln Ala Gly Phe Phe Leu Leu Thr Arg
1               5                   10

<210> SEQ ID NO 62
<211> LENGTH: 9
<212> TYPE: PRT
<213> ORGANISM: Hepatitis B virus

<400> SEQUENCE: 62

Gln Ala Gly Phe Phe Leu Leu Thr Lys
1               5

<210> SEQ ID NO 63
<211> LENGTH: 9
<212> TYPE: PRT
<213> ORGANISM: Hepatitis B virus

<400> SEQUENCE: 63

Gln Ala Gly Phe Phe Ser Leu Thr Lys
1               5

<210> SEQ ID NO 64
<211> LENGTH: 8
<212> TYPE: PRT
<213> ORGANISM: Hepatitis B virus

<400> SEQUENCE: 64

Ala Gly Phe Phe Leu Leu Thr Lys
1               5

<210> SEQ ID NO 65
<211> LENGTH: 8
<212> TYPE: PRT
<213> ORGANISM: Hepatitis B virus

<400> SEQUENCE: 65

Ala Gly Phe Phe Ser Leu Thr Lys
1               5

<210> SEQ ID NO 66
<211> LENGTH: 11
<212> TYPE: PRT
<213> ORGANISM: Hepatitis B virus

<400> SEQUENCE: 66

Thr Ser Leu Asn Phe Leu Gly Gly Ala Pro Lys
1               5                   10

<210> SEQ ID NO 67
<211> LENGTH: 10
<212> TYPE: PRT
<213> ORGANISM: Hepatitis B virus

<400> SEQUENCE: 67

Ser Leu Asn Phe Leu Gly Gly Ala Pro Lys
1               5                   10

<210> SEQ ID NO 68
<211> LENGTH: 11
<212> TYPE: PRT
<213> ORGANISM: Hepatitis B virus

<400> SEQUENCE: 68

Thr Ser Cys Pro Pro Ile Cys Pro Gly Tyr Arg
1               5                   10

<210> SEQ ID NO 69
<211> LENGTH: 10
<212> TYPE: PRT
<213> ORGANISM: Hepatitis B virus

<400> SEQUENCE: 69

Leu Ile Phe Leu Leu Val Leu Leu Asp Tyr
1               5                   10

<210> SEQ ID NO 70
<211> LENGTH: 11
<212> TYPE: PRT
<213> ORGANISM: Hepatitis B virus

<400> SEQUENCE: 70

Gly Thr Ser Thr Thr Ser Thr Gly Pro Cys Lys
1               5                   10

<210> SEQ ID NO 71
<211> LENGTH: 11
<212> TYPE: PRT
<213> ORGANISM: Hepatitis B virus

<400> SEQUENCE: 71

Gly Ser Ser Thr Thr Ser Thr Gly Pro Cys Lys
1               5                   10

```
<210> SEQ ID NO 72
<211> LENGTH: 10
<212> TYPE: PRT
<213> ORGANISM: Hepatitis B virus

<400> SEQUENCE: 72

Ser Ser Thr Thr Ser Thr Gly Pro Cys Lys
1               5                   10

<210> SEQ ID NO 73
<211> LENGTH: 10
<212> TYPE: PRT
<213> ORGANISM: Hepatitis B virus

<400> SEQUENCE: 73

Thr Ser Thr Thr Ser Thr Gly Pro Cys Lys
1               5                   10

<210> SEQ ID NO 74
<211> LENGTH: 9
<212> TYPE: PRT
<213> ORGANISM: Hepatitis B virus

<400> SEQUENCE: 74

Ser Thr Thr Ser Thr Gly Pro Cys Lys
1               5

<210> SEQ ID NO 75
<211> LENGTH: 8
<212> TYPE: PRT
<213> ORGANISM: Hepatitis B virus

<400> SEQUENCE: 75

Thr Thr Ser Thr Gly Pro Cys Lys
1               5

<210> SEQ ID NO 76
<211> LENGTH: 11
<212> TYPE: PRT
<213> ORGANISM: Hepatitis B virus

<400> SEQUENCE: 76

Thr Ser Met Phe Pro Ser Cys Cys Cys Thr Lys
1               5                   10

<210> SEQ ID NO 77
<211> LENGTH: 10
<212> TYPE: PRT
<213> ORGANISM: Hepatitis B virus

<400> SEQUENCE: 77

Ser Met Phe Pro Ser Cys Cys Cys Thr Lys
1               5                   10

<210> SEQ ID NO 78
<211> LENGTH: 10
<212> TYPE: PRT
<213> ORGANISM: Hepatitis B virus

<400> SEQUENCE: 78

Ser Met Tyr Pro Ser Cys Cys Cys Thr Lys
1               5                   10

<210> SEQ ID NO 79
<211> LENGTH: 11
```

```
<212> TYPE: PRT
<213> ORGANISM: Hepatitis B virus

<400> SEQUENCE: 79

Ile Pro Ile Pro Ser Ser Trp Ala Phe Ala Lys
1               5                   10

<210> SEQ ID NO 80
<211> LENGTH: 10
<212> TYPE: PRT
<213> ORGANISM: Hepatitis B virus

<400> SEQUENCE: 80

Pro Ile Pro Ser Ser Trp Ala Phe Ala Lys
1               5                   10

<210> SEQ ID NO 81
<211> LENGTH: 9
<212> TYPE: PRT
<213> ORGANISM: Hepatitis B virus

<400> SEQUENCE: 81

Ile Pro Ser Ser Trp Ala Phe Ala Lys
1               5

<210> SEQ ID NO 82
<211> LENGTH: 8
<212> TYPE: PRT
<213> ORGANISM: Hepatitis B virus

<400> SEQUENCE: 82

Pro Ser Ser Trp Ala Phe Ala Lys
1               5

<210> SEQ ID NO 83
<211> LENGTH: 8
<212> TYPE: PRT
<213> ORGANISM: Hepatitis B virus

<400> SEQUENCE: 83

Ser Ser Trp Ala Phe Ala Lys Tyr
1               5

<210> SEQ ID NO 84
<211> LENGTH: 8
<212> TYPE: PRT
<213> ORGANISM: Hepatitis B virus

<400> SEQUENCE: 84

Ser Val Ile Trp Met Met Trp Tyr
1               5

<210> SEQ ID NO 85
<211> LENGTH: 9
<212> TYPE: PRT
<213> ORGANISM: Hepatitis B virus

<400> SEQUENCE: 85

Ser Val Ile Trp Met Met Trp Phe Trp
1               5

<210> SEQ ID NO 86
<211> LENGTH: 9
<212> TYPE: PRT
<213> ORGANISM: Hepatitis B virus
```

<400> SEQUENCE: 86

Ser Val Ile Trp Met Met Trp Tyr Trp
1               5

<210> SEQ ID NO 87
<211> LENGTH: 11
<212> TYPE: PRT
<213> ORGANISM: Hepatitis B virus

<400> SEQUENCE: 87

Trp Met Met Trp Phe Trp Gly Pro Ser Leu Tyr
1               5                   10

<210> SEQ ID NO 88
<211> LENGTH: 11
<212> TYPE: PRT
<213> ORGANISM: Hepatitis B virus

<400> SEQUENCE: 88

Trp Met Met Trp Tyr Trp Gly Pro Ser Leu Tyr
1               5                   10

<210> SEQ ID NO 89
<211> LENGTH: 10
<212> TYPE: PRT
<213> ORGANISM: Hepatitis B virus

<400> SEQUENCE: 89

Met Met Trp Phe Trp Gly Pro Ser Leu Tyr
1               5                   10

<210> SEQ ID NO 90
<211> LENGTH: 10
<212> TYPE: PRT
<213> ORGANISM: Hepatitis B virus

<400> SEQUENCE: 90

Met Pro Leu Ser Tyr Leu His Phe Arg Lys
1               5                   10

<210> SEQ ID NO 91
<211> LENGTH: 10
<212> TYPE: PRT
<213> ORGANISM: Hepatitis B virus

<400> SEQUENCE: 91

Met Pro Leu Ser Tyr Gln His Phe Arg Lys
1               5                   10

<210> SEQ ID NO 92
<211> LENGTH: 9
<212> TYPE: PRT
<213> ORGANISM: Hepatitis B virus

<400> SEQUENCE: 92

Pro Leu Ser Tyr Leu His Phe Arg Lys
1               5

<210> SEQ ID NO 93
<211> LENGTH: 9
<212> TYPE: PRT
<213> ORGANISM: Hepatitis B virus

<400> SEQUENCE: 93

```
Pro Leu Ser Tyr Gln His Phe Arg Lys
1               5

<210> SEQ ID NO 94
<211> LENGTH: 8
<212> TYPE: PRT
<213> ORGANISM: Hepatitis B virus

<400> SEQUENCE: 94

Leu Ser Tyr Leu His Phe Arg Lys
1               5

<210> SEQ ID NO 95
<211> LENGTH: 8
<212> TYPE: PRT
<213> ORGANISM: Hepatitis B virus

<400> SEQUENCE: 95

Leu Ser Tyr Gln His Phe Arg Lys
1               5

<210> SEQ ID NO 96
<211> LENGTH: 11
<212> TYPE: PRT
<213> ORGANISM: Hepatitis B virus

<400> SEQUENCE: 96

Asn Leu Asn Val Ser Ile Pro Trp Thr His Lys
1               5                   10

<210> SEQ ID NO 97
<211> LENGTH: 9
<212> TYPE: PRT
<213> ORGANISM: Hepatitis B virus

<400> SEQUENCE: 97

Asn Val Ser Ile Pro Trp Thr His Lys
1               5

<210> SEQ ID NO 98
<211> LENGTH: 8
<212> TYPE: PRT
<213> ORGANISM: Hepatitis B virus

<400> SEQUENCE: 98

Val Ser Ile Pro Trp Thr His Lys
1               5

<210> SEQ ID NO 99
<211> LENGTH: 9
<212> TYPE: PRT
<213> ORGANISM: Hepatitis B virus

<400> SEQUENCE: 99

Lys Val Gly Asn Phe Thr Gly Leu Tyr
1               5

<210> SEQ ID NO 100
<211> LENGTH: 11
<212> TYPE: PRT
<213> ORGANISM: Hepatitis B virus

<400> SEQUENCE: 100

Tyr Ser Ser Thr Val Pro Cys Phe Asn Pro Lys
```

```
<210> SEQ ID NO 101
<211> LENGTH: 10
<212> TYPE: PRT
<213> ORGANISM: Hepatitis B virus

<400> SEQUENCE: 101

Ser Ser Thr Val Pro Cys Phe Asn Pro Lys
1               5                   10

<210> SEQ ID NO 102
<211> LENGTH: 9
<212> TYPE: PRT
<213> ORGANISM: Hepatitis B virus

<400> SEQUENCE: 102

Ser Thr Val Pro Cys Phe Asn Pro Lys
1               5

<210> SEQ ID NO 103
<211> LENGTH: 8
<212> TYPE: PRT
<213> ORGANISM: Hepatitis B virus

<400> SEQUENCE: 103

Thr Val Pro Cys Phe Asn Pro Lys
1               5

<210> SEQ ID NO 104
<211> LENGTH: 11
<212> TYPE: PRT
<213> ORGANISM: Hepatitis B virus

<400> SEQUENCE: 104

Gln Thr Pro Ser Phe Pro His Ile His Leu Lys
1               5                   10

<210> SEQ ID NO 105
<211> LENGTH: 10
<212> TYPE: PRT
<213> ORGANISM: Hepatitis B virus

<400> SEQUENCE: 105

Thr Pro Ser Phe Pro His Ile His Leu Lys
1               5                   10

<210> SEQ ID NO 106
<211> LENGTH: 9
<212> TYPE: PRT
<213> ORGANISM: Hepatitis B virus

<400> SEQUENCE: 106

Pro Ser Phe Pro His Ile His Leu Lys
1               5

<210> SEQ ID NO 107
<211> LENGTH: 8
<212> TYPE: PRT
<213> ORGANISM: Hepatitis B virus

<400> SEQUENCE: 107

Ser Phe Pro His Ile His Leu Lys
1               5
```

```
<210> SEQ ID NO 108
<211> LENGTH: 10
<212> TYPE: PRT
<213> ORGANISM: Hepatitis B virus

<400> SEQUENCE: 108

Tyr Val Gly Pro Leu Thr Val Asn Glu Lys
1               5                   10

<210> SEQ ID NO 109
<211> LENGTH: 10
<212> TYPE: PRT
<213> ORGANISM: Hepatitis B virus

<400> SEQUENCE: 109

Leu Thr Ile Asn Glu Asn Arg Arg Leu Lys
1               5                   10

<210> SEQ ID NO 110
<211> LENGTH: 10
<212> TYPE: PRT
<213> ORGANISM: Hepatitis B virus

<400> SEQUENCE: 110

Leu Thr Val Asn Glu Thr Arg Arg Leu Lys
1               5                   10

<210> SEQ ID NO 111
<211> LENGTH: 10
<212> TYPE: PRT
<213> ORGANISM: Hepatitis B virus

<400> SEQUENCE: 111

Leu Thr Val Asn Glu Asn Arg Arg Leu Lys
1               5                   10

<210> SEQ ID NO 112
<211> LENGTH: 10
<212> TYPE: PRT
<213> ORGANISM: Hepatitis B virus

<400> SEQUENCE: 112

Leu Thr Val Asn Glu Lys Arg Arg Leu Lys
1               5                   10

<210> SEQ ID NO 113
<211> LENGTH: 9
<212> TYPE: PRT
<213> ORGANISM: Hepatitis B virus

<400> SEQUENCE: 113

Thr Val Asn Glu Thr Arg Arg Leu Lys
1               5

<210> SEQ ID NO 114
<211> LENGTH: 9
<212> TYPE: PRT
<213> ORGANISM: Hepatitis B virus

<400> SEQUENCE: 114

Thr Val Asn Glu Asn Arg Arg Leu Lys
1               5

<210> SEQ ID NO 115
```

```
<211> LENGTH: 9
<212> TYPE: PRT
<213> ORGANISM: Hepatitis B virus

<400> SEQUENCE: 115

Thr Val Asn Glu Lys Arg Arg Leu Lys
1               5

<210> SEQ ID NO 116
<211> LENGTH: 9
<212> TYPE: PRT
<213> ORGANISM: Hepatitis B virus

<400> SEQUENCE: 116

Thr Ile Asn Glu Asn Arg Arg Leu Lys
1               5

<210> SEQ ID NO 117
<211> LENGTH: 9
<212> TYPE: PRT
<213> ORGANISM: Hepatitis B virus

<400> SEQUENCE: 117

Lys Leu Ile Met Pro Ala Arg Phe Tyr
1               5

<210> SEQ ID NO 118
<211> LENGTH: 8
<212> TYPE: PRT
<213> ORGANISM: Hepatitis B virus

<400> SEQUENCE: 118

Leu Val Met Pro Ala Arg Phe Tyr
1               5

<210> SEQ ID NO 119
<211> LENGTH: 8
<212> TYPE: PRT
<213> ORGANISM: Hepatitis B virus

<400> SEQUENCE: 119

Arg Phe Tyr Pro Asn Leu Thr Lys
1               5

<210> SEQ ID NO 120
<211> LENGTH: 8
<212> TYPE: PRT
<213> ORGANISM: Hepatitis B virus

<400> SEQUENCE: 120

Arg Phe Tyr Pro Asn Val Thr Lys
1               5

<210> SEQ ID NO 121
<211> LENGTH: 10
<212> TYPE: PRT
<213> ORGANISM: Hepatitis B virus

<400> SEQUENCE: 121

Asn Val Thr Lys Tyr Leu Pro Leu Asp Lys
1               5                   10

<210> SEQ ID NO 122
<211> LENGTH: 9
<212> TYPE: PRT
```

<213> ORGANISM: Hepatitis B virus

<400> SEQUENCE: 122

Val Thr Lys Tyr Leu Pro Leu Asp Lys
1               5

<210> SEQ ID NO 123
<211> LENGTH: 9
<212> TYPE: PRT
<213> ORGANISM: Hepatitis B virus

<400> SEQUENCE: 123

Leu Thr Lys Tyr Leu Pro Leu Asp Lys
1               5

<210> SEQ ID NO 124
<211> LENGTH: 8
<212> TYPE: PRT
<213> ORGANISM: Hepatitis B virus

<400> SEQUENCE: 124

His Thr Val Asn His Tyr Phe Lys
1               5

<210> SEQ ID NO 125
<211> LENGTH: 10
<212> TYPE: PRT
<213> ORGANISM: Hepatitis B virus

<400> SEQUENCE: 125

His Thr Val Asn His Tyr Phe Gln Thr Arg
1               5                   10

<210> SEQ ID NO 126
<211> LENGTH: 10
<212> TYPE: PRT
<213> ORGANISM: Hepatitis B virus

<400> SEQUENCE: 126

His Val Val Asp His Tyr Phe Gln Thr Arg
1               5                   10

<210> SEQ ID NO 127
<211> LENGTH: 10
<212> TYPE: PRT
<213> ORGANISM: Hepatitis B virus

<400> SEQUENCE: 127

His Val Val Asn His Tyr Phe Gln Thr Arg
1               5                   10

<210> SEQ ID NO 128
<211> LENGTH: 9
<212> TYPE: PRT
<213> ORGANISM: Hepatitis B virus

<400> SEQUENCE: 128

Thr Val Asn His Tyr Phe Gln Thr Arg
1               5

<210> SEQ ID NO 129
<211> LENGTH: 9
<212> TYPE: PRT
<213> ORGANISM: Hepatitis B virus

<400> SEQUENCE: 129

Val Val Asn His Tyr Phe Gln Thr Arg
1               5

<210> SEQ ID NO 130
<211> LENGTH: 9
<212> TYPE: PRT
<213> ORGANISM: Hepatitis B virus

<400> SEQUENCE: 130

Thr Val Asn His Tyr Phe Lys Thr Arg
1               5

<210> SEQ ID NO 131
<211> LENGTH: 9
<212> TYPE: PRT
<213> ORGANISM: Hepatitis B virus

<400> SEQUENCE: 131

Ile Val Asn His Tyr Phe Gln Thr Arg
1               5

<210> SEQ ID NO 132
<211> LENGTH: 11
<212> TYPE: PRT
<213> ORGANISM: Hepatitis B virus

<400> SEQUENCE: 132

Thr Val Asn His Tyr Phe Gln Thr Arg His Tyr
1               5                   10

<210> SEQ ID NO 133
<211> LENGTH: 11
<212> TYPE: PRT
<213> ORGANISM: Hepatitis B virus

<400> SEQUENCE: 133

Thr Val Asn His Tyr Phe Lys Thr Arg His Tyr
1               5                   10

<210> SEQ ID NO 134
<211> LENGTH: 9
<212> TYPE: PRT
<213> ORGANISM: Hepatitis B virus

<400> SEQUENCE: 134

Val Val His His Tyr Phe Gln Thr Arg
1               5

<210> SEQ ID NO 135
<211> LENGTH: 9
<212> TYPE: PRT
<213> ORGANISM: Hepatitis B virus

<400> SEQUENCE: 135

Val Val Asp His Tyr Phe Gln Thr Arg
1               5

<210> SEQ ID NO 136
<211> LENGTH: 11
<212> TYPE: PRT
<213> ORGANISM: Hepatitis B virus

<400> SEQUENCE: 136

Val Val Asn His Tyr Phe Gln Thr Arg His Tyr
1               5                   10

<210> SEQ ID NO 137
<211> LENGTH: 11
<212> TYPE: PRT
<213> ORGANISM: Hepatitis B virus

<400> SEQUENCE: 137

Lys Thr Arg His Tyr Leu His Thr Leu Trp Lys
1               5                   10

<210> SEQ ID NO 138
<211> LENGTH: 11
<212> TYPE: PRT
<213> ORGANISM: Hepatitis B virus

<400> SEQUENCE: 138

Gln Thr Arg His Tyr Leu His Thr Leu Trp Lys
1               5                   10

<210> SEQ ID NO 139
<211> LENGTH: 9
<212> TYPE: PRT
<213> ORGANISM: Hepatitis B virus

<400> SEQUENCE: 139

Arg His Tyr Leu His Thr Leu Trp Lys
1               5

<210> SEQ ID NO 140
<211> LENGTH: 11
<212> TYPE: PRT
<213> ORGANISM: Hepatitis B virus

<400> SEQUENCE: 140

His Thr Leu Trp Lys Ala Gly Ile Leu Tyr Lys
1               5                   10

<210> SEQ ID NO 141
<211> LENGTH: 11
<212> TYPE: PRT
<213> ORGANISM: Hepatitis B virus

<400> SEQUENCE: 141

His Thr Leu Trp Glu Ala Gly Ile Leu Tyr Lys
1               5                   10

<210> SEQ ID NO 142
<211> LENGTH: 10
<212> TYPE: PRT
<213> ORGANISM: Hepatitis B virus

<400> SEQUENCE: 142

His Thr Leu Trp Lys Ala Gly Ile Leu Tyr
1               5                   10

<210> SEQ ID NO 143
<211> LENGTH: 10
<212> TYPE: PRT
<213> ORGANISM: Hepatitis B virus

<400> SEQUENCE: 143

His Thr Leu Trp Glu Ala Gly Ile Leu Tyr
1               5                   10

<210> SEQ ID NO 144
<211> LENGTH: 10
<212> TYPE: PRT
<213> ORGANISM: Hepatitis B virus

<400> SEQUENCE: 144

Thr Leu Trp Glu Ala Gly Ile Leu Tyr Lys
1               5                   10

<210> SEQ ID NO 145
<211> LENGTH: 10
<212> TYPE: PRT
<213> ORGANISM: Hepatitis B virus

<400> SEQUENCE: 145

Thr Leu Trp Lys Ala Gly Ile Leu Tyr Lys
1               5                   10

<210> SEQ ID NO 146
<211> LENGTH: 8
<212> TYPE: PRT
<213> ORGANISM: Hepatitis B virus

<400> SEQUENCE: 146

Ser Thr Arg Ser Ala Ser Phe Tyr
1               5

<210> SEQ ID NO 147
<211> LENGTH: 10
<212> TYPE: PRT
<213> ORGANISM: Hepatitis B virus

<400> SEQUENCE: 147

Arg Ser Ala Ser Phe Tyr Gly Ser Pro Tyr
1               5                   10

<210> SEQ ID NO 148
<211> LENGTH: 10
<212> TYPE: PRT
<213> ORGANISM: Hepatitis B virus

<400> SEQUENCE: 148

Arg Ser Ala Ser Phe Cys Gly Ser Pro Tyr
1               5                   10

<210> SEQ ID NO 149
<211> LENGTH: 9
<212> TYPE: PRT
<213> ORGANISM: Hepatitis B virus

<400> SEQUENCE: 149

Ser Ala Ser Phe Tyr Gly Ser Pro Tyr
1               5

<210> SEQ ID NO 150
<211> LENGTH: 9
<212> TYPE: PRT
<213> ORGANISM: Hepatitis B virus

<400> SEQUENCE: 150

Ser Ala Ser Phe Cys Gly Ser Pro Tyr
1               5

```
<210> SEQ ID NO 151
<211> LENGTH: 8
<212> TYPE: PRT
<213> ORGANISM: Hepatitis B virus

<400> SEQUENCE: 151

Ala Ser Phe Tyr Gly Ser Pro Tyr
1               5

<210> SEQ ID NO 152
<211> LENGTH: 8
<212> TYPE: PRT
<213> ORGANISM: Hepatitis B virus

<400> SEQUENCE: 152

Ala Ser Phe Cys Gly Ser Pro Tyr
1               5

<210> SEQ ID NO 153
<211> LENGTH: 8
<212> TYPE: PRT
<213> ORGANISM: Hepatitis B virus

<400> SEQUENCE: 153

Arg Leu Val Phe Gln Thr Ser Lys
1               5

<210> SEQ ID NO 154
<211> LENGTH: 8
<212> TYPE: PRT
<213> ORGANISM: Hepatitis B virus

<400> SEQUENCE: 154

Leu Val Phe Gln Thr Ser Glu Arg
1               5

<210> SEQ ID NO 155
<211> LENGTH: 8
<212> TYPE: PRT
<213> ORGANISM: Hepatitis B virus

<400> SEQUENCE: 155

Leu Val Phe Gln Thr Ser Thr Arg
1               5

<210> SEQ ID NO 156
<211> LENGTH: 8
<212> TYPE: PRT
<213> ORGANISM: Hepatitis B virus

<400> SEQUENCE: 156

Leu Val Phe Gln Thr Ser Lys Arg
1               5

<210> SEQ ID NO 157
<211> LENGTH: 9
<212> TYPE: PRT
<213> ORGANISM: Hepatitis B virus

<400> SEQUENCE: 157

Gln Thr Ser Glu Arg His Gly Asp Lys
1               5

<210> SEQ ID NO 158
<211> LENGTH: 9
```

```
<212> TYPE: PRT
<213> ORGANISM: Hepatitis B virus

<400> SEQUENCE: 158

Gln Thr Ser Lys Arg His Gly Asp Lys
1               5

<210> SEQ ID NO 159
<211> LENGTH: 8
<212> TYPE: PRT
<213> ORGANISM: Hepatitis B virus

<400> SEQUENCE: 159

Thr Ser Glu Arg His Gly Asp Lys
1               5

<210> SEQ ID NO 160
<211> LENGTH: 8
<212> TYPE: PRT
<213> ORGANISM: Hepatitis B virus

<400> SEQUENCE: 160

Thr Ser Lys Arg His Gly Asp Lys
1               5

<210> SEQ ID NO 161
<211> LENGTH: 10
<212> TYPE: PRT
<213> ORGANISM: Hepatitis B virus

<400> SEQUENCE: 161

Cys Ser Gln Ser Ser Gly Ile Leu Ser Arg
1               5                   10

<210> SEQ ID NO 162
<211> LENGTH: 9
<212> TYPE: PRT
<213> ORGANISM: Hepatitis B virus

<400> SEQUENCE: 162

Ser Gln Ser Ser Gly Ile Leu Ser Arg
1               5

<210> SEQ ID NO 163
<211> LENGTH: 8
<212> TYPE: PRT
<213> ORGANISM: Hepatitis B virus

<400> SEQUENCE: 163

Gln Ser Ser Gly Ile Leu Ser Arg
1               5

<210> SEQ ID NO 164
<211> LENGTH: 11
<212> TYPE: PRT
<213> ORGANISM: Hepatitis B virus

<400> SEQUENCE: 164

Gly Ile Leu Pro Arg Ser Ser Val Gly Pro Arg
1               5                   10

<210> SEQ ID NO 165
<211> LENGTH: 11
<212> TYPE: PRT
<213> ORGANISM: Hepatitis B virus
```

```
<400> SEQUENCE: 165

Ser Val Gly Ser Cys Ile Gln Ser Gln Leu Arg
1               5                   10

<210> SEQ ID NO 166
<211> LENGTH: 11
<212> TYPE: PRT
<213> ORGANISM: Hepatitis B virus

<400> SEQUENCE: 166

Ser Val Gly Pro Arg Ile Gln Ser Gln Leu Arg
1               5                   10

<210> SEQ ID NO 167
<211> LENGTH: 11
<212> TYPE: PRT
<213> ORGANISM: Hepatitis B virus

<400> SEQUENCE: 167

Ser Val Gly Pro Cys Ile Gln Ser Gln Leu Arg
1               5                   10

<210> SEQ ID NO 168
<211> LENGTH: 10
<212> TYPE: PRT
<213> ORGANISM: Hepatitis B virus

<400> SEQUENCE: 168

Gly Ser Cys Ile Gln Ser Gln Leu Arg Lys
1               5                   10

<210> SEQ ID NO 169
<211> LENGTH: 9
<212> TYPE: PRT
<213> ORGANISM: Hepatitis B virus

<400> SEQUENCE: 169

Gly Ser Cys Ile Gln Ser Gln Leu Arg
1               5

<210> SEQ ID NO 170
<211> LENGTH: 9
<212> TYPE: PRT
<213> ORGANISM: Hepatitis B virus

<400> SEQUENCE: 170

Ser Cys Ile Gln Ser Gln Leu Arg Lys
1               5

<210> SEQ ID NO 171
<211> LENGTH: 8
<212> TYPE: PRT
<213> ORGANISM: Hepatitis B virus

<400> SEQUENCE: 171

Arg Ile Gln Ser Gln Leu Arg Lys
1               5

<210> SEQ ID NO 172
<211> LENGTH: 8
<212> TYPE: PRT
<213> ORGANISM: Hepatitis B virus

<400> SEQUENCE: 172
```

```
Gly Ile Gln Ser Gln Leu Arg Lys
1               5
```

<210> SEQ ID NO 173
<211> LENGTH: 8
<212> TYPE: PRT
<213> ORGANISM: Hepatitis B virus

<400> SEQUENCE: 173

```
Cys Ile Gln Ser Gln Leu Arg Lys
1               5
```

<210> SEQ ID NO 174
<211> LENGTH: 8
<212> TYPE: PRT
<213> ORGANISM: Hepatitis B virus

<400> SEQUENCE: 174

```
Arg Ser Gln Phe Lys Gln Ser Arg
1               5
```

<210> SEQ ID NO 175
<211> LENGTH: 11
<212> TYPE: PRT
<213> ORGANISM: Hepatitis B virus

<400> SEQUENCE: 175

```
Ser Gln Leu Arg Lys Ser Arg Leu Gly Pro Lys
1               5                   10
```

<210> SEQ ID NO 176
<211> LENGTH: 9
<212> TYPE: PRT
<213> ORGANISM: Hepatitis B virus

<400> SEQUENCE: 176

```
Gln Gln Gly Ser Met Ala Ser Gly Lys
1               5
```

<210> SEQ ID NO 177
<211> LENGTH: 10
<212> TYPE: PRT
<213> ORGANISM: Hepatitis B virus

<400> SEQUENCE: 177

```
Arg Ser Met Ala Ser Gly Lys Pro Gly Arg
1               5                   10
```

<210> SEQ ID NO 178
<211> LENGTH: 10
<212> TYPE: PRT
<213> ORGANISM: Hepatitis B virus

<400> SEQUENCE: 178

```
Gly Ser Met Ala Ser Gly Lys Pro Gly Arg
1               5                   10
```

<210> SEQ ID NO 179
<211> LENGTH: 10
<212> TYPE: PRT
<213> ORGANISM: Hepatitis B virus

<400> SEQUENCE: 179

```
Gly Ser Met Ala Arg Gly Lys Ser Gly Arg
```

```
<210> SEQ ID NO 180
<211> LENGTH: 11
<212> TYPE: PRT
<213> ORGANISM: Hepatitis B virus

<400> SEQUENCE: 180

Ser Ile Arg Ala Arg Val His Pro Thr Ser Arg
1               5                   10

<210> SEQ ID NO 181
<211> LENGTH: 8
<212> TYPE: PRT
<213> ORGANISM: Hepatitis B virus

<400> SEQUENCE: 181

Arg Val His Ser Ser Pro Trp Arg
1               5

<210> SEQ ID NO 182
<211> LENGTH: 8
<212> TYPE: PRT
<213> ORGANISM: Hepatitis B virus

<400> SEQUENCE: 182

Arg Val His Pro Thr Ser Arg Arg
1               5

<210> SEQ ID NO 183
<211> LENGTH: 10
<212> TYPE: PRT
<213> ORGANISM: Hepatitis B virus

<400> SEQUENCE: 183

Ser Ala Ser Ser Ala Ser Ser Cys Leu Tyr
1               5                   10

<210> SEQ ID NO 184
<211> LENGTH: 10
<212> TYPE: PRT
<213> ORGANISM: Hepatitis B virus

<400> SEQUENCE: 184

Ser Thr Ser Ser Ala Ser Tyr Cys Leu His
1               5                   10

<210> SEQ ID NO 185
<211> LENGTH: 9
<212> TYPE: PRT
<213> ORGANISM: Hepatitis B virus

<400> SEQUENCE: 185

Ala Ser Ser Ala Ser Ser Cys Leu Tyr
1               5

<210> SEQ ID NO 186
<211> LENGTH: 8
<212> TYPE: PRT
<213> ORGANISM: Hepatitis B virus

<400> SEQUENCE: 186

Ser Ser Ala Ser Ser Cys Leu Tyr
1               5
```

<210> SEQ ID NO 187
<211> LENGTH: 11
<212> TYPE: PRT
<213> ORGANISM: Hepatitis B virus

<400> SEQUENCE: 187

Ala Ser Tyr Cys Leu His Gln Ser Ala Val Arg
1               5                   10

<210> SEQ ID NO 188
<211> LENGTH: 11
<212> TYPE: PRT
<213> ORGANISM: Hepatitis B virus

<400> SEQUENCE: 188

Ser Ser Ser Cys Leu His Gln Pro Ala Val Arg
1               5                   10

<210> SEQ ID NO 189
<211> LENGTH: 11
<212> TYPE: PRT
<213> ORGANISM: Hepatitis B virus

<400> SEQUENCE: 189

Ser Ser Ser Cys Leu His Gln Ser Ala Val Arg
1               5                   10

<210> SEQ ID NO 190
<211> LENGTH: 11
<212> TYPE: PRT
<213> ORGANISM: Hepatitis B virus

<400> SEQUENCE: 190

Ala Ser Ser Cys Leu His Gln Ser Ala Val Arg
1               5                   10

<210> SEQ ID NO 191
<211> LENGTH: 11
<212> TYPE: PRT
<213> ORGANISM: Hepatitis B virus

<400> SEQUENCE: 191

Ala Ser Ser Cys Leu Tyr Gln Ser Ala Val Arg
1               5                   10

<210> SEQ ID NO 192
<211> LENGTH: 11
<212> TYPE: PRT
<213> ORGANISM: Hepatitis B virus

<400> SEQUENCE: 192

Ser Ser Cys Leu His Gln Pro Ala Val Arg Lys
1               5                   10

<210> SEQ ID NO 193
<211> LENGTH: 11
<212> TYPE: PRT
<213> ORGANISM: Hepatitis B virus

<400> SEQUENCE: 193

Ser Ser Cys Leu Tyr Gln Ser Ala Val Arg Lys
1               5                   10

<210> SEQ ID NO 194

```
<211> LENGTH: 11
<212> TYPE: PRT
<213> ORGANISM: Hepatitis B virus

<400> SEQUENCE: 194

Ser Ser Cys Leu His Gln Ser Ala Val Arg Lys
1               5                   10

<210> SEQ ID NO 195
<211> LENGTH: 10
<212> TYPE: PRT
<213> ORGANISM: Hepatitis B virus

<400> SEQUENCE: 195

Ser Ser Cys Leu Tyr Gln Ser Ala Val Arg
1               5                   10

<210> SEQ ID NO 196
<211> LENGTH: 10
<212> TYPE: PRT
<213> ORGANISM: Hepatitis B virus

<400> SEQUENCE: 196

Ser Ser Cys Leu His Gln Pro Ala Val Arg
1               5                   10

<210> SEQ ID NO 197
<211> LENGTH: 10
<212> TYPE: PRT
<213> ORGANISM: Hepatitis B virus

<400> SEQUENCE: 197

Ser Ser Cys Leu His Gln Ser Ala Val Arg
1               5                   10

<210> SEQ ID NO 198
<211> LENGTH: 11
<212> TYPE: PRT
<213> ORGANISM: Hepatitis B virus

<400> SEQUENCE: 198

Ser Tyr Cys Leu His Gln Ser Ala Val Arg Lys
1               5                   10

<210> SEQ ID NO 199
<211> LENGTH: 9
<212> TYPE: PRT
<213> ORGANISM: Hepatitis B virus

<400> SEQUENCE: 199

Cys Leu Tyr Gln Ser Ala Val Arg Lys
1               5

<210> SEQ ID NO 200
<211> LENGTH: 10
<212> TYPE: PRT
<213> ORGANISM: Hepatitis B virus

<400> SEQUENCE: 200

Cys Leu Tyr Gln Ser Ala Val Arg Lys Lys
1               5                   10

<210> SEQ ID NO 201
<211> LENGTH: 9
<212> TYPE: PRT
```

<213> ORGANISM: Hepatitis B virus

<400> SEQUENCE: 201

Cys Leu His Gln Pro Ala Val Arg Lys
1               5

<210> SEQ ID NO 202
<211> LENGTH: 9
<212> TYPE: PRT
<213> ORGANISM: Hepatitis B virus

<400> SEQUENCE: 202

Cys Leu His Gln Ser Ala Val Arg Lys
1               5

<210> SEQ ID NO 203
<211> LENGTH: 8
<212> TYPE: PRT
<213> ORGANISM: Hepatitis B virus

<400> SEQUENCE: 203

Tyr Gln Ser Ala Val Arg Lys Lys
1               5

<210> SEQ ID NO 204
<211> LENGTH: 11
<212> TYPE: PRT
<213> ORGANISM: Hepatitis B virus

<400> SEQUENCE: 204

Lys Thr Ala Tyr Ser His Leu Ser Thr Ser Lys
1               5                   10

<210> SEQ ID NO 205
<211> LENGTH: 11
<212> TYPE: PRT
<213> ORGANISM: Hepatitis B virus

<400> SEQUENCE: 205

Lys Thr Ala Tyr Ser Leu Ile Ser Thr Ser Lys
1               5                   10

<210> SEQ ID NO 206
<211> LENGTH: 11
<212> TYPE: PRT
<213> ORGANISM: Hepatitis B virus

<400> SEQUENCE: 206

Lys Ala Ala Tyr Ser Leu Ile Ser Thr Ser Lys
1               5                   10

<210> SEQ ID NO 207
<211> LENGTH: 11
<212> TYPE: PRT
<213> ORGANISM: Hepatitis B virus

<400> SEQUENCE: 207

Lys Ala Ala Tyr Ser Leu Asn Ser Thr Ser Lys
1               5                   10

<210> SEQ ID NO 208
<211> LENGTH: 10
<212> TYPE: PRT
<213> ORGANISM: Hepatitis B virus

```
<400> SEQUENCE: 208

Lys Ala Tyr Ser His Leu Ser Ser Ser Lys
1               5                   10

<210> SEQ ID NO 209
<211> LENGTH: 10
<212> TYPE: PRT
<213> ORGANISM: Hepatitis B virus

<400> SEQUENCE: 209

Thr Ala Tyr Ser His Leu Ser Thr Ser Lys
1               5                   10

<210> SEQ ID NO 210
<211> LENGTH: 10
<212> TYPE: PRT
<213> ORGANISM: Hepatitis B virus

<400> SEQUENCE: 210

Thr Ala Tyr Ser Leu Ile Ser Thr Ser Lys
1               5                   10

<210> SEQ ID NO 211
<211> LENGTH: 10
<212> TYPE: PRT
<213> ORGANISM: Hepatitis B virus

<400> SEQUENCE: 211

Ala Ala Tyr Ser Leu Ile Ser Thr Ser Lys
1               5                   10

<210> SEQ ID NO 212
<211> LENGTH: 10
<212> TYPE: PRT
<213> ORGANISM: Hepatitis B virus

<400> SEQUENCE: 212

Ala Ala Tyr Ser Leu Asn Ser Thr Ser Lys
1               5                   10

<210> SEQ ID NO 213
<211> LENGTH: 11
<212> TYPE: PRT
<213> ORGANISM: Hepatitis B virus

<400> SEQUENCE: 213

Thr Ala Tyr Ser His Leu Ser Thr Ser Lys Arg
1               5                   10

<210> SEQ ID NO 214
<211> LENGTH: 11
<212> TYPE: PRT
<213> ORGANISM: Hepatitis B virus

<400> SEQUENCE: 214

Thr Ala Tyr Ser Leu Ile Ser Thr Ser Lys Arg
1               5                   10

<210> SEQ ID NO 215
<211> LENGTH: 11
<212> TYPE: PRT
<213> ORGANISM: Hepatitis B virus

<400> SEQUENCE: 215
```

```
Lys Ala Tyr Ser His Leu Ser Ser Ser Lys Arg
1               5                   10

<210> SEQ ID NO 216
<211> LENGTH: 9
<212> TYPE: PRT
<213> ORGANISM: Hepatitis B virus

<400> SEQUENCE: 216

Ala Tyr Ser His Leu Ser Ser Ser Lys
1               5

<210> SEQ ID NO 217
<211> LENGTH: 9
<212> TYPE: PRT
<213> ORGANISM: Hepatitis B virus

<400> SEQUENCE: 217

Ala Tyr Ser His Leu Ser Thr Ser Lys
1               5

<210> SEQ ID NO 218
<211> LENGTH: 9
<212> TYPE: PRT
<213> ORGANISM: Hepatitis B virus

<400> SEQUENCE: 218

Ala Tyr Ser Leu Ile Ser Thr Ser Lys
1               5

<210> SEQ ID NO 219
<211> LENGTH: 9
<212> TYPE: PRT
<213> ORGANISM: Hepatitis B virus

<400> SEQUENCE: 219

Ala Tyr Ser Leu Asn Ser Thr Ser Lys
1               5

<210> SEQ ID NO 220
<211> LENGTH: 8
<212> TYPE: PRT
<213> ORGANISM: Hepatitis B virus

<400> SEQUENCE: 220

Tyr Ser Leu Asn Ser Thr Ser Lys
1               5

<210> SEQ ID NO 221
<211> LENGTH: 8
<212> TYPE: PRT
<213> ORGANISM: Hepatitis B virus

<400> SEQUENCE: 221

Tyr Ser Leu Ile Ser Thr Ser Lys
1               5

<210> SEQ ID NO 222
<211> LENGTH: 8
<212> TYPE: PRT
<213> ORGANISM: Hepatitis B virus

<400> SEQUENCE: 222

Tyr Ser His Leu Ser Ser Ser Lys
1               5
```

<210> SEQ ID NO 223
<211> LENGTH: 8
<212> TYPE: PRT
<213> ORGANISM: Hepatitis B virus

<400> SEQUENCE: 223

Tyr Ser His Leu Ser Thr Ser Lys
1               5

<210> SEQ ID NO 224
<211> LENGTH: 8
<212> TYPE: PRT
<213> ORGANISM: Hepatitis B virus

<400> SEQUENCE: 224

Ser Leu Ile Ser Thr Ser Lys Arg
1               5

<210> SEQ ID NO 225
<211> LENGTH: 10
<212> TYPE: PRT
<213> ORGANISM: Hepatitis B virus

<400> SEQUENCE: 225

Ser Thr Ser Lys Gly His Ser Ser Ser Arg
1               5                   10

<210> SEQ ID NO 226
<211> LENGTH: 11
<212> TYPE: PRT
<213> ORGANISM: Hepatitis B virus

<400> SEQUENCE: 226

Ser Thr Ser Lys Gly His Ser Ser Ser Gly Arg
1               5                   10

<210> SEQ ID NO 227
<211> LENGTH: 9
<212> TYPE: PRT
<213> ORGANISM: Hepatitis B virus

<400> SEQUENCE: 227

Thr Ser Lys Gly His Ser Ser Ser Arg
1               5

<210> SEQ ID NO 228
<211> LENGTH: 10
<212> TYPE: PRT
<213> ORGANISM: Hepatitis B virus

<400> SEQUENCE: 228

Ser Ser Ser Arg His Ala Val Glu Leu Arg
1               5                   10

<210> SEQ ID NO 229
<211> LENGTH: 9
<212> TYPE: PRT
<213> ORGANISM: Hepatitis B virus

<400> SEQUENCE: 229

Arg Gln Phe Pro Pro Asn Thr Ser Arg
1               5

```
<210> SEQ ID NO 230
<211> LENGTH: 9
<212> TYPE: PRT
<213> ORGANISM: Hepatitis B virus

<400> SEQUENCE: 230

Ser Ser Ala Arg Ser Gln Ser Glu Arg
1               5

<210> SEQ ID NO 231
<211> LENGTH: 11
<212> TYPE: PRT
<213> ORGANISM: Hepatitis B virus

<400> SEQUENCE: 231

Ser Val Leu Ser Cys Trp Trp Leu Gln Phe Arg
1               5                   10

<210> SEQ ID NO 232
<211> LENGTH: 9
<212> TYPE: PRT
<213> ORGANISM: Hepatitis B virus

<400> SEQUENCE: 232

Ser Val Leu Ser Cys Trp Trp Leu Gln
1               5

<210> SEQ ID NO 233
<211> LENGTH: 11
<212> TYPE: PRT
<213> ORGANISM: Hepatitis B virus

<400> SEQUENCE: 233

Pro Val Leu Ser Cys Trp Trp Leu Gln Phe Arg
1               5                   10

<210> SEQ ID NO 234
<211> LENGTH: 10
<212> TYPE: PRT
<213> ORGANISM: Hepatitis B virus

<400> SEQUENCE: 234

Val Leu Ser Cys Trp Trp Leu Gln Phe Arg
1               5                   10

<210> SEQ ID NO 235
<211> LENGTH: 10
<212> TYPE: PRT
<213> ORGANISM: Hepatitis B virus

<400> SEQUENCE: 235

Ile Leu Ser Cys Trp Trp Leu Gln Phe Arg
1               5                   10

<210> SEQ ID NO 236
<211> LENGTH: 9
<212> TYPE: PRT
<213> ORGANISM: Hepatitis B virus

<400> SEQUENCE: 236

Leu Ser Cys Trp Trp Leu Gln Phe Arg
1               5

<210> SEQ ID NO 237
<211> LENGTH: 9
```

<212> TYPE: PRT
<213> ORGANISM: Hepatitis B virus

<400> SEQUENCE: 237

Pro Ser Cys Trp Trp Leu Gln Phe Arg
1               5

<210> SEQ ID NO 238
<211> LENGTH: 8
<212> TYPE: PRT
<213> ORGANISM: Hepatitis B virus

<400> SEQUENCE: 238

Trp Leu Gln Phe Arg Asn Ser Lys
1               5

<210> SEQ ID NO 239
<211> LENGTH: 11
<212> TYPE: PRT
<213> ORGANISM: Hepatitis B virus

<400> SEQUENCE: 239

Arg Val Thr Gly Gly Val Phe Leu Val Asp Lys
1               5                   10

<210> SEQ ID NO 240
<211> LENGTH: 11
<212> TYPE: PRT
<213> ORGANISM: Hepatitis B virus

<400> SEQUENCE: 240

Arg Ile Thr Gly Gly Val Phe Leu Val Asp Lys
1               5                   10

<210> SEQ ID NO 241
<211> LENGTH: 10
<212> TYPE: PRT
<213> ORGANISM: Hepatitis B virus

<400> SEQUENCE: 241

Val Thr Gly Gly Val Phe Leu Val Asp Lys
1               5                   10

<210> SEQ ID NO 242
<211> LENGTH: 10
<212> TYPE: PRT
<213> ORGANISM: Hepatitis B virus

<400> SEQUENCE: 242

Ile Thr Gly Gly Val Phe Leu Val Asp Lys
1               5                   10

<210> SEQ ID NO 243
<211> LENGTH: 9
<212> TYPE: PRT
<213> ORGANISM: Hepatitis B virus

<400> SEQUENCE: 243

Val Val Asp Phe Ser Gln Phe Ser Arg
1               5

<210> SEQ ID NO 244
<211> LENGTH: 9
<212> TYPE: PRT
<213> ORGANISM: Hepatitis B virus

<400> SEQUENCE: 244

Ser Gln Phe Ser Arg Gly Ser Thr Arg
1               5

<210> SEQ ID NO 245
<211> LENGTH: 9
<212> TYPE: PRT
<213> ORGANISM: Hepatitis B virus

<400> SEQUENCE: 245

Ser Gln Phe Ser Arg Gly Asn Thr Arg
1               5

<210> SEQ ID NO 246
<211> LENGTH: 10
<212> TYPE: PRT
<213> ORGANISM: Hepatitis B virus

<400> SEQUENCE: 246

Arg Gly Asn Thr Arg Val Ser Trp Pro Lys
1               5                   10

<210> SEQ ID NO 247
<211> LENGTH: 10
<212> TYPE: PRT
<213> ORGANISM: Hepatitis B virus

<400> SEQUENCE: 247

Arg Gly Ser Thr His Val Ser Trp Pro Lys
1               5                   10

<210> SEQ ID NO 248
<211> LENGTH: 10
<212> TYPE: PRT
<213> ORGANISM: Hepatitis B virus

<400> SEQUENCE: 248

Arg Gly Ser Thr Arg Val Ser Trp Pro Lys
1               5                   10

<210> SEQ ID NO 249
<211> LENGTH: 9
<212> TYPE: PRT
<213> ORGANISM: Hepatitis B virus

<400> SEQUENCE: 249

Gly Ser Thr His Val Ser Trp Pro Lys
1               5

<210> SEQ ID NO 250
<211> LENGTH: 9
<212> TYPE: PRT
<213> ORGANISM: Hepatitis B virus

<400> SEQUENCE: 250

Gly Ser Thr Arg Val Ser Trp Pro Lys
1               5

<210> SEQ ID NO 251
<211> LENGTH: 9
<212> TYPE: PRT
<213> ORGANISM: Hepatitis B virus

<400> SEQUENCE: 251

```
Gly Ser Thr Gln Val Ser Trp Pro Lys
1               5

<210> SEQ ID NO 252
<211> LENGTH: 8
<212> TYPE: PRT
<213> ORGANISM: Hepatitis B virus

<400> SEQUENCE: 252

Ser Thr Gln Val Ser Trp Pro Lys
1               5

<210> SEQ ID NO 253
<211> LENGTH: 8
<212> TYPE: PRT
<213> ORGANISM: Hepatitis B virus

<400> SEQUENCE: 253

Ser Thr His Val Ser Trp Pro Lys
1               5

<210> SEQ ID NO 254
<211> LENGTH: 8
<212> TYPE: PRT
<213> ORGANISM: Hepatitis B virus

<400> SEQUENCE: 254

Ser Thr Arg Val Ser Trp Pro Lys
1               5

<210> SEQ ID NO 255
<211> LENGTH: 8
<212> TYPE: PRT
<213> ORGANISM: Hepatitis B virus

<400> SEQUENCE: 255

Asn Thr Arg Val Ser Trp Pro Lys
1               5

<210> SEQ ID NO 256
<211> LENGTH: 9
<212> TYPE: PRT
<213> ORGANISM: Hepatitis B virus

<400> SEQUENCE: 256

Ala Ala Phe Tyr His Leu Pro Leu His
1               5

<210> SEQ ID NO 257
<211> LENGTH: 9
<212> TYPE: PRT
<213> ORGANISM: Hepatitis B virus

<400> SEQUENCE: 257

Leu Val Gly Ser Ser Gly Leu Pro Arg
1               5

<210> SEQ ID NO 258
<211> LENGTH: 9
<212> TYPE: PRT
<213> ORGANISM: Hepatitis B virus

<400> SEQUENCE: 258

Leu Val Gly Ser Ser Gly Leu Ser Arg
```

```
1               5
```

<210> SEQ ID NO 259
<211> LENGTH: 11
<212> TYPE: PRT
<213> ORGANISM: Hepatitis B virus

<400> SEQUENCE: 259

```
Gly Ser Ser Gly Leu Ser Arg Tyr Val Ala Arg
1               5                   10
```

<210> SEQ ID NO 260
<211> LENGTH: 11
<212> TYPE: PRT
<213> ORGANISM: Hepatitis B virus

<400> SEQUENCE: 260

```
Gly Ser Ser Gly Leu Pro Arg Tyr Val Ala Arg
1               5                   10
```

<210> SEQ ID NO 261
<211> LENGTH: 10
<212> TYPE: PRT
<213> ORGANISM: Hepatitis B virus

<400> SEQUENCE: 261

```
Ser Ser Gly Leu Ser Arg Tyr Val Ala Arg
1               5                   10
```

<210> SEQ ID NO 262
<211> LENGTH: 10
<212> TYPE: PRT
<213> ORGANISM: Hepatitis B virus

<400> SEQUENCE: 262

```
Ser Ser Gly Leu Pro Arg Tyr Val Ala Arg
1               5                   10
```

<210> SEQ ID NO 263
<211> LENGTH: 10
<212> TYPE: PRT
<213> ORGANISM: Hepatitis B virus

<400> SEQUENCE: 263

```
Tyr Val Ala Arg Leu Ser Ser Thr Ser Arg
1               5                   10
```

<210> SEQ ID NO 264
<211> LENGTH: 10
<212> TYPE: PRT
<213> ORGANISM: Hepatitis B virus

<400> SEQUENCE: 264

```
Tyr Val Ala Arg Leu Ser Ser Asn Ser Arg
1               5                   10
```

<210> SEQ ID NO 265
<211> LENGTH: 9
<212> TYPE: PRT
<213> ORGANISM: Hepatitis B virus

<400> SEQUENCE: 265

```
Ser Ser Thr Ser Arg Asn Ile Asn Tyr
1               5
```

<210> SEQ ID NO 266
<211> LENGTH: 11
<212> TYPE: PRT
<213> ORGANISM: Hepatitis B virus

<400> SEQUENCE: 266

Ser Thr Ser Arg Ile Ile Asn Asn Gln His Arg
1               5                   10

<210> SEQ ID NO 267
<211> LENGTH: 8
<212> TYPE: PRT
<213> ORGANISM: Hepatitis B virus

<400> SEQUENCE: 267

Ser Thr Ser Arg Asn Ile Asn Tyr
1               5

<210> SEQ ID NO 268
<211> LENGTH: 11
<212> TYPE: PRT
<213> ORGANISM: Hepatitis B virus

<400> SEQUENCE: 268

Ser Thr Ser Arg Ile Ile Asn Asp Gln His Arg
1               5                   10

<210> SEQ ID NO 269
<211> LENGTH: 8
<212> TYPE: PRT
<213> ORGANISM: Hepatitis B virus

<400> SEQUENCE: 269

Arg Ile Ile Asn Asn Gln His Arg
1               5

<210> SEQ ID NO 270
<211> LENGTH: 11
<212> TYPE: PRT
<213> ORGANISM: Hepatitis B virus

<400> SEQUENCE: 270

Thr Met Gln Asn Leu His Ser Ser Cys Ser Arg
1               5                   10

<210> SEQ ID NO 271
<211> LENGTH: 11
<212> TYPE: PRT
<213> ORGANISM: Hepatitis B virus

<400> SEQUENCE: 271

Thr Met Gln Asp Leu His Asn Ser Cys Ser Arg
1               5                   10

<210> SEQ ID NO 272
<211> LENGTH: 11
<212> TYPE: PRT
<213> ORGANISM: Hepatitis B virus

<400> SEQUENCE: 272

Thr Met Gln Asn Leu His Asn Ser Cys Ser Arg
1               5                   10

<210> SEQ ID NO 273

```
<211> LENGTH: 11
<212> TYPE: PRT
<213> ORGANISM: Hepatitis B virus

<400> SEQUENCE: 273

Thr Met Gln Asp Leu His Asp Ser Cys Ser Arg
1               5                   10

<210> SEQ ID NO 274
<211> LENGTH: 11
<212> TYPE: PRT
<213> ORGANISM: Hepatitis B virus

<400> SEQUENCE: 274

Thr Met Gln Asn Leu His Asp Ser Cys Ser Arg
1               5                   10

<210> SEQ ID NO 275
<211> LENGTH: 11
<212> TYPE: PRT
<213> ORGANISM: Hepatitis B virus

<400> SEQUENCE: 275

Ala Met Gln Asp Leu His Asp Ser Cys Ser Arg
1               5                   10

<210> SEQ ID NO 276
<211> LENGTH: 10
<212> TYPE: PRT
<213> ORGANISM: Hepatitis B virus

<400> SEQUENCE: 276

Met Gln Asn Leu His Ser Ser Cys Ser Arg
1               5                   10

<210> SEQ ID NO 277
<211> LENGTH: 8
<212> TYPE: PRT
<213> ORGANISM: Hepatitis B virus

<400> SEQUENCE: 277

Ser Ser Cys Ser Arg Asn Leu Tyr
1               5

<210> SEQ ID NO 278
<211> LENGTH: 11
<212> TYPE: PRT
<213> ORGANISM: Hepatitis B virus

<400> SEQUENCE: 278

Asn Leu Tyr Val Ser Leu Met Leu Leu Tyr Lys
1               5                   10

<210> SEQ ID NO 279
<211> LENGTH: 11
<212> TYPE: PRT
<213> ORGANISM: Hepatitis B virus

<400> SEQUENCE: 279

Asn Leu Tyr Val Ser Leu Leu Leu Leu Tyr Lys
1               5                   10

<210> SEQ ID NO 280
<211> LENGTH: 10
<212> TYPE: PRT
```

<213> ORGANISM: Hepatitis B virus

<400> SEQUENCE: 280

Asn Leu Tyr Val Ser Leu Met Leu Leu Tyr
1               5                   10

<210> SEQ ID NO 281
<211> LENGTH: 10
<212> TYPE: PRT
<213> ORGANISM: Hepatitis B virus

<400> SEQUENCE: 281

Asn Leu Tyr Val Ser Leu Leu Leu Leu Tyr
1               5                   10

<210> SEQ ID NO 282
<211> LENGTH: 10
<212> TYPE: PRT
<213> ORGANISM: Hepatitis B virus

<400> SEQUENCE: 282

Leu Tyr Val Ser Leu Met Leu Leu Tyr Lys
1               5                   10

<210> SEQ ID NO 283
<211> LENGTH: 10
<212> TYPE: PRT
<213> ORGANISM: Hepatitis B virus

<400> SEQUENCE: 283

Leu Tyr Val Ser Leu Leu Leu Leu Tyr Lys
1               5                   10

<210> SEQ ID NO 284
<211> LENGTH: 9
<212> TYPE: PRT
<213> ORGANISM: Hepatitis B virus

<400> SEQUENCE: 284

Tyr Val Ser Leu Leu Leu Leu Tyr Lys
1               5

<210> SEQ ID NO 285
<211> LENGTH: 9
<212> TYPE: PRT
<213> ORGANISM: Hepatitis B virus

<400> SEQUENCE: 285

Tyr Val Ser Leu Met Leu Leu Tyr Lys
1               5

<210> SEQ ID NO 286
<211> LENGTH: 8
<212> TYPE: PRT
<213> ORGANISM: Hepatitis B virus

<400> SEQUENCE: 286

Tyr Val Ser Leu Met Leu Leu Tyr
1               5

<210> SEQ ID NO 287
<211> LENGTH: 8
<212> TYPE: PRT
<213> ORGANISM: Hepatitis B virus

```
<400> SEQUENCE: 287

Tyr Val Ser Leu Leu Leu Tyr
1               5

<210> SEQ ID NO 288
<211> LENGTH: 8
<212> TYPE: PRT
<213> ORGANISM: Hepatitis B virus

<400> SEQUENCE: 288

Val Ser Leu Met Leu Leu Tyr Lys
1               5

<210> SEQ ID NO 289
<211> LENGTH: 8
<212> TYPE: PRT
<213> ORGANISM: Hepatitis B virus

<400> SEQUENCE: 289

Val Ser Leu Leu Leu Leu Tyr Lys
1               5

<210> SEQ ID NO 290
<211> LENGTH: 11
<212> TYPE: PRT
<213> ORGANISM: Hepatitis B virus

<400> SEQUENCE: 290

Ser Leu Met Leu Leu Tyr Lys Thr Tyr Gly Arg
1               5                   10

<210> SEQ ID NO 291
<211> LENGTH: 11
<212> TYPE: PRT
<213> ORGANISM: Hepatitis B virus

<400> SEQUENCE: 291

Ser Leu Leu Leu Leu Tyr Lys Thr Phe Gly Arg
1               5                   10

<210> SEQ ID NO 292
<211> LENGTH: 11
<212> TYPE: PRT
<213> ORGANISM: Hepatitis B virus

<400> SEQUENCE: 292

Leu Met Leu Leu Tyr Lys Thr Tyr Gly Arg Lys
1               5                   10

<210> SEQ ID NO 293
<211> LENGTH: 11
<212> TYPE: PRT
<213> ORGANISM: Hepatitis B virus

<400> SEQUENCE: 293

Leu Leu Leu Leu Tyr Lys Thr Phe Gly Arg Lys
1               5                   10

<210> SEQ ID NO 294
<211> LENGTH: 10
<212> TYPE: PRT
<213> ORGANISM: Hepatitis B virus

<400> SEQUENCE: 294
```

```
Met Leu Leu Tyr Lys Thr Tyr Gly Arg Lys
1               5                   10
```

<210> SEQ ID NO 295
<211> LENGTH: 10
<212> TYPE: PRT
<213> ORGANISM: Hepatitis B virus

<400> SEQUENCE: 295

```
Leu Leu Leu Tyr Lys Thr Phe Gly Arg Lys
1               5                   10
```

<210> SEQ ID NO 296
<211> LENGTH: 9
<212> TYPE: PRT
<213> ORGANISM: Hepatitis B virus

<400> SEQUENCE: 296

```
Met Leu Leu Tyr Lys Thr Tyr Gly Arg
1               5
```

<210> SEQ ID NO 297
<211> LENGTH: 9
<212> TYPE: PRT
<213> ORGANISM: Hepatitis B virus

<400> SEQUENCE: 297

```
Leu Leu Tyr Lys Thr Phe Gly Arg Lys
1               5
```

<210> SEQ ID NO 298
<211> LENGTH: 9
<212> TYPE: PRT
<213> ORGANISM: Hepatitis B virus

<400> SEQUENCE: 298

```
Leu Leu Tyr Lys Thr Tyr Gly Arg Lys
1               5
```

<210> SEQ ID NO 299
<211> LENGTH: 8
<212> TYPE: PRT
<213> ORGANISM: Hepatitis B virus

<400> SEQUENCE: 299

```
Leu Leu Tyr Lys Thr Phe Gly Arg
1               5
```

<210> SEQ ID NO 300
<211> LENGTH: 10
<212> TYPE: PRT
<213> ORGANISM: Hepatitis B virus

<400> SEQUENCE: 300

```
Lys Thr Tyr Gly Arg Lys Leu His Leu Tyr
1               5                   10
```

<210> SEQ ID NO 301
<211> LENGTH: 10
<212> TYPE: PRT
<213> ORGANISM: Hepatitis B virus

<400> SEQUENCE: 301

```
Lys Thr Phe Gly Arg Lys Leu His Leu Tyr
1               5                   10
```

<210> SEQ ID NO 302
<211> LENGTH: 11
<212> TYPE: PRT
<213> ORGANISM: Hepatitis B virus

<400> SEQUENCE: 302

Tyr Ser His Pro Ile Ile Leu Gly Phe Arg Lys
1               5                   10

<210> SEQ ID NO 303
<211> LENGTH: 8
<212> TYPE: PRT
<213> ORGANISM: Hepatitis B virus

<400> SEQUENCE: 303

Pro Ile Ile Leu Gly Phe Arg Lys
1               5

<210> SEQ ID NO 304
<211> LENGTH: 11
<212> TYPE: PRT
<213> ORGANISM: Hepatitis B virus

<400> SEQUENCE: 304

Phe Thr Ser Ala Ile Cys Ser Val Val Arg Arg
1               5                   10

<210> SEQ ID NO 305
<211> LENGTH: 10
<212> TYPE: PRT
<213> ORGANISM: Hepatitis B virus

<400> SEQUENCE: 305

Thr Ser Ala Ile Cys Ser Val Val Arg Arg
1               5                   10

<210> SEQ ID NO 306
<211> LENGTH: 9
<212> TYPE: PRT
<213> ORGANISM: Hepatitis B virus

<400> SEQUENCE: 306

Thr Ser Ala Ile Cys Ser Val Val Arg
1               5

<210> SEQ ID NO 307
<211> LENGTH: 9
<212> TYPE: PRT
<213> ORGANISM: Hepatitis B virus

<400> SEQUENCE: 307

Ser Ala Ile Cys Ser Val Val Arg Arg
1               5

<210> SEQ ID NO 308
<211> LENGTH: 8
<212> TYPE: PRT
<213> ORGANISM: Hepatitis B virus

<400> SEQUENCE: 308

Ser Ala Ile Cys Ser Val Val Arg
1               5

```
<210> SEQ ID NO 309
<211> LENGTH: 8
<212> TYPE: PRT
<213> ORGANISM: Hepatitis B virus

<400> SEQUENCE: 309

Ala Ile Cys Ser Val Val Arg Arg
1               5

<210> SEQ ID NO 310
<211> LENGTH: 9
<212> TYPE: PRT
<213> ORGANISM: Hepatitis B virus

<400> SEQUENCE: 310

Ser Val Val Arg Arg Ala Phe Pro His
1               5

<210> SEQ ID NO 311
<211> LENGTH: 11
<212> TYPE: PRT
<213> ORGANISM: Hepatitis B virus

<400> SEQUENCE: 311

Arg Ala Phe Pro His Cys Leu Ala Phe Ser Tyr
1               5                   10

<210> SEQ ID NO 312
<211> LENGTH: 11
<212> TYPE: PRT
<213> ORGANISM: Hepatitis B virus

<400> SEQUENCE: 312

Ser Tyr Met Asp Asp Val Val Leu Gly Ala Lys
1               5                   10

<210> SEQ ID NO 313
<211> LENGTH: 10
<212> TYPE: PRT
<213> ORGANISM: Hepatitis B virus

<400> SEQUENCE: 313

Tyr Met Asp Asp Val Val Leu Gly Ala Lys
1               5                   10

<210> SEQ ID NO 314
<211> LENGTH: 9
<212> TYPE: PRT
<213> ORGANISM: Hepatitis B virus

<400> SEQUENCE: 314

Ser Val Gln His Leu Glu Ser Leu Tyr
1               5

<210> SEQ ID NO 315
<211> LENGTH: 9
<212> TYPE: PRT
<213> ORGANISM: Hepatitis B virus

<400> SEQUENCE: 315

Ser Val Gln His Leu Glu Ser Val Tyr
1               5

<210> SEQ ID NO 316
<211> LENGTH: 11
```

```
<212> TYPE: PRT
<213> ORGANISM: Hepatitis B virus

<400> SEQUENCE: 316

Ser Val Tyr Ala Ala Val Thr Asn Phe Leu Leu
1               5                   10

<210> SEQ ID NO 317
<211> LENGTH: 11
<212> TYPE: PRT
<213> ORGANISM: Hepatitis B virus

<400> SEQUENCE: 317

Leu Ser Leu Gly Ile His Leu Asn Pro Asn Lys
1               5                   10

<210> SEQ ID NO 318
<211> LENGTH: 11
<212> TYPE: PRT
<213> ORGANISM: Hepatitis B virus

<400> SEQUENCE: 318

Leu Ser Leu Gly Ile His Leu Asn Pro His Lys
1               5                   10

<210> SEQ ID NO 319
<211> LENGTH: 10
<212> TYPE: PRT
<213> ORGANISM: Hepatitis B virus

<400> SEQUENCE: 319

Ser Leu Gly Ile His Leu Asn Pro Asn Lys
1               5                   10

<210> SEQ ID NO 320
<211> LENGTH: 10
<212> TYPE: PRT
<213> ORGANISM: Hepatitis B virus

<400> SEQUENCE: 320

Ser Leu Gly Ile His Leu Asn Pro His Lys
1               5                   10

<210> SEQ ID NO 321
<211> LENGTH: 8
<212> TYPE: PRT
<213> ORGANISM: Hepatitis B virus

<400> SEQUENCE: 321

Gly Ile His Leu Asn Pro Asn Lys
1               5

<210> SEQ ID NO 322
<211> LENGTH: 8
<212> TYPE: PRT
<213> ORGANISM: Hepatitis B virus

<400> SEQUENCE: 322

Gly Ile His Leu Asn Pro His Lys
1               5

<210> SEQ ID NO 323
<211> LENGTH: 10
<212> TYPE: PRT
<213> ORGANISM: Hepatitis B virus
```

<400> SEQUENCE: 323

Gly Ile His Leu Asn Pro His Lys Thr Lys
1               5                   10

<210> SEQ ID NO 324
<211> LENGTH: 10
<212> TYPE: PRT
<213> ORGANISM: Hepatitis B virus

<400> SEQUENCE: 324

Gly Ile His Leu Asn Pro Asn Lys Thr Lys
1               5                   10

<210> SEQ ID NO 325
<211> LENGTH: 8
<212> TYPE: PRT
<213> ORGANISM: Hepatitis B virus

<400> SEQUENCE: 325

Tyr Ser Leu Asn Phe Met Gly Tyr
1               5

<210> SEQ ID NO 326
<211> LENGTH: 11
<212> TYPE: PRT
<213> ORGANISM: Hepatitis B virus

<400> SEQUENCE: 326

Gly Thr Leu Pro Gln Glu His Ile Val Leu Lys
1               5                   10

<210> SEQ ID NO 327
<211> LENGTH: 11
<212> TYPE: PRT
<213> ORGANISM: Hepatitis B virus

<400> SEQUENCE: 327

Gly Thr Leu Pro Gln Glu His Ile Val Gln Lys
1               5                   10

<210> SEQ ID NO 328
<211> LENGTH: 10
<212> TYPE: PRT
<213> ORGANISM: Hepatitis B virus

<400> SEQUENCE: 328

Thr Leu Pro Gln Glu His Ile Val Leu Lys
1               5                   10

<210> SEQ ID NO 329
<211> LENGTH: 10
<212> TYPE: PRT
<213> ORGANISM: Hepatitis B virus

<400> SEQUENCE: 329

Thr Leu Pro Gln Glu His Ile Val Gln Lys
1               5                   10

<210> SEQ ID NO 330
<211> LENGTH: 11
<212> TYPE: PRT
<213> ORGANISM: Hepatitis B virus

<400> SEQUENCE: 330

His Ile Val Gln Lys Ile Lys Met Cys Phe Lys
1               5                   10

<210> SEQ ID NO 331
<211> LENGTH: 11
<212> TYPE: PRT
<213> ORGANISM: Hepatitis B virus

<400> SEQUENCE: 331

Ile Val Gln Lys Ile Lys Met Cys Phe Arg Lys
1               5                   10

<210> SEQ ID NO 332
<211> LENGTH: 10
<212> TYPE: PRT
<213> ORGANISM: Hepatitis B virus

<400> SEQUENCE: 332

Ile Val Gln Lys Ile Lys Met Cys Phe Lys
1               5                   10

<210> SEQ ID NO 333
<211> LENGTH: 11
<212> TYPE: PRT
<213> ORGANISM: Hepatitis B virus

<400> SEQUENCE: 333

Ile Val Gln Lys Ile Lys Leu Cys Phe Arg Lys
1               5                   10

<210> SEQ ID NO 334
<211> LENGTH: 11
<212> TYPE: PRT
<213> ORGANISM: Hepatitis B virus

<400> SEQUENCE: 334

Ile Val Gln Lys Ile Lys Met Cys Phe Lys Lys
1               5                   10

<210> SEQ ID NO 335
<211> LENGTH: 11
<212> TYPE: PRT
<213> ORGANISM: Hepatitis B virus

<400> SEQUENCE: 335

Ile Val Leu Lys Leu Lys Gln Cys Phe Arg Lys
1               5                   10

<210> SEQ ID NO 336
<211> LENGTH: 11
<212> TYPE: PRT
<213> ORGANISM: Hepatitis B virus

<400> SEQUENCE: 336

Ile Val Gln Lys Ile Lys Gln Cys Phe Arg Lys
1               5                   10

<210> SEQ ID NO 337
<211> LENGTH: 10
<212> TYPE: PRT
<213> ORGANISM: Hepatitis B virus

<400> SEQUENCE: 337

Ile Val Gln Lys Ile Lys Met Cys Phe Arg

```
1               5                   10

<210> SEQ ID NO 338
<211> LENGTH: 10
<212> TYPE: PRT
<213> ORGANISM: Hepatitis B virus

<400> SEQUENCE: 338

Ile Val Gln Lys Ile Lys Leu Cys Phe Arg
1               5                   10

<210> SEQ ID NO 339
<211> LENGTH: 10
<212> TYPE: PRT
<213> ORGANISM: Hepatitis B virus

<400> SEQUENCE: 339

Ile Val Leu Lys Leu Lys Gln Cys Phe Arg
1               5                   10

<210> SEQ ID NO 340
<211> LENGTH: 10
<212> TYPE: PRT
<213> ORGANISM: Hepatitis B virus

<400> SEQUENCE: 340

Ile Val Gln Lys Ile Lys Gln Cys Phe Arg
1               5                   10

<210> SEQ ID NO 341
<211> LENGTH: 9
<212> TYPE: PRT
<213> ORGANISM: Hepatitis B virus

<400> SEQUENCE: 341

Val Gln Lys Ile Lys Met Cys Phe Lys
1               5

<210> SEQ ID NO 342
<211> LENGTH: 10
<212> TYPE: PRT
<213> ORGANISM: Hepatitis B virus

<400> SEQUENCE: 342

Val Gln Lys Ile Lys Met Cys Phe Arg Lys
1               5                   10

<210> SEQ ID NO 343
<211> LENGTH: 10
<212> TYPE: PRT
<213> ORGANISM: Hepatitis B virus

<400> SEQUENCE: 343

Val Gln Lys Ile Lys Leu Cys Phe Arg Lys
1               5                   10

<210> SEQ ID NO 344
<211> LENGTH: 10
<212> TYPE: PRT
<213> ORGANISM: Hepatitis B virus

<400> SEQUENCE: 344

Val Gln Lys Ile Lys Met Cys Phe Lys Lys
1               5                   10
```

<210> SEQ ID NO 345
<211> LENGTH: 10
<212> TYPE: PRT
<213> ORGANISM: Hepatitis B virus

<400> SEQUENCE: 345

Val Leu Lys Leu Lys Gln Cys Phe Arg Lys
1               5                   10

<210> SEQ ID NO 346
<211> LENGTH: 10
<212> TYPE: PRT
<213> ORGANISM: Hepatitis B virus

<400> SEQUENCE: 346

Val Gln Lys Ile Lys Gln Cys Phe Arg Lys
1               5                   10

<210> SEQ ID NO 347
<211> LENGTH: 8
<212> TYPE: PRT
<213> ORGANISM: Hepatitis B virus

<400> SEQUENCE: 347

Lys Ile Lys Met Cys Phe Arg Lys
1               5

<210> SEQ ID NO 348
<211> LENGTH: 8
<212> TYPE: PRT
<213> ORGANISM: Hepatitis B virus

<400> SEQUENCE: 348

Lys Ile Lys Met Cys Phe Lys Lys
1               5

<210> SEQ ID NO 349
<211> LENGTH: 8
<212> TYPE: PRT
<213> ORGANISM: Hepatitis B virus

<400> SEQUENCE: 349

Lys Ile Lys Leu Cys Phe Arg Lys
1               5

<210> SEQ ID NO 350
<211> LENGTH: 8
<212> TYPE: PRT
<213> ORGANISM: Hepatitis B virus

<400> SEQUENCE: 350

Lys Ile Lys Gln Cys Phe Arg Lys
1               5

<210> SEQ ID NO 351
<211> LENGTH: 8
<212> TYPE: PRT
<213> ORGANISM: Hepatitis B virus

<400> SEQUENCE: 351

Lys Leu Lys Gln Cys Phe Arg Lys
1               5

<210> SEQ ID NO 352

```
<211> LENGTH: 11
<212> TYPE: PRT
<213> ORGANISM: Hepatitis B virus

<400> SEQUENCE: 352

Lys Met Cys Phe Arg Lys Leu Pro Val Asn Arg
1               5                   10

<210> SEQ ID NO 353
<211> LENGTH: 11
<212> TYPE: PRT
<213> ORGANISM: Hepatitis B virus

<400> SEQUENCE: 353

Lys Gln Cys Phe Arg Lys Leu Pro Ile Asn Arg
1               5                   10

<210> SEQ ID NO 354
<211> LENGTH: 11
<212> TYPE: PRT
<213> ORGANISM: Hepatitis B virus

<400> SEQUENCE: 354

Lys Met Cys Phe Lys Lys Leu Pro Val Asn Arg
1               5                   10

<210> SEQ ID NO 355
<211> LENGTH: 11
<212> TYPE: PRT
<213> ORGANISM: Hepatitis B virus

<400> SEQUENCE: 355

Lys Gln Cys Phe Arg Lys Leu Pro Val Asn Arg
1               5                   10

<210> SEQ ID NO 356
<211> LENGTH: 11
<212> TYPE: PRT
<213> ORGANISM: Hepatitis B virus

<400> SEQUENCE: 356

Lys Leu Cys Phe Arg Lys Leu Pro Val Asn Arg
1               5                   10

<210> SEQ ID NO 357
<211> LENGTH: 9
<212> TYPE: PRT
<213> ORGANISM: Hepatitis B virus

<400> SEQUENCE: 357

Pro Val Asn Arg Pro Ile Asp Trp Lys
1               5

<210> SEQ ID NO 358
<211> LENGTH: 9
<212> TYPE: PRT
<213> ORGANISM: Hepatitis B virus

<400> SEQUENCE: 358

Pro Leu Tyr Ala Cys Ile Gln Ala Lys
1               5

<210> SEQ ID NO 359
<211> LENGTH: 9
<212> TYPE: PRT
```

```
<213> ORGANISM: Hepatitis B virus

<400> SEQUENCE: 359

Pro Leu Tyr Ala Cys Ile Gln Thr Lys
1               5

<210> SEQ ID NO 360
<211> LENGTH: 11
<212> TYPE: PRT
<213> ORGANISM: Hepatitis B virus

<400> SEQUENCE: 360

Lys Gln Ala Phe Thr Phe Ser Pro Thr Tyr Lys
1               5                   10

<210> SEQ ID NO 361
<211> LENGTH: 10
<212> TYPE: PRT
<213> ORGANISM: Hepatitis B virus

<400> SEQUENCE: 361

Lys Gln Ala Phe Thr Phe Ser Pro Thr Tyr
1               5                   10

<210> SEQ ID NO 362
<211> LENGTH: 10
<212> TYPE: PRT
<213> ORGANISM: Hepatitis B virus

<400> SEQUENCE: 362

Gln Ala Phe Thr Phe Ser Pro Thr Tyr Lys
1               5                   10

<210> SEQ ID NO 363
<211> LENGTH: 9
<212> TYPE: PRT
<213> ORGANISM: Hepatitis B virus

<400> SEQUENCE: 363

Gln Ala Phe Thr Phe Ser Pro Thr Tyr
1               5

<210> SEQ ID NO 364
<211> LENGTH: 9
<212> TYPE: PRT
<213> ORGANISM: Hepatitis B virus

<400> SEQUENCE: 364

Ala Phe Thr Phe Ser Pro Thr Tyr Lys
1               5

<210> SEQ ID NO 365
<211> LENGTH: 8
<212> TYPE: PRT
<213> ORGANISM: Hepatitis B virus

<400> SEQUENCE: 365

Phe Thr Phe Ser Pro Thr Tyr Lys
1               5

<210> SEQ ID NO 366
<211> LENGTH: 11
<212> TYPE: PRT
<213> ORGANISM: Hepatitis B virus
```

```
<400> SEQUENCE: 366

Phe Ser Pro Thr Tyr Lys Ala Phe Leu Ser Lys
1               5                   10

<210> SEQ ID NO 367
<211> LENGTH: 11
<212> TYPE: PRT
<213> ORGANISM: Hepatitis B virus

<400> SEQUENCE: 367

Phe Ser Pro Thr Tyr Lys Ala Phe Leu Cys Lys
1               5                   10

<210> SEQ ID NO 368
<211> LENGTH: 10
<212> TYPE: PRT
<213> ORGANISM: Hepatitis B virus

<400> SEQUENCE: 368

Ser Pro Thr Tyr Lys Ala Phe Leu Cys Lys
1               5                   10

<210> SEQ ID NO 369
<211> LENGTH: 10
<212> TYPE: PRT
<213> ORGANISM: Hepatitis B virus

<400> SEQUENCE: 369

Ser Pro Thr Tyr Lys Ala Phe Leu Ser Lys
1               5                   10

<210> SEQ ID NO 370
<211> LENGTH: 9
<212> TYPE: PRT
<213> ORGANISM: Hepatitis B virus

<400> SEQUENCE: 370

Pro Thr Tyr Lys Ala Phe Leu Ser Lys
1               5

<210> SEQ ID NO 371
<211> LENGTH: 9
<212> TYPE: PRT
<213> ORGANISM: Hepatitis B virus

<400> SEQUENCE: 371

Pro Thr Tyr Lys Ala Phe Leu Cys Lys
1               5

<210> SEQ ID NO 372
<211> LENGTH: 8
<212> TYPE: PRT
<213> ORGANISM: Hepatitis B virus

<400> SEQUENCE: 372

Thr Tyr Lys Ala Phe Leu Ser Lys
1               5

<210> SEQ ID NO 373
<211> LENGTH: 8
<212> TYPE: PRT
<213> ORGANISM: Hepatitis B virus

<400> SEQUENCE: 373
```

```
Thr Tyr Lys Ala Phe Leu Cys Lys
1               5
```

<210> SEQ ID NO 374
<211> LENGTH: 11
<212> TYPE: PRT
<213> ORGANISM: Hepatitis B virus

<400> SEQUENCE: 374

```
Lys Gln Tyr Leu His Leu Tyr Pro Val Ala Arg
1               5                   10
```

<210> SEQ ID NO 375
<211> LENGTH: 11
<212> TYPE: PRT
<213> ORGANISM: Hepatitis B virus

<400> SEQUENCE: 375

```
Lys Gln Tyr Leu Asn Leu Tyr Pro Val Ala Arg
1               5                   10
```

<210> SEQ ID NO 376
<211> LENGTH: 8
<212> TYPE: PRT
<213> ORGANISM: Hepatitis B virus

<400> SEQUENCE: 376

```
Ala Ala Cys Phe Ala Arg Ser Arg
1               5
```

<210> SEQ ID NO 377
<211> LENGTH: 11
<212> TYPE: PRT
<213> ORGANISM: Hepatitis B virus

<400> SEQUENCE: 377

```
Gly Thr Asp Asn Ser Val Val Leu Ser Arg Lys
1               5                   10
```

<210> SEQ ID NO 378
<211> LENGTH: 10
<212> TYPE: PRT
<213> ORGANISM: Hepatitis B virus

<400> SEQUENCE: 378

```
Gly Thr Asp Asn Ser Val Val Leu Ser Arg
1               5                   10
```

<210> SEQ ID NO 379
<211> LENGTH: 8
<212> TYPE: PRT
<213> ORGANISM: Hepatitis B virus

<400> SEQUENCE: 379

```
Asn Ser Val Val Leu Ser Arg Lys
1               5
```

<210> SEQ ID NO 380
<211> LENGTH: 8
<212> TYPE: PRT
<213> ORGANISM: Hepatitis B virus

<400> SEQUENCE: 380

```
Cys Ala Ala Asn Trp Ile Leu Arg
1               5
```

<210> SEQ ID NO 381
<211> LENGTH: 11
<212> TYPE: PRT
<213> ORGANISM: Hepatitis B virus

<400> SEQUENCE: 381

Ser Ala Leu Asn Pro Ala Asp Asp Pro Ser Arg
1               5                   10

<210> SEQ ID NO 382
<211> LENGTH: 8
<212> TYPE: PRT
<213> ORGANISM: Hepatitis B virus

<400> SEQUENCE: 382

Gly Leu Tyr Arg Pro Leu Leu Arg
1               5

<210> SEQ ID NO 383
<211> LENGTH: 11
<212> TYPE: PRT
<213> ORGANISM: Hepatitis B virus

<400> SEQUENCE: 383

Gly Leu Tyr Arg Pro Leu Leu Arg Leu Leu Tyr
1               5                   10

<210> SEQ ID NO 384
<211> LENGTH: 11
<212> TYPE: PRT
<213> ORGANISM: Hepatitis B virus

<400> SEQUENCE: 384

Gly Leu Tyr Arg Pro Leu Leu Arg Leu Val Tyr
1               5                   10

<210> SEQ ID NO 385
<211> LENGTH: 9
<212> TYPE: PRT
<213> ORGANISM: Hepatitis B virus

<400> SEQUENCE: 385

Leu Val Tyr Arg Pro Thr Thr Gly Arg
1               5

<210> SEQ ID NO 386
<211> LENGTH: 8
<212> TYPE: PRT
<213> ORGANISM: Hepatitis B virus

<400> SEQUENCE: 386

Thr Thr Gly Arg Thr Ser Leu Tyr
1               5

<210> SEQ ID NO 387
<211> LENGTH: 9
<212> TYPE: PRT
<213> ORGANISM: Hepatitis B virus

<400> SEQUENCE: 387

Ser Val Pro Ser His Leu Pro Val Arg
1               5

-continued

```
<210> SEQ ID NO 388
<211> LENGTH: 9
<212> TYPE: PRT
<213> ORGANISM: Hepatitis B virus

<400> SEQUENCE: 388

Ser Val Pro Phe His Leu Pro Asp Arg
1               5

<210> SEQ ID NO 389
<211> LENGTH: 9
<212> TYPE: PRT
<213> ORGANISM: Hepatitis B virus

<400> SEQUENCE: 389

Ser Val Pro Ser His Leu Pro Asp Arg
1               5

<210> SEQ ID NO 390
<211> LENGTH: 9
<212> TYPE: PRT
<213> ORGANISM: Hepatitis B virus

<400> SEQUENCE: 390

Ser Val Pro Ser His Pro Pro Asp Arg
1               5

<210> SEQ ID NO 391
<211> LENGTH: 10
<212> TYPE: PRT
<213> ORGANISM: Hepatitis B virus

<400> SEQUENCE: 391

Phe Ala Ser Pro Leu His Val Ala Trp Lys
1               5                   10

<210> SEQ ID NO 392
<211> LENGTH: 9
<212> TYPE: PRT
<213> ORGANISM: Hepatitis B virus

<400> SEQUENCE: 392

Ala Ser Pro Leu His Val Ala Trp Lys
1               5

<210> SEQ ID NO 393
<211> LENGTH: 8
<212> TYPE: PRT
<213> ORGANISM: Hepatitis B virus

<400> SEQUENCE: 393

Ser Pro Leu His Val Ala Trp Lys
1               5

<210> SEQ ID NO 394
<211> LENGTH: 11
<212> TYPE: PRT
<213> ORGANISM: Hepatitis B virus

<400> SEQUENCE: 394

Ala Val Val Arg Arg Arg Cys Arg Ser Pro Arg
1               5                   10

<210> SEQ ID NO 395
<211> LENGTH: 11
```

```
<212> TYPE: PRT
<213> ORGANISM: Hepatitis B virus

<400> SEQUENCE: 395

Thr Val Val Arg Arg Arg Gly Arg Ser Pro Arg
1               5                   10

<210> SEQ ID NO 396
<211> LENGTH: 11
<212> TYPE: PRT
<213> ORGANISM: Hepatitis B virus

<400> SEQUENCE: 396

Thr Val Ile Arg Arg Arg Gly Arg Ser Pro Arg
1               5                   10

<210> SEQ ID NO 397
<211> LENGTH: 11
<212> TYPE: PRT
<213> ORGANISM: Hepatitis B virus

<400> SEQUENCE: 397

Thr Val Val Gly Arg Arg Gly Arg Ser Pro Arg
1               5                   10

<210> SEQ ID NO 398
<211> LENGTH: 10
<212> TYPE: PRT
<213> ORGANISM: Hepatitis B virus

<400> SEQUENCE: 398

Arg Val Cys Cys Gln Leu Asp Pro Ala Arg
1               5                   10

<210> SEQ ID NO 399
<211> LENGTH: 9
<212> TYPE: PRT
<213> ORGANISM: Hepatitis B virus

<400> SEQUENCE: 399

Ser Ser Ala Gly Pro Cys Ala Leu Arg
1               5

<210> SEQ ID NO 400
<211> LENGTH: 9
<212> TYPE: PRT
<213> ORGANISM: Hepatitis B virus

<400> SEQUENCE: 400

Ser Ser Thr Gly Pro Cys Ala Leu Arg
1               5

<210> SEQ ID NO 401
<211> LENGTH: 8
<212> TYPE: PRT
<213> ORGANISM: Hepatitis B virus

<400> SEQUENCE: 401

Ser Thr Gly Pro Cys Ala Leu Arg
1               5

<210> SEQ ID NO 402
<211> LENGTH: 11
<212> TYPE: PRT
<213> ORGANISM: Hepatitis B virus
```

```
<400> SEQUENCE: 402

Thr Thr Val Asn Ala His Trp Asn Leu Pro Lys
1               5                   10

<210> SEQ ID NO 403
<211> LENGTH: 11
<212> TYPE: PRT
<213> ORGANISM: Hepatitis B virus

<400> SEQUENCE: 403

Thr Thr Val Asn Ala Leu Gly Asn Leu Pro Lys
1               5                   10

<210> SEQ ID NO 404
<211> LENGTH: 11
<212> TYPE: PRT
<213> ORGANISM: Hepatitis B virus

<400> SEQUENCE: 404

Thr Thr Val Asn Ala His Gly Asn Leu Pro Lys
1               5                   10

<210> SEQ ID NO 405
<211> LENGTH: 11
<212> TYPE: PRT
<213> ORGANISM: Hepatitis B virus

<400> SEQUENCE: 405

Thr Thr Val Asn Ala Pro Gly Asn Leu Pro Lys
1               5                   10

<210> SEQ ID NO 406
<211> LENGTH: 11
<212> TYPE: PRT
<213> ORGANISM: Hepatitis B virus

<400> SEQUENCE: 406

Thr Thr Val Asn Ala His Gln Val Leu Pro Lys
1               5                   10

<210> SEQ ID NO 407
<211> LENGTH: 11
<212> TYPE: PRT
<213> ORGANISM: Hepatitis B virus

<400> SEQUENCE: 407

Thr Thr Val Asn Ala His Arg Asn Leu Pro Lys
1               5                   10

<210> SEQ ID NO 408
<211> LENGTH: 11
<212> TYPE: PRT
<213> ORGANISM: Hepatitis B virus

<400> SEQUENCE: 408

Thr Thr Val Asn Ala Arg Gln Val Leu Pro Lys
1               5                   10

<210> SEQ ID NO 409
<211> LENGTH: 10
<212> TYPE: PRT
<213> ORGANISM: Hepatitis B virus

<400> SEQUENCE: 409
```

Thr Val Asn Ala His Gln Val Leu Pro Lys
1               5                   10

<210> SEQ ID NO 410
<211> LENGTH: 10
<212> TYPE: PRT
<213> ORGANISM: Hepatitis B virus

<400> SEQUENCE: 410

Thr Val Asn Ala His Arg Asn Leu Pro Lys
1               5                   10

<210> SEQ ID NO 411
<211> LENGTH: 10
<212> TYPE: PRT
<213> ORGANISM: Hepatitis B virus

<400> SEQUENCE: 411

Thr Val Asn Ala His Trp Asn Leu Pro Lys
1               5                   10

<210> SEQ ID NO 412
<211> LENGTH: 10
<212> TYPE: PRT
<213> ORGANISM: Hepatitis B virus

<400> SEQUENCE: 412

Thr Val Asn Ala His Gly Asn Leu Pro Lys
1               5                   10

<210> SEQ ID NO 413
<211> LENGTH: 10
<212> TYPE: PRT
<213> ORGANISM: Hepatitis B virus

<400> SEQUENCE: 413

Thr Val Asn Ala Leu Gly Asn Leu Pro Lys
1               5                   10

<210> SEQ ID NO 414
<211> LENGTH: 10
<212> TYPE: PRT
<213> ORGANISM: Hepatitis B virus

<400> SEQUENCE: 414

Thr Val Asn Ala Pro Gly Asn Leu Pro Lys
1               5                   10

<210> SEQ ID NO 415
<211> LENGTH: 10
<212> TYPE: PRT
<213> ORGANISM: Hepatitis B virus

<400> SEQUENCE: 415

Thr Val Asn Ala Arg Gln Val Leu Pro Lys
1               5                   10

<210> SEQ ID NO 416
<211> LENGTH: 9
<212> TYPE: PRT
<213> ORGANISM: Hepatitis B virus

<400> SEQUENCE: 416

Val Asn Ala His Trp Asn Leu Pro Lys

```
1               5
```

<210> SEQ ID NO 417
<211> LENGTH: 8
<212> TYPE: PRT
<213> ORGANISM: Hepatitis B virus

<400> SEQUENCE: 417

```
Asn Ala His Trp Asn Leu Pro Lys
1               5
```

<210> SEQ ID NO 418
<211> LENGTH: 8
<212> TYPE: PRT
<213> ORGANISM: Hepatitis B virus

<400> SEQUENCE: 418

```
Asn Ala Leu Gly Asn Leu Pro Lys
1               5
```

<210> SEQ ID NO 419
<211> LENGTH: 8
<212> TYPE: PRT
<213> ORGANISM: Hepatitis B virus

<400> SEQUENCE: 419

```
Asn Ala His Gln Val Leu Pro Lys
1               5
```

<210> SEQ ID NO 420
<211> LENGTH: 8
<212> TYPE: PRT
<213> ORGANISM: Hepatitis B virus

<400> SEQUENCE: 420

```
Asn Ala His Gly Asn Leu Pro Lys
1               5
```

<210> SEQ ID NO 421
<211> LENGTH: 8
<212> TYPE: PRT
<213> ORGANISM: Hepatitis B virus

<400> SEQUENCE: 421

```
Asn Ala His Arg Asn Leu Pro Lys
1               5
```

<210> SEQ ID NO 422
<211> LENGTH: 11
<212> TYPE: PRT
<213> ORGANISM: Hepatitis B virus

<400> SEQUENCE: 422

```
Ala Leu Gly Asn Leu Pro Lys Val Leu His Lys
1               5                   10
```

<210> SEQ ID NO 423
<211> LENGTH: 10
<212> TYPE: PRT
<213> ORGANISM: Hepatitis B virus

<400> SEQUENCE: 423

```
Arg Gln Val Leu Pro Lys Val Leu His Lys
1               5                   10
```

<210> SEQ ID NO 424
<211> LENGTH: 10
<212> TYPE: PRT
<213> ORGANISM: Hepatitis B virus

<400> SEQUENCE: 424

His Gln Val Leu Pro Lys Val Leu His Lys
1               5                   10

<210> SEQ ID NO 425
<211> LENGTH: 9
<212> TYPE: PRT
<213> ORGANISM: Hepatitis B virus

<400> SEQUENCE: 425

Gln Val Leu Pro Lys Val Leu His Lys
1               5

<210> SEQ ID NO 426
<211> LENGTH: 10
<212> TYPE: PRT
<213> ORGANISM: Hepatitis B virus

<400> SEQUENCE: 426

Gln Val Leu Pro Lys Val Leu His Lys Arg
1               5                   10

<210> SEQ ID NO 427
<211> LENGTH: 8
<212> TYPE: PRT
<213> ORGANISM: Hepatitis B virus

<400> SEQUENCE: 427

Val Leu Pro Lys Val Leu His Lys
1               5

<210> SEQ ID NO 428
<211> LENGTH: 11
<212> TYPE: PRT
<213> ORGANISM: Hepatitis B virus

<400> SEQUENCE: 428

Ser Val Met Ser Met Thr Asp Leu Glu Ala Tyr
1               5                   10

<210> SEQ ID NO 429
<211> LENGTH: 11
<212> TYPE: PRT
<213> ORGANISM: Hepatitis B virus

<400> SEQUENCE: 429

Ser Val Met Ser Thr Thr Asp Leu Glu Ala Tyr
1               5                   10

<210> SEQ ID NO 430
<211> LENGTH: 11
<212> TYPE: PRT
<213> ORGANISM: Hepatitis B virus

<400> SEQUENCE: 430

Ser Ala Met Ser Thr Thr Asp Leu Glu Ala Tyr
1               5                   10

<210> SEQ ID NO 431

```
<211> LENGTH: 11
<212> TYPE: PRT
<213> ORGANISM: Hepatitis B virus

<400> SEQUENCE: 431

Ser Ala Met Ser Ala Thr Asp Leu Glu Ala Tyr
1               5                   10

<210> SEQ ID NO 432
<211> LENGTH: 11
<212> TYPE: PRT
<213> ORGANISM: Hepatitis B virus

<400> SEQUENCE: 432

Met Ser Met Thr Asp Leu Glu Ala Tyr Phe Lys
1               5                   10

<210> SEQ ID NO 433
<211> LENGTH: 11
<212> TYPE: PRT
<213> ORGANISM: Hepatitis B virus

<400> SEQUENCE: 433

Met Ser Ala Thr Asp Leu Glu Ala Tyr Phe Lys
1               5                   10

<210> SEQ ID NO 434
<211> LENGTH: 11
<212> TYPE: PRT
<213> ORGANISM: Hepatitis B virus

<400> SEQUENCE: 434

Met Ser Thr Thr Asp Leu Glu Ala Tyr Phe Lys
1               5                   10

<210> SEQ ID NO 435
<211> LENGTH: 9
<212> TYPE: PRT
<213> ORGANISM: Hepatitis B virus

<400> SEQUENCE: 435

Met Ser Met Thr Asp Leu Glu Ala Tyr
1               5

<210> SEQ ID NO 436
<211> LENGTH: 10
<212> TYPE: PRT
<213> ORGANISM: Hepatitis B virus

<400> SEQUENCE: 436

Ser Thr Thr Asp Leu Glu Ala Tyr Phe Lys
1               5                   10

<210> SEQ ID NO 437
<211> LENGTH: 10
<212> TYPE: PRT
<213> ORGANISM: Hepatitis B virus

<400> SEQUENCE: 437

Ser Met Thr Asp Leu Glu Ala Tyr Phe Lys
1               5                   10

<210> SEQ ID NO 438
<211> LENGTH: 10
<212> TYPE: PRT
```

<213> ORGANISM: Hepatitis B virus

<400> SEQUENCE: 438

Ser Ala Thr Asp Leu Glu Ala Tyr Phe Lys
1               5                   10

<210> SEQ ID NO 439
<211> LENGTH: 8
<212> TYPE: PRT
<213> ORGANISM: Hepatitis B virus

<400> SEQUENCE: 439

Ser Thr Thr Asp Leu Glu Ala Tyr
1               5

<210> SEQ ID NO 440
<211> LENGTH: 9
<212> TYPE: PRT
<213> ORGANISM: Hepatitis B virus

<400> SEQUENCE: 440

Thr Thr Asp Leu Glu Ala Tyr Phe Lys
1               5

<210> SEQ ID NO 441
<211> LENGTH: 9
<212> TYPE: PRT
<213> ORGANISM: Hepatitis B virus

<400> SEQUENCE: 441

Met Thr Asp Leu Glu Ala Tyr Phe Lys
1               5

<210> SEQ ID NO 442
<211> LENGTH: 9
<212> TYPE: PRT
<213> ORGANISM: Hepatitis B virus

<400> SEQUENCE: 442

Ala Thr Asp Leu Glu Ala Tyr Phe Lys
1               5

<210> SEQ ID NO 443
<211> LENGTH: 10
<212> TYPE: PRT
<213> ORGANISM: Hepatitis B virus

<400> SEQUENCE: 443

Glu Ala Tyr Phe Lys Asp Cys Val Phe Lys
1               5                   10

<210> SEQ ID NO 444
<211> LENGTH: 9
<212> TYPE: PRT
<213> ORGANISM: Hepatitis B virus

<400> SEQUENCE: 444

Ala Tyr Phe Lys Asp Cys Val Phe Lys
1               5

<210> SEQ ID NO 445
<211> LENGTH: 11
<212> TYPE: PRT
<213> ORGANISM: Hepatitis B virus

```
<400> SEQUENCE: 445

Arg Leu Met Ile Phe Val Leu Gly Gly Cys Arg
1               5                   10

<210> SEQ ID NO 446
<211> LENGTH: 11
<212> TYPE: PRT
<213> ORGANISM: Hepatitis B virus

<400> SEQUENCE: 446

Lys Val Phe Val Leu Gly Gly Cys Arg His Lys
1               5                   10

<210> SEQ ID NO 447
<211> LENGTH: 11
<212> TYPE: PRT
<213> ORGANISM: Hepatitis B virus

<400> SEQUENCE: 447

Met Ile Phe Val Leu Gly Gly Cys Arg His Lys
1               5                   10

<210> SEQ ID NO 448
<211> LENGTH: 11
<212> TYPE: PRT
<213> ORGANISM: Hepatitis B virus

<400> SEQUENCE: 448

Lys Ile Tyr Val Leu Gly Gly Cys Arg His Lys
1               5                   10

<210> SEQ ID NO 449
<211> LENGTH: 9
<212> TYPE: PRT
<213> ORGANISM: Hepatitis B virus

<400> SEQUENCE: 449

Lys Val Phe Val Leu Gly Gly Cys Arg
1               5

<210> SEQ ID NO 450
<211> LENGTH: 9
<212> TYPE: PRT
<213> ORGANISM: Hepatitis B virus

<400> SEQUENCE: 450

Lys Ile Tyr Val Leu Gly Gly Cys Arg
1               5

<210> SEQ ID NO 451
<211> LENGTH: 9
<212> TYPE: PRT
<213> ORGANISM: Hepatitis B virus

<400> SEQUENCE: 451

Met Ile Phe Val Leu Gly Gly Cys Arg
1               5

<210> SEQ ID NO 452
<211> LENGTH: 9
<212> TYPE: PRT
<213> ORGANISM: Hepatitis B virus

<400> SEQUENCE: 452
```

Tyr Val Leu Gly Gly Cys Arg His Lys
1               5

<210> SEQ ID NO 453
<211> LENGTH: 9
<212> TYPE: PRT
<213> ORGANISM: Hepatitis B virus

<400> SEQUENCE: 453

Tyr Val Asn Val Asn Met Gly Leu Lys
1               5

<210> SEQ ID NO 454
<211> LENGTH: 9
<212> TYPE: PRT
<213> ORGANISM: Hepatitis B virus

<400> SEQUENCE: 454

Tyr Val Asn Thr Asn Met Gly Leu Lys
1               5

<210> SEQ ID NO 455
<211> LENGTH: 9
<212> TYPE: PRT
<213> ORGANISM: Hepatitis B virus

<400> SEQUENCE: 455

Tyr Val Asn Val Asn Met Gly Pro Lys
1               5

<210> SEQ ID NO 456
<211> LENGTH: 9
<212> TYPE: PRT
<213> ORGANISM: Hepatitis B virus

<400> SEQUENCE: 456

Tyr Val Asn Val Asn Thr Gly Leu Lys
1               5

<210> SEQ ID NO 457
<211> LENGTH: 9
<212> TYPE: PRT
<213> ORGANISM: Hepatitis B virus

<400> SEQUENCE: 457

Tyr Val Asn Val Asn Met Gly Ile Lys
1               5

<210> SEQ ID NO 458
<211> LENGTH: 9
<212> TYPE: PRT
<213> ORGANISM: Hepatitis B virus

<400> SEQUENCE: 458

Tyr Ala Asn Val Asn Met Gly Ile Lys
1               5

<210> SEQ ID NO 459
<211> LENGTH: 9
<212> TYPE: PRT
<213> ORGANISM: Hepatitis B virus

<400> SEQUENCE: 459

Tyr Val Asn Val Asn Met Arg Leu Lys
1               5

<210> SEQ ID NO 460
<211> LENGTH: 9
<212> TYPE: PRT
<213> ORGANISM: Hepatitis B virus

<400> SEQUENCE: 460

Tyr Val Asn Val Ile Met Gly Leu Lys
1               5

<210> SEQ ID NO 461
<211> LENGTH: 10
<212> TYPE: PRT
<213> ORGANISM: Hepatitis B virus

<400> SEQUENCE: 461

Cys Ser Cys Pro Thr Val Gln Ala Ser Lys
1               5                   10

<210> SEQ ID NO 462
<211> LENGTH: 10
<212> TYPE: PRT
<213> ORGANISM: Hepatitis B virus

<400> SEQUENCE: 462

Cys Ser Cys Ser Thr Val Gln Ala Ser Lys
1               5                   10

<210> SEQ ID NO 463
<211> LENGTH: 10
<212> TYPE: PRT
<213> ORGANISM: Hepatitis B virus

<400> SEQUENCE: 463

Cys Ser Cys Pro Thr Val Gln Thr Ser Lys
1               5                   10

<210> SEQ ID NO 464
<211> LENGTH: 10
<212> TYPE: PRT
<213> ORGANISM: Hepatitis B virus

<400> SEQUENCE: 464

Cys Thr Cys Pro Thr Val Gln Ala Ser Lys
1               5                   10

<210> SEQ ID NO 465
<211> LENGTH: 10
<212> TYPE: PRT
<213> ORGANISM: Hepatitis B virus

<400> SEQUENCE: 465

Cys Ser Cys Pro Thr Val Gln Val Ser Lys
1               5                   10

<210> SEQ ID NO 466
<211> LENGTH: 8
<212> TYPE: PRT
<213> ORGANISM: Hepatitis B virus

<400> SEQUENCE: 466

Cys Ser Thr Val Gln Ala Ser Lys
1               5

```
<210> SEQ ID NO 467
<211> LENGTH: 11
<212> TYPE: PRT
<213> ORGANISM: Hepatitis B virus

<400> SEQUENCE: 467

Thr Val Gln Ala Ser Lys Leu Cys Leu Gly Arg
1               5                   10

<210> SEQ ID NO 468
<211> LENGTH: 8
<212> TYPE: PRT
<213> ORGANISM: Hepatitis B virus

<400> SEQUENCE: 468

Thr Val Gln Ala Ser Lys Leu Tyr
1               5

<210> SEQ ID NO 469
<211> LENGTH: 11
<212> TYPE: PRT
<213> ORGANISM: Hepatitis B virus

<400> SEQUENCE: 469

Arg Leu Trp Gly Met Asp Ile Asp Pro Tyr Lys
1               5                   10

<210> SEQ ID NO 470
<211> LENGTH: 8
<212> TYPE: PRT
<213> ORGANISM: Hepatitis B virus

<400> SEQUENCE: 470

Gly Met Asp Ile Asp Pro Tyr Lys
1               5

<210> SEQ ID NO 471
<211> LENGTH: 8
<212> TYPE: PRT
<213> ORGANISM: Hepatitis B virus

<400> SEQUENCE: 471

Gly Met Asn Ile Asp Pro Tyr Lys
1               5

<210> SEQ ID NO 472
<211> LENGTH: 8
<212> TYPE: PRT
<213> ORGANISM: Hepatitis B virus

<400> SEQUENCE: 472

Gly Met Asp Ile Asp Ala Tyr Lys
1               5

<210> SEQ ID NO 473
<211> LENGTH: 8
<212> TYPE: PRT
<213> ORGANISM: Hepatitis B virus

<400> SEQUENCE: 473

Gly Met Asp Ile Asp Thr Tyr Lys
1               5

<210> SEQ ID NO 474
<211> LENGTH: 10
```

```
<212> TYPE: PRT
<213> ORGANISM: Hepatitis B virus

<400> SEQUENCE: 474

Val Val Ser Tyr Val Asn Val Asn Met Arg
1               5                   10

<210> SEQ ID NO 475
<211> LENGTH: 11
<212> TYPE: PRT
<213> ORGANISM: Hepatitis B virus

<400> SEQUENCE: 475

Val Ser Tyr Val Asn Val Asn Met Gly Leu Lys
1               5                   10

<210> SEQ ID NO 476
<211> LENGTH: 11
<212> TYPE: PRT
<213> ORGANISM: Hepatitis B virus

<400> SEQUENCE: 476

Val Ser Tyr Val Asn Val Asn Met Gly Pro Lys
1               5                   10

<210> SEQ ID NO 477
<211> LENGTH: 11
<212> TYPE: PRT
<213> ORGANISM: Hepatitis B virus

<400> SEQUENCE: 477

Val Ser Tyr Val Asn Val Asn Thr Gly Leu Lys
1               5                   10

<210> SEQ ID NO 478
<211> LENGTH: 11
<212> TYPE: PRT
<213> ORGANISM: Hepatitis B virus

<400> SEQUENCE: 478

Val Ser Tyr Val Asn Val Asn Met Gly Ile Lys
1               5                   10

<210> SEQ ID NO 479
<211> LENGTH: 11
<212> TYPE: PRT
<213> ORGANISM: Hepatitis B virus

<400> SEQUENCE: 479

Val Ser Tyr Ala Asn Val Asn Met Gly Ile Lys
1               5                   10

<210> SEQ ID NO 480
<211> LENGTH: 11
<212> TYPE: PRT
<213> ORGANISM: Hepatitis B virus

<400> SEQUENCE: 480

Val Ser Tyr Val Asn Val Asn Met Arg Leu Lys
1               5                   10

<210> SEQ ID NO 481
<211> LENGTH: 11
<212> TYPE: PRT
<213> ORGANISM: Hepatitis B virus
```

<400> SEQUENCE: 481

Val Ser Tyr Val Asn Val Ile Met Gly Leu Lys
1               5                   10

<210> SEQ ID NO 482
<211> LENGTH: 9
<212> TYPE: PRT
<213> ORGANISM: Hepatitis B virus

<400> SEQUENCE: 482

Val Ser Tyr Val Asn Val Asn Met Arg
1               5

<210> SEQ ID NO 483
<211> LENGTH: 10
<212> TYPE: PRT
<213> ORGANISM: Hepatitis B virus

<400> SEQUENCE: 483

Ser Tyr Val Asn Val Asn Met Gly Leu Lys
1               5                   10

<210> SEQ ID NO 484
<211> LENGTH: 10
<212> TYPE: PRT
<213> ORGANISM: Hepatitis B virus

<400> SEQUENCE: 484

Ser Tyr Val Asn Val Asn Met Gly Pro Lys
1               5                   10

<210> SEQ ID NO 485
<211> LENGTH: 10
<212> TYPE: PRT
<213> ORGANISM: Hepatitis B virus

<400> SEQUENCE: 485

Ser Tyr Val Asn Val Asn Thr Gly Leu Lys
1               5                   10

<210> SEQ ID NO 486
<211> LENGTH: 10
<212> TYPE: PRT
<213> ORGANISM: Hepatitis B virus

<400> SEQUENCE: 486

Gly Tyr Val Asn Val Asn Met Gly Leu Lys
1               5                   10

<210> SEQ ID NO 487
<211> LENGTH: 10
<212> TYPE: PRT
<213> ORGANISM: Hepatitis B virus

<400> SEQUENCE: 487

Ser Tyr Val Asn Val Asn Met Arg Leu Lys
1               5                   10

<210> SEQ ID NO 488
<211> LENGTH: 10
<212> TYPE: PRT
<213> ORGANISM: Hepatitis B virus

<400> SEQUENCE: 488

```
Ser Tyr Val Asn Val Ile Met Gly Leu Lys
1               5                   10

<210> SEQ ID NO 489
<211> LENGTH: 11
<212> TYPE: PRT
<213> ORGANISM: Hepatitis B virus

<400> SEQUENCE: 489

Arg Gln Leu Leu Trp Phe His Ile Ser Cys Arg
1               5                   10

<210> SEQ ID NO 490
<211> LENGTH: 9
<212> TYPE: PRT
<213> ORGANISM: Hepatitis B virus

<400> SEQUENCE: 490

His Ile Ser Cys Leu Thr Phe Gly Arg
1               5

<210> SEQ ID NO 491
<211> LENGTH: 11
<212> TYPE: PRT
<213> ORGANISM: Hepatitis B virus

<400> SEQUENCE: 491

Leu Thr Phe Gly Arg Glu Thr Val Leu Glu Tyr
1               5                   10

<210> SEQ ID NO 492
<211> LENGTH: 11
<212> TYPE: PRT
<213> ORGANISM: Hepatitis B virus

<400> SEQUENCE: 492

Arg Thr Phe Gly Arg Glu Thr Val Leu Glu Tyr
1               5                   10

<210> SEQ ID NO 493
<211> LENGTH: 11
<212> TYPE: PRT
<213> ORGANISM: Hepatitis B virus

<400> SEQUENCE: 493

Leu Thr Phe Gly Arg Gln Thr Val Leu Glu Tyr
1               5                   10

<210> SEQ ID NO 494
<211> LENGTH: 11
<212> TYPE: PRT
<213> ORGANISM: Hepatitis B virus

<400> SEQUENCE: 494

Gly Val Trp Ile Arg Thr Pro Pro Ala Tyr Arg
1               5                   10

<210> SEQ ID NO 495
<211> LENGTH: 11
<212> TYPE: PRT
<213> ORGANISM: Hepatitis B virus

<400> SEQUENCE: 495

Gly Val Trp Ile Arg Thr Pro Pro Ala Phe Arg
```

```
1               5                   10

<210> SEQ ID NO 496
<211> LENGTH: 11
<212> TYPE: PRT
<213> ORGANISM: Hepatitis B virus

<400> SEQUENCE: 496

Gly Val Trp Ile Arg Thr Pro Thr Ala Tyr Arg
1               5                   10

<210> SEQ ID NO 497
<211> LENGTH: 11
<212> TYPE: PRT
<213> ORGANISM: Hepatitis B virus

<400> SEQUENCE: 497

Gly Val Trp Ile Arg Thr Pro Ser Ala Tyr Arg
1               5                   10

<210> SEQ ID NO 498
<211> LENGTH: 11
<212> TYPE: PRT
<213> ORGANISM: Hepatitis B virus

<400> SEQUENCE: 498

Gly Val Trp Ile Arg Thr Pro Leu Ala Tyr Arg
1               5                   10

<210> SEQ ID NO 499
<211> LENGTH: 11
<212> TYPE: PRT
<213> ORGANISM: Hepatitis B virus

<400> SEQUENCE: 499

Gly Val Trp Ile Arg Ala Pro Pro Ala Tyr Arg
1               5                   10

<210> SEQ ID NO 500
<211> LENGTH: 10
<212> TYPE: PRT
<213> ORGANISM: Hepatitis B virus

<400> SEQUENCE: 500

Ser Thr Leu Pro Glu Thr Thr Val Val Arg
1               5                   10

<210> SEQ ID NO 501
<211> LENGTH: 10
<212> TYPE: PRT
<213> ORGANISM: Hepatitis B virus

<400> SEQUENCE: 501

Ser Thr Leu Pro Glu Thr Thr Val Ile Arg
1               5                   10

<210> SEQ ID NO 502
<211> LENGTH: 10
<212> TYPE: PRT
<213> ORGANISM: Hepatitis B virus

<400> SEQUENCE: 502

Ser Thr Ile Pro Glu Thr Thr Val Val Arg
1               5                   10
```

<210> SEQ ID NO 503
<211> LENGTH: 8
<212> TYPE: PRT
<213> ORGANISM: Hepatitis B virus

<400> SEQUENCE: 503

Thr Val Ile Arg Arg Arg Gly Arg
1               5

<210> SEQ ID NO 504
<211> LENGTH: 8
<212> TYPE: PRT
<213> ORGANISM: Hepatitis B virus

<400> SEQUENCE: 504

Arg Thr Gln Ser Pro Arg Arg Arg
1               5

<210> SEQ ID NO 505
<211> LENGTH: 9
<212> TYPE: PRT
<213> ORGANISM: Hepatitis B virus

<400> SEQUENCE: 505

Arg Thr Gln Ser Pro Arg Arg Arg Arg
1               5

<210> SEQ ID NO 506
<211> LENGTH: 11
<212> TYPE: PRT
<213> ORGANISM: Hepatitis B virus

<400> SEQUENCE: 506

Arg Ser Gln Ser Pro Arg Arg Arg Arg Ser Lys
1               5                   10

<210> SEQ ID NO 507
<211> LENGTH: 10
<212> TYPE: PRT
<213> ORGANISM: Hepatitis B virus

<400> SEQUENCE: 507

Ser Gln Ser Pro Arg Arg Arg Arg Ser Lys
1               5                   10

<210> SEQ ID NO 508
<211> LENGTH: 9
<212> TYPE: PRT
<213> ORGANISM: cytomegalovirus

<400> SEQUENCE: 508

Ala Thr Val Gln Gly Gln Asn Leu Lys
1               5

<210> SEQ ID NO 509
<211> LENGTH: 8
<212> TYPE: PRT
<213> ORGANISM: HCV-GPP-2

<400> SEQUENCE: 509

Ser Thr Asn Pro Lys Pro Gln Lys
1               5

<210> SEQ ID NO 510

```
<211> LENGTH: 10
<212> TYPE: PRT
<213> ORGANISM: Survivin-53

<400> SEQUENCE: 510

Asp Leu Ala Gln Cys Phe Phe Cys Phe Lys
1               5                   10

<210> SEQ ID NO 511
<211> LENGTH: 10
<212> TYPE: PRT
<213> ORGANISM: EBV-EBNA3B

<400> SEQUENCE: 511

Ala Val Phe Asp Arg Lys Ser Asp Ala Lys
1               5                   10

<210> SEQ ID NO 512
<211> LENGTH: 9
<212> TYPE: PRT
<213> ORGANISM: EBV-EBNA3B-416

<400> SEQUENCE: 512

Ile Val Thr Asp Phe Ser Val Ile Lys
1               5

<210> SEQ ID NO 513
<211> LENGTH: 9
<212> TYPE: PRT
<213> ORGANISM: HIV-Nef-85

<400> SEQUENCE: 513

Ala Val Asp Leu Ser His Phe Leu Lys
1               5

<210> SEQ ID NO 514
<211> LENGTH: 9
<212> TYPE: PRT
<213> ORGANISM: HPV33-E6-86

<400> SEQUENCE: 514

Asn Thr Leu Glu Gln Thr Val Lys Lys
1               5

<210> SEQ ID NO 515
<211> LENGTH: 10
<212> TYPE: PRT
<213> ORGANISM: DENV1-1-PP*

<400> SEQUENCE: 515

Gly Thr Ser Gly Ser Pro Ile Val Asn Arg
1               5                   10

<210> SEQ ID NO 516
<211> LENGTH: 10
<212> TYPE: PRT
<213> ORGANISM: DENV1-1-PP*

<400> SEQUENCE: 516

Gly Thr Ser Gly Ser Pro Ile Ile Asp Lys
1               5                   10

<210> SEQ ID NO 517
<211> LENGTH: 10
<212> TYPE: PRT
```

<213> ORGANISM: DENV1-1-PP*

<400> SEQUENCE: 517

Gly Thr Ser Gly Ser Pro Ile Val Asp Arg
1               5                   10

<210> SEQ ID NO 518
<211> LENGTH: 10
<212> TYPE: PRT
<213> ORGANISM: DENV1-1-PP*

<400> SEQUENCE: 518

Gly Thr Ser Gly Ser Pro Ile Val Asp Lys
1               5                   10

<210> SEQ ID NO 519
<211> LENGTH: 10
<212> TYPE: PRT
<213> ORGANISM: DENV1-1-PP*

<400> SEQUENCE: 519

Gly Thr Ser Gly Ser Pro Ile Ala Asp Lys
1               5                   10

<210> SEQ ID NO 520
<211> LENGTH: 10
<212> TYPE: PRT
<213> ORGANISM: DENV1-1-PP*

<400> SEQUENCE: 520

Gly Thr Ser Gly Ser Pro Ile Ile Asn Arg
1               5                   10

<210> SEQ ID NO 521
<211> LENGTH: 10
<212> TYPE: PRT
<213> ORGANISM: DENV1-1-PP*

<400> SEQUENCE: 521

Gly Thr Ser Gly Ser Pro Ile Ile Asp Lys
1               5                   10

<210> SEQ ID NO 522
<211> LENGTH: 12
<212> TYPE: PRT
<213> ORGANISM: CMV-pp65_2

<400> SEQUENCE: 522

Ser Val Leu Gly Pro Ile Ser Gly His Val Leu Lys
1               5                   10

<210> SEQ ID NO 523
<211> LENGTH: 15
<212> TYPE: PRT
<213> ORGANISM: CMV-2

<400> SEQUENCE: 523

Thr Val Arg Ala Phe Ser Arg Ala Tyr His His Arg Ile Asn Arg
1               5                   10                  15

<210> SEQ ID NO 524
<211> LENGTH: 9
<212> TYPE: PRT
<213> ORGANISM: MTB-EsxR

```
<400> SEQUENCE: 524

Gln Ile Met Tyr Asn Tyr Pro Ala Met
1               5

<210> SEQ ID NO 525
<211> LENGTH: 9
<212> TYPE: PRT
<213> ORGANISM: MTB-EsxH

<400> SEQUENCE: 525

Ala Asn Thr Met Ala Met Met Ala Arg
1               5

<210> SEQ ID NO 526
<211> LENGTH: 9
<212> TYPE: PRT
<213> ORGANISM: TG-MS*

<400> SEQUENCE: 526

Lys Ser Phe Lys Asp Ile Leu Pro Lys
1               5

<210> SEQ ID NO 527
<211> LENGTH: 9
<212> TYPE: PRT
<213> ORGANISM: TG-MS*

<400> SEQUENCE: 527

Arg Ser Phe Lys Asp Leu Leu Lys Lys
1               5

<210> SEQ ID NO 528
<211> LENGTH: 9
<212> TYPE: PRT
<213> ORGANISM: TG-DG_1

<400> SEQUENCE: 528

Ala Met Leu Thr Ala Phe Phe Leu Arg
1               5

<210> SEQ ID NO 529
<211> LENGTH: 9
<212> TYPE: PRT
<213> ORGANISM: TG-SAG_1

<400> SEQUENCE: 529

Ser Thr Phe Trp Pro Cys Leu Leu Arg
1               5

<210> SEQ ID NO 530
<211> LENGTH: 9
<212> TYPE: PRT
<213> ORGANISM: TG-SAG_2

<400> SEQUENCE: 530

Ser Ser Ala Tyr Val Phe Ser Val Lys
1               5

<210> SEQ ID NO 531
<211> LENGTH: 10
<212> TYPE: PRT
<213> ORGANISM: TG-DG_2

<400> SEQUENCE: 531
```

```
Ala Val Val Ser Leu Leu Arg Leu Leu Lys
1               5                   10

<210> SEQ ID NO 532
<211> LENGTH: 10
<212> TYPE: PRT
<213> ORGANISM: IAV-MP1_1

<400> SEQUENCE: 532

Ala Ser Cys Met Gly Leu Ile Tyr Asn Arg
1               5                   10

<210> SEQ ID NO 533
<211> LENGTH: 10
<212> TYPE: PRT
<213> ORGANISM: IAV-MP2

<400> SEQUENCE: 533

Arg Leu Phe Phe Lys Cys Ile Tyr Arg Arg
1               5                   10

<210> SEQ ID NO 534
<211> LENGTH: 10
<212> TYPE: PRT
<213> ORGANISM: IAV-NPv1

<400> SEQUENCE: 534

Ser Val Gln Pro Thr Phe Ser Val Gln Arg
1               5                   10

<210> SEQ ID NO 535
<211> LENGTH: 10
<212> TYPE: PRT
<213> ORGANISM: IAV-NPv2

<400> SEQUENCE: 535

Ser Val Gln Arg Asn Leu Pro Phe Glu Arg
1               5                   10

<210> SEQ ID NO 536
<211> LENGTH: 10
<212> TYPE: PRT
<213> ORGANISM: IAV-PA_1

<400> SEQUENCE: 536

Lys Phe Leu Pro Asp Leu Tyr Asp Tyr Lys
1               5                   10

<210> SEQ ID NO 537
<211> LENGTH: 10
<212> TYPE: PRT
<213> ORGANISM: IAV-PCS_1

<400> SEQUENCE: 537

Lys Leu Val Gly Ile Asn Met Ser Lys Lys
1               5                   10

<210> SEQ ID NO 538
<211> LENGTH: 10
<212> TYPE: PRT
<213> ORGANISM: IAV-PCS_2

<400> SEQUENCE: 538

Gly Thr Phe Glu Phe Thr Ser Phe Phe Tyr
1               5                   10
```

<210> SEQ ID NO 539
<211> LENGTH: 10
<212> TYPE: PRT
<213> ORGANISM: IAV-PB2_1

<400> SEQUENCE: 539

Ser Phe Ser Phe Gly Gly Phe Thr Phe Lys
1               5                   10

<210> SEQ ID NO 540
<211> LENGTH: 10
<212> TYPE: PRT
<213> ORGANISM: IAV-PB2_2

<400> SEQUENCE: 540

Val Leu Arg Gly Phe Leu Ile Leu Gly Lys
1               5                   10

<210> SEQ ID NO 541
<211> LENGTH: 9
<212> TYPE: PRT
<213> ORGANISM: DENV2-5-PP

<400> SEQUENCE: 541

Ser Gln Ile Gly Ala Gly Val Tyr Lys
1               5

<210> SEQ ID NO 542
<211> LENGTH: 9
<212> TYPE: PRT
<213> ORGANISM: DENV2-7-PP

<400> SEQUENCE: 542

Lys Thr Phe Asp Ser Glu Tyr Val Lys
1               5

<210> SEQ ID NO 543
<211> LENGTH: 10
<212> TYPE: PRT
<213> ORGANISM: DENV2-8-PP

<400> SEQUENCE: 543

Arg Ile Tyr Ser Asp Pro Leu Ala Leu Lys
1               5                   10

<210> SEQ ID NO 544
<211> LENGTH: 9
<212> TYPE: PRT
<213> ORGANISM: DENV2-9-PP

<400> SEQUENCE: 544

Ala Thr Val Leu Met Gly Leu Gly Lys
1               5

<210> SEQ ID NO 545
<211> LENGTH: 9
<212> TYPE: PRT
<213> ORGANISM: DENV2-10-PP*

<400> SEQUENCE: 545

Ser Thr Tyr Gly Trp Asn Leu Val Arg
1               5

-continued

<210> SEQ ID NO 546
<211> LENGTH: 9
<212> TYPE: PRT
<213> ORGANISM: DENV2-10-PP*

<400> SEQUENCE: 546

Ala Thr Tyr Gly Trp Asn Leu Val Lys
1               5

<210> SEQ ID NO 547
<211> LENGTH: 9
<212> TYPE: PRT
<213> ORGANISM: DENV2-10-PP*

<400> SEQUENCE: 547

Ser Thr Tyr Gly Trp Asn Ile Val Lys
1               5

<210> SEQ ID NO 548
<211> LENGTH: 9
<212> TYPE: PRT
<213> ORGANISM: DENV1-2-PP

<400> SEQUENCE: 548

Thr Val Met Asp Ile Ile Ser Arg Arg
1               5

<210> SEQ ID NO 549
<211> LENGTH: 9
<212> TYPE: PRT
<213> ORGANISM: DENV2-11-PP

<400> SEQUENCE: 549

Arg Thr Thr Trp Ser Ile His Ala Lys
1               5

<210> SEQ ID NO 550
<211> LENGTH: 10
<212> TYPE: PRT
<213> ORGANISM: DENV2-12-PP

<400> SEQUENCE: 550

Arg Gln Met Glu Gly Glu Gly Val Phe Lys
1               5                   10

<210> SEQ ID NO 551
<211> LENGTH: 9
<212> TYPE: PRT
<213> ORGANISM: IAV-MP2-70

<400> SEQUENCE: 551

Lys Ser Met Arg Glu Glu Tyr Arg Lys
1               5

<210> SEQ ID NO 552
<211> LENGTH: 10
<212> TYPE: PRT
<213> ORGANISM: IAV-MP1-178

<400> SEQUENCE: 552

Arg Met Val Leu Ala Ser Thr Thr Ala Lys
1               5                   10

<210> SEQ ID NO 553
<211> LENGTH: 9

```
<212> TYPE: PRT
<213> ORGANISM: IAV-MP1-13

<400> SEQUENCE: 553

Ser Ile Ile Pro Ser Gly Pro Leu Lys
1               5

<210> SEQ ID NO 554
<211> LENGTH: 10
<212> TYPE: PRT
<213> ORGANISM: EBV-LMP2-340*

<400> SEQUENCE: 554

Ser Ser Cys Ser Ser Cys Pro Leu Ser Lys
1               5                   10

<210> SEQ ID NO 555
<211> LENGTH: 10
<212> TYPE: PRT
<213> ORGANISM: EBV-LMP2-340*

<400> SEQUENCE: 555

Ser Ser Cys Ser Ser Cys Pro Leu Ser Lys
1               5                   10

<210> SEQ ID NO 556
<211> LENGTH: 10
<212> TYPE: PRT
<213> ORGANISM: DENV2-PP

<400> SEQUENCE: 556

Ala Val Gln Thr Lys Pro Gly Leu Phe Lys
1               5                   10

<210> SEQ ID NO 557
<211> LENGTH: 10
<212> TYPE: PRT
<213> ORGANISM: DENV3-PP

<400> SEQUENCE: 557

Gly Ala Met Leu Phe Leu Ile Ser Gly Lys
1               5                   10

<210> SEQ ID NO 558
<211> LENGTH: 9
<212> TYPE: PRT
<213> ORGANISM: DENV4-PP

<400> SEQUENCE: 558

Lys Ser Gly Ala Ile Lys Val Leu Lys
1               5

<210> SEQ ID NO 559
<211> LENGTH: 9
<212> TYPE: PRT
<213> ORGANISM: DENV5-PP

<400> SEQUENCE: 559

Lys Thr Phe Val Asp Leu Met Arg Arg
1               5

<210> SEQ ID NO 560
<211> LENGTH: 10
<212> TYPE: PRT
<213> ORGANISM: DENV6-PP
```

<400> SEQUENCE: 560

Met Ala Asn Glu Met Gly Phe Leu Glu Lys
1               5                   10

<210> SEQ ID NO 561
<211> LENGTH: 10
<212> TYPE: PRT
<213> ORGANISM: DENV7-PP*

<400> SEQUENCE: 561

Met Ala Thr Tyr Gly Trp Asn Leu Val Lys
1               5                   10

<210> SEQ ID NO 562
<211> LENGTH: 10
<212> TYPE: PRT
<213> ORGANISM: DENV7-PP*

<400> SEQUENCE: 562

Met Ser Thr Tyr Gly Trp Asn Ile Val Lys
1               5                   10

<210> SEQ ID NO 563
<211> LENGTH: 9
<212> TYPE: PRT
<213> ORGANISM: DENV9-PP

<400> SEQUENCE: 563

Met Ser Tyr Thr Met Cys Ser Gly Lys
1               5

<210> SEQ ID NO 564
<211> LENGTH: 9
<212> TYPE: PRT
<213> ORGANISM: DENV10-PP

<400> SEQUENCE: 564

Met Val Ser Arg Leu Leu Leu Asn Arg
1               5

<210> SEQ ID NO 565
<211> LENGTH: 9
<212> TYPE: PRT
<213> ORGANISM: DENV11-PP

<400> SEQUENCE: 565

Arg Gln Leu Ala Asn Ala Ile Phe Lys
1               5

<210> SEQ ID NO 566
<211> LENGTH: 10
<212> TYPE: PRT
<213> ORGANISM: DENV12-PP*

<400> SEQUENCE: 566

Arg Val Ile Asp Pro Arg Arg Cys Leu Lys
1               5                   10

<210> SEQ ID NO 567
<211> LENGTH: 10
<212> TYPE: PRT
<213> ORGANISM: DENV12-PP*

<400> SEQUENCE: 567

```
Arg Val Ile Asp Pro Arg Arg Cys Met Lys
1               5                   10

<210> SEQ ID NO 568
<211> LENGTH: 9
<212> TYPE: PRT
<213> ORGANISM: DENV15-PP

<400> SEQUENCE: 568

Thr Ser Gly Ser Pro Ile Ile Asp Lys
1               5

<210> SEQ ID NO 569
<211> LENGTH: 10
<212> TYPE: PRT
<213> ORGANISM: DENV16-PP

<400> SEQUENCE: 569

Thr Thr Lys Arg Asp Leu Gly Met Ser Lys
1               5                   10

<210> SEQ ID NO 570
<211> LENGTH: 10
<212> TYPE: PRT
<213> ORGANISM: DENV17-PP

<400> SEQUENCE: 570

Val Thr Arg Gly Ala Val Leu Met His Lys
1               5                   10

<210> SEQ ID NO 571
<211> LENGTH: 10
<212> TYPE: PRT
<213> ORGANISM: DENV18-PP

<400> SEQUENCE: 571

Tyr Val Ser Ala Ile Ala Gln Thr Glu Lys
1               5                   10

<210> SEQ ID NO 572
<211> LENGTH: 15
<212> TYPE: PRT
<213> ORGANISM: DENV19-PP

<400> SEQUENCE: 572

Ser Pro Gly Thr Ser Gly Ser Pro Ile Ile Asp Lys Lys Gly Lys
1               5                   10                  15

<210> SEQ ID NO 573
<211> LENGTH: 9
<212> TYPE: PRT
<213> ORGANISM: EBV-BRLF1

<400> SEQUENCE: 573

Ala Thr Ile Gly Thr Ala Met Tyr Lys
1               5

<210> SEQ ID NO 574
<211> LENGTH: 9
<212> TYPE: PRT
<213> ORGANISM: CMV-pp65_3

<400> SEQUENCE: 574

Gly Pro Ile Ser Gly His Val Leu Lys
```

```
1               5

<210> SEQ ID NO 575
<211> LENGTH: 10
<212> TYPE: PRT
<213> ORGANISM: IAV-MP1_2

<400> SEQUENCE: 575

Ala Tyr Gln Lys Arg Met Gly Val Gln Met
1               5                   10

<210> SEQ ID NO 576
<211> LENGTH: 10
<212> TYPE: PRT
<213> ORGANISM: IAV-PA_2

<400> SEQUENCE: 576

Leu Tyr Ala Ser Pro Gln Leu Glu Gly Phe
1               5                   10

<210> SEQ ID NO 577
<211> LENGTH: 10
<212> TYPE: PRT
<213> ORGANISM: LMAV-GP

<400> SEQUENCE: 577

Leu Val Thr Phe Leu Leu Leu Cys Gly Arg
1               5                   10

<210> SEQ ID NO 578
<211> LENGTH: 10
<212> TYPE: PRT
<213> ORGANISM: LCMV-GP_1

<400> SEQUENCE: 578

Leu Val Ser Phe Leu Leu Leu Ala Gly Arg
1               5                   10

<210> SEQ ID NO 579
<211> LENGTH: 9
<212> TYPE: PRT
<213> ORGANISM: LCMV-GP_2

<400> SEQUENCE: 579

Phe Thr Asn Asp Ser Ile Ile Ser His
1               5

<210> SEQ ID NO 580
<211> LENGTH: 10
<212> TYPE: PRT
<213> ORGANISM: LCMV-RING-Z

<400> SEQUENCE: 580

Thr Thr Tyr Leu Gly Pro Leu Ser Cys Lys
1               5                   10

<210> SEQ ID NO 581
<211> LENGTH: 9
<212> TYPE: PRT
<213> ORGANISM: Mus musculus-GP

<400> SEQUENCE: 581

Ala Ile Asn Ser Glu Met Phe Leu Arg
1               5
```

<210> SEQ ID NO 582
<211> LENGTH: 10
<212> TYPE: PRT
<213> ORGANISM: Mus musculus-Insulin-1

<400> SEQUENCE: 582

Leu Ala Leu Glu Val Ala Arg Gln Lys Arg
1               5                   10

<210> SEQ ID NO 583
<211> LENGTH: 10
<212> TYPE: PRT
<213> ORGANISM: Mus musculus-Insulin-1

<400> SEQUENCE: 583

Thr Leu Ala Leu Glu Val Ala Arg Gln Lys
1               5                   10

<210> SEQ ID NO 584
<211> LENGTH: 10
<212> TYPE: PRT
<213> ORGANISM: Mus musculus-Insulin-2

<400> SEQUENCE: 584

Thr Leu Ala Leu Glu Val Ala Gln Gln Lys
1               5                   10

<210> SEQ ID NO 585
<211> LENGTH: 9
<212> TYPE: PRT
<213> ORGANISM: MTB-Ag85B

<400> SEQUENCE: 585

Ala Met Gly Asp Ala Gly Gly Tyr Lys
1 5

<210> SEQ ID NO 586
<211> LENGTH: 9
<212> TYPE: PRT
<213> ORGANISM: Hepatitis B virus

<400> SEQUENCE: 586

Ser Thr Asn Arg Gln Ser Gly Arg Gln
1 5

<210> SEQ ID NO 587
<211> LENGTH: 11
<212> TYPE: PRT
<213> ORGANISM: Hepatitis B virus

<400> SEQUENCE: 587

Arg Ser Gln Ser Pro Arg Arg Arg Arg Ser Gln
1 5 10

<210> SEQ ID NO 588
<211> LENGTH: 11
<212> TYPE: PRT
<213> ORGANISM: Hepatitis B virus

<400> SEQUENCE: 588

Lys Ala Ala His Ser Leu Ile Ser Thr Ser Lys
1 5 10

<210> SEQ ID NO 589

```
<211> LENGTH: 11
<212> TYPE: PRT
<213> ORGANISM: Hepatitis B virus

<400> SEQUENCE: 589

Thr Val Val Arg Arg Arg Cys Arg Ser Pro Arg
1               5                   10

<210> SEQ ID NO 590
<211> LENGTH: 9
<212> TYPE: PRT
<213> ORGANISM: Hepatitis B virus

<400> SEQUENCE: 590

Val Val Ser His Tyr Phe Gln Thr Arg
1               5

<210> SEQ ID NO 591
<211> LENGTH: 11
<212> TYPE: PRT
<213> ORGANISM: Hepatitis B virus

<400> SEQUENCE: 591

Glu Thr Ala Tyr Ser His Leu Thr Thr Ser Lys
1               5                   10

<210> SEQ ID NO 592
<211> LENGTH: 11
<212> TYPE: PRT
<213> ORGANISM: Hepatitis B virus

<400> SEQUENCE: 592

Glu Ala Ala Tyr Ser Phe Ile Ser Thr Ser Glu
1               5                   10

<210> SEQ ID NO 593
<211> LENGTH: 11
<212> TYPE: PRT
<213> ORGANISM: Hepatitis B virus

<400> SEQUENCE: 593

Ser Thr Leu Pro Glu Thr Thr Val Val Arg Cys
1               5                   10

<210> SEQ ID NO 594
<211> LENGTH: 11
<212> TYPE: PRT
<213> ORGANISM: Hepatitis B virus

<400> SEQUENCE: 594

Thr Val Val Arg Cys Arg Gly Arg Ser Thr Arg
1               5                   10

<210> SEQ ID NO 595
<211> LENGTH: 11
<212> TYPE: PRT
<213> ORGANISM: Hepatitis B virus

<400> SEQUENCE: 595

Thr Val Ile Arg Arg Arg Gly Arg Thr Pro Arg
1               5                   10

<210> SEQ ID NO 596
<211> LENGTH: 9
<212> TYPE: PRT
```

<213> ORGANISM: Hepatitis B virus

<400> SEQUENCE: 596

Ser Asn Asn Arg Gln Ser Gly Arg Gln
1               5

<210> SEQ ID NO 597
<211> LENGTH: 11
<212> TYPE: PRT
<213> ORGANISM: Hepatitis B virus

<400> SEQUENCE: 597

Lys Ala Ala Asn Ser Leu Ile Ser Thr Ser Lys
1               5                   10

<210> SEQ ID NO 598
<211> LENGTH: 11
<212> TYPE: PRT
<213> ORGANISM: Hepatitis B virus

<400> SEQUENCE: 598

Lys Ala Ala Tyr Ser Leu Ile Ser Thr Ser Thr
1               5                   10

<210> SEQ ID NO 599
<211> LENGTH: 11
<212> TYPE: PRT
<213> ORGANISM: Hepatitis B virus

<400> SEQUENCE: 599

Lys Ala Ala Tyr Ser Arg Ile Ser Thr Ser Lys
1               5                   10

<210> SEQ ID NO 600
<211> LENGTH: 9
<212> TYPE: PRT
<213> ORGANISM: Hepatitis B virus

<400> SEQUENCE: 600

Tyr Asp Ser Leu Ile Leu Leu Tyr Lys
1               5

<210> SEQ ID NO 601
<211> LENGTH: 9
<212> TYPE: PRT
<213> ORGANISM: Hepatitis B virus

<400> SEQUENCE: 601

Tyr Asp Ser Leu Met Leu Leu Tyr Lys
1               5

<210> SEQ ID NO 602
<211> LENGTH: 11
<212> TYPE: PRT
<213> ORGANISM: Hepatitis B virus

<400> SEQUENCE: 602

Thr Thr Val Asn Thr His Gly Asn Leu Pro Lys
1               5                   10

<210> SEQ ID NO 603
<211> LENGTH: 11
<212> TYPE: PRT
<213> ORGANISM: Hepatitis B virus -continued

```
<400> SEQUENCE: 603

Arg Thr Gln Ser Pro Arg Arg Arg Ser Gln
1               5                   10

<210> SEQ ID NO 604
<211> LENGTH: 11
<212> TYPE: PRT
<213> ORGANISM: Hepatitis B virus

<400> SEQUENCE: 604

Thr Val Val Arg Arg Arg Gly Arg Ser Thr Arg
1               5                   10

<210> SEQ ID NO 605
<211> LENGTH: 11
<212> TYPE: PRT
<213> ORGANISM: Hepatitis B virus

<400> SEQUENCE: 605

Thr Thr Val Asn Ala His Glu Asn Leu Pro Lys
1               5                   10

<210> SEQ ID NO 606
<211> LENGTH: 9
<212> TYPE: PRT
<213> ORGANISM: Hepatitis B virus

<400> SEQUENCE: 606

Val Val Asn His Tyr Leu Gln Thr Arg
1               5

<210> SEQ ID NO 607
<211> LENGTH: 11
<212> TYPE: PRT
<213> ORGANISM: Hepatitis B virus

<400> SEQUENCE: 607

Lys Ala Ser Tyr Ser Leu Ile Ser Thr Ser Lys
1               5                   10

<210> SEQ ID NO 608
<211> LENGTH: 11
<212> TYPE: PRT
<213> ORGANISM: Hepatitis B virus

<400> SEQUENCE: 608

Lys Ala Ala Tyr Ser Ile Ile Ser Thr Ser Lys
1               5                   10

<210> SEQ ID NO 609
<211> LENGTH: 9
<212> TYPE: PRT
<213> ORGANISM: Hepatitis B virus

<400> SEQUENCE: 609

Tyr Asp Ser Leu Met Leu Leu Tyr Lys
1               5

<210> SEQ ID NO 610
<211> LENGTH: 11
<212> TYPE: PRT
<213> ORGANISM: Hepatitis B virus

<400> SEQUENCE: 610
```

Ser Thr Leu Pro Glu Ile Thr Val Val Arg Arg
1               5                   10

<210> SEQ ID NO 611
<211> LENGTH: 8
<212> TYPE: PR

```
<211> LENGTH: 12
<212> TYPE: PRT
<213> ORGANISM: Hepatitis B virus

<400> SEQUENCE: 617

Lys Ala Ala His Ser Leu Ile Ser Thr Ser Lys Gly
1               5                   10

<210> SEQ ID NO 618
<211> LENGTH: 12
<212> TYPE: PRT
<213> ORGANISM: Hepatitis B virus

<400> SEQUENCE: 618

Lys Ala Ser Tyr Ser Leu Ile Ser Thr Ser Lys Gly
1               5                   10

<210> SEQ ID NO 619
<211> LENGTH: 11
<212> TYPE: PRT
<213> ORGANISM: Hepatitis B virus

<400> SEQUENCE: 619

Ser Thr Leu Pro Glu Thr Thr Val Val Arg Gln
1               5                   10

<210> SEQ ID NO 620
<211> LENGTH: 11
<212> TYPE: PRT
<213> ORGANISM: Hepatitis B virus

<400> SEQUENCE: 620

Ser Thr Leu Pro Glu Thr Ala Val Val Arg Arg
1               5                   10

<210> SEQ ID NO 621
<211> LENGTH: 11
<212> TYPE: PRT
<213> ORGANISM: Hepatitis B virus

<400> SEQUENCE: 621

Ser Thr Leu Pro Glu Thr Ala Val Val Arg Pro
1               5                   10
```